(12) United States Patent
Bacon et al.

(10) Patent No.: US 8,513,232 B2
(45) Date of Patent: Aug. 20, 2013

(54) SUBSTITUTED SPIROCYCLIC PIPERIDINE DERIVATIVES AS HISTAMINE-3 (H3) RECEPTOR LIGANDS

(75) Inventors: Edward R. Bacon, Audobon, PA (US); Nadine C. Becknell, Coatesville, PA (US); Reddeppa reddy Dandu, Downingtown, PA (US); Lisa Guise-Zawacki, Yardley, PA (US); Tao Guo, Dayton, NJ (US); Chia-yu Huang, Princeton Junction, NJ (US); Robert L. Hudkins, Chester Springs, PA (US); Babu G. Sundar, West Chester, PA (US); Ming Tao, Maple Glen, PA (US); Minglang Wu, Monmouth Junction, NJ (US); Allison L. Zulli, Wayne, PA (US)

(73) Assignees: Cephalon, Inc., Frazer, PA (US); Pharmacopeia, LLC, San Diego, CA (US)

( * ) Notice: Subject to any disclaimer, the term of this patent is extended or adjusted under 35 U.S.C. 154(b) by 284 days.

(21) Appl. No.: 12/846,100

(22) Filed: Jul. 29, 2010

(65) Prior Publication Data

US 2011/0071131 A1 Mar. 24, 2011

Related U.S. Application Data

(63) Continuation of application No. PCT/US2009/032709, filed on Jan. 30, 2009.

(60) Provisional application No. 61/062,907, filed on Jan. 30, 2008.

(51) Int. Cl.
| | |
|---|---|
| *C07D 491/10* | (2006.01) |
| *C07D 401/14* | (2006.01) |
| *C07D 471/10* | (2006.01) |
| *A61K 31/397* | (2006.01) |
| *A61K 31/438* | (2006.01) |
| *A61K 31/506* | (2006.01) |
| *A61P 11/00* | (2006.01) |
| *A61P 1/00* | (2006.01) |
| *A61P 25/00* | (2006.01) |
| *A61P 29/00* | (2006.01) |

(52) U.S. Cl.
USPC ...... 514/210.21; 514/274; 514/278; 544/230; 544/70; 546/17

(58) Field of Classification Search
USPC ......... 514/210.21, 232.8, 274, 278; 544/230, 544/70; 546/17
See application file for complete search history.

(56) References Cited

U.S. PATENT DOCUMENTS

| | | | |
|---|---|---|---|
| 4,166,120 A | 8/1979 | Effland et al. | |
| 2005/0159438 A1* | 7/2005 | Dolle et al. | 514/278 |

FOREIGN PATENT DOCUMENTS

| | | | |
|---|---|---|---|
| EP | 1 481 679 A1 | 12/2004 | |
| WO | WO2004/005295 A1 | 1/2004 | |
| WO | WO2007/063385 A2 | 6/2007 | |
| WO | WO2007/088462 A1 | 8/2007 | |
| WO | WO2009/039431 A2 | 3/2009 | |
| WO | WO2009/097567 A1 | 8/2009 | |

OTHER PUBLICATIONS

Alguacil et al., "Histamine $H_3$ Receptor: A Potential Drug Target for the Treatment of Central Nervous System Disorders", *Current Drug Targets—CNS & Neurological Disorders* (2003), 2, pp. 303-313.
Arrang et al., "Auto-Inhibition of Brain Histamine Release Mediated by a Novel Class ($H_3$) of Histamine Receptor", *Nature* (1983), 302, pp. 832-837.
Celanire et al, "Histamine $H_3$ Receptor Antagonists Reach Out for the Clinic", *Drug Discovery Today* (2005), 10(23-24), pp. 1613-1627.
Chazot et al., "$H_3$ Histamine Receptor Isoforms: New Therapeutic Targets in the CNS?", *Current Opinion in Investigational Drugs* (2001), 2(10), pp. 1428-1431.
Chen, "Effect of Histamine $H_3$-Receptor Antagonist Clobenpropit on Spatial Memory of Radial Maze Performance in Rats", *Acta Pharmacol. Sin.* (2000), 21(10), pp. 905-910.
Esbenshade et al., "Histamine $H_3$ Receptor Antagonists: Preclinical Promise for Treating Obesity and Cognitive Disorders", *Molecular Interventions* (2006), 6(2), pp. 77-88.
Fletcher et al., "4-(Phenylsulfonyl)piperidines: Novel, Selective, and Bioavailable 5-$HT_{2A}$ Receptor Antagonists", *J. Med. Chem.* (2002), 45, pp. 492-503.
Fox et al., "Effects of Histamine $H_3$ Receptor Ligands GT-2331 and Ciproxifan in a Repeated Acquisition Avoidance Response in the Spontaneously Hypertensive Rat Pup", *Behavioural Brain Res.* (2002), 131, pp. 151-161.
Fox et al. "Two Novel and Selective Nonimidazole $H_3$ Receptor Antagonists A-304121 and A-317920: II. In vivo Behavioral and Neurophysiological Characterization", *J. Pharmacol. Exper. Ther.* (2003), 305(3), pp. 897-908.
Hancock et al., "Genetic and Pharmacological Aspects of Histamine $H_3$ Receptor Heterogeneity", *Life Sci.* (2003), 73(24), pp. 3043-3072.
Hancock et al., "Perspectives on Cognitive Domains, $H_3$ Receptor Ligands and Neurological Disease", *Expert Opin. Investig. Drugs* (2004), 13, pp. 1237-1248.
Komater et al., "$H_3$ Receptor Blockade by Thioperamide Enhances Cognition in Rats Without Inducing Locomotor Sensitization", *Psychopharmacology* (2003), 167, pp. 363-372.
Leurs et al., "Therapeutic Potential of Histamine $H_3$ Receptor Agonists and Antagonists", *Trends in Pharmacology* (1998), 19, pp. 177-183.
Leurs et al., "The Histamine $H_3$ Receptor: From Gene Cloning to $H_3$ Receptor Drugs", *Nat. Rev. Drug Discovery* (2005), 4(2), pp. 107-120.
Lin et al., "Involvement of Histaminergic Neurons in Arousal Mechanisms Demonstrated with $H_3$-Receptor Ligands in the Cat", *Brain Res.* (1990), 523(2), pp. 325-330.

(Continued)

*Primary Examiner* — Sreeni Padmanabhan
*Assistant Examiner* — Uma Ramachandran

(57) ABSTRACT

The present invention provides compounds of Formula (I):

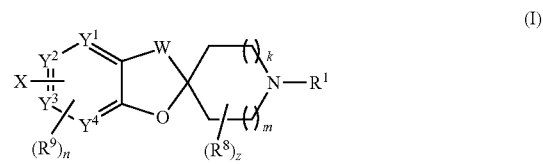

their use as $H_3$ antagonists/inverse agonists, processes for their preparation, and pharmaceuticals compositions thereof.

30 Claims, No Drawings

(56) References Cited

OTHER PUBLICATIONS

Lloyd et al., "Neuronal Nicotinic Acetylcholine Receptors as Novel Drug Targets", *J. Pharmacol. And Exper. Ther.* (2000), 292(2), pp. 461-467.

Monti et al., Sleep and Waking During Acute Histamine $H_3$ Agonist BP 2.94 or $H_3$ Antagonist Carboperamide (MR16155) Administration in Rats, *Neuropsychopharmacology* (1996), 15(1), pp. 31-35.

Orsetti et al., "Histamine $H_3$-Receptor Blockade in the Rat Nucleus *Basalis magnocellularis* Improves Place Recognition Memory", *Psychopharmacology* (2002), 159, pp. 133-137.

Parmentier et al., Anatomical, Physiological, and Pharmacological Characteristics of Histidine Decarboxylase Knock-Out Mice: Evidence for the Role of Brain Histamine in Behavioral and Sleep-Wake Control, *J. Neurosci.* (2002), 22(17), pp. 7695-7711.

Passani et al., The Histamine $H_3$ Receptor as a Novel Therapeutic Target for Cognitive and Sleep Disorders, *Trends Pharmacol, Sci.* (2004), 25(12), pp. 618-625.

Repka-Ramirez, "New Concepts of Histamine Receptors and Actions", *Current Allergy & Asthma Reports* (2003), 3, pp. 227-231.

Rizk et al., "Anxiety and Cognition in Histamine $H_3$ Receptor −/− Mice", *Eur. J. Neurosci.* (2004), 19, pp. 1992-1996.

Rouleau et al., "Cloning and Expression of the Mouse Histamine $H_3$ Receptor: Evidence for Multiple Isoforms", *J. Neurochem.* (2004), 90, pp. 1331-1338.

Vanni-Mercier et al., "Waking Selective Neurons in the Posterior Hypothalamus and Their Response to Histamine $H_3$-Receptor Ligands: an Electrophysiological Study in Freely Moving Cats", *Behavioural Brain Res.* (2003), 144, pp. 227-241.

Witkin et al., "Selective Histamine $H_3$ Receptor Antagonists for Treatment of Cognitive Deficiencies and Other Disorders of the Central Nervous System", *Pharmacol. & Therap.* (2004), 103, pp. 1-20.

Yao et al., "Cloning and Pharmacological Characterization of the Monkey Histamine $H_3$ Receptor", *Euro. J. Pharmacol.* (2003), 482, pp. 49-60.

\* cited by examiner

SUBSTITUTED SPIROCYCLIC PIPERIDINE DERIVATIVES AS HISTAMINE-3 (H3) RECEPTOR LIGANDS

CROSS-REFERENCE TO RELATED APPLICATIONS

This application is a continuation of International Application No. PCT/US2009/097309, filed Jan. 28, 2009, which claims priority to U.S. Provisional Application Ser. No. 61/062,909, filed Jan. 30, 2008. The disclosures of the aforementioned applications are incorporated herein by reference in their entireties for all purposes.

FIELD OF THE INVENTION

The present invention is related to substituted spirocyclic piperidine derivatives, their use as $H_3$ antagonists/inverse agonists, processes for their preparation, and pharmaceutical compositions thereof.

BACKGROUND OF THE INVENTION

Publications cited throughout this disclosure are incorporated in their entirety herein by reference.

Histamine is a well established modulator of neuronal activity. At least four subtypes of histamine receptors have been reported in the literature—$H_1$, $H_2$, $H_3$, $H_4$. The histamine $H_3$ receptors play a key role in neurotransmission in the central nervous system. The $H_3$ receptor was discovered in 1983 originally on histamine-containing neurons where it was shown to function presynaptically, regulating the release and synthesis of the biogenic amine histamine (Arrang et al, 1983) now a well established neurotransmitter. $H_3$ receptors are predominately expressed in the brain, localizing to the cerebral cortex, amygdala, hippocampus, striatum, thalamus and hypothalamus. $H_3$ receptors are also localized presynaptically on histaminergic nerve terminals and act as inhibitory autoreceptors (Alguacil and Perez-Garcia, 2003; Passani et al, 2004; Leurs at al, 2005; Celanire et al, 2005; Witkin and Nelson, 2004). When these receptors are activated by histamine, histamine release is inhibited. $H_3$ receptors can also be found in the periphery (skin, lung, cardiovascular system, intestine, GI tract, etc). $H_3$ receptors are also involved in presynaptic regulation of the release of acetylcholine, dopamine, GABA, glutamate and serotonin (see Repka-Ramirez, 2003; Chazot and Hann, 2001; Leurs et al, 1998). The $H_3$ receptor demonstrates a high degree of constitutive or spontaneous activity (e.g., receptor is active in the absence of agonist stimulation) in vitro and in vivo, thus, ligands to the receptor can display, agonist, neutral antagonist or inverse agonist effects.

The location and function of histaminergic neurons in the CNS suggests that compounds interacting with the $H_3$ receptor may have utility in a number of therapeutic applications including narcolepsy or sleep/wake disorders, feeding behavior, eating disorders, obesity, cognition, arousal, memory, mood disorders, mood attention alteration, attention deficit hyperactivity disorder (ADHD), Alzheimer's disease/dementia, schizophrenia, pain, stress, migraine, motion sickness, depression, psychiatric disorders and epilepsy (Leurs et al, 2005; Witkin and Nelson, 2004, Hancock and Fox 2004; Esbenshade et al. 2006). An $H_3$ antagonist/inverse agonist could be important for gastrointestinal disorders, respiratory disorders such as asthma, inflammation, and myocardial infarction.

Ohtake et al. (US 2006/0178375 A1) disclosed compounds that reportedly exhibit histamine receptor $H_3$ antagonist or inverse agonist activity and may be useful for the treatment or prevention of obesity, diabetes, hormonal secretion abnormality, or sleep disorders.

Celanire et al. (WO 2006/103057 A1 and WO 2006/103045) have disclosed compounds comprising an oxazoline or thiazoline moiety, processes for preparing them, their pharmaceutical compositions and their uses as $H_3$ ligands.

Bertrand et al. (WO 2006/117609 A2) disclosed novel histamine $H_3$ receptor ligands, processes for their preparation, and their therapeutic applications.

Schwartz et al. (WO 2006/103546 A2) disclosed certain methods of treatment for Parkinson's disease, obstructive sleep apnea, narcolepsy, dementia with Lewy bodies, and/or vascular dementia using non-imidazole alkylamine derivatives that are antagonists of the $H_3$ receptors of histamine.

Apodaca et al. (EP 1 311 482 B1) disclosed certain non-imidazole aryloxypiperidines as $H_3$ receptor ligands, their synthesis, and their use for the treatment of disorders and conditions mediated by the histamine receptor.

Xu et al. disclosed certain 6-substituted phenyl-4,5-dihydro-3(2H)-pyridazinones, their synthesis, and rabbit platelet aggregation inhibitory activity induced by ADP in vitro.

Barker et al. (US 2006/0217375) discloses spiro[benzodioxane] compounds as active antagonists of the orexin-1 receptor and potentially useful in the prophylaxis and treatment of orexin-1 receptor related disorders and orexin-2 receptor related disorders.

Thus, there is a need for novel classes of compounds that possess the beneficial properties. It has been discovered that currently disclosed class of compounds, referred to herein as substituted spirocycle derivatives, are useful as agents for treating or preventing various diseases or disorders disclosed herein.

SUMMARY OF THE INVENTION

The present invention in one aspect is directed to novel compounds which are useful as $H_3$ antagonists/inverse agonists. These compounds have the structure of Formula (I):

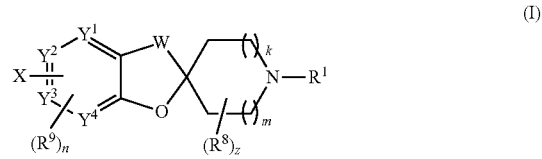

and its stereoisomeric forms, mixtures of stereoisomeric forms, N-oxide forms, and pharmaceutically acceptable salt forms thereof, wherein the constituent members are defined infra. More specifically, the novel compounds are substituted spiropiperidines.

The compounds of the present invention may be used to treat the following diseases and disorders: narcolepsy or other sleep/wake disorders, such as obstructive sleep apnea/hypopnea syndrome, and shift work sleep disorder; feeding behavior disorders, eating disorders, obesity, cognition disorders, arousal disorders, memory disorders, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders (such as asthma), inflammation, and myocardial infarction.

In another aspect, the present invention is directed to pharmaceutical compositions which comprise a pharmaceutically acceptable carrier and a compound of the present invention, preferably in a therapeutically effective amount.

DETAILED DESCRIPTION OF THE INVENTION

The present invention is directed to compounds of Formula I:

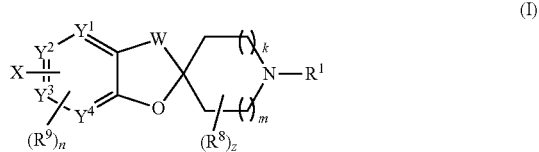

(I)

and stereoisomeric forms, mixtures of stereoisomeric forms, N-oxide forms, or pharmaceutically acceptable salt forms thereof, wherein:

$R^1$ is a $C_1$-$C_8$ alkyl, $C_3$-$C_8$ cycloalkyl ring, $C_3$-$C_8$ heterocycloalkyl ring, or —($C_1$-$C_3$alkyl)-$C_3$-$C_8$ heterocycloalkyl ring, each optionally substituted with 1-3 $R^{20}$;

k is 0, 1, or 2; m is 0, 1, or 2; and the sum of m and k is 1, 2, or 3;

$Y^1$, $Y^2$, $Y^3$, and $Y^4$ are independently selected from —CH= and —N=;

provided that when $Y^1$, $Y^2$, $Y^3$, and $Y^4$ are independently selected from —N= with the proviso that no more than of $Y^1$, $Y^2$, $Y^3$, and $Y^4$ may be —N=;

W is —O—, —$CH_2$—, —$CH_2$—O—, —C(=O)—$CH_2$—, —C(OH)—$CH_2$—, —$CH_2$—$CH_2$—, —O—$CH_2$—$CH_2$— or —$CH_2$—$CH_2$—O—;

X is $R^2$, —$OR^2$, —($C_1$-$C_3$ alkyl)-$R^2$; —($C_2$-$C_6$ alkenyl)-$R^2$; —O($C_1$-$C_3$ alkyl)-$R^2$, —O($C_2$-$C_6$ alkenyl)-$R^2$; —$NR^{29}R^{29}$, —$NR^{29}R^2$, —$NR^{29}(C_1$-$C_3$ alkyl)-$R^2$, —($C_1$-$C_3$ alkyl)$NR^{29}R^2$, —$NR^{29}C(=O)R^2$, —$NR^{29}C(=O)(C_1$-$C_3$ alkyl)-$R^2$, or —$NR^{29}C(=O)NHR^2$; wherein each of said ($C_1$-$C_3$ alkyl) is optionally substituted with —OH or —$OC_1$-$C_3$alkyl;

$R^2$ is selected from the group consisting of $C_1$-$C_8$ alkyl optionally substituted with 1-3 $R^{20}$;

$C_2$-$C_6$ alkenyl optionally substituted with 1-3 $R^{20}$;

$C_3$-$C_2$ cycloalkyl optionally substituted with 1-3 $R^{20}$;

$C_6$-$C_{10}$ aryl optionally substituted with 1-3 $R^{20}$;

5 to 10 membered heteroaryl ring system containing one, two, or three heteroatoms selected from N, O, and S, wherein said heteroaryl ring system is optionally substituted with 1-3 $R^{20}$; and 3 to 10 membered heterocycloalkyl ring system containing one, two, or three heteroatoms selected from N, O, S, SO, and $SO_2$, wherein said heterocycloalkyl ring system is optionally substituted with 1-3 $R^{20}$;

with the proviso that $R^2$ is not:

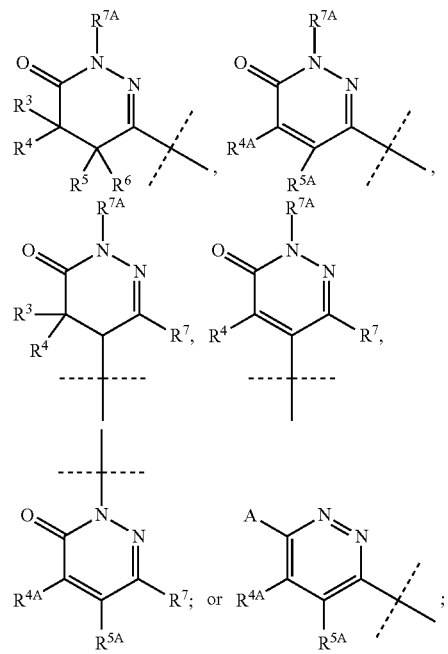

wherein:
A is F, Cl, or Br;
$R^3$ is H, F, or $C_1$-$C_4$ alkyl;
$R^4$ is H, F, or $C_1$-$C_4$ alkyl;
$R^{4A}$ is H, F, Cl, Br, or $C_1$-$C_4$ alkyl;
$R^5$ is H, F, or $C_1$-$C_4$ alkyl;
$R^{5A}$ is H, F, Cl, Br, $C_1$-$C_4$ alkyl; or phenyl;
or wherein, $R^4$ and $R^5$, together with the carbon atoms to which they are attached, may form a fused $C_3$-$C_6$ cycloalkyl ring optionally substituted with 1, 2, or 3 $R^{14}$;
or wherein, $R^{4A}$ and $R^{5A}$, together with the carbon atoms to which they are attached, may form a fused phenyl ring optionally substituted with 1, 2, or 3 $R^{14}$;
a $C_3$-$C_6$ cycloalkyl ring optionally substituted with 1, 2 or 3 $R^{14}$;
a 5 to 6 membered fused heteroaryl ring system containing one, two, or three heteroatoms selected from N, O, and S, wherein said heteroaryl ring system is optionally substituted with 1, 2, or 3 $R^{14}$; or
a 5 to 6 membered fused heterocycloalkyl ring system containing one, two, or three heteroatoms selected from N, O, S, SO, and $SO_2$, wherein said heterocycloalkyl ring system is optionally substituted with 1, 2, or 3 $R^{14}$;
$R^6$ is H, F, or $C_1$-$C_4$ alkyl;
$R^7$ is H, F, Cl, Br, or $C_1$-$C_4$ alkyl;
$R^{7A}$ is H, —C(=O)$R^{270}$, —$CO_2R^{270}$, $C_1$-$C_6$ alkyl optionally substituted by 1-3 $R^{200}$;
$C_3$-$C_8$ cycloalkyl optionally substituted by 1-3 $R^{200A}$;
$C_6$-$C_{10}$ aryl optionally substituted by 1-3 $R^{200A}$;
$C_7$-$C_{15}$ arylalkyl optionally substituted by 1-3 $R^{200A}$; or
a 5 to 10 membered heteroaryl ring system containing one, two, or three heteroatoms selected from N, O, and S, wherein said heteroaryl ring system is optionally substituted with 1-3 $R^{200A}$;
$R^{14}$ at each occurrence is independently F, Br, I, —$OR^{210}$, —$OR^{220}$, —$NR^{230}R^{240}$, —NHOH, —$NO_2$, —CN, —$CF_3$, (=O), —C(=O)$R^{210}$, —$CO_2R^{210}$, —OC(=O)$R^{206}$, —C(=O)$NR^{230}R^{240}$, —NR$^{270}$C(=O)R$^{210}$, NR$^{270}$C(=O)OR$^{210}$, —OC(=O)NR$^{230}$R$^{240}$, —NR$^{270}$C(=S)R$^{210}$, —SR$^{210}$, —S(O)R$^{210}$, or —S(O)$_2$R$^{210}$; C$_1$-C$_6$ alkyl optionally substituted with OR$^{260}$; C$_2$-C$_6$ alkenyl, or C$_2$-C$_6$ alkynyl;

R$^{200}$ at each occurrence is independently F, Cl, Br, I, —OR$^{210}$, —OR$^{220}$, —NR$^{230}$R$^{240}$, —NHOH, —NO$_2$, —CN, —CF$_3$, (=O), —C(=O)R$^{210}$, —CO$_2$R$^{210}$, —OC(=O)R$^{210}$, —C(=O)NR$^{230}$R$^{240}$, —NR$^{270}$C(=O)R$^{210}$, —NR$^{270}$C(=O)OR$^{210}$, —OC(=O)NR$^{230}$R$^{240}$, —NR$^{270}$C(=S)R$^{210}$, —SR$^{210}$, —S(O)R$^{210}$, or —S(O)$_2$R$^{210}$; C$_1$-C$_6$ alkyl optionally substituted with OR$^{260}$; C$_2$-C$_6$ alkenyl, C$_2$-C$_6$ alkynyl, C$_3$-C$_7$ cycloalkyl, phenyl, 3- to 7-membered heterocycloalkyl group, or 5- or 6-membered heteroaryl group;

R$^{200A}$ at each occurrence is independently F, Cl, Br, I, —OR$^{210}$, —OR$^{220}$, —NR$^{230}$R$^{240}$, —NHOH, —NO$_2$, —CN, —CF$_3$, (=O), —C(=O)R$^{210}$, —CO$_2$R$^{210}$, —OC(=O)R$^{210}$, —C(=O)NR$^{230}$R$^{240}$, —NR$^{270}$C(=O)R$^{210}$, —NR$^{270}$C(=O)OR$^{210}$, —OC(=O)NR$^{230}$R$^{240}$, —NR$^{270}$C(=S)R$^{210}$, —SR$^{210}$, —S(O)R$^{210}$, or —S(O)$_2$R$^{210}$; C$_1$-C$_6$ alkyl optionally substituted with OR$^{260}$; C$_2$-C$_6$ alkenyl, or C$_2$-C$_6$ alkynyl;

R$^{210}$ at each occurrence is independently H, C$_1$-C$_6$ alkyl, C$_6$-C$_{10}$ aryl, or C$_7$-C$_{15}$ arylalkyl;

R$^{220}$ at each occurrence is independently the residue of an amino acid after the hydroxyl group of the carboxyl group is removed;

R$^{230}$ and R$^{240}$ at each occurrence is independently selected from H, C$_1$-C$_6$ alkyl, and C$_6$-C$_{10}$ aryl; alternatively, R$^{230}$ and R$^{240}$, together with the nitrogen atom to which they are attached, form a 3 to 7 membered heterocycloalkyl ring system containing one, two, or three heteroatoms selected from N, O, and S, wherein said heterocycloalkyl ring system is optionally substituted with =O;

R$^{260}$ is H or C$_1$-C$_6$ alkyl;
R$^{270}$ is H or C$_1$-C$_6$ alkyl;
R$^8$ is F, C$_1$-C$_3$ alkyl, or C$_1$-C$_3$ alkoxy;
R$^9$, at each occurrence, is independently, F, Cl, Br, C$_1$-C$_4$ alkyl, or C$_1$-C$_4$ alkoxy;
R$^{20}$ at each occurrence is independently selected from the group consisting of
—H, —F, —Cl, —Br, —I, —OR$^{21}$, —NR$^{23}$R$^{24}$, —NHOH, —NO$_2$, —CN, —CF$_3$, —CHF$_2$, —CH$_2$F, (=O), —C(=O)R$^{25}$, —C(=O)OR$^{25}$, —OC(=O)R$^{25}$, —OC(=O)NR$^{23}$R$^{24}$, —C(=O)NR$^{23}$R$^{24}$, —NR$^{27}$C(=O)NR$^{23}$R$^{24}$, —NR$^{27}$C(=O)R$^{25}$, —NR$^{27}$C(=O)OR$^{25}$, —NR$^{27}$C(=S)R$^{25}$, —SR$^{25}$, —S(=O)R$^{25}$, —S(=O)$_2$R$^{25}$, —S(=O)$_2$NR$^{23}$R$^{24}$, —NR$^{27}$SR$^{25}$, —NR$^{27}$S(=O)R$^{25}$, —NR$^{27}$S(=O)$_2$R$^{25}$, methylenedioxy, ethylenedioxy, propylenedioxy, C$_1$-C$_6$ alkyl optionally substituted by 1-3 R$^{31}$;
C$_2$-C$_6$ alkenyl optionally substituted by 1-3 R$^{31}$;
C$_2$-C$_6$ alkynyl optionally substituted by 1-3 R$^{31}$;
C$_3$-C$_7$ cycloalkyl optionally substituted with 1-3 R$^{30}$;
C$_6$-C$_{10}$ aryl optionally substituted with 1-3 R$^{30}$;
5 to 6 membered heteroaryl ring system containing one, two, or three heteroatoms selected from N, O, and S, wherein said heteroaryl ring system is optionally substituted with 1-3 R$^{30}$; and
3 to 7 membered heterocycloalkyl ring system containing one, two, or three heteroatoms selected from N, O, S, SO, and SO$_2$, wherein said heterocycloalkyl ring system is optionally substituted with 1-3 R$^{30}$;

R$^{21}$ at each occurrence is independently H, C$_1$-C$_4$ haloalkyl, C$_1$-C$_4$ alkyl optionally substituted with 1-3 R$^{22}$; C$_2$-C$_6$ alkenyl optionally substituted with 1-3 R$^{22}$; C$_6$-C$_{10}$ aryl optionally substituted with 1-3 R$^{30}$; 5 to 6 membered heteroaryl ring system containing one, two, or three heteroatoms selected from N, O, and S, wherein said heteroaryl ring system is optionally substituted with 1-3 R$^{30}$; and 3 to 7 membered heterocycloalkyl ring system containing one, two, or three heteroatoms selected from N, O, S, SO, and SO$_2$, wherein said heterocycloalkyl ring system is optionally substituted with 1-3 R$^{30}$;

R$^{22}$ at each occurrence is independently selected from the group consisting of
—H, —F, —Cl, —Br, —I, —C$_1$-C$_6$ alkoxy, phenyl, —NR$^{23}$R$^{24}$, —NHOH, —NO$_2$, —CN, —CF$_3$, —CHF$_2$, —CH$_2$F, (=O), —C(=O)R$^{28}$, —C(=O)OR$^{28}$, —OC(=O)R$^{28}$, —OC(=O)NR$^{23}$R$^{24}$, —C(=O)NR$^{23}$R$^{24}$, —NR$^{27}$C(=O)NR$^{23}$R$^{24}$, —NR$^{27}$C(=O)R$^{28}$, —NR$^{27}$C(=O)OR$^{28}$, —NR$^{27}$C(=S)R$^{28}$, —SR$^{28}$, —S(=O)R$^{28}$, —S(=O)$_2$R$^{28}$, —S(=O)$_2$NR$^{23}$R$^{24}$, —NR$^{27}$SR$^{28}$, —NR$^{27}$S(=O)R$^{28}$, —NR$^{27}$S(=O)$_2$R$^{28}$, and C$_3$-C$_7$ cycloalkyl;

R$^{23}$ and R$^{24}$ at each occurrence are each independently selected from H, C$_1$-C$_6$ alkyl optionally substituted with 1-3 R$^{31}$; C$_3$-C$_7$ cycloalkyl; C$_6$-C$_{10}$ aryl optionally substituted with 1-3 R$^{30}$; 5 to 6 membered heteroaryl ring system containing one, two, or three heteroatoms selected from N, O, and S, said heteroaryl optionally substituted with 1-3 R$^{30}$; and 3 to 7 membered heterocycloalkyl ring system containing one, two, or three heteroatoms selected from N, O, S, SO, and SO$_2$ said heterocycloalkyl optionally substituted with 1-3 R$^{30}$;

alternatively R$^{23}$ and R$^{24}$, together with the nitrogen atom to which they are attached, may form a 3 to 7 membered heterocycloalkyl ring containing 1 nitrogen atom and optionally a second heteroatom selected from nitrogen, oxygen, and sulfur, wherein said heterocycloalkyl ring is optionally substituted with 1-3 R$^{30}$;

R$^{25}$ at each occurrence is independently H, C$_1$-C$_6$ alkyl, C$_1$-C$_4$ haloalkyl, —(C$_1$-C$_3$ alkyl)C$_6$-C$_{10}$aryl; C$_6$-C$_{10}$ aryl; C$_3$-C$_7$ cycloalkyl; 5 to 6 membered heteroaryl ring system containing one, two, or three heteroatoms selected from N, O, and S; or 3 to 7 membered heterocycloalkyl ring system containing one, two, or three heteroatoms selected from N, O, S, SO, and SO$_2$;

R$^{27}$ at each occurrence is independently H or C$_1$-C$_3$ alkyl;
R$^{28}$ at each occurrence is independently H or C$_1$-C$_3$ alkyl;
R$^{29}$ at each occurrence is independently H, C$_1$-C$_3$ alkyl, or —C(=O)CH$_3$;
R$^{30}$ at each occurrence is independently H, —F, —Cl, —Br, —I, —OH, =O, C$_1$-C$_6$ alkyl, C$_1$-C$_6$ alkoxy, C$_1$-C$_4$ haloalkyl, —C(=O)N(R$^{32}$)$_2$, —NHC(=O)N(R$^{32}$)$_2$, or —S(=O)$_2$R$^{32}$, R$^{31}$ at each occurrence is independently H, —F, —Cl, —Br, —I, —OH, =O, C$_1$-C$_6$ alkoxy, C$_1$-C$_4$ haloalkyl, —C(=O)N(R$^{32}$)$_2$, —NHC(=O)N(R$^{32}$)$_2$, C$_6$-C$_{10}$ aryl optionally substituted with 1-3 R$^{30}$; or 3 to 7 membered heterocycloalkyl ring system containing one, two, or three heteroatoms selected from N, O, S, SO, and SO$_2$;

R$^{32}$ at each occurrence is independently H, C$_1$-C$_3$ alkyl, or C$_1$-C$_3$ alkoxy;

n is 0, 1, 2, or 3; and
z is 0, 1, 2, 3, 4, 5, or 6;
provided when Y$^1$, Y$^2$, Y$^3$, and Y$^4$ are each CH, W is —O— or —CH$_2$—O—, k is 1, m is 0 or 1, and X is R$^2$ then R$^1$ is C$_3$-C$_8$ cycloalkyl ring.

The present invention is directed to compounds of Formula I:

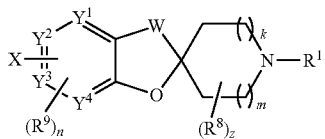

and stereoisomeric forms, mixtures of stereoisomeric forms, N-oxide forms, or pharmaceutically acceptable salt forms thereof, wherein:

$R^1$ is a $C_1$-$C_8$ alkyl, $C_3$-$C_8$ cycloalkyl ring, $C_3$-$C_8$ heterocycloalkyl ring, or —($C_1$-$C_3$alkyl)-$C_3$-$C_8$ heterocycloalkyl ring, each optionally substituted with 1-3 $R^{20}$;

k is 0, 1, or 2; m is 0, 1, or 2; and the sum of m and k is 1, 2, or 3;

$Y^1$, $Y^2$, $Y^3$, and $Y^4$ are independently selected from —CH= and —N=;

provided that when $Y^1$, $Y^2$, $Y^3$, and $Y^4$ are independently selected from —N= with the proviso that no more than of $Y^1$, $Y^2$, $Y^3$, and $Y^4$ may be —N=;

W is —O—, —$CH_2$—, —$CH_2$—O—, —C(=O)—$CH_2$—, —C(OH)—$CH_2$—, —$CH_2$—$CH_2$—, —O—$CH_2$—$CH_2$— or —$CH_2$—$CH_2$—O—;

X is $R^2$, —$OR^2$, —($C_1$-$C_3$ alkyl)-$R^2$; —($C_2$-$C_6$ alkenyl)-$R^2$; —O($C_1$-$C_3$ alkyl)-$R^2$, —O($C_2$-$C_6$ alkenyl)-$R^2$; —$NR^{29}R^{29}$, —$NR^{29}R^2$, —$NR^{29}$($C_1$-$C_3$ alkyl)-$R^2$, —($C_1$-$C_3$ alkyl)$NR^{29}R^2$, —$NR^{29}$C(=O)$R^2$, —$NR^{29}$C(=O)($C_1$-$C_3$ alkyl)-$R^2$, or —$NR^{29}$C(=O)$NHR^2$; wherein each of said ($C_1$-$C_3$ alkyl) is optionally substituted with —OH or —$OC_1$-$C_3$alkyl;

$R^2$ is selected from the group consisting of
  $C_1$-$C_8$ alkyl optionally substituted with 1-3 $R^{20}$;
  $C_2$-$C_6$ alkenyl optionally substituted with 1-3 $R^{20}$;
  $C_3$-$C_7$ cycloalkyl optionally substituted with 1-3 $R^{20}$;
  $C_6$-$C_{10}$ aryl optionally substituted with 1-3 $R^{20}$;
  5 to 10 membered heteroaryl ring system containing one, two, or three heteroatoms selected from N, O, and S, wherein said heteroaryl ring system is optionally substituted with 1-3 $R^{20}$; and
  3 to 10 membered heterocycloalkyl ring system containing one, two, or three heteroatoms selected from N, O, S, SO, and $SO_2$, wherein said heterocycloalkyl ring system is optionally substituted with 1-3 $R^{20}$;
  with the proviso that $R^2$ is not a substituted or unsubstituted pyridazinone ring or a substituted or unsubstituted pyridazine ring;

$R^8$ is F, $C_1$-$C_3$ alkyl, or $C_1$-$C_3$ alkoxy;

$R^9$, at each occurrence, is independently, F, Cl, Br, $C_1$-$C_4$ alkyl, or $C_1$-$C_4$ alkoxy;

$R^{20}$ at each occurrence is independently selected from the group consisting of
  —H, —F, —Cl, —Br, —I, —$OR^{21}$, —$NR^{23}R^{24}$, NHOH, —$NO_2$, —CN, —$CF_3$, —$CHF_2$, —$CH_2F$, (=O), —C(=O)$R^{25}$, —C(=O)$OR^{25}$, —OC(=O)$R^{25}$, —OC(=O)$NR^{23}R^{24}$, —C(=O)$NR^{23}R^{24}$, —$NR^{27}$C(=O)$NR^{23}R^{24}$, —$NR^{27}$C(=O)$R^{25}$, —$NR^{27}$C(=O)$OR^{25}$, —$NR^{27}$C(=S)$R^{25}$, —$SR^{25}$, —S(=O)$R^{25}$, —S(=O)$_2R^{25}$, —S(=O)$_2NR^{23}R^{24}$, —$NR^{27}SR^{25}$, —$NR^{27}$S(=O)$R^{25}$, —$NR^{27}$S(=O)$_2R^{25}$, methylenedioxy, ethylenedioxy, propylenedioxy, $C_1$-$C_6$ alkyl optionally substituted by 1-3 $R^{31}$;
  $C_2$-$C_6$ alkenyl optionally substituted by 1-3 $R^{31}$;
  $C_2$-$C_6$ alkynyl optionally substituted by 1-3 $R^{31}$;
  $C_3$-$C_7$ cycloalkyl optionally substituted with 1-3 $R^{30}$;
  $C_6$-$C_{10}$ aryl optionally substituted with 1-3 $R^{30}$;
  5 to 6 membered heteroaryl ring system containing one, two, or three heteroatoms selected from N, O, and S, wherein said heteroaryl ring system is optionally substituted with 1-3 $R^{30}$; and
  3 to 7 membered heterocycloalkyl ring system containing one, two, or three heteroatoms selected from N, O, S, SO, and $SO_2$, wherein said heterocycloalkyl ring system is optionally substituted with 1-3 $R^{30}$;

$R^{21}$ at each occurrence is independently H, $C_1$-$C_4$ haloalkyl, $C_1$-$C_4$ alkyl optionally substituted with 1-3 $R^{22}$; $C_2$-$C_6$ alkenyl optionally substituted with 1-3 $R^{22}$; $C_6$-$C_{10}$ aryl optionally substituted with 1-3 $R^{30}$; 5 to 6 membered heteroaryl ring system containing one, two, or three heteroatoms selected from N, O, and S, wherein said heteroaryl ring system is optionally substituted with 1-3 $R^{30}$; and 3 to 7 membered heterocycloalkyl ring system containing one, two, or three heteroatoms selected from N, O, S, SO, and $SO_2$, wherein said heterocycloalkyl ring system is optionally substituted with 1-3 $R^{30}$;

$R^{22}$ at each occurrence is independently selected from the group consisting of
  —H, —F, —Cl, —Br, —I, —$C_1$-$C_6$ alkoxy, phenyl, —$NR^{23}R^{24}$, —NHOH, —$NO_2$, —CN, —$CF_3$, —$CHF_2$, —$CH_2F$, (=O), —C(=O)$R^{28}$, —C(=O)$OR^{28}$, —OC(=O)$R^{28}$, —OC(=O)$NR^{23}R^{24}$, —C(=O)$NR^{23}R^{24}$, —$NR^{27}$C(=O)$NR^{23}R^{24}$, —$NR^{27}$C(=O)$R^{28}$, —$NR^{27}$C(=O)$OR^{28}$, —$NR^{27}$C(=S)$R^{28}$, —$SR^{28}$, —S(=O)$R^{28}$, —S(=O)$_2R^{28}$, —S(=O)$_2NR^{23}R^{24}$, —$NR^{27}SR^{28}$, —$NR^{27}$S(=O)$R^{28}$, —$NR^{27}$S(=O)$_2R^{28}$, and $C_3$-$C_7$ cycloalkyl;

$R^{23}$ and $R^{24}$ at each occurrence are each independently selected from H, $C_1$-$C_6$ alkyl optionally substituted with 1-3 $R^{31}$; $C_3$-$C_7$ cycloalkyl; $C_6$-$C_{10}$ aryl optionally substituted with 1-3 $R^{30}$; 5 to 6 membered heteroaryl ring system containing one, two, or three heteroatoms selected from N, O, and S, said heteroaryl optionally substituted with 1-3 $R^{30}$; and 3 to 7 membered heterocycloalkyl ring system containing one, two, or three heteroatoms selected from N, O, S, SO, and $SO_2$ said heterocycloalkyl optionally substituted with 1-3 $R^{30}$;

alternatively $R^{23}$ and $R^{24}$, together with the nitrogen atom to which they are attached, may form a 3 to 7 membered heterocycloalkyl ring containing 1 nitrogen atom and optionally a second heteroatom selected from nitrogen, oxygen, and sulfur, wherein said heterocycloalkyl ring is optionally substituted with 1-3 $R^{30}$;

$R^{25}$ at each occurrence is independently H, $C_1$-$C_6$ alkyl, $C_1$-$C_4$ haloalkyl, —($C_1$-$C_3$ alkyl)$C_6$-$C_{10}$aryl; $C_6$-$C_{10}$ aryl; $C_3$-$C_7$ cycloalkyl; 5 to 6 membered heteroaryl ring system containing one, two, or three heteroatoms selected from N, O, and S; or 3 to 7 membered heterocycloalkyl ring system containing one, two, or three heteroatoms selected from N, O, S, SO, and $SO_2$;

$R^{27}$ at each occurrence is independently H or $C_1$-$C_3$ alkyl;
$R^{28}$ at each occurrence is independently H or $C_1$-$C_3$ alkyl;
$R^{29}$ at each occurrence is independently H, $C_1$-$C_3$ alkyl, or —C(=O)$CH_3$;
$R^{30}$ at each occurrence is independently H, —F, —Cl, —Br, —I, —OH, =O, $C_1$-$C_6$ alkyl, $C_1$-$C_6$ alkoxy, $C_1$-$C_4$ haloalkyl, —C(=O)N($R^{32}$)$_2$, —NHC(=O)N($R^{32}$)$_2$, or —S(=O)$_2R^{32}$, $R^{31}$ at each occurrence is independently H, —F, —Cl, —Br, —I, —OH, =O, $C_1$-$C_6$ alkoxy, $C_1$-$C_4$ haloalkyl, —C(=O)N($R^{32}$)$_2$, —NHC(=O)N($R^{32}$)$_2$, $C_6$-$C_{10}$ aryl optionally substituted with 1-3 $R^{30}$; or 3 to 7 membered heterocycloalkyl ring system containing one, two, or three heteroatoms selected from N, O, S, SO, and $SO_2$;

$R^{32}$ at each occurrence is independently H, $C_1$-$C_3$ alkyl, or $C_1$-$C_3$ alkoxy;

n is 0, 1, 2, or 3; and z is 0, 1, 2, 3, 4, 5, or 6;
provided when $Y^1$, $Y^2$, $Y^3$, and $Y^4$ are each CH, W is —O— or —$CH_2$—O—, k is 1, m is 0 or 1, and X is $R^2$ then $R^1$ is $C_3$-$C_8$ cycloalkyl ring.

In preferred embodiments $R^2$ is not a substituted or unsubstituted pyridazine or pyridazinone.

In certain embodiments, the present invention provides compounds of Formula (I) and stereoisomeric forms, mixtures of stereoisomeric forms, or pharmaceutically acceptable salt forms thereof.

In preferred embodiments, the present invention provides novel compounds of Formula (IA):

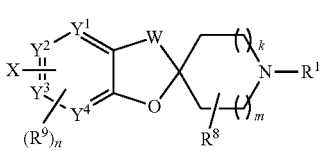

(IA)

and stereoisomeric forms, mixtures of stereoisomeric forms or pharmaceutically acceptable salt forms thereof, wherein:

$R^1$ is a $C_1$-$C_8$ alkyl or $C_3$-$C_8$ cycloalkyl ring;

k is 0, 1, or 2; m is 0, 1, or 2; and the sum of m and k is 1, 2, or 3;

$Y^1$, $Y^2$, $Y^3$, and $Y^4$ are independently selected from —CH= and —N=;

provided that when $Y^1$, $Y^2$, $Y^3$, and $Y^4$ are independently selected from —N= then only one of $Y^1$, $Y^2$, $Y^3$, and $Y^4$ may be —N=;

W is —O—, —$CH_2$—, —$CH_2$—O—, —C(=O)—$CH_2$—, —C(OH)—$CH_2$—, —$CH_2$—$CH_2$—, or —$CH_2$—$CH_2$—O—;

X is $R^2$, —$OR^2$, —O($C_1$-$C_3$ alkyl)-$R^2$, —$NR^{29}R^2$, —$NR^{29}$($C_1$-$C_3$ alkyl)-$R^2$, —($C_1$-$C_3$ alkyl)$NR^{29}R^2$, —$NR^{29}$C(=O)$R^2$, —$NR^{29}$C(=O)($C_1$-$C_3$ alkyl)-$R^2$, or —$NR^{29}$C(=O)$NHR^2$;

$R^2$ is selected from the group consisting of
$C_3$-$C_7$ cycloalkyl optionally substituted with 1-3 $R^{20}$;
$C_6$-$C_{10}$ aryl optionally substituted with 1-3 $R^{20}$;
5 to 10 membered heteroaryl ring system containing one, two, or three heteroatoms selected from N, O, and S, wherein said heteroaryl ring system is optionally substituted with 1-3 $R^{20}$; and
5 to 10 membered heterocycloalkyl ring system containing one, two, or three heteroatoms selected from N, O, S, SO, and $SO_2$, wherein said heterocycloalkyl ring system is optionally substituted with 1-3 $R^{20}$;

$R^8$ is H, F, $C_1$-$C_3$ alkyl, or $C_1$-$C_3$ alkoxy;

$R^9$, at each occurrence, is independently, F, Cl, Br, $C_1$-$C_4$ alkyl, or $C_1$-$C_4$ alkoxy;

$R^{20}$ at each occurrence is independently selected from the group consisting of
—H, —F, —Cl, —Br, —I, —$OR^{21}$, —$NR^{23}R^{24}$, NHOH, —$NO_2$, —CN, —$CF_3$, —CHF, —$CH_2$F, (=O), —C(=O)$R^{25}$, —C(=O)$OR^{25}$, —OC(=O)$R^{25}$, —OC(=O)$NR^{23}R^{24}$, C(=O)$NR^{23}R^{24}$, —$NR^{27}$C(=O)$NR^{23}R^{24}$, —$NR^{27}$C(=O)$R^{25}$, —$NR^{27}$C(=O)$OR^{25}$, —$NR^{27}$C(=S)$R^{25}$, —$SR^{25}$, —S(=O)$R^{25}$, —S(=O)$_2R^{25}$, —S(=O)$_2NR^{23}R^{24}$, —$NR^{27}SR^{25}$, —$NR^{27}$S(=O)$R^{25}$, —$NR^{27}$S(=O)$_2R^{25}$, methylenedioxy, ethylenedioxy, propylenedioxy,
$C_1$-$C_6$ alkyl optionally substituted by 1-3 $R^{31}$;
$C_2$-$C_6$ alkenyl optionally substituted by 1-3 $R^{31}$;
$C_2$-$C_6$ alkynyl optionally substituted by 1-3 $R^{31}$;
$C_3$-$C_7$ cycloalkyl optionally substituted with 1-3 $R^{30}$;
$C_6$-$C_{10}$ aryl optionally substituted with 1-3 $R^{30}$;
5 to 6 membered heteroaryl ring system containing one, two, or three heteroatoms selected from N, O, and S, wherein said heteroaryl ring system is optionally substituted with 1-3 $R^{30}$; and
3 to 7 membered heterocycloalkyl ring system containing one, two, or three heteroatoms selected from N, O, S, SO, and $SO_2$, wherein said heterocycloalkyl ring system is optionally substituted with 1-3 $R^{30}$;

$R^{21}$ at each occurrence is independently H, $C_1$-$C_4$ haloalkyl, $C_1$-$C_4$ alkyl optionally substituted with 1-3 $R^{22}$; $C_6$-$C_{10}$ aryl optionally substituted with 1-3 $R^{30}$; 5 to 6 membered heteroaryl ring system containing one, two, or three heteroatoms selected from N, O, and S, wherein said heteroaryl ring system is optionally substituted with 1-3 $R^{30}$; and 3 to 7 membered heterocycloalkyl ring system containing one, two, or three heteroatoms selected from N, O, S, SO, and $SO_2$, wherein said heterocycloalkyl ring system is optionally substituted with 1-3 $R^{30}$;

$R^{22}$ at each occurrence is independently selected from the group consisting of
—H, —F, —Cl, —Br, —I, —$C_1$-$C_6$ alkoxy, —$NR^{23}R^{24}$, —NHOH, —$NO_2$, —CN, —$CF_3$, —$CHF_2$, —$CH_2F$, (=O), —C(=O)$R^{28}$, —C(=O)$OR^{28}$, —OC(=O)$R^{28}$, —OC(=O)$NR^{23}R^{24}$, —C(=O)$NR^{23}R^{24}$, —$NR^{27}$C(=O)$NR^{23}R^{24}$, —$NR^{27}$C(=O)$R^{28}$, —$NR^{27}$C(=O)$OR^{28}$, —$NR^{27}$C(=S)$R^{28}$, —$SR^{28}$, —S(=O)$R^{28}$, —S(=O)$_2R^{28}$, —S(=O)$_2NR^{23}R^{24}$, —$NR^{27}SR^{28}$, —$NR^{27}$S(=O)$R^{28}$, —$NR^{27}$S(=O)$_2R^{28}$, and $C_3$-$C_7$ cycloalkyl;

$R^{23}$ and $R^{24}$ at each occurrence are each independently selected from H, $C_1$-$C_6$ alkyl optionally substituted with 1-3 $R^{31}$; $C_3$-$C_7$ cycloalkyl; $C_6$-$C_{10}$ aryl optionally substituted with 1-3 $R^{30}$; 5 to 6 membered heteroaryl ring system containing one, two, or three heteroatoms selected from N, O, and S, said heteroaryl optionally substituted with 1-3 $R^{30}$; and 3 to 7 membered heterocycloalkyl ring system containing one, two, or three heteroatoms selected from N, O, S, SO, and $SO_2$ said heterocycloalkyl optionally substituted with 1-3 $R^{30}$;

alternatively $R^{23}$ and $R^{24}$, together with the nitrogen atom to which they are attached, may form a 3 to 7 membered heterocycloalkyl ring containing 1 nitrogen atom and optionally a second heteroatom selected from nitrogen, oxygen, and sulfur, wherein said heterocycloalkyl ring is optionally substituted with 1-3 $R^{30}$;

$R^{25}$ at each occurrence is independently H, $C_1$-$C_6$ alkyl, $C_1$-$C_4$ haloalkyl, $C_6$-$C_{10}$ aryl; $C_3$-$C_7$ cycloalkyl; 5 to 6 membered heteroaryl ring system containing one, two, or three heteroatoms selected from N, O, and S; or 3 to 7 membered heterocycloalkyl ring system containing one, two, or three heteroatoms selected from N, O, S, SO, and $SO_2$;

$R^{27}$ at each occurrence is independently H or $C_1$-$C_3$ alkyl;

$R^{28}$ at each occurrence is independently H or $C_1$-$C_3$ alkyl;

$R^{29}$ at each occurrence is independently H, $C_1$-$C_3$ alkyl, or —C(=O)$CH_3$;

$R^{30}$ at each occurrence is independently H, —F, —Cl, —Br, —I, —OH, =O, $C_1$-$C_6$ alkyl, $C_1$-$C_6$ alkoxy, $C_1$-$C_4$ haloalkyl, —C(=O)N($R^{32}$)$_2$, —NHC(=O)N($R^{32}$)$_2$, or —S(=O)$_2$$R^{32}$;

$R^{31}$ at each occurrence is independently H, —F, —Cl, —Br, —I, —OH, =O, $C_1$-$C_6$ alkoxy, $C_1$-$C_4$ haloalkyl, —C(=O)N($R^{32}$)$_2$, —NHC(=O)N($R^{32}$)$_2$, $C_6$-$C_{10}$ aryl optionally substituted with 1-3 $R^{30}$; or 3 to 7 membered heterocycloalkyl ring system containing one, two, or three heteroatoms selected from N, O, S, SO, and $SO_2$;

$R^{32}$ at each occurrence is independently H or $C_1$-$C_3$ alkyl;

n is 0, 1, 2, or 3;

provided when $Y^1$, $Y^2$, $Y^3$, and $Y^4$ are each CH, W is —O— or —CH$_2$—O—, k is 1, m is 0 or 1, and X is $R^2$ then $R^1$ is $C_3$-$C_8$ cycloalkyl ring.

In a preferred embodiment the present invention provides novel compounds wherein $R^1$ is $C_3$-$C_8$ cycloalkyl ring. In another preferred embodiment the present invention provides a novel compound wherein $R^1$ is cyclobutyl or cyclopentyl. In another preferred embodiment the present invention provides a novel compound wherein $R^1$ is cyclobutyl. In another preferred embodiment the present invention provides a novel compound wherein $R^1$ is cyclopentyl.

In a preferred embodiment the present invention provides a novel compound wherein $Y^1$, $Y^2$, $Y^3$, and $Y^4$ are each —CH=. Another preferred embodiment of the invention provides compounds wherein $Y^1$ is —CH= or —N= and $Y^2$=$Y^3$ is —C(X)=CH— or —CH=C(X)—. In a preferred embodiment the present invention provides a novel compound wherein $Y^1$ is —N=, and $Y^2$, $Y^3$, and $Y^4$ are each —CH=. In preferred embodiments, W is —CH$_2$—O— or —CH$_2$—CH$_2$—.

In other preferred embodiments, $R^1$ is cyclobutyl or cyclopentyl

In a preferred embodiment the present invention provides compounds of Formula (I) that are compounds of Formula (II):

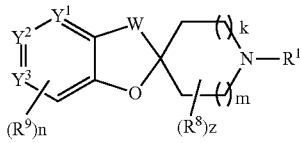

(II)

and stereoisomeric forms, mixtures of stereoisomeric forms, N-oxide forms, or pharmaceutically acceptable salt forms thereof;

wherein $Y^1$ is —CH= or —N=; and $Y^2$=$Y^3$ is —C(X)=CH— or —CH=C(X)—.

In a preferred embodiment the present invention provides a novel compound of Formula (II) wherein W is —CH$_2$—O— or —CH$_2$—CH$_2$—. In another preferred embodiment the present invention provides a novel compound of Formula (II) wherein W is —CH$_2$—O—. In another preferred embodiment the present invention provides a novel compound of Formula (II) wherein W is —CH$_2$—CH$_2$—.

In a preferred embodiment the present invention provides a novel compound of Formula (I) or (II) wherein $R^1$ is cyclobutyl or cyclopentyl.

In certain preferred embodiments, k is 0. In others, k is 1. In other embodiments, m is 0. In others, m is 1. In still other embodiments, the sum of m and k is 1. In others, the sum of m and k is 2.

In preferred embodiments, W is —O—, —CH$_2$—O—, —CH$_2$—CH$_2$—, or —CH$_2$—CH$_2$—O—. Preferably, W is —CH$_2$—O— or —CH$_2$—CH$_2$—.

In preferred embodiments of the present invention, z is 0.

In a preferred embodiment the present invention provides a novel compound of Formula (I) that is a compound of Formula (II'):

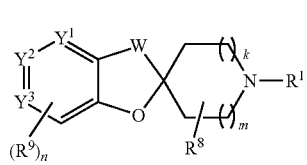

(II')

wherein $Y^1$ is —CH= or —N=; and $Y^2$=$Y^3$ is —C(X)=CH— or —CH=C(X)—.

In a preferred embodiment the present invention provides a novel compound of Formula (II') wherein W is —CH$_2$—O— or —CH$_2$—CH$_2$—. In another preferred embodiment the present invention provides a novel compound of Formula (II') wherein W is —CH$_2$—O—. In another preferred embodiment the present invention provides a novel compound of Formula (II') wherein W is —CH$_2$—CH$_2$—.

In a preferred embodiment the present invention provides a novel compound of Formula (II') wherein $R^1$ is cyclobutyl or cyclopentyl.

In a preferred embodiment the present invention provides novel compounds of Formula (I) that are compounds of Formula (III)

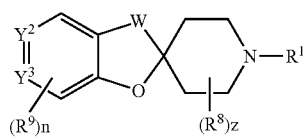

(III)

and stereoisomeric forms, mixtures of stereoisomeric forms, N-oxide forms, or pharmaceutically acceptable salt forms thereof, wherein:

$Y^2$=$Y^3$ is —C(X)=CH— or —CH=C(X)—.

In a preferred embodiment the present invention provides a novel compound of Formula (III) wherein W is —CH$_2$—O— or —CH$_2$—CH$_2$—. In another preferred embodiment the present invention provides a novel compound of Formula (III) wherein W is —CH$_2$—O—. In another preferred embodiment the present invention provides a novel compound of Formula (III) wherein W is —CH$_2$—CH$_2$—.

In a preferred embodiment the present invention provides a novel compound of Formula (III) wherein $R^1$ is cyclobutyl or cyclopentyl. In another preferred embodiment the present invention provides a novel compound of Formula (III) wherein $R^1$ is cyclobutyl. In another preferred embodiment the present invention provides a novel compound of Formula (III) wherein $R^1$ is cyclopentyl.

In a preferred embodiment the present invention provides a novel compound of Formula (III')

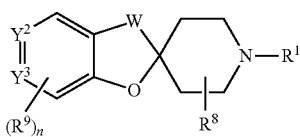

(III')

wherein $Y^2$=$Y^3$ is —C(X)=CH— or —CH=C(X)—.

In a preferred embodiment the present invention provides a novel compound of Formula (III') wherein W is —CH$_2$—O— or —CH$_2$—CH$_2$—. In another preferred embodiment the present invention provides a novel compound of Formula (III') wherein W is —CH$_2$—O—. In another preferred embodiment the present invention provides a novel compound of Formula (III') wherein W is —CH$_2$—CH$_2$—.

In a preferred embodiment the present invention provides a novel compound of Formula (III') wherein $R^1$ is cyclobutyl or cyclopentyl. In another preferred embodiment the present invention provides a novel compound of Formula (III') wherein $R^1$ is cyclobutyl. In another preferred embodiment the present invention provides a novel compound of Formula (III') wherein $R^1$ is cyclopentyl.

In a preferred embodiment the present invention provides a novel compound of Formula (IV):

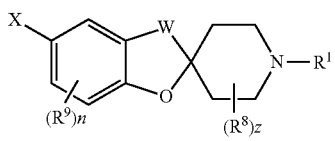

(IV)

and stereoisomeric forms, mixtures of stereoisomeric forms, N-oxide forms, or pharmaceutically acceptable salt forms thereof.

In a preferred embodiment the present invention provides a novel compound of Formula (IV), wherein:
$R^1$ is a $C_3$-$C_8$ cycloalkyl ring;
W is —O—, —CH$_2$—O—, —C(=O)—CH$_2$—, —C(OH)—CH$_2$—, —CH$_2$—CH$_2$—, or —CH$_2$—CH$_2$—O—;
$R^{23}$ at each occurrence are each independently selected from H, methyl, ethyl, and propyl;
$R^{24}$ at each occurrence are each independently selected from H, $C_1$-$C_6$ alkyl optionally substituted with 1-3 $R^{31}$; $C_3$-$C_7$ cycloalkyl; $C_6$-$C_{10}$ aryl optionally substituted with 1-3 $R^{30}$; 5 to 6 membered heteroaryl ring system containing one, two, or three heteroatoms selected from N, O, and S, said heteroaryl optionally substituted with 1-3 $R^{30}$; and 3 to 7 membered heterocycloalkyl ring system containing one, two, or three heteroatoms selected from N, O, S, SO, and SO$_2$ said heterocycloalkyl optionally substituted with 1-3 $R^{30}$;
alternatively $R^{23}$ and $R^{24}$, together with the nitrogen atom to which they are attached, may form a 3 to 7 membered heterocycloalkyl ring containing 1 nitrogen atom and optionally a second heteroatom selected from nitrogen, oxygen, and sulfur, wherein said heterocycloalkyl ring is optionally substituted with 1-3 $R^{30}$.

In a preferred embodiment the present invention provides a novel compound of Formula (IV):

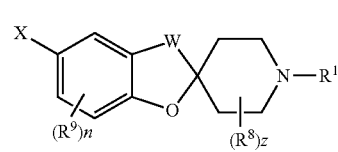

(IV)

and stereoisomeric forms, mixtures of stereoisomeric forms or pharmaceutically acceptable salt forms thereof, wherein:
$R^1$ is a $C_3$-$C_8$ cycloalkyl ring;
W is —O—, —CH$_2$—O—, —C(=O)—CH$_2$—, —C(OH)—CH$_2$—, —CH$_2$—CH$_2$—, or —CH$_2$—CH$_2$—O—;
$R^2$ is selected from the group consisting of
  $C_1$-$C_8$ alkyl optionally substituted with 1-3 $R^{20}$;
  $C_2$-$C_6$ alkenyl optionally substituted with 1-3 $R^{20}$;
  $C_3$-$C_{10}$ cycloalkyl optionally substituted with 1-3 $R^{20}$;
  $C_6$-$C_{10}$ aryl optionally substituted with 1-3 $R^{20}$;
  5 to 10 membered heteroaryl ring system containing one, two, or three heteroatoms selected from N, O, and S, wherein said heteroaryl ring system is optionally substituted with 1-3 $R^{20}$; and
  5 to 10 membered heterocycloalkyl ring system containing one, two, or three heteroatoms selected from N, O, S, SO, and SO$_2$, wherein said heterocycloalkyl ring system is optionally substituted with 1-3 $R^{20}$;
  with the proviso that $R^2$ is not a substituted or unsubstituted pyridazinone ring or a substituted or unsubstituted pyridazine ring;
$R^{23}$ at each occurrence are each independently selected from H, methyl, ethyl, and propyl;
$R^{24}$ at each occurrence are each independently selected from H, $C_1$-$C_6$ alkyl optionally substituted with 1-3 $R^{31}$; $C_3$-$C_7$ cycloalkyl; $C_6$-$C_{10}$ aryl optionally substituted with 1-3 $R^{30}$; 5 to 6 membered heteroaryl ring system containing one, two, or three heteroatoms selected from N, O, and S, said heteroaryl optionally substituted with 1-3 $R^{30}$; and 3 to 7 membered heterocycloalkyl ring system containing one, two, or three heteroatoms selected from N, O, S, SO, and SO$_2$ said heterocycloalkyl optionally substituted with 1-3 $R^{30}$;
alternatively $R^{23}$ and $R^{24}$, together with the nitrogen atom to which they are attached, may form a 3 to 7 membered heterocycloalkyl ring containing 1 nitrogen atom and optionally a second heteroatom selected from nitrogen, oxygen, and sulfur, wherein said heterocycloalkyl ring is optionally substituted with 1-3 $R^{30}$.

In a preferred embodiment the present invention provides a novel compound of Formula (IV) wherein W is —CH$_2$—O— or —CH$_2$—CH$_2$—. In a preferred embodiment the present invention provides a novel compound of Formula (IV) wherein W is —CH$_2$—O—. In a preferred embodiment the present invention provides a novel compound of Formula (IV) wherein W is —CH$_2$—CH$_2$—.

In a preferred embodiment the present invention provides a novel compound of Formula (IV) wherein $R^1$ is cyclobutyl or cyclopentyl. In a preferred embodiment the present invention provides a novel compound of Formula (IV) wherein $R^1$ is cyclobutyl. In a preferred embodiment the present invention provides a novel compound of Formula (IV) wherein $R^1$ is cyclopentyl.

In a preferred embodiment the present invention provides a novel compound of Formula (IV) wherein X is $R^2$, —O$R^2$, —OCH$_2$—$R^2$, —N$R^{29}R^2$, —N($R^{29}$)CH$_2$—$R^2$, —CH$_2$N$R^{29}R^2$, —N$R^{29}$C(=O)$R^2$, —N$R^{29}$C(=O)CH$_2$—$R^2$, or —N$R^{29}$C(=O)NH$R^2$.

In a preferred embodiment the present invention provides a novel compounds of Formula (I) that are compounds of Formula (IV'):

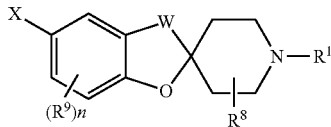

and stereoisomeric forms, mixtures of stereoisomeric forms or pharmaceutically acceptable salt forms thereof.

In a preferred embodiment the present invention provides a novel compounds of Formula (I) that are compounds of Formula (IV'):

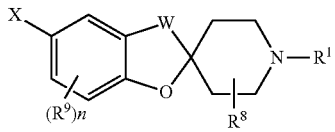

and stereoisomeric forms, mixtures of stereoisomeric forms or pharmaceutically acceptable salt forms thereof, wherein:
$R^1$ is a $C_3$-$C_s$ cycloalkyl ring;
W is —O—, —CH$_2$—O—, —C(=O)—CH$_2$—, —C(OH)—CH$_2$—, —CH$_2$—CH$_2$—, or —CH$_2$—CH$_2$—O—;
X is $R^2$, —O$R^2$, —O($C_1$-$C_3$ alkyl)-$R^2$, —N$R^{29}R^2$, —N$R^{29}$($C_1$-$C_3$ alkyl)-$R^2$, —($C_1$-$C_3$ alkyl)N$R^{29}R^2$, —N$R^{29}$C(=O)$R^2$, —N$R^{29}$C(=O)($C_1$-$C_3$ alkyl)-$R^2$, or —N$R^{29}$C(=O)NH$R^2$;
$R^2$ is selected from the group consisting of
  $C_3$-$C_7$ cycloalkyl optionally substituted with 1-3 $R^{20}$;
  $C_6$-$C_{10}$ aryl optionally substituted with 1-3 $R^{20}$;
  5 to 10 membered heteroaryl ring system containing one, two, or three heteroatoms selected from N, O, and S, wherein said heteroaryl ring system is optionally substituted with 1-3 $R^{20}$; and
  5 to 10 membered heterocycloalkyl ring system containing one, two, or three heteroatoms selected from N, O, S, SO, and SO$_2$, wherein said heterocycloalkyl ring system is optionally substituted with 1-3 $R^{20}$;
$R^8$ is F, $C_1$-$C_3$ alkyl, or $C_1$-$C_3$ alkoxy;
$R^9$, at each occurrence, is independently, F, Cl, Br, $C_1$-$C_4$ alkyl, or $C_1$-$C_4$ alkoxy;
$R^{20}$ at each occurrence is independently selected from the group consisting of
  —H, —F, —Cl, —Br, —I, —O$R^{21}$, —N$R^{23}R^{24}$, —NHOH, —NO$_2$, —CN, —CF$_3$, —CHF$_2$, —CH$_2$F, (=O), —C(=O)$R^{25}$, —C(=O)O$R^{25}$, —OC(=O)$R^{25}$, —OC(=O)N$R^{23}R^{24}$, —C(=O)N$R^{23}R^{24}$, —N$R^{27}$C(=O)N$R^{23}R^{24}$, N$R^{27}$C(=O)$R^{25}$, —N$R^{27}$C(O)O$R^{25}$, —N$R^{27}$C(=S)$R^{25}$, —S$R^{25}$, —S(=O)$R^{25}$, —S(=O)$_2$$R^{25}$, —S(=O)$_2$N$R^{23}R^{24}$, N$R^{27}$S$R^{25}$, —N$R^{27}$S(=O)$R^{25}$, —N$R^{27}$S(=O)$_2$$R^{25}$, methylenedioxy, ethylenedioxy, propylenedioxy,
  $C_1$-$C_6$ alkyl optionally substituted by 1-3 $R^{31}$;
  $C_2$-$C_6$ alkenyl optionally substituted by 1-3 $R^{31}$;
  $C_2$-$C_6$ alkynyl optionally substituted by 1-3 $R^{31}$;
  $C_3$-$C_7$ cycloalkyl optionally substituted with 1-3 $R^{30}$;
  $C_6$-$C_{10}$ aryl optionally substituted with 1-3 $R^{30}$;
  5 to 6 membered heteroaryl ring system containing one, two, or three heteroatoms selected from N, O, and S, wherein said heteroaryl ring system is optionally substituted with 1-3 $R^{30}$; and
  3 to 7 membered heterocycloalkyl ring system containing one, two, or three heteroatoms selected from N, O, S, SO, and SO$_2$, wherein said heterocycloalkyl ring system is optionally substituted with 1-3 $R^{30}$;
$R^{21}$ at each occurrence is independently H, $C_1$-$C_4$ haloalkyl, $C_1$-$C_4$ alkyl optionally substituted with 1-3 $R^{22}$; $C_6$-$C_{10}$ aryl optionally substituted with 1-3 $R^{30}$; 5 to 6 membered heteroaryl ring system containing one, two, or three heteroatoms selected from N, O, and S, wherein said heteroaryl ring system is optionally substituted with 1-3 $R^{30}$; and 3 to 7 membered heterocycloalkyl ring system containing one, two, or three heteroatoms selected from N, O, S, SO, and SO$_2$, wherein said heterocycloalkyl ring system is optionally substituted with 1-3 $R^{30}$;
$R^{22}$ at each occurrence is independently selected from the group consisting of
  —H, —F, —Cl, —Br, —I, —$C_1$-$C_6$ alkoxy, —N$R^{23}R^{24}$, —NHOH, —NO$_2$, —CN, —CF$_3$, —CHF$_2$, —CH$_2$F, (=O), —C(=O)$R^{28}$, —C(=O)O$R^{28}$, —OC(=O)$R^{28}$, —OC(=O)N$R^{23}R^{24}$, —C(=O)N$R^{23}R^{24}$, —N$R^{27}$C(=O)N$R^{23}R^{24}$, —N$R^{27}$C(=O)$R^{28}$, —N$R^{27}$C(=O)O$R^{28}$, —N$R^{27}$C(=S)$R^{28}$, —S$R^{28}$, —S(=O)$R^{28}$, —S(=O)$_2$$R^{28}$, —S(=O)$_2$N$R^{23}R^{24}$, —N$R^{27}$S$R^{28}$, —N$R^{27}$S(=O)$R^{28}$, —N$R^{27}$S(=O)$_2$$R^{28}$, and $C_3$-$C_7$ cycloalkyl;
$R^{23}$ at each occurrence are each independently selected from H, methyl, ethyl, and propyl;
$R^{24}$ at each occurrence are each independently selected from H, $C_1$-$C_6$ alkyl optionally substituted with 1-3 $R^{31}$; $C_3$-$C_7$ cycloalkyl; $C_6$-$C_{10}$ aryl optionally substituted with 1-3 $R^{30}$; 5 to 6 membered heteroaryl ring system containing one, two, or three heteroatoms selected from N, O, and S, said heteroaryl optionally substituted with 1-3 $R^{30}$; and 3 to 7 membered heterocycloalkyl ring system containing one, two, or three heteroatoms selected from N, O, S, SO, and SO$_2$ said heterocycloalkyl optionally substituted with 1-3 $R^{30}$;
alternatively $R^{23}$ and $R^{24}$, together with the nitrogen atom to which they are attached, may form a 3 to 7 membered heterocycloalkyl ring containing 1 nitrogen atom and optionally a second heteroatom selected from nitrogen, oxygen, and sulfur, wherein said heterocycloalkyl ring is optionally substituted with 1-3 $R^{30}$;
$R^{25}$ at each occurrence is independently H, $C_1$-$C_6$ alkyl, $C_1$-$C_4$ haloalkyl, $C_6$-$C_{10}$ aryl; $C_3$-$C_7$ cycloalkyl; 5 to 6 membered heteroaryl ring system containing one, two, or three heteroatoms selected from N, O, and S; or 3 to 7 membered heterocycloalkyl ring system containing one, two, or three heteroatoms selected from N, O, S, SO, and SO$_2$;
$R^{27}$ at each occurrence is independently H or $C_1$-$C_3$ alkyl;
$R^{28}$ at each occurrence is independently H or $C_1$-$C_3$ alkyl;
$R^{29}$ at each occurrence is independently H, $C_1$-$C_3$ alkyl, or —C(=O)CH$_3$;
$R^{30}$ at each occurrence is independently H, —F, —Cl, —Br, —I, —OH, =O, $C_1$-$C_6$ alkyl, $C_1$-$C_6$ alkoxy, $C_1$-$C_4$ haloalkyl, —C(=O)N($R^{32}$)$_2$, —NHC(=O)N($R^{32}$)$_2$, or —S(=O)$_2$$R^{32}$;
$R^{31}$ at each occurrence is independently H, —F, —Cl, —Br, —I, —OH, =O, $C_1$-$C_6$ alkoxy, $C_1$-$C_4$ haloalkyl, —C(=O)N($R^{32}$)$_2$, —NHC(=O)N($R^{32}$)$_2$, $C_6$-$C_{10}$ aryl optionally substituted with 1-3 $R^{30}$; or 3 to 7 membered heterocycloalkyl ring system containing one, two, or three heteroatoms selected from N, O, S, SO, and $SO_2$;

$R^{32}$ at each occurrence is independently H or $C_1$-$C_3$ alkyl;

n is 0, 1, 2, or 3.

In a preferred embodiment the present invention provides a novel compound of Formula (IV') wherein W is —$CH_2$—O— or —$CH_2$—$CH_2$—. In a preferred embodiment the present invention provides a novel compound of Formula (IV') wherein W is —$CH_2$—O—. In a preferred embodiment the present invention provides a novel compound of Formula (IV') wherein W is —$CH_2$—$CH_2$—.

In a preferred embodiment the present invention provides a novel compound of Formula (IV') wherein $R^1$ is cyclobutyl or cyclopentyl. In a preferred embodiment the present invention provides a novel compound of Formula (IV') wherein $R^1$ is cyclobutyl. In a preferred embodiment the present invention provides a novel compound of Formula (IV') wherein $R^1$ is cyclopentyl.

In a preferred embodiment the present invention provides a novel compound of Formula (IV') wherein X is $R^2$, —$OR^2$, —$OCH_2$—$R^2$ $NR^{29}R^2$, —$N(R^{29})CH_2$—$R^2$, —$CH_2NR^{29}R^2$, —$NR^{29}C(=O)R^2$, —$NR^{29}C(O)CH_2$—$R^2$, or —$NR^{29}C(=O)NHR^2$.

In a preferred embodiment the present invention provides a novel compound of Formula (IVa):

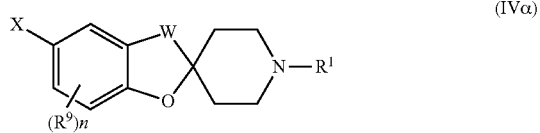

(IVα)

and stereoisomeric forms, mixtures of stereoisomeric forms or pharmaceutically acceptable salt forms thereof, wherein:

$R^1$ is cyclobutyl or cyclopentyl;

W is —$CH_2$—O— or —$CH_2$—$CH_2$—;

X is $R^2$, —$OR^2$, —$OCH_2$—$R^2$, —$NR^{29}R^2$, —$N(R^{29})CH_2$—$R^2$, —$CH_2NR^{29}R^2$, —$NR^{29}C(=O)R^2$, —$NR^{29}C(=O)CH_2$—$R^2$, or —$NR^{29}C(=O)NHR^2$;

$R^2$ is selected from the group consisting of
  $C_3$-$C_6$ cycloalkyl optionally substituted with 1-3 $R^{20}$;
  phenyl optionally substituted with 1-3 $R^{20}$;
  5 to 10 membered heteroaryl ring system containing one, two, or three heteroatoms selected from N, O, and S, wherein said heteroaryl ring system is optionally substituted with 1-3 $R^{20}$; and
  5 to 10 membered heterocycloalkyl ring system containing one, two, or three heteroatoms selected from N, O, S, SO, and $SO_2$, wherein said heterocycloalkyl ring system is optionally substituted with 1-3 $R^{20}$;

$R^9$, at each occurrence, is independently, F, Cl, methyl, ethyl, methoxy, or ethoxy;

$R^{20}$ at each occurrence is independently selected from the group consisting of
  —H, —F, Cl, —$OR^{21}$, —$NR^{23}R^{24}$, —NHOH, —$NO_2$, —CN, —$CF_3$, —$CHF_2$, —$CH_2F$, (=O), —$C(=O)R^{25}$, —$C(=O)OR^{25}$, —$OC(=O)R^{25}$, —$OC(=O)NR^{23}R^{24}$, —$C(=O)NR^{23}R^{24}$, —$NR^{27}C(=O)NR^{23}R^{24}$, $NR^{27}C(=O)R^{25}$, —$NR^{27}C(=O)OR^{25}$, —$NR^{27}C(=S)R^{25}$, —$SR^{25}$, —$S(=O)R^{25}$, —$S(=O)_2R^{25}$, —$S(=O)_2NR^{23}R^{24}$, —$NR^{27}SR^{25}$, —$NR^{27}S(=O)R^{25}$, —$NR^{27}S(=O)_2R^{25}$, methylenedioxy, ethylenedioxy,
  $C_1$-$C_4$ alkyl optionally substituted by 1-3 $R^{31}$;
  $C_3$-$C_6$ cycloalkyl optionally substituted with 1-3 $R^{30}$;
  phenyl optionally substituted with 1-3 $R^{30}$;
  5 to 6 membered heteroaryl ring system containing one, two, or three heteroatoms selected from N, O, and S, wherein said heteroaryl ring system is optionally substituted with 1-3 $R^{30}$; and
  3 to 7 membered heterocycloalkyl ring system containing one, two, or three heteroatoms selected from N, O, S, SO, and $SO_2$, wherein said heterocycloalkyl ring system is optionally substituted with 1-3 $R^{30}$;

$R^{21}$ at each occurrence is independently H, —$CF_3$, methyl, ethyl, propyl, butyl, or $C_1$-$C_4$ alkyl substituted with 1-2 $R^{22}$; phenyl optionally substituted with 1-3 $R^{30}$; 5 to 6 membered heteroaryl ring system containing one, two, or three heteroatoms selected from N, O, and S, wherein said heteroaryl ring system is optionally substituted with 1-3 $R^{30}$; and 3 to 7 membered heterocycloalkyl ring system containing one, two, or three heteroatoms selected from N, O, S, SO, and $SO_2$, wherein said heterocycloalkyl ring system is optionally substituted with 1-3 $R^{30}$;

$R^{22}$ at each occurrence is independently selected from the group consisting of
  —H, —F, —Cl, methoxy, ethoxy, propoxy, butoxy, —$NR^{23}R^{24}$, —NHOH, —$NO_2$, —CN, —$CF_3$, —$CHF_2$, —$CH_2F$, (=O), —$C(=O)R^{28}$, —$C(=O)OR^{28}$, —$OC(=O)R^{28}$, —$OC(=O)NR^{23}R^{24}$, —$C(=O)NR^{23}R^{24}$, —$NR^{27}C(=O)NR^{23}R^{24}$, —$NR^{27}C(=O)R^{28}$, —$NR^{27}C(=O)OR^{28}$, —$NR^{27}C(=S)R^{28}$, —$SR^{28}$, —$S(=O)R^{28}$, —$S(=O)_2R^{28}$, —$S(=O)_2NR^{23}R^{24}$, —$NR^{27}SR^{28}$, —$NR^{27}S(=O)R^{28}$, —$NR^{27}S(=O)_2R^{28}$, and $C_3$-$C_6$ cycloalkyl;

$R^{23}$ at each occurrence are each independently selected from H, methyl, ethyl, and propyl;

$R^{24}$ at each occurrence are each independently selected from H, cyclopropyl, cyclobutyl, cyclopentyl, cyclohexyl, $C_1$-$C_6$ alkyl optionally substituted with 1-3 $R^{31}$; phenyl optionally substituted with 1-3 $R^{30}$;
  5 to 6 membered heteroaryl ring system containing one, two, or three heteroatoms selected from N, O, and S, said heteroaryl optionally substituted with 1-3 $R^{30}$; and
  3 to 7 membered heterocycloalkyl ring system containing one, two, or three heteroatoms selected from N, O, S, SO, and $SO_2$ said heterocycloalkyl optionally substituted with 1-3 $R^{30}$;

alternatively $R^{23}$ and $R^{24}$, together with the nitrogen atom to which they are attached, may form a 3 to 7 membered heterocycloalkyl ring containing 1 nitrogen atom and optionally a second heteroatom selected from nitrogen, oxygen, and sulfur, wherein said heterocycloalkyl ring is optionally substituted with 1-3 $R^{30}$;

$R^{25}$ at each occurrence is independently H, methyl, ethyl, propyl, butyl, $CF_3$, phenyl, cyclopropyl, cyclobutyl, cyclopentyl, cyclohexyl, 5 to 6 membered heteroaryl ring system containing one, two, or three heteroatoms selected from N, O, and S; or 3 to 7 membered heterocycloalkyl ring system containing one, two, or three heteroatoms selected from N, O, S, SO, and $SO_2$;

$R^{27}$ at each occurrence is independently H or methyl;

$R^{28}$ at each occurrence is independently H or methyl;

$R^{29}$ at each occurrence is independently H, methyl, ethyl, or —$C(=O)CH_3$;

$R^{30}$ at each occurrence is independently H, —F, —Cl, —OH, =O, methyl, ethyl, propyl, butyl, methoxy, ethoxy, propoxy, butoxy, $CF_3$, —$C(=O)N(R^{32})_2$, —$NHC(=O)N(R^{32})_2$, or —$S(=O)_2R^{32}$;

$R^{31}$ at each occurrence is independently H, —F, —Cl, —OH, =O, methoxy, ethoxy, propoxy, butoxy, $CF_3$, —$C(=O)N(R^{32})_2$, —$NHC(=O)N(R^{32})_2$, phenyl optionally substituted with 1-3 $R^{30}$; or 3 to 7 membered heterocycloalkyl ring system containing one, two, or three heteroatoms selected from N, O, S, SO, and $SO_2$;
$R^{32}$ at each occurrence is independently H or methyl;
n is 0, 1, or 2.

In a preferred embodiment the present invention provides a novel compound of Formula (IVa):

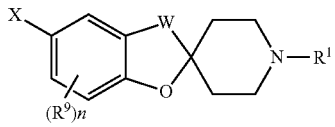

(IVa)

and stereoisomeric forms, mixtures of stereoisomeric forms or pharmaceutically acceptable salt forms thereof, wherein:
$R^1$ is cyclobutyl or cyclopentyl;
W is —$CH_2$—O— or —$CH_2$—$CH_2$—;
X is $R^2$, —$OR^2$, —$OCH_2$—$R^2$, —$NR^{29}R^2$, —$N(R^{29})CH_2$—$R^2$, —$CH_2NR^{29}R^2$, —$NR^{29}C(=O)R^2$, —$NR^{29}C(=O)CH_2$—$R^2$, or —$NR^{29}C(=O)NHR^2$;
$R^2$ is selected from the group consisting of phenyl optionally substituted with 1-3 $R^{20}$;
5 to 10 membered heteroaryl ring system selected from benzofuranyl, benzimidazolyl, benzothiazolyl, benzooxazolyl, benzooxadiazolyl, cinnolinyl, furanyl, imidazolyl, imidazopyridinyl, 1H-indazolyl, indolyl, isoxazolyl, isothiazolyl, oxazolyl, oxadiazolyl, pyrazolyl, pyrazinyl, pyridazinyl, pyridinyl, pyrimidinyl, pyrrolyl, thiazolyl, and thienyl, wherein said heteroaryl ring system is optionally substituted with 1-3 $R^{20}$; and
5 to 10 membered heterocycloalkyl ring system selected from azetidinyl, 1,1-dioxo-thiomorpholinyl, 1,4-diazapinyl, 2,3-dihydrobenzofuranyl, 3H-benzooxazolyl, imidazolidinyl, morpholinyl, piperidinyl, piperazinyl, pyrrolidinyl, oxazolidinyl, thiomorpholinyl, tetrahydropyranyl, tetrahydropyrazolopyridinyl, tetrahydro-1,3a,7-triaza-azulenyl, and tetrahydrofuran, wherein said heterocycloalkyl ring system is optionally substituted with 1-3 $R^{20}$;
$R^9$, at each occurrence, is independently, F or Cl;
$R^{20}$ at each occurrence is independently selected from the group consisting of
—H, —F, —Cl, —$OR^{21}$, —$NR^{23}R^{24}$, —CN, —$CF_3$, (=O), —$C(=O)R^{25}$, —$C(=O)OR^{25}$, —$OC(=O)R^{25}$, —$OC(=O)NR^{23}R^{24}$, —$C(=O)NR^{23}R^{24}$, —$NR^{27}C(=O)NR^{23}R^{24}$, —$NR^{27}C(=O)R^{25}$, —$NR^{27}C(=O)OR^{25}$, —$NR^{27}C(=S)R^{25}$, —$SR^{25}$, —$S(=O)R^{25}$, —$S(=O)_2R^{25}$, —$S(=O)_2NR^{23}R^{24}$, —$NR^{27}SR^{25}$, —$NR^{27}S(=O)R^{25}$, —$NR^{27}S(=O)_2R^{25}$, methyl, ethyl, propyl, butyl, ethylenedioxy,
methyl substituted with $R^{31}$;
phenyl optionally substituted with 1-3 $R^{30}$; and
5 to 6 membered heteroaryl ring system selected from oxadiazolyl, thiazolyl, pyridinyl, pyridazinyl, pyrimidinyl, and pyrazinyl, wherein said heteroaryl ring system is optionally substituted with 1-3 $R^{30}$;
3 to 7 membered heterocycloalkyl ring system selected from dihydro-oxazolyl, morpholinyl, piperidinyl, piperazinyl, and pyrrolidinyl, wherein said heterocycloalkyl ring system is optionally substituted with 1-3 $R^{30}$;
$R^{21}$ at each occurrence is independently H, —$CF_3$, methyl, ethyl, propyl, butyl, methoxyethyl, cyclopropylmethyl, phenyl, or pyridyl;
$R^{22}$ at each occurrence is independently selected from the group consisting of
—H, —F, —Cl, methoxy, ethoxy, propoxy, butoxy, —$NR^{23}R^{24}$, —NHOH, —$NO_2$, —CN, —$CF_3$, —$CHF_2$, —$CH_2F$, (=O), —$C(=O)R^{28}$, —$C(=O)OR^{28}$, —$OC(=O)R^{28}$, —$OC(=O)NR^{23}R^{24}$, —$C(=O)NR^{23}R^{24}$, —$NR^{27}C(=O)NR^{23}R^{24}$, —$NR^{27}C(=O)R^{28}$, —$NR^{27}C(=O)OR^{28}$, —$NR^{27}C(=S)R^{28}$, —$SR^{28}$, —$S(=O)R^{28}$, —$S(=O)_2R^{28}$, —$S(=O)_2NR^{23}R^{24}$, —$NR^{27}SR^{28}$, —$NR^{27}S(=O)R^{28}$, and —$NR^{27}S(=O)_2R^{28}$;
$R^{23}$ at each occurrence are each independently selected from H, methyl, ethyl, and propyl;
$R^{24}$ at each occurrence are each independently selected from H, methyl, ethyl, propyl, butyl, hydroxyethyl, methoxyethyl, ethoxyethyl, cyclopropyl, cyclobutyl, phenyl optionally substituted with 1-3 $R^{30}$;
3 to 7 membered heterocycloalkyl ring system selected from morpholinyl, piperidinyl, piperazinyl, pyrrolidinyl, tetrahydrofuranyl, and tetrahydropyranyl, said heterocycloalkyl optionally substituted with 1-3 $R^{30}$;
alternatively $R^{23}$ and $R^{24}$, together with the nitrogen atom to which they are attached, may form a 3 to 7 membered heterocycloalkyl ring selected from azetidinyl, morpholinyl, piperidinyl, piperazinyl, pyrrolidinyl, wherein said heterocycloalkyl ring is optionally substituted with 1-3 $R^{30}$;
$R^{25}$ at each occurrence is independently H, methyl, ethyl, propyl, butyl, $CF_3$, phenyl, cyclopropyl, cyclobutyl, cyclopentyl, cyclohexyl, cyclopropyl, cyclobutyl, cyclopentyl, cyclohexyl, morpholinyl and furanyl;
$R^{27}$ at each occurrence is independently H or methyl;
$R^{28}$ at each occurrence is independently H or methyl;
$R^{29}$ at each occurrence is independently H, methyl, ethyl, or —$C(=O)CH_3$;
$R^{30}$ at each occurrence is independently H, —F, —Cl, —OH, =O, methyl, ethyl, propyl, butyl, methoxy, ethoxy, propoxy, butoxy, $CF_3$, —$C(=O)N(R^{32})_2$, —$NHC(=O)N(R^{32})_2$, or —$S(=O)_2CH_3$;
$R^{31}$ at each occurrence is independently H, —F, —Cl, —OH, =O, methoxy, ethoxy, propoxy, butoxy, $CF_3$, —$C(=O)N(R^{32})_2$, —$NHC(=O)N(R^{32})_2$, phenyl optionally substituted with 1-3 $R^{30}$; or tetrahydrofuranyl;
$R^{32}$ at each occurrence is independently H or methyl;
n is 0, 1, or 2.

In another embodiment the present invention provides novel compounds of Formula (V):

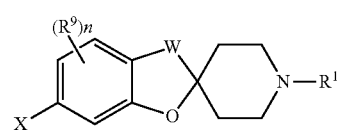

(V)

and stereoisomeric forms, mixtures of stereoisomeric forms or pharmaceutically acceptable salt forms thereof.

Preferred embodiments in elude compounds of Formula (V) wherein:
$R^1$ is a $C_3$-$C_8$ cycloalkyl ring;
W is —O—, —$CH_2$—O—, —C(=O)—$CH_2$—, —C(OH)—$CH_2$—, —$CH_2$—$CH_2$—, or —$CH_2$—$CH_2$—O—;
$R^{23}$ at each occurrence are each independently selected from H, methyl, ethyl, and propyl; and
$R^{24}$ at each occurrence are each independently selected from H, $C_1$-$C_6$ alkyl optionally substituted with 1-3 $R^{31}$; $C_3$-$C_7$ cycloalkyl; $C_6$-$C_{10}$ aryl optionally substituted with 1-3 $R^{30}$; 5 to 6 membered heteroaryl ring system containing one, two, or three heteroatoms selected from N, O, and S, said heteroaryl optionally substituted with 1-3 $R^{30}$; and 3 to 7 membered heterocycloalkyl ring system containing one, two, or three heteroatoms selected from N, O, S, SO, and $SO_2$ said heterocycloalkyl optionally substituted with 1-3 $R^{30}$;

alternatively $R^{23}$ and $R^{24}$, together with the nitrogen atom to which they are attached, may form a 3 to 7 membered heterocycloalkyl ring containing 1 nitrogen atom and optionally a second heteroatom selected from nitrogen, oxygen, and sulfur, wherein said heterocycloalkyl ring is optionally substituted with 1-3 $R^{30}$.

Preferred compounds of Formula (V) include those where W is —$CH_2$—O— or —$CH_2$—$CH_2$—.

Other preferred compounds of Formula (V) include those where $R^1$ is cyclobutyl or cyclopentyl Still other preferred compounds of Formula (V) include those where $R^2$, —$OR^2$, —$OCH_2$—$R^2$, —OCH(OH)—$R^2$, —OCH(OCH_3)—$R^2$, —($CH_2$—CH=CH—$CH_2$)—$R^2$, —O—($CH_2$—CH=CH—$CH_2$)—$R^2$, —$NR^{29}R^2$, —N($R^{29}$)$CH_2$—$R^2$, —$CH_2NR^{29}R^2$, —$NR^{29}$C(=O)$R^2$, —$NR^{29}$C(=O)$CH_2$—$R^2$, or —$NR^{29}$C(=O)NH$R^2$.

Most preferred compounds of Formula (V) are those wherein:
$R^1$ is cyclobutyl or cyclopentyl;
W is —$CH_2$—O— or —$CH_2$—$CH_2$—;
X is $R^2$, —$OR^2$, —$OCH_2$—$R^2$, —$NR^{29}R^2$, —N($R^{29}$)$CH_2$—$R^2$, —$CH_2NR^{29}R^2$, —$NR^{29}$C(=O)$R^2$, —$NR^{29}$C(=O)$CH_2$—$R^2$, or —$NR^{29}$C(=O)NH$R^2$;
$R^2$ is selected from the group consisting of
  phenyl optionally substituted with 1-3 $R^{20}$;
  5 to 10 membered heteroaryl ring system selected from benzofuranyl, benzimidazolyl, benzothiazolyl, benzooxazolyl, benzooxadiazolyl, cinnolinyl, furanyl, imidazolyl, imidazopyridinyl, 1H-indazolyl, indolyl, isoxazolyl, isothiazolyl, oxazolyl, oxadiazolyl, pyrazolyl, pyrazinyl, pyridazinyl, pyridinyl, pyrimidinyl, pyrrolyl, thiazolyl, and thienyl, wherein said heteroaryl ring system is optionally substituted with 1-3 $R^{20}$; and
  5 to 10 membered heterocycloalkyl ring system selected from azetidinyl, 1,1-dioxo-thiomorpholinyl, 1,4-diazapinyl, 2,3-dihydrobenzofuranyl, 3H-benzooxazolyl, imidazolidinyl, morpholinyl, piperidinyl, piperazinyl, pyrrolidinyl, oxazolidinyl, thiomorpholinyl, tetrahydropyranyl, tetrahydropyrazolopyridinyl, tetrahydro-1,3a, 7-triaza-azulenyl, and tetrahydrofuran, wherein said heterocycloalkyl ring system is optionally substituted with 1-3 $R^{20}$;
$R^9$, at each occurrence, is independently, F or Cl;
$R^{20}$ at each occurrence is independently selected from the group consisting of
  —H, —F, —Cl, —$OR^{21}$, —$NR^{23}R^{24}$, —CN, —$CF_3$, (=O), —C(=O)$R^{25}$, —C(=O)$OR^{25}$, —OC(=O)$R^{25}$, —OC(=O)$NR^{23}R^{24}$, —C(=O)$NR^{23}R^{24}$, —$NR^{27}$C(=O)$NR^{23}R^{24}$, —$NR^{27}$C(=O)$R^{25}$, —$NR^{27}$C(=O)$OR^{25}$, —$NR^{27}$C(=S)$R^{25}$, —$SR^{25}$, —S(=O)$R^{25}$, —S(=O)$_2R^{25}$, —S(=O)$_2NR^{23}R^{24}$, —$NR^{27}SR^{25}$, —$NR^{27}$S(=O)$R^{25}$, —$NR^{27}$S(=O)$_2R^{25}$, methyl, ethyl, propyl, butyl, ethylenedioxy,
  methyl substituted with $R^{31}$;
  phenyl optionally substituted with 1-3 $R^{30}$; and
  5 to 6 membered heteroaryl ring system selected from oxadiazolyl, thiazolyl, pyridinyl, pyridazinyl, pyrimidinyl, and pyrazinyl, wherein said heteroaryl ring system is optionally substituted with 1-3 $R^{30}$;
  3 to 7 membered heterocycloalkyl ring system selected from dihydro-oxazolyl, morpholinyl, piperidinyl, piperazinyl, and pyrrolidinyl, wherein said heterocycloalkyl ring system is optionally substituted with 1-3 $R^{30}$;
$R^{21}$ at each occurrence is independently H, —$CF_3$, methyl, ethyl, propyl, butyl, methoxyethyl, cyclopropylmethyl, phenyl, or pyridyl;
$R^{22}$ at each occurrence is independently selected from the group consisting of
  —H, —F, —Cl, methoxy, ethoxy, propoxy, butoxy, —$NR^{23}R^{24}$, —NHOH, —$NO_2$, —CN, —$CF_3$, —$CHF_2$, —$CH_2F$, (=O), —C(=O)$R^{28}$, —C(=O)$OR^{28}$, —OC(=O)$R^{28}$, —OC(=O)$NR^{23}R^{24}$,
  —C(=O)$NR^{23}R^{24}$, —$NR^{27}$C(=O)$NR^{23}R^{24}$, —$NR^{27}$C(=O)$R^{28}$, —$NR^{27}$C(=O)$OR^{28}$, —$NR^{27}$C(=S)$R^{28}$, —$SR^{28}$, —S(=O)$R^{28}$, —S(=O)$_2R^{28}$, —S(=O)$_2NR^{23}R^{24}$, —$NR^{27}SR^{28}$, —$NR^{27}$S(=O)$R^{28}$, and —$NR^{27}$S(=O)$_2R^{28}$;
$R^{23}$ at each occurrence are each independently selected from H, methyl, ethyl, and propyl;
$R^{24}$ at each occurrence are each independently selected from H, methyl, ethyl, propyl, butyl, hydroxyethyl, methoxyethyl, ethoxyethyl, cyclopropyl, cyclobutyl, phenyl optionally substituted with 1-3 $R^{30}$;
  3 to 7 membered heterocycloalkyl ring system selected from morpholinyl, piperidinyl, piperazinyl, pyrrolidinyl, tetrahydrofuranyl, and tetrahydropyranyl, said heterocycloalkyl optionally substituted with 1-3 $R^{30}$;
alternatively $R^{23}$ and $R^{24}$, together with the nitrogen atom to which they are attached, may form a 3 to 7 membered heterocycloalkyl ring selected from azetidinyl, morpholinyl, piperidinyl, piperazinyl, pyrrolidinyl, wherein said heterocycloalkyl ring is optionally substituted with 1-3 $R^{30}$;
$R^{25}$ at each occurrence is independently H, methyl, ethyl, propyl, butyl, $CF_3$, phenyl, cyclopropyl, cyclobutyl, cyclopentyl, cyclohexyl, morpholinyl and furanyl;
$R^{27}$ at each occurrence is independently H or methyl;
$R^{28}$ at each occurrence is independently H or methyl;
$R^{29}$ at each occurrence is independently H, methyl, ethyl, or —C(=O)$CH_3$;
$R^{30}$ at each occurrence is independently H, —F, —Cl, —OH, =O, methyl, ethyl, propyl, butyl, methoxy, ethoxy, propoxy, butoxy, $CF_3$, —C(=O)N($R^{32}$)$_2$, —NHC(=O)N($R^{32}$)$_2$, or —S(=O)$_2CH_3$;
$R^{31}$ at each occurrence is independently H, —F, —Cl, —OH, =O, methoxy, ethoxy, propoxy, butoxy, $CF_3$, —C(=O)N($R^{32}$)$_2$, —NHC(=O)N($R^{32}$)$_2$, phenyl optionally substituted with 1-3 $R^{30}$; or tetrahydrofuranyl;
$R^{32}$ at each occurrence is independently H or methyl;
n is 0, 1, or 2; and
z is 0.

In a second embodiment the present invention provides pharmaceutical composition comprising a compound according to the present invention and one or more pharmaceutically acceptable excipients.

In a third embodiment the present invention provides for methods for treating a disorder selected from the group consisting of narcolepsy or sleep/wake disorders, feeding behavior disorders, eating disorders, obesity, cognition disorders, arousal disorders, memory disorders, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders, inflammation, and myocardial infarction comprising administering to a subject in need of such treatment a therapeutically effective amount of a compound of the present invention. In a preferred embodiment the present invention provides for methods of treating narcolepsy or sleep/wake disorders. In a preferred embodiment the present invention provides for methods of treating attention deficit hyperactivity disorder. In a preferred embodiment the present invention provides for method of treating cognition disorders.

In a fourth embodiment the present invention provides for use of the compounds of the present invention for use in therapy.

In a fifth embodiment the present invention provides for use of the compounds of the present invention in the manufacture of a medicament for treating a disorder selected from the group consisting of narcolepsy or sleep/wake disorders, feeding behavior disorders, eating disorders, obesity, cognition disorders, arousal disorders, memory disorders, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders, inflammation, and myocardial infarction comprising administering to a subject in need of such treatment a therapeutically effective amount of a compound of the present invention.

Definitions

In the formulas described and claimed herein, it is intended that when any symbol appears more than once in a particular formula or substituent, its meaning in each instance is independent of the other.

The following terms and expressions have the indicated meanings.

As used herein, the term "about" refers to a range of values from ±10% of a specified value. For example, the phrase "about 50" includes ±10% of 50, or from 45 to 55. The phrase "from about 10 to 100" includes ±10% of 10 and ±10% of 100, or from 9 to 110.

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

As used herein, "substituted" refers to any one or more hydrogen atoms on the indicated atom is replaced with a selected group referred to herein as a "substituent", provided that the substituted atom's valency is not exceeded, and that the substitution results in a stable compound.

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups has the same meaning as alkyl defined above. A designation such as "$C_1$-$C_6$ alkyl" refers to straight-chain, or branched alkyl group having 1 to 6 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, etc. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms, such as methyl, ethyl, propyl, isopropyl, butyl, isobutyl, sec-butyl, and tert-butyl. A designation such as "$C_1$-$C_3$ alkyl" refers to an alkyl radical containing from 1 to 3 carbon atoms, such as methyl, ethyl, propyl, and isopropyl.

As used herein, the term "alkenyl" refers to a straight chain, or branched hydrocarbon chains of 2 to 6 carbon atoms having at least one carbon-carbon double bond. A designation "$C_2$-$C_6$ alkenyl" refers to an alkenyl radical containing from 2 to 6 carbon atoms. Examples of alkenyl groups include ethenyl, propenyl, isopropenyl, 2,4-pentadienyl, etc.

As used herein, the term "alkynyl" refers to a straight chain, or branched hydrocarbon chains of 2 to 6 carbon atoms having at least one carbon-carbon triple bond. A designation "$C_2$-$C_6$ alkynyl" refers to an alkynyl radical containing from 2 to 6 carbon atoms. Examples include ethynyl, propynyl, isopropynyl, 3,5-hexadiynyl, etc.

As used herein, the term "$C_1$-$C_4$ haloalkyl" refers to an "alkyl" group as defined herein substituted by one or more halogen atoms to form a stable compound. Examples of haloalkyl, include but are not limited to, —$CF_3$, —$CHF_2$ and —$CH_2F$.

As used herein, the term "$C_1$-$C_4$ alkoxy" refers to an "alkyl" group as defined herein bonded to and oxygen atom.

As used herein, the term "halo" refers to an F, Cl, Br, and I. Preferred halo substituents are F and Cl.

As used herein, the term "cycloalkyl" refers to a saturated or partially saturated mono- or bicyclic alkyl ring system containing 3 to 11 carbon atoms. Certain embodiments contain 3 to 10 carbon atoms, other embodiments contain 3 to 7 carbon atmons, other embodiments contain 3 to 6 carbon atoms, and other embodiments contain 5 or 6 carbon atoms. A designation such as "$C_3$-$C_7$ cycloalkyl" refers to a cycloalkyl radical containing from 3 to 7 ring carbon atoms. Examples of cycloalkyl groups include such groups as cyclopropyl, cyclobutyl, cyclopentyl, cyclohexyl, cyclohexenyl, and cycloheptyl.

As used herein, the term "aryl" refers to a substituted or unsubstituted, mono- or bicyclic hydrocarbon aromatic ring system having 6 to 10 ring carbon atoms. Examples include phenyl and naphthyl.

As used herein, the term "heteroaryl" refers to an aromatic group or ring system containing 5 to 10 ring carbon atoms in which one or more ring carbon atoms are replaced by at least one hetero atom such as O, N, or S. Certain embodiments include 5 or 6 membered rings. Examples of heteroaryl groups include pyrrolyl, furanyl, thienyl, pyrazolyl, imidazolyl, thiazolyl, isothiazolyl, isoxazolyl, oxazolyl, oxathiolyl, oxadiazolyl, triazolyl, oxatriazolyl, furazanyl, tetrazolyl, pyridyl, pyrazinyl, pyrimidinyl, pyridazinyl, triazinyl, picolinyl, imidazopyridinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzooxadiazolyl, benzisoxazolyl, cinnolinyl, phthalazinyl, naphthyridinyl, and quinoxalinyl.

As used herein, the term "heterocycloalkyl" refers to a cycloalkyl group in which one or more ring carbon atoms are replaced by at least one hetero atom such as O, N, S, SO, and $SO_2$. Certain embodiments include 3 to 6 membered rings, and other embodiments include 5 or 6 membered rings. Examples of heterocycloalkyl groups include azetidinyl, 3H-benzooxazolyl, 1,1-dioxo-thiomorpholinyl, 1,4-diazapinyl, pyrrolidinyl, pyrrolinyl, imidazolidinyl, imidazolinyl, imidazolidinyl, oxazolidinyl, pirazolidinyl, pirazolinyl, pyrazalinyl, piperidinyl, piperazinyl, hexahydropyrimidinyl, morpholinyl, thiomorpholinyl, dihydrobenzofuranyl, tetrahydrofuranyl, tetrahydropyranyl, tetrahydropyrazolopyridinyl, tetrahydro-1,3a,7-triaza-azulenyl, dihydro-oxazolyl, dithiolyl, oxathiolyl, dioxazolyl, oxathiazolyl, pyranyl, oxazinyl, oxathiazinyl, and oxadiazinyl. Included within the definition of "heterocycloalkyl" are fused ring systems, including, for example, ring systems in which an aromatic ring is fused to a heterocycloalkyl ring and ring systems in which a heteroaromatic ring is fused to a cycloalkyl ring or a heterocycloalkyl ring. Examples of such fused ring systems include, for example, 2,3-dihydrobenzofuran, 2,3-dihydro-1,3-benzoxazole, phthalamide, phthalic anhydride, indoline, isoindoline, tetrahydroisoquinoline, chroman, isochroman, chromene, and isochromene.

As used herein, the term "methylenedioxy", "ethylenedioxy", or "propylenedioxy" refer to a —O—CH$_2$—O—, —O—CH$_2$CH$_2$—O—, or —O—CH$_2$CH$_2$CH$_2$—O— group, respectively, bonded to a cycloalkyl, aryl, heteroaryl, or heterocycloalkyl moiety, as defined herein, through the two oxygen atoms of the methylenedioxy, ethylenedioxy, or propylenedioxy. The methylenedioxy, ethylenedioxy, or propylenedioxy groups may be bonded to the cyclic moiety through one carbon atom of the cyclic moiety (i.e. a spirocyclic bond) or through two adjacent carbons of the cyclic moiety (i.e. fused).

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity of the receptors described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described hereinafter.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

The present invention also encompasses the pharmaceutically acceptable prodrugs of the compounds disclosed herein. As used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be delivered in prodrug form. Conventional procedures for the selection and preparation of suitable prodrug derivatives are described, for example, in *Prodrugs*, Sloane, K. B., Ed.; Marcel Dekker: New York, 1992, incorporated by reference herein in its entirety It is recognized that compounds of the present invention may exist in various stereoisomeric forms. As such, the compounds of the present invention include both diastereomers and enantiomers. The compounds are normally prepared as racemates and can conveniently be used as such, but individual enantiomers can be isolated or synthesized by conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

It is further recognized that functional groups present on the compounds of Formula I may contain protecting groups. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred groups for protecting lactams include silyl groups such as t-butyldimethylsilyl ("TBDMS"), dimethoxybenzhydryl ("DMB"), acyl, benzyl ("Bn"), and methoxybenzyl groups. Preferred groups for protecting hydroxy groups include TBS, acyl, benzyl, benzyloxycarbonyl ("CBZ"), t-butyloxycarbonyl ("Boc"), and methoxymethyl. Many other standard protecting groups employed by one skilled in the art can be found in Greene, T. W. and Wuts, P. G. M., "Protective Groups in Organic Synthesis" 2d. Ed., Wiley & Sons, 1991.

Synthesis

The compounds of the present invention may be prepared in a number of methods well known to those skilled in the art, including, but not limited to those described below, or through modifications of these methods by applying standard techniques known to those skilled in the art of organic synthesis. All processes disclosed in association with the present invention are contemplated to be practiced on any scale, including milligram, gram, multigram, kilogram, multikilogram or commercial industrial scale.

The general routes to prepare the examples shown herein are shown in the general Schemes 1-9. The reagents and starting materials are commercially available, or readily synthesized by well-known techniques by one of ordinary skill in the arts. All substituents in the synthetic Schemes, unless otherwise indicated, are as previously defined.

EXAMPLES

Other features of the invention will become apparent in the course of the following descriptions of exemplary embodiments as shown below. The compounds shown herein have activity in the targets described herein at concentrations ranging from 0.1 nM to 10 nM. These examples are given for illustration of the invention and are not intended to be limiting thereof.

Example 1

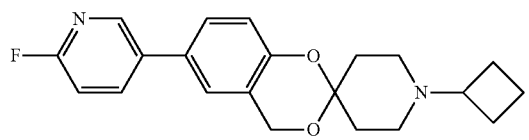 [SMILES: Fc1ccc(-c2ccc3c(c2)COC2(CCN(C4CCC4)CC2)O3)cn1]

Example 1 was prepared according to Scheme 1 and the procedures described below:

Scheme 1

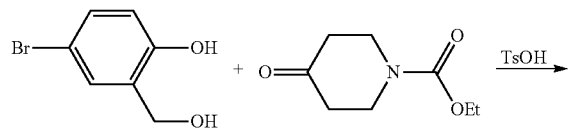

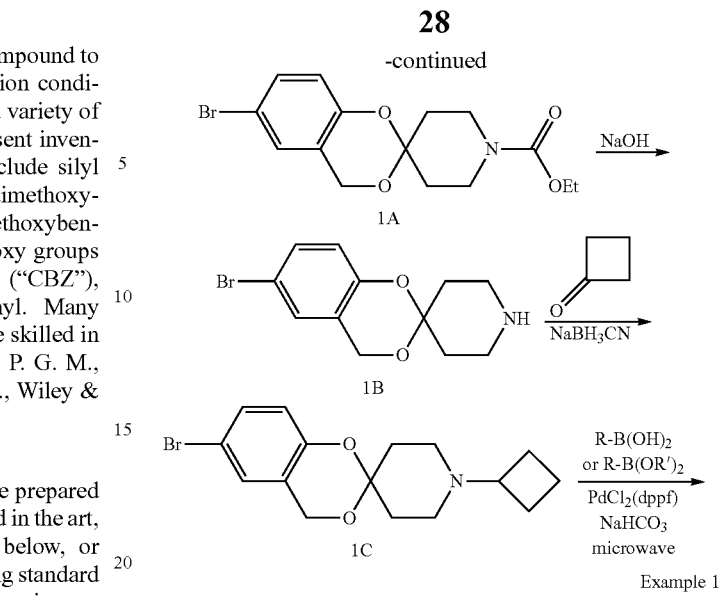

Example 1

1a) To a solution of 5-bromo-2-hydroxybenzyl alcohol (10 g, 49.2 mmol) in $CHCl_3$ (150 mL) was added 4-ethoxycarbonylpiperidone (9.8 g, 57.3 mmol) and p-toluenesulfonic acid (0.84 g, 4.43 mmol). The reaction was equipped with a Dean Stark trap and refluxed for 18 h. The mixture cooled to room temperature. The mixture was washed with 2 N NaOH and brine, then dried ($Na_2SO_4$), filtered and concentrated. Purification by ISCO chromatography (80 gram column, $SiO_2$, gradient 5% to 30% EtOAc in hexane) gave compound 1A (10 g, 58%). $^1$H-NMR ($CDCl_3$) δ 7.37 (m, 1H), 7.21 (s, 1H), 6.82 (d, 1H), 4.93 (s, 2H), 4.25 (m, 2H), 3.73, (m, 2H), 3.62 (m, 2H), 1.98 (m, 4H); LC/MS (ESI+): 355 (M+H).

1b) A solution of 1A (10 g, 28 mmol) in EtOH (150 mL) was treated with 6N NaOH (40 mL), and refluxed overnight. After cooling to room temperature, solvent was removed and the residue was diluted with water, and extracted with EtOAc three times. The organic layer was dried ($Na_2SO_4$), filtered and concentrated to give compound 1B (7.6 g, 96%) as a yellow oil. $^1$H-NMR ($CDCl_3$) δ 7.24 (m, 1H), 7.03 (s, 1H), 6.72 (m, 1H), 4.79 (s, 2H), 2.92 (m, 4H), 1.81 (m, 1H), 1.52 (br, 1H); LC/MS (ESI+): 284 (M+H).

1c) Compound 1B (7.6 g, 26.9 mmol) was dissolved in THF (100 mL). Water (1 mL), acetic acid (10 mL) and cyclobutanone (3 mL, 40.3 mmol) was added, followed by sodium cyanoborohydride (2.5 g, 39.8 mmol). The reaction was heated at 60° C. overnight. The mixture was cooled to room temperature and concentrated. To the residue was added saturated $NaHCO_3$ solution. The mixture was extracted with EtOAc three times. The organic layer was dried ($Na_2SO_4$), filtered and concentrated to give compound 1C (8.9 g, 99%) as a white solid. $^1$H-NMR ($CDCl_3$) δ 7.38 (m, 1H), 7.20 (s, 1H), 6.81 (d, 1H), 4.91 (s, 2H), 2.92 (m, 1H), 2.41-2.65 (m, 4H), 1.95-2.23 (m, 8H); LC/MS (ESI+): 338 (M+H).

1d) Compound 1C (250 mg, 0.74 mmol) was dissolved in 80% EtOH (8 mL) in a 20 mL microwave vial, sodium bicarbonate (0.18 g, 2.23 mmol), 2-fluoropyridine-5-boronic acid (125 mg, 0.89 mmol), and $PdCl_2$(dppf) (27 mg, 0.037 mmol) was added. The vial was capped and microwaved at 120° C. for 25 min. (Ermy's Optimizer). The reaction mixture was filtered through a small pad of celite. The celite was washed with MeOH. The combined filterate was concentrated, diluted with water and extracted with EtOAc three times. The organic layer was washed with saturated $NaHCO_3$ solution, dried ($Na_2SO_4$), filtered and concentrated. Purification by ISCO chromatography (40 gram column, SiO$_2$, gradient 0% to 10% MeOH in DCM) gave 114 mg of Example 1. Example 1 can be further purified by reverse phase HPLC (Sunfired column C$_{18}$OBD™ 5 μm, 19×100 mm, gradient 10% to 90% CH$_3$CN in H$_2$O with 0.01% TFA). The pure fraction from HPLC was concentrated and stirred with MP-carbonate resin (3 equi.) overnight in MeOH to remove TFA salt and give 71 mg pure Example 1. $^1$H NMR (CDCl$_3$) δ 8.32 (d, J=2.1 Hz, 1H), 7.87 (m, 1H), 7.31 (dd, J$_1$=8.4 Hz, J$_2$=2.4 Hz, 1H), 7.11 (d, J=2.4 Hz, 1H), 6.96 (m, 2H), 4.88 (s, 2H), 2.79 (m, 1H), 2.43 (bs, 4H), 1.80-2.10 (m, 8H), 1.60-1.78 (m, 2H); LC/MS (ESI+): 355.1 (M+H$^+$).

Employing similar procedure as described in Example 1, compounds in Table 1 can be prepared by coupling compound 1C and the appropriate R-boronic acid or R-boronic ester, followed by ISCO purification. Some examples require HPLC purification at the final stage.

TABLE 1

| example | R | MS (MH$^+$) | MP (° C.) | $^1$H NMR |
|---|---|---|---|---|
| 1 | 6-fluoropyridin-3-yl | 355.1 | | (CDCl$_3$) δ 8.32 (d, J = 2.1 Hz, 1H), 7.87 (m, 1H), 7.31 (dd, J$_1$ = 8.4 Hz, J$_2$ = 2.4 Hz, 1H), 7.11 (d, J = 2.4 Hz, 1H), 6.96 (m, 2H), 4.88 (s, 2H), 2.79 (m, 1H), 2.43 (bs, 4H), 1.80-2.10 (m, 8H), 1.60-1.78 (m, 2H) |
| 2 | 2,3-dihydrobenzofuran-5-yl | 378 | | (CDCl$_3$) δ 7.28-7.37 (m, 2H), 7.22 (d, J = 7.65 Hz, 1H), 7.09 (s, 1H), 6.88 (d, J = 8.4 Hz, 1H), 6.79 (d, J = 8.4 Hz, 1H),), 4.87 (s, 2H), 4.58 (t, J = 8.4 Hz, 2H), 3.22 (t, J = 8.4 Hz, 2H), 2.78-2.95 (m, 1H), 2.38-2.62 (m, 4H), 2.85-2.17 (m, 6H), 1.60-2.78 (m, 4H) |
| 3 | 4-cyanophenyl | 361.3 | | (CDCl$_3$) δ 7.67 (d, J = 9.0 Hz, 2H), 7.59 (d, J = 9.0 Hz, 2H), 7.39 (dd, J$_1$ = 7.5 Hz, J$_2$ = 2.4 Hz, 1H), 7.18 (s, 1H), 6.95 (d, J = 8.7 Hz, 1H), 4.88 (s, 2H), 2.79 (m, 1H), 2.44 (bs, 4H), 1.84-2.10 (m, 8H), 1.60-1.80 (m, 2H) |
| 4 | 5-fluoropyridin-3-yl | 355 | 140-145 | (CDCl$_3$) δ 8.98 (s, 1H), 8.61 (s, 1H), 8.15 (br s, 1H), 7.58 (br s, 1H), 7.43 (s, 1H), 7.19 (br s, 1H), 5.01 (br s, 2H), 3.43-3.72 (m, 3H), 2.62-3.02 (m, 6H), 2.22-2.45 (m, 4H), 2.01-2.21 (m, 1H), 1.80-2.00 (m, 1H) |
| 5 | furan-3-yl | 326 | 150-152 | (CDCl$_3$) δ 7.52 (s, 1H), 7.47 (s, 1H), 7.32 (d, J = 8.4 Hz, 1H), 7.00 (s, 1H), 6.78 (d, J = 8.4 Hz, 1H), 6.52 (s, 1H), 4.89 (s, 2H), 2.68-2.86 (m, 1H), 2.34-2.48 (m, 4H), 1.73-1.98 (m, 8H), 1.52-1.93 (m, 3H) |
| 6 | benzofuran-2-yl | 376 | | (CDCl$_3$) δ 7.76 (d, J = 8.55 Hz, 1H), 7.56-7.7.68 (m, 3H), 7.28-7.38 (m, 2H), 7.05 (d, J = 8.4 Hz, 1H), 6.98 (s, 1H), 5.02 (s, 2H), 2.86-3.00 (m, 1H), 2.43-2.65 (m, 4H), 1.98-2.24 (m, 7H), 1.72-1.68 (m, 2H) |
| 7 | pyridin-3-yl | 337 | | (CD$_3$OD) δ 8.88 (br s, 1H), 8.60 (br s, 1H), 8.19 (d, J = 8.4 Hz, 1H), 7.62 (d, J = 8.4 Hz, 2H), 7.43 (s, 1H), 7.06 (d, J = 8.4 Hz, 1H), 5.02 (s, 2H), 2.98-3.12 (m, 1H), 2.58-2.72 (m, 4H), 2.18-2.32 (m, 2H), 2.01-2.16 (m, 6H), 1.82-1.98 (m, 2H) |
| 8 | 4-(pyrrolidine-1-carbonyl)phenyl | 433 | | (CDCl$_3$) δ 7.62-7.74 (m, 4H), 7.53 (d, J = 8.4 Hz, 1H), 7.38 (s, 1H), 7.02 (d, J = 8.4 Hz, 1H), 5.01 (s, 2H), 3.78 (t, J = 7.5 Hz, 2H), 3.60 (t, J = 7.5 Hz, 2H), 2.88-3.00 (m, 1H), 2.42-2.76 (m, 4H), 1.96-2.24 (m, 11H), 1.72-1.93 (m, 3H) |

TABLE 1-continued

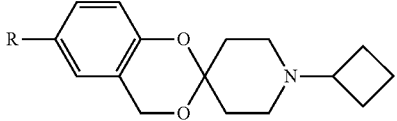

| example | R | MS (MH+) | MP (° C.) | ¹H NMR |
|---|---|---|---|---|
| 9 | 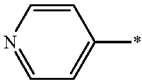 | 449 | | (CDCl₃) δ 7.66 (d, J = 8.4, 2H), 7.55 (d, J = 8.4 Hz, 2H), 7.50 (d, J = 8.4 Hz, 1H), 7.29 (br s, 1H), 7.04 (d, J = 8.4 Hz, 1H), 5.01 (s, 2H), 3.58-3.98 (m, 8H), 2.81-3.00 (m, 1H), 2.43-2.71 (m, 4H), 1.96-2.24 (m, 8H), 1.61-1.90 (m, 2H) |
| 10 | 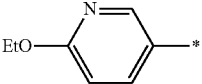 [SMILES: *c1ccc(OCC)nc1] | 337 | | (CD₃OD) δ 8.88 (br s, 2H), 7.71-7.82 (m, 3H), 7.62 (s, 1H), 7.02 (d, J = 8.4 Hz, 1H), 5.09 (s, 2H), 2.98-3.12 (m, 1H), 2.62-2.82 (m, 4H), 2.01-2.35 (m, 8H), 1.82-1.98 (m, 2H) |
| 11 | 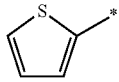 | 381 | | (CDCl₃) δ 8.28 (d, J = 2.4 Hz, 1H), 7.64-7.75 (m, 1H), 7.31 (d, J = 8.4 Hz, 1H), 7.09 (d, J = 11 Hz, 1H), 6.91 (t, J = 8.7 Hz, 1H), 6.77 (d, J = 8.7 Hz, 1H), 4.87 (d, J = 19.8 Hz, 2H), 4.36 (m, J = 7.2 Hz, 2H), 3.32-3.54 (m, 3H), 2.72-2.91 (m, 2H), 2.53-2.70 (m, 2H), 2.35-2.51 (m, 2H), 2.16-2.33 (m, 4H), 1.86-1.98 (m, 1H), 1.70-1.84 (m, 1H), 1.40 (t, J = 7.2 Hz, 3H) |
| 12 | 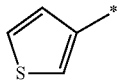 | 342 | | (CDCl₃) δ 7.52 (dd, J₁ = 9 Hz, J₂ = 2.1 Hz, 1H), 7.27-7.33 (m, 3H), 7.15 (m, 1H), 6.98 (d, J = 8.4 Hz, 1H), 4.98 (s, 2H), 2.91 (m, 1H), 2.54 (bs, 4H), 1.92-2.22 (m, 8H), 1.70-1.82 (m, 2H) |
| 13 | 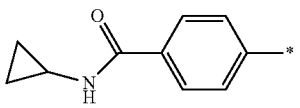 [SMILES: *c1ccc(C(=O)NC2CC2)cc1] | 342 | | (CDCl₃) δ 7.28-7.41 (m, 4H), 7.18 (s, 1H), 6.85 (d, J = 9 Hz, 1H), 4.84 (s, 2H), 2.90 (bs, 1H), 2.54 (bs, 3H), 2.15 (bs, 8H), 1.60-1.80 (m, 3H) |
| 14 | 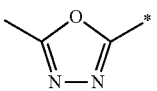 [SMILES: *c1nnc(C)o1] | 419.1 | | (CDCl₃) δ 7.75 (d, J = 8.4 Hz, 2H), 7.53 (d, J = 8.4 Hz, 2H), 7.39 (dd, J₁ = 7.5 Hz, J₂ = 2.1 Hz, 1H), 7.18 (s, 1H), 6.92 (d, J = 8.4 Hz, 1H), 6.30 (s, 1H), 4.88 (s, 2H), 2.89 (m, 1H), 2.49 (s, 4H), 1.85-2.18 (m, 8H), 1.66-1.75 (m, 2H), 0.82-0.90 (m, 2H), 0.60-0.68 (m, 2H) |
| 15 | 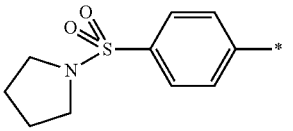 [SMILES: *c1ccc(S(=O)(=O)N2CCCC2)cc1] | 418.1 | | (CDCl₃) δ 8.04 (d, J = 9 Hz, 2H), 7.64 (d, J = 9 Hz, 2H), 7.44 (d, J = 8.4 Hz, 1H), 7.23 (s, 1H), 6.95 (d, J = 8.7 Hz, 1H), 4.90 (s, 2H), 2.80 (m, 1H), 2.62 (s, 3H), 2.44 (bs, 4H), 1.85-2.10 (m, 8H), 1.66-1.75 (m, 2H) |
| 16 | 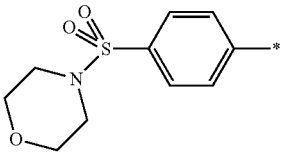 [SMILES: *c1ccc(S(=O)(=O)N2CCOCC2)cc1] | 469 | | (CDCl₃) δ 7.83 (d, J = 8.46 Hz, 2H), 7.63 (d, J = 8.6 Hz, 2H), 7.41 (dd, J = 2.26 Hz, J = 8.52 Hz, 1H), 7.20 (d, J = 2.22 Hz, 1H), 6.94 (d, J = 8.48 Hz, 1H), 4.89 (s, 2H), 3.26 (m, 4H), 2.80 (m, 1H), 2.43 (m, 3H), 1.97 (m, 7H), 1.76 (m, 6H) |
| 17 | 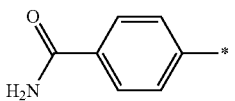 | 485 | | (CDCl₃) δ 7.79 (d, J = 8.5 Hz, 2H), 7.67 (d, J = 8.5 Hz, 2H), 7.43 (dd, J = 2.4 Hz, J = 8.5 Hz, 1H), 7.22 (d, J = 2.13 Hz, 1H), 6.98 (d, J = 8.5 Hz, 1H), 4.9 (S, 2H), 3.76 (t, J = 4.6 Hz, J = 5.6 Hz, 4H), 3.04 (T, J = 3.0 Hz, J = 6.0 Hz, 4H), 2.81 (m, 1H), 2.4 (m, 4H), 2.0 (m, 8H), 1.7 (m, 2H) |
| 18 | | 379.1 | | (CDCl₃) δ 7.83 (d, J = 6 Hz, 2H), 7.56 (d, J = 6 Hz, 2H), 7.41 (d, J = 7.5 Hz, 1H), 7.01 (s, 1H), 6.93 (d, J = 8.4 Hz, 1H), 4.88 (s, 2H), 2.87 (m, 1H), 2.52 (s, 4H), 2.02 (bm, 8H), 1.66-1.75 (m, 2H) |

TABLE 1-continued

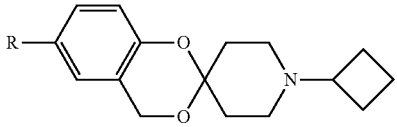

| example | R | MS (MH+) | MP (° C.) | ¹H NMR |
|---|---|---|---|---|
| 19 | 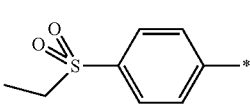 | 376 | 64.5-66 | δ 8.21 (s, 1H), 7.59-7.64 (m, 3H), 7.3 (d, J = 9.3 Hz, 2H), 7.14 (s, 1H), 6.94 (d, J = 8.7 Hz, 1H), 4.89 (s, 2H), 2.82 (m, 2H), 2.47 (s, 4H), 1.85-2.18 (m, 8H), 1.62-1.75 (m, 2H) |
| 20 | 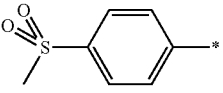 [SMILES: *c1ccc(S(C)(=O)=O)cc1] | 428 | | (CDCl₃) δ 7.9 (d, J = 8.6 Hz, 2H), 7.7 (d, J = 8.6 Hz, 2H), 7.43 (dd, J = 2.14 Hz, J = 8.5 Hz, 1H), 7.22 (d, J = 2.32 Hz, 1H), 6.96 (d, J = 8.5 Hz, 1H), 4.9 (S, 2H), 3.1 (q, J = 7.5 Hz, 2H), 2.9 (m, 1H), 2.6 (m, 4H), 2.08 (m, 8H), 1.7 (m, 2H), 1.3 (t, J = 7.5 Hz, 3H) |
| 21 | 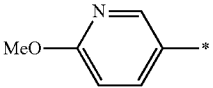 [SMILES: *c1ccc(OC)nc1] | 414 | | (CDCl₃) δ 7.97 (d, J = 8.45 Hz, 2H), 7.69 (d, J = 8.45 Hz, 2H), 7.45 (d, J = 2.26 Hz, J = 8.45 Hz, 1H), 7.24 (d, J = 1.96 Hz, 1H), 6.98 (d J 8.45 Hz, 1H), 4.92 (s, 2H), 3.31 (m, 2H), 3.09 (s, 3H), 2.91 (m, 4H), 2.53 (m, 2H), 2.26 (m, 7H), 1.83 (m, 2H) |
| 22 | 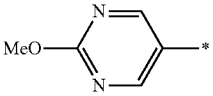 | 367 | 122-124 | (CDCl₃) δ 8.28 (d, J = 2.7 Hz, 1H), 7.69 (dd, J₁ = 7.7 Hz, J₂ = 3.3 Hz, 1H), 7.30 (d, J = 8.7 Hz, 1H), 7.08 (s, 1H), 6.92 (d, J = 8.4 Hz, 1H), 6.77 (d, J = 8.7 Hz, 1H), 4.88 (s, 2H), 3.95 (s, 3H) 2.95 (m, 2H), 2.50-2.75 (m, 4H), 1.95-2.18 (m, 8H), 1.62-1.75 (m, 2H) |
| 23 | 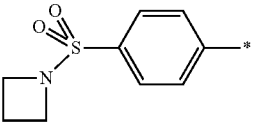 [SMILES: *c1ccc(S(=O)(=O)N2CCC2)cc1] | 368.1 | | (CDCl₃) δ 8.62 (s, 2H), 7.29 (d, J = 9 Hz, 1H), 7.1 (s, 1H), 6.95 (d, J = 9 Hz, 1H), 4.95 (s, 2H), 4.03 (s, 3H), 2.8 (m, 1H), 2.42 (br, 4H), 1.9-2.05 (m, 8H), 1.7 (m, 2H) |
| 24 | 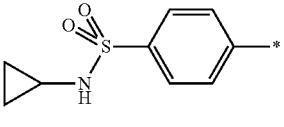 [SMILES: *c1ccc(S(=O)(=O)NC2CC2)cc1] | 455 | | (CDCl₃) δ 7.87 (d, J = 8.5 Hz, 2H), 7.70 (d, 8.6 Hz, 2H), 7.66 (dd, J = 2.37 Hz, J = 8.64 Hz, 1H), 7.25 (d, J = 2.16 Hz, 1H), 6.98 (d, J = 8.4 Hz, 1H), 4.92 (s, 2H), 3.81 (t, J = 7.56 Hz, 4H), 3.10 (m, 1H), 2.79 (m, 3.5H), 2.16 (m, 10.5H), 1.76 (m, 2H) |
| 25 | 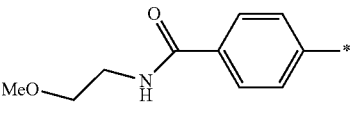 [SMILES: *c1ccc(C(=O)NCCOC)cc1] | 455 | | (CDCl₃) δ 7.91 (d, J = 8.68 Hz, 2H), 7.62 (d, J = 8.53 Hz, 2H), 7.42 (dd, J = 2.24 Hz, J = 8.38 Hz, 1H), 7.21 (d, J = 2.09 Hz, 1H), 6.95 (d, J = 8.52 Hz, 1H), 5.02 (s, 1H), 4.90 (s, 2H), 3.15 (m, 1H), 2.84 (m, 3H), 2.20 (m, 9H), 1.77 (m, 2H), 0.60 (m, 4H) |
| 26 | 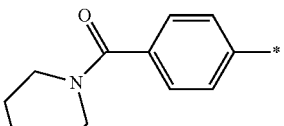 | 437 | 145-147 | (CDCl₃) δ 7.79 (d, J = 8.4 Hz, 2H), 7.54 (d, J = 8.4 Hz, 2H), 7.40 (d, J = 8.4 Hz, 1H), 7.18 (s, 1H), 6.91 (d, J = 8.4 Hz, 1H), 6.61 (s, 1H), 4.87 (s, 2H), 3.60-3.69 (m, 2H), 3.52-3.57 (m, 2H), 3.37 (s, 3H), 2.90-3.00 (m, 1H), 2.54-2.74 (m, 4H), 1.98-2.22 (m, 8H), 1.70-1.82 (m, 2H) |
| 27 | 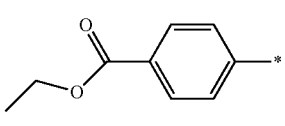 [SMILES: *c1ccc(C(=O)OCC)cc1] | 447 | 59-62 | (CDCl₃) δ 7.48 (d, J = 8.4 Hz, 2H), 7.40 (d, J = 8.4 Hz, 2H), 7.35 (s, 1H), 7.19 (s, 1H), 6.92 (d, J = 8.4 Hz, 1H), 4.86 (s, 2H), 3.68 (br s, 2H), 3.31 (br s, 2H), 3.00 (m, 1H), 2.58-2.82 (m, 4H), 1.96-2.19 (m, 10H), 1.41-1.83 (m, 6H) |
| 28 |  | 408 | 148-149 | (CDCl₃) δ 8.17 (d, J = 8.4 Hz, 2H), 7.61 (d, J = 8.4 Hz, 2H), 7.52 (d, J = 8.4 Hz, 1H), 7.33 (s, 1H), 7.05 (d, J = 8.4 Hz, 1H), 5.00 (s, 2H), 4.44-4.53 (m, J = 7.2 Hz, 2H), 2.88-3.00 (m, 1H), 2.45-2.64 (m, 4H), 1.92-2.42 (m, 8H), 1.72-1.88 (m, 2H), 1.51 (t, J = 7.2 Hz, 3H) |

TABLE 1-continued

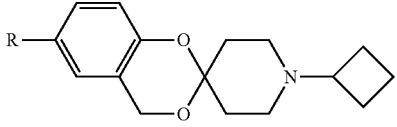

| example | R | MS (MH+) | MP (° C.) | ¹H NMR |
|---|---|---|---|---|
| 29 | 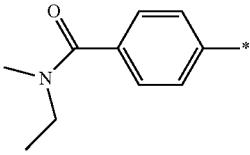 [SMILES: *c1ccc(C(=O)N(C)CC)cc1] | 407 | 187-190 | (CDCl₃) δ 7.48 (d, J = 8.4 Hz, 2H), 7.40 (d, J = 8.4 Hz, 2H), 7.38 (d, J = 8.4 Hz, 1H), 7.19 (s, 1H) 6.92 (d, J = 8.4 Hz, 1H), 4.86 (s, 2H), 2.83-3.19 (m, 7H), 2.42-2.63 (m, 4H), 1.96-2.19 (m, 8H), 1.61-1.83 (m, 2H) |
| 30 | 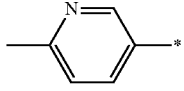 [SMILES: *c1ccc(C)nc1] | 421 | 140-141 | (CDCl₃) δ 7.62 (d, J = 8.4 Hz, 2H), 7.52 (d, J = 8.4 Hz, 2H), 7.48 (s, 1H), 7.32 (s, 1H), 7.02 (d, J = 8.4 Hz, 1H), 5.00 (s, 2H), 3.60-3.76 (m, 1H), 3.28-3.52 (m, 1H), 3.02-3.27 (m, 3H), 2.85-3.00 (m, 1H), 2.43-2.71 (m, 4H), 1.96-2.22 (m, 8H), 1.70-1.92 (m, 2H), 1.18-1.43 (m, 3H) |
| 31 | 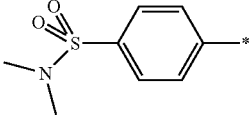 [SMILES: *c1ccc(S(=O)(=O)N(C)C)cc1] | 351 | 137-139 | (CDCl₃) δ 8.62 (s, 1H), 7.68 (d, J = 9Hz, 1H), 7.38 (d, J = 9 Hz, 1H), 7.10-7.19 (m, 2H), 6.92 (d, J = 8.4 Hz, 1H), 4.86 (s, 2H), 2.88-3.00 (m, 1H), 2.51-2.78 (m, 5H), 1.96-2.19 (m, 10H), 1.61-1.83 (m, 2H) |
| 32 | 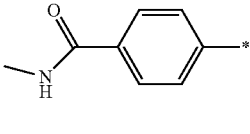 [SMILES: *c1ccc(C(=O)NC)cc1] | 443 | | (CDCl₃) δ 7.78 (d, J = 8.57 Hz, 2H), 7.64 (d, J = 8.66 Hz, 2H), 7.42 (dd, J = 2.39 Hz, J = 8.66 Hz, 1H), 7.21 (d, J = 2.12 Hz, 1H), 6.95 (d, J 8.48 Hz, 1H), 4.90 (s, 2H), 2.97 (m, 1H), 2.72 (m, 10H), 2.68 (m, 6H), 2.09 (m, 8H), 1.72 (m, 2H) |
| 33 | 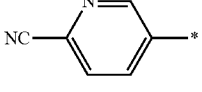 | 393 | 198-199 | (CDCl₃) δ 7.90 (d, J = 8.4 Hz, 2H), 7.67 (d, J = 8.4 Hz, 2H), 7.53 (d, J = 8.4 Hz, 1H), 7.31 (s, 1H), 7.05 (d, J = 8.4 Hz, 1H), 6.28 (s, 1H), 5.00 (s, 2H), 3.14 (d, J = 5.1 Hz, 3H), 2.85-3.00 (m, 1H), 2.45-2.47 (m, 4H), 1.94-2.22 (m, 8H), 1.70-1.89 (m, 2H) |
| 34 | 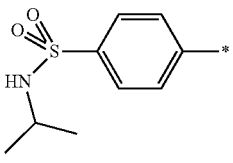 [SMILES: *c1ccc(S(=O)(=O)NC(C)C)cc1] | 362.1 | 159.8-160.7 | (CDCl₃) δ 8.86 (s, 1H), 7.91 (d, J = 8.4 Hz, 1H), 7.71 (d, J = 8.4 Hz, 1H), 7.41 (d, J = 8.4 Hz, 1H), 7.20 (s, 1H), 6.99 (d, J = 8.7 Hz, 1H), 4.90 (s, 2H), 2.79 (m, 2H), 2.38-2.55 (m, 4H), 1.85-2.12 (m, 8H), 1.62-1.75 (m, 2H) |
| 35 | 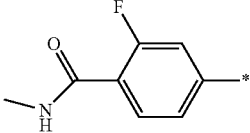 [SMILES: *c1ccc(C(=O)NC)c(F)c1] | 457 | 85-90 | (CDCl₃) δ 7.90 (d, J = 8.6 Hz, 2H), 7.63 (d, J = 8.78 Hz, 2H), 7.43 (dd, J = 2.19 Hz, J = 8.44 Hz, 1H), 7.23 (d, J = 2.19 Hz, 1H), 6.96 (d, J = 8.61 Hz, 1H), 4.91 (s, 2H), 4.5 (d, 1H), 3.50 (m, 1H), 3.10 (m, 1H), 2.77 (m, 4H), 2.17 (m, 8H), 1.77 (m, 2H), 1.10 (m, 6H) |
| 36 | 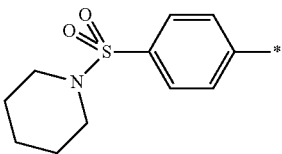 | 411 | 147.8-149 | (CDCl₃) δ 8.23 (t, J = 8.4 Hz, 1H), 7.51 (d, J = 8.4 Hz, 2H), 7.28-7.40 (m, 3H), 7.04 (d, J = 8.4 Hz, 1H), 6.86 (m, 1H), 4.99 (s, 2H), 3.15 (d, J = 3.9 Hz, 3H), 2.84-2.98 (m, 1H), 2.42-2.63 (m, 4H), 1.92-2.22 (m, 8H), 1.74-1.88 (m, 2H) |
| 37 | 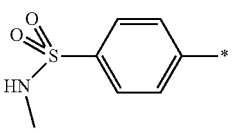 | 483 | 85-90 | (CDCl₃) δ 7.77 (d, J = 8.6 Hz, 2H), 7.64 (d, J = 8.6 Hz, 2H), 7.43 (dd, J = 2.25 Hz, J = 8.5 Hz, 1H), 7.22 (d, J = 2.12 Hz, 1H), 6.95 (d, J = 8.5 Hz, 1H), 4.9 (S, 2H), 3.01 (m, 6H), 2.56 (m, 3H), 2.05 (m, 8H), 1.64 (m, 6H), 1.42 (m, 2H) |
| 38 | | 428 | 80-85 | (CDCl₃) δ 7.89 (d, J = 8.7 Hz, 2H), 7.65 (d, J = 8.7 Hz, 2H), 7.43 (dd, J = 2.28 Hz, J = 8.4 Hz, 1H), 7.22 (d, J = 2.4 Hz, 1H), 6.96 (d, J 8.56 Hz, 1H), 4.91 (s, 2H), 4.44 (q, 1H), 3.03 (m, 2H), 2.68 (m, 6H), 2.13 (m, 8H), 1.73 (m, 2H) |

TABLE 1-continued

[Structure: R-substituted benzo-dioxaspiro-piperidine-cyclobutane scaffold]

| example | R | MS (MH+) | MP (° C.) | ¹H NMR |
|---|---|---|---|---|
| 39 | phenyl* | 336.2 | 127.8-128.6 | (CDCl₃) δ 7.51 (m, 2H), 7.41 (m, 3H), 7.22-7.26 (m, 1H), 7.17 (s, 1H), 6.92 (d, J = 8.7 Hz, 1H), 4.89 (s, 2H), 2.79 (m, 2H), 2.38-2.55 (m, 4H), 1.85-2.12 (m, 8H), 1.62-1.75 (m, 2H) |
| 40 | 2-F,4-(N,N-dimethylcarbamoyl)phenyl* | 425 | 172.9-173.5 | (CDCl₃) δ 7.42-7.56 (m, 3H), 7.24-7.38 (m, 2H), 7.04 (d, J = 8.4 Hz, 1H), 4.99 (s, 2H), 3.24 (s, 3H), 3.07 (s, 3H), 2.84-2.98 (m, 1H), 2.42-2.63 (m, 4H), 1.92-2.22 (m, 8H), 1.74-1.88 (m, 2H) |
| 41 | 2-F,4-(pyrrolidin-1-ylcarbonyl)phenyl* | 451.2 | 171-172.5 | (CDCl₃) δ 7.3-7.45 (m, 3H), 7.15-7.24 (m, 2H), 6.92 (d, J = 9 Hz, 1H), 4.85 (s, 2H), 3.64 (t, J = 9 Hz, 2H), 3.34 (t, J = 9 Hz, 2H), 2.8 (m, 1H), 2.42 (br, 4H), 1.85-2.1 (m, 12H) 1.7 (m, 2H) |
| 42 | 2-(dimethylamino)pyrimidin-5-yl* | 381.1 | 204.8-205.8 | (CDCl₃) δ 8.45 (s, 2H), 7.24 (d, J = 9 Hz, 1H), 7.02 (s, 1H), 6.90 (d, J = 8.4 Hz, 1H), 4.87 (s, 2H), 3.21 (s, 6H), 2.79 (m, 2H), 2.38-2.55 (m, 4H), 1.85-2.12 (m, 8H), 1.62-1.75 (m, 2H) |
| 43 | 4-(thiazol-2-ylcarbamoyl)phenyl* | 462 | 242-243 | (CDCl₃) δ 8.04 (d, J = 8.7 Hz, 2H), 7.66 (d, J = 8.7 Hz, 2H), 7.46 (d, J = 8.7 Hz, 1H), 7.18-7.28 (m, 3H), 6.94-6.98 (m, 2H), 4.91 (s, 2H), 2.75-2.85 (m, 1H), 2.42-2.53 (m, 4H), 1.84-2.14 (m, 8H), 1.61-1.78 (m, 2H) |
| 44 | 4-(hydroxymethyl)phenyl* | 366.2 | 131-134 | (CDCl₃) δ 7.50 (d, J = 6.4 Hz, 2H), 7.35-7.49 (m, 3H), 7.16 (s, 1H), 6.91 (d, J = 8.7 Hz, 1H), 4.87 (s, 2H), 4.71 (s, 2H), 2.81 (m, 1H), 2.35-2.59 (m, 4H), 1.87-2.12 (m, 8H), 1.63-1.75 (m, 2H) |
| 45 | pyrimidin-5-yl* | 338.1 | 153-155 | (CDCl₃) δ 9.13 (s, 1H), 8.85 (s, 2H), 7.36 (d, J = 8.7 Hz, 1H), 7.16 (s, 1H), 6.98 (d, J = 8.7 Hz, 1H), 4.89 (s, 2H), 2.81 (m, 1H), 2.37-2.56 (m, 4H), 1.82-2.12 (m, 8H), 1.62-1.74 (m, 2H) |
| 46 | 6-(acetylamino)pyridin-3-yl* | 394.2 | 186-187 | (CDCl3) δ 8.27 (s, 1H), 8.06 (d, J = 8 Hz, 1H), 7.7 (d, J = 8 Hz, 1H), 7.24 (d, J = 6 Hz, 1H), 7.0 (s, 1H), 6.8 (d, J = 6 Hz, 1H), 4.75 (s, 2H), 2.76 (m, 1H), 2.4 (br, 4H), 2.1 (s, 3H), 1.75-1.95 (m, 8H), 1.6 (m, 2H) |
| 47 | 2-fluoropyridin-3-yl* | 355 | 95-100 | (CDCl3) δ 8.14 (d, J = 4.9 Hz, 1H), 7.82 (m, 1H), 7.36 (d, J = 8.5 Hz, 1H), 7.24 (m, 1H), 7.20 (s, 1H), 6.95 (d, J = 8.4 Hz, 1H), 4.89 (s, 2H), 2.81 (m, 1H), 2.44 (m, 4H), 1.97 (m, 8H), 1.70 (m, 2H) |
| 48 | 4-sulfamoylphenyl* | 415 | 195-200 | (CDCl3) δ 7.92 (d, J = 8.54 Hz, 2H), 7.72 (d, J = 8.53 Hz, 2H), 7.49 (dd, J = 8.52 Hz, J = 2.3 Hz, 1H), 7.37 (d, J = 2.1 Hz, 1H), 6.92 (d, J = 8.62 Hz, 1H), 4.92 (s, 2H), 1.97 (m, 8H), 1.70 (m, 4H), 2.08 (m, 2H), 1.95 (m, 6H), 1.74 (m, 2H) |

TABLE 1-continued

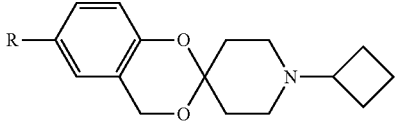

| example | R | MS (MH+) | MP (° C.) | 1H NMR |
|---|---|---|---|---|
| 49 | 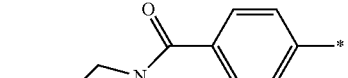 | 393.1 | | (CDCl3) δ 7.35-7.45 (m, 4H), 7.16-7.22 (m, 2H), 6.92 (d, J = 9 Hz, 1H), 5.4 (br, 2H), 4.85 (s, 2H), 3.6 (s, 2H), 2.82 (m, 1H), 2.46 (br, 4H), 1.9-2.1 (m, 8H), 1.66 (m, 2H) |
| 50 | 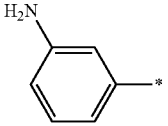 [SMILES: *c1cccc(N)c1] | 423.2 | 185-187 | (CDCl3) δ 7.93 (d, J = 8.1 Hz, 2H), 7.65 (d, J = 8.1 Hz, 2H), 7.50 (d, J = 8.1 Hz, 1H), 7.29 (s, 1H), 7.03 (d, J = 8.1 Hz, 1H), 6.89 (s, 1H), 4.98 (s, 2H), 3.96 (m, 2H), 3.76 (m, 2H), 2.95 (m, 1H), 2.52-2.60 (m, 4H), 1.98-2.18 (m, 8H), 1.74-1.86 (m, 2H) |
| 51 | 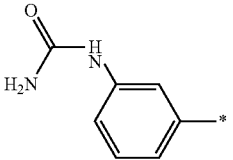 [SMILES: *c1cccc(NC(N)=O)c1] | 351 | | (CDCl3) δ 7.34 (d, J = 8.4 Hz, 1H), 7.11-7.22 (m, 2H), 6.88 (d, J = 8.4 Hz, 2H), 6.79 (s, 1H), 6.60 (d, J = 8.4 Hz, 1H), 4.86 (s, 2H), 3.70 (br s, 2H), 2.80-2.92 (m, 1H), 2.39-2.62 (m, 4H), 1.89-2.14 (m, 8H), 1.60-1.80 (m, 2H) |
| 52 | 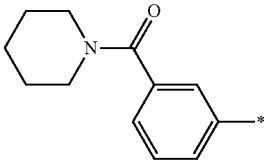 [SMILES: *c1cccc(C(=O)N2CCCCC2)c1] | 394 | | (CDCl3) δ 7.96-8.08 (m, 4H), 7.35-7.71 (m, 7H), 7.03 (d, J = 8.4 Hz, 1H), 5.00 (s, 2H), 2.68-2.86 (m, 4H), 1.94-2.19 (m, 6H), 1.76-1.86 (m, 2H), 1.52-1.74 (m, 4H), 1.36 (s, 1H) |
| 53 | 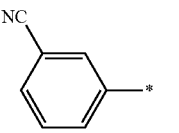 [SMILES: *c1cccc(C#N)c1] | 447 | | (CDCl3) δ 7.62-7.68 (m, 2H), 7.47-7.56 (m, 2H), 7.38 (m, 1H), 7.29 (s, 1H), 7.03 (d, J = 8.4 Hz, 1H), 4.99 (s, 2H), 3.83 (br S, 2H), 3.47 (br s, 2H), 2.86-2.95 (m, 1H), 2.46-2.64 (m, 4H), 1.94-2.22 (m, 8H), 1.52-1.89 (m, 7H), 1.03 (br s, 1H) |
| 54 | 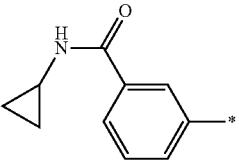 [SMILES: *c1cccc(C(=O)NC2CC2)c1] | 361.3 | | (CDCl3) δ 7.67 (d, J = 9.0 Hz, 2H), 7.59 (d, J = 9.0 Hz, 2H), 7.39 (dd, J1 = 7.5 Hz, J2 = 2.4 Hz, 1H), 7.18 (s, 1H), 6.95 (d, J = 8.7 Hz, 1H), 4.88 (s, 2H), 2.79 (m, 1H), 2.44 (bs, 4H), 1.84-2.10 (m, 8H), 1.60-1.80 (m, 2H) |
| 55 | 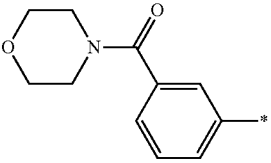 [SMILES: *c1cccc(C(=O)N2CCOCC2)c1] | 419 | | (CDCl3) δ 7.92 (s, 1H), 7.62 (t, J = 7.5 Hz, 2H), 7.38-7.50 (m, 2H), 7.20 (s, 1H), 6.96 (d, J = 8.4 Hz, 1H), 6.46 (s, 1H), 4.87 (s, 2H), 2.81-3.00 (m, 2H), 2.43-2.71 (m, 4H), 1.96-2.18 (m, 8H), 1.61-1.82 (m, 2H), 0.81-0.97 (m, 2H), 0.58-0.64 (m, 2H) |
| 56 | 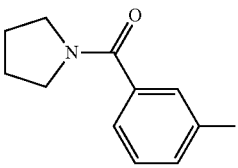 | 449.1 | | HCl salt: (CD3OD) δ 7.84 (d, J = 7.5 Hz, 1H), 7.76 (s, 1H), 7.66 (m, 2H), 7.52 (m, 2H), 7.13 (dd, J1 = 27 Hz, J2 = 8.7 Hz, 1H), 5.12 (m, 2H), 3.92 (m, 3H); 3.78 (m, 1H), 3.64 (m, 2H), 3.47 (m, 6H), 3.18-3.32 (m, 2H), 2.42-2.62 (m, 6H), 2.10-2.18 (m, 2H ), 1.95-2.08 (m, 2H) |
| 57 |  | 433 | 221.7 | (CDCl3) δ 7.62 (s, 1H), 7.47-7.57 (m, 1H), 7.36-7.45 (m, 3H), 7.19 (s, 1H), 6.87 (d, J = 8.4 Hz, 1H), 4.87 (s, 2H), 3.62 (t, J = 7.5 Hz, 2H), 3.41 (t, J = 7.5 Hz, 2H), 3.03-3.21 (m, 1H), 2.72-2.98 (m, 3H), 2.39-2.60 (m, 2H), 2.08-2.38 (m, 5H), 1.80-2.01 (m, 5H), 1.62-1.80 (m, 1H), 1.20-1.38 (m, 2H) |

TABLE 1-continued

| example | R | MS (MH+) | MP (° C.) | 1H NMR |
|---|---|---|---|---|
| 58 | 3-carbamoylphenyl (H2N-C(O)-C6H4-*) | 379 | 109.3 | (CDCl$_3$) δ 7.98 (s, 1H), 7.62-7.72 (m, 2H), 7.47 (d, J = 8.4 Hz, 1H), 7.38-7.47 (m, 1H), 7.20 (s, 1H), 6.93 (d, J = 8.4 Hz, 1H), 4.87 (s, 2H), 2.80 (m, 1H), 2.38-2.58 (m, 4H), 1.86-2.11 (m, 8H), 1.62-1.78 (m, 2H) |
| 59 | ethyl nicotinate-5-yl (EtO-C(O)-pyridin-3-yl-*) | 409 | 239.2 | (CDCl$_3$) δ 9.11 (s, 1H), 8.89 (s, 1H), 8.39 (s, 1H), 7.42 (d, J = 8.4 Hz, 1H), 7.20 (s, 1H), 6.98 (d, J = 8.4 Hz, 1H), 4.87 (s, 2H), 4.41 (m, J = 7.5 Hz, 2H), 2.79 (m, 1H), 2.36-2.58 (m, 4H), 1.80-2.12 (m, 8H), 1.78-1.80 (m, 2H), 1.42 (t, J = 7.5 Hz, 2H) |

Employing similar procedure as described for Example 1 and Scheme 1, except replacing the cyclobutanone in step 1c with cyclopentanone or acetone, the compounds disclosed in Table 2 can be prepared by one skilled in the art. Purification was carried out with ISCO chromatography. Some examples require HPLC purification at the final stage.

TABLE 2

| Ex. | R | X | MS (MH+) | MP (° C.) | 1H NMR |
|---|---|---|---|---|---|
| 60 | 2,3-dihydrobenzofuran-5-yl | cyclopentyl | 391 | | (CDCl$_3$) δ 7.25-7.42 (m, 2H), 7.15-7.7.24 (m, 2H), 7.02 (s, 1H), 6.86 (d, J = 8.4 Hz, 1H), 6.76 (d, J = 8.4 Hz, 1H),), 4.80 (s, 2H), 4.52 (t, J = 8.55 Hz, 2H), 3.18 (t, J = 8.55 Hz, 2H), 2.50-2.80 (m, 4H), 1.90-2.07 (m, 4H), 1.85 (br s, 2H), 1.67 (br s, 2H), 1.49-1.51 (m, 4H) |
| 61 | 3-aminophenyl | cyclopentyl | 365 | | (CDCl$_3$) δ 7.45 (d, J = 7.35 Hz, 1H), 7.25-7.7.32 (m, 2H), 7.02 (D, J = 8.25 Hz, 1H), 6.95 (s, 1H), 6.75 (d, J = 7.35 Hz, 1H), 5.00 (s, 2H), 4.83 (br s, 2H), 2.78-3.00 (m, 4H), 2.18-2.30 (m, 4H), 1.90-2.10 (m, 2H), 1.80-1.95 (m, 2H), 1.60-1.80 (m, 3H) |
| 62 | 3-benzamidophenyl | cyclopentyl | 469 | | (CDCl$_3$) δ 7.96-8.08 (m, 4H), 7.35-7.71 (m, 7H), 7.03 (d, J = 8.4 Hz, 1H), 5.00 (s, 2H), 2.68-2.86 (m, 4H), 1.94-2.19 (m, 6H), 1.76-1.86 (m, 2H), 1.52-1.74 (m, 4H), 1.36 (s, 1H) |
| 63 | 3-aminophenyl | isopropyl | 339 | | (CDCl$_3$) δ 7.36 (d, J = 8.4 Hz, 1H), 7.11-7.22 (m, 2H), 6.84-6.90 (m, 2H), 6.79 (s, 1H), 6.62 (d, J = 8.4 Hz, 1H), 4.86 (s, 2H), 3.25-3.40 (m, 1H), 3.02-3.18 (m, 4H), 2.27 (t, J = 5.7 Hz, 4H), 1.30 (d, J = 6.6 Hz, 6H) |

TABLE 2-continued

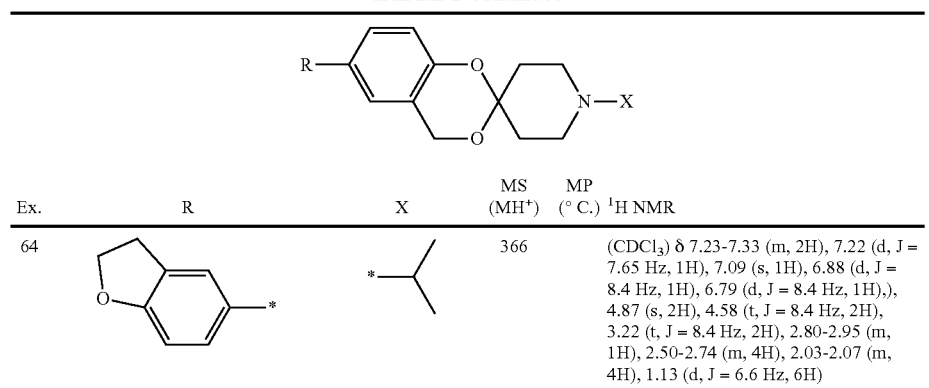

| Ex. | R | X | MS (MH+) | MP (° C.) | 1H NMR |
|---|---|---|---|---|---|
| 64 | (benzofuran) | isopropyl | 366 | | (CDCl3) δ 7.23-7.33 (m, 2H), 7.22 (d, J = 7.65 Hz, 1H), 7.09 (s, 1H), 6.88 (d, J = 8.4 Hz, 1H), 6.79 (d, J = 8.4 Hz, 1H),), 4.87 (s, 2H), 4.58 (t, J = 8.4 Hz, 2H), 3.22 (t, J = 8.4 Hz, 2H), 2.80-2.95 (m, 1H), 2.50-2.74 (m, 4H), 2.03-2.07 (m, 4H), 1.13 (d, J = 6.6 Hz, 6H) |

Example 65

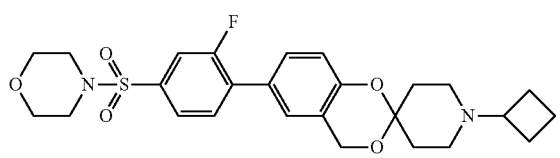 [SMILES: O=S(=O)(c1ccc(-c2ccc3c(c2)COC2(CCN(C4CCC4)CC2)O3)c(F)c1)N1CCOCC1]

Example 65 was prepared according to Scheme 2 and the procedures described below:

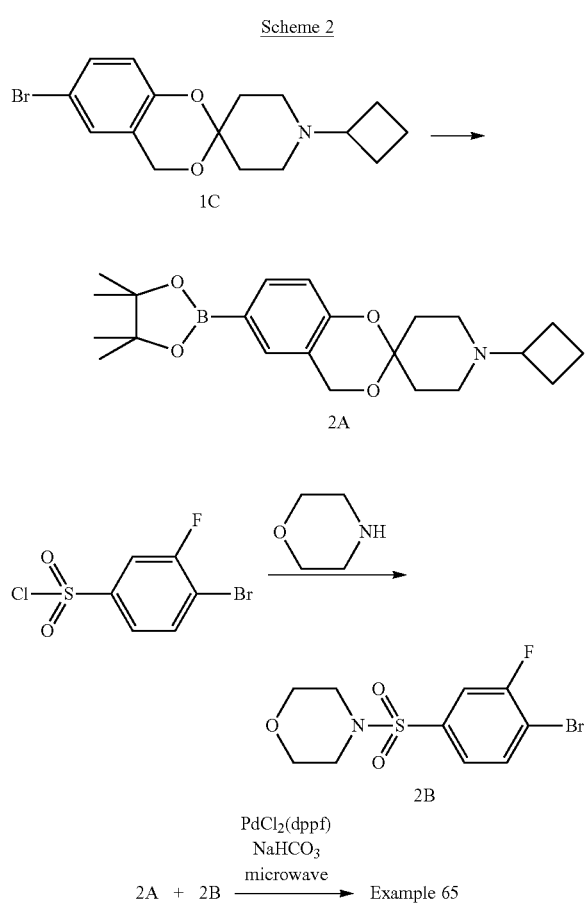

2a) To a solution of compound 1C (0.2 g, 0.6 mmol) in DMSO (3 mL), was added Bis(pinacolato)diboron (0.17 g, 0.66) and Potassium acetate (0.18 g, 1.8 mmol). The reaction mixture was degassed by Argon and was added 1,1'-Bis (diphenylphosphino)-ferrocene palladium dichloride (0.013 g, 0.018). The reaction was stirred at 80° C. under inert atmosphere for 3 h. Reaction mixture was diluted with ethyl acetate and was washed with water and brine. The ethyl acetate layer was dried over MgSO4 and was concentrated to get crude compound 2A. The crude material was used as such for the next reaction.

2b) To a stirred solution of 3-fluoro-4-bromo-benzenesulfonyl chloride (1 g, 3.94 mmol) in pyridine (10 mL) at 0° C. was added morpholine (0.5 mL, 5.9 mmol). The mixture was stirred at 0° C. for 3 h. Solvent was removed and water was added to the reaction. The mixture was extracted with EtOA three times. The organic layer was washed with brine, dried (MgSO4), and concentrated. Purification by ISCO chromatography (40 gram column, SiO2, gradient 5% to 30% MeOH in DCM) gave compound 2B (1.3 g, 100%). 1H-NMR (CDCl3) δ 7.76 (dd, J=8.25 Hz, J=6.4 Hz, 1H), 7.50 (dd, J=7.65 Hz, J=1.95 Hz, 1H), 7.42 (d, J=8.1 Hz, 1H), 3.75 (t, J=4.8 Hz, 2H), 3.03 (t, J=5.1 Hz, 2H).

2c) Compound 2A and 2B was coupled using procedure as described in step 1d to give Example 65 after purification. 1H-NMR (CDCl3) δ 7.55 (m, 3H), 7.40 (d, J=8.6 Hz, 1H), 7.22 (m, 1H), 6.99 (t, J=10.2 Hz, 1H), 4.91 (d, J=19.2 Hz, 2H), 3.77 (t, J=4.54 Hz, 4H), 3.48 (m, 3H), 3.06 (t, J=4.79 Hz, 4H), 2.81 (m, 2H), 2.38 (m, 8H), 1.86 (m, 2H); LC/MS (ESI+): 503 (M+H).

Employing similar procedure as described for Example 65, step 2c, compounds in Table 3 can be prepared by coupling compound 2A and the appropriate R-halide, followed by ISCO purification. Some examples require HPLC purification at the final stage.

The appropriate R-halide used in Examples 67, 68, 69, and 72 was prepared by coupling 4-bromobenzoic acid (1 eq.) and the corresponding amine, NH(R')(R'') (1 eq.) using EDC (2.5 eq.) as the coupling reagent with HOBt in DIEA/DMF overnight. After solvent was removed, the residue was dissolved in CH2Cl2 and washed with saturated NaHCO3 solution. The organic layer was dried (Na2SO4) and concentrated to give crude substituted 4-bromo-benzoamide which was used directly for the next reaction.

TABLE 3

| Ex. | R | MS (MH+) | MP (° C.) | 1H NMR |
|---|---|---|---|---|
| 66 | 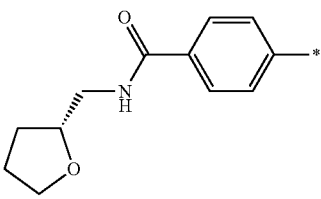 | 343.1 | 165-166 | (CDCl₃) δ 8.82 (s, 1H), 7.66 (d, J = 7.2 Hz, 1H), 7.59 (s, 1H), 7.37 (s, 1H), 6.90 (d, J = 8.4 Hz, 1H), 4.88 (s, 2H), 2.79 (m, 2H), 2.38-2.55 (m, 4H), 1.85-2.12 (m, 8H), 1.62-1.75 (m, 2H) |
| 67 | 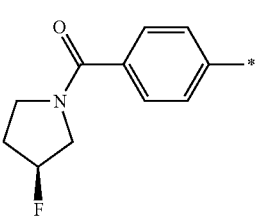 | 463.2 | 184-186 | (CDCl₃) δ 7.80 (d, J = 8.1 Hz, 2H), 7.55 (d, J = 8.1 Hz, 2H), 7.40 (d, J = 6.0 Hz, 1H), 7.20 (s, 1H), 6.93 (d, J = 8.1 Hz, 1H), 6.50 (t, d = 5.4 Hz, 1H), 4.89 (s, 2H), 4.07 (m, 1H), 3.74-3.92 (m, 4H), 3.31-3.38 (m, 1H), 2.76-2.81 (m, 1H), 2.42 (b, 4H), 1.84-2.05 (m, 8H), 1.61-1.78 (m, 5H) |
| 68 | 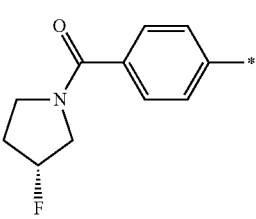 | 451.2 | 184-186 | (CDCl₃) δ 7.54-7.61 (m, 4H) 7.39 (d, J = 8.7 Hz, 1H), 7.19 (s, 1H), 6.93 (d, J = 8.7 Hz, 1H), 5.11-5.42 (m, 1H), 4.89 (s, 2H), 3.63-3.96 (m, 4H), 2.79 (m, 1H), 2.34-2.53 (m, 5H), 1.84-2.14 (m, 8H), 1.61-1.78 (m, 3H) |
| 69 | 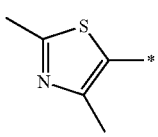 | 451.2 | 185-186 | (CDCl₃) δ 7.66-7.72 (m, 4H), 7.51 (d, J = 8.7 Hz, 1H), 7.30 (s, 1H), 7.05 (d, J = 8.7 Hz, 1H), 5.21-5.57 (m, 1H), 5.01 (s, 2H), 3.70-4.09 (m, 4H), 2.93 (m, 1H), 2.34-2.62 (m, 5H), 1.96-2.22 (m, 8H), 1.75-1.81 (m, 3H) |
| 70 | 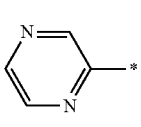 | 371.1 | 225-227 (HCl Salt) | (CDCl₃) δ 7.15 (s, 1H), 6.97 (s, 1H), 6.85 (s, 1H), 4.84 (s, 2H), 3.39 (m, 3H), 2.73 (m, 9H), 2.40 (b, 3H), 2.19 (m, 4H), 1.90 (m, 1H), 1.71 (m, 1H) |
| 71 | 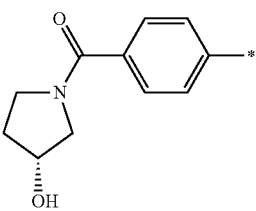 | 338.2 | 114-115 | (CDCl₃) δ 8.94 (s, 1H), 8.55 (s, 1H), 8.43 (s, 1H), 7.79 (d, J = 8.1 Hz, 1H), 7.699s, 1H), 6.97 (d, J = 8.7 Hz, 1H), 4.92 (s, 2H), 2.81 (m, 1H), 2.45 (b, 4H), 1.87-2.12 (m, 6H), 1.52-1.71 (m, 4H) |
| 72 | 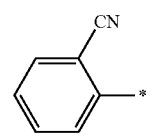 | 449.2 | 180-182 | (CDCl₃) δ 7.42-7.58 (m, 4H), 7.39 (d, J = 8.4 Hz, 1H), 7.18 (s, 1H), 6.91 (d, 8.7 Hz, 1H), 4.87 (s, 2H), 4.46-4.59 (m, 1H), 3.44-3.78 (m, 4H), 2.80 (m, 1H), 2.44 (b, 4H), 1.87-2.12 (m, 8H), 1.63-1.71 (m, 4 H) |
| 73 |  | 361 | | (CDCl3) δ 7.73 (d, J = 7.89 Hz, 2H), 7.61 (m, 1H), 7.46 (d, J = 7.85 Hz, 1H), 7.38 (m, 2H), 7.18 (d, J = 2.28 Hz, 1H), 6.97 (d, J = 8.47 Hz, 1H), 4.91 (s, 2H), 2.83 (m, 1H), 2.45 (m, 3H), 2.0 (m, 9H), 1.71 (m, 2H) |

TABLE 3-continued

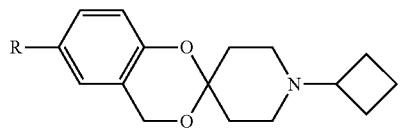

| Ex. | R | MS (MH+) | MP (° C.) | 1H NMR |
|---|---|---|---|---|
| 74 | 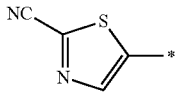 | 357.1 | 151-153 | (CDCl$_3$) δ 7.71 (d, J = 8.4 Hz, 1H), 7.65 (s, 1H), 7.25 (s, 1H), 6.97 (s, 1H), 6.99 (d, J = 8.4 Hz, 1H), 4.97 (s, 2H), 2.90 (m, 1H), 2.85 (s, 3H), 2.52-2.55 (m, 4H), 1.98-2.18 (m, 8H), 1.74-1.86 (m, 2H) |
| 75 | 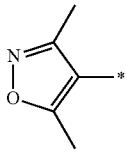 | 368 | | (CDCl3) δ 8.22 (s, 1H), 7.74 (dd, J = 8.59 Hz, J = 2.1 Hz, 1H), 7.64 (s, 1H), 6.95 (d, J = 8.56 Hz, 1H), 4.90 (s, 2H), 2.80 (m, 1H), 2.44 (m, 3H), 1.97 (m, 9H), 1.71 (m, 2H) |
| 76 | 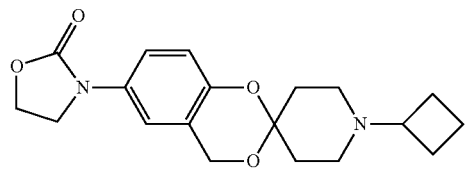 | 355.2 | 123-127 | (CDCl$_3$) δ 7.01 (d, J = 8.1 Hz, 1H), 6.89 (d, J = 8.1 Hz, 1H), 6.80 (s, 1H), 4.85 (s, 2H), 2.79 (m, 1H), 2.40-2.56 (m, 4H), 2.35 (s, 3H), 2.21 (s, 3H), 1.92-2.12 (m, 8H), 1.62-1.74 (m, 2H) |

Example 77

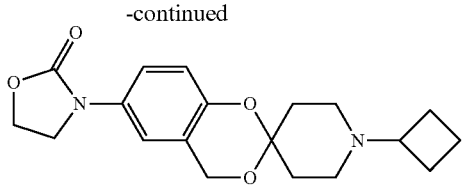

Example 77 was prepared using the procedures described below:

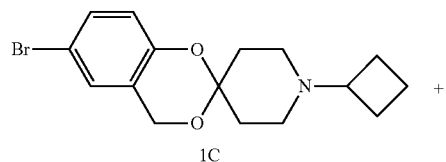

1C

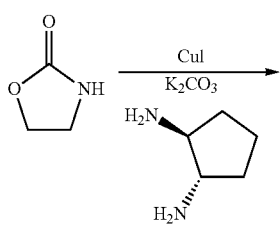

-continued

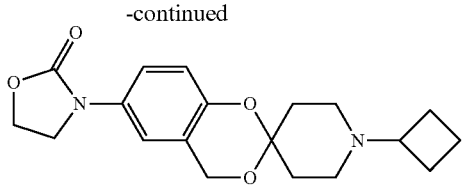

Example 77

To a round bottomed flask with a condenser was added copper iodide (0.005 g, 0.022 mmol), potassium carbonate (0.121 g, 0.88 mmol) and oxazolidinone (0.039 g, 0.44 mmol). After the system was flushed with argon, dioxane (3 mL) was added followed by trans-1,2-cyclohexanediamine (0.005 mL, 0.44 mmol) and compound 1C (0.150 g, 0.44 mmol). The resulting solution was heated at 110° C. for 48 h. After cooling to room temperature, the solution was diluted with DCM (3 mL) and filtered through a syringe filter. The solvent was removed in vacuo and the residue purified by preparative TLC (10% MeOH/DCM) and preparative HPLC (Sunfired column C$_{18}$ OBD™ 5 μm, 19×100 mm, gradient 10% to 90% CH$_3$CN in H$_2$O with 0.01% TFA). The resulting salt was neutralized with MP-carbonate (150 mg) in DCM (5 mL) overnight. The solution was filtered and solvent removed in vacuo to provide Example 77 (28.5 mg, 19%). MP=165-168° C. $^1$H-NMR (CDCl$_3$) δ 7.28 (d, J=2.7 Hz, 1H), 7.14 (dd, J=2.4, 9.0 Hz, 1H), 6.85 (d, J=8.4 Hz, 1H), 4.82 (s, 2H), 4.45 (t, J=8.4 Hz, 2H), 3.99 (t, J=7.5 Hz, 2H) 2.77 (m, 1H), 2.39 (m, 4H), 1.92 (m, 8H), 1.68 (m, 2H); LC/MS (ESI+): 345.1 (M+H).

Employing similar procedure as described for Example 77, compounds in Table 4 can be prepared by coupling 1C and the appropriate R—H, followed by preparative TLC and/or HPLC purification at the final stage.

TABLE 4

![structure: R-substituted benzodioxine spiro piperidine N-cyclobutyl]

| Ex. | R | MS (MH+) | MP (° C.) | 1H NMR |
|---|---|---|---|---|
| 78 | ![pyrrolidinone] | 343 | 187-188 | (CDCl3) δ 7.3 (d, J = 2.4 Hz, 1H), 7.2 (dd J = 2.7, 9 Hz, 1H), 6.83 (d, J = 9 Hz, 1H), 4.82 (s, 2H), 3.79 (t, J = 6.9 Hz, 2H), 2.77 (m, 1H), 2.57 (t, J = 8.7 Hz, 2H), 2.39 (m, 4H), 2.13 (m, 2H), 1.95 (m, 8H), 1.68 (m, 2H) |
| 79 | ![4-hydroxy pyrrolidinone] | 359.1 | 117-120 | (CDCl3) δ 7.30 (d, J = 2.4 Hz, 1H), 7.17 (dd, J = 2.7, 8.1 Hz, 1H), 6.82 (d, J = 8.7 Hz, 1H), 4.80 (s, 2H), 4.58 (m, 1H), 4.02 (dd, J = 5.4, 3.0 Hz, 1H), 3.68 (dd, J = 1.8, 12 Hz, 1H), 2.86 (dd, J = 6.3. 16.5 Hz, 1H), 2.77 (m, 1H), 2.55 (dd, J = 2.1, 18 Hz, 1H), 2.39 (m, 4H), 2.01 (m, 2H), 1.88 (m, 6H), 1.69 (m, 2H) |
| 80 | ![morpholinone] | 359.1 | 148-152 | (CDCl3) δ 7.05 (dd, J = 2.4, 8.7 Hz, 1H), 6.92 (d, J = 2.4 Hz, 1H), 6.87 (d, J = 9 Hz, 1H), 4.80 (s, 2H), 4.29 (s, 2H), 3.98 (t, J = 5.1 Hz, 2H), 3.67 (t, J = 5.4 Hz, 2H) 2.76 (m, 1H), 2.38 (m, 4H), 1.93 (m, 8H), 1.68 (m, 2H) |
| 80 | ![benzoxazolone] | 393.3 | 172-175 | (CDCl3) δ 7.39 (m, 2H), 7.27 (m, 3H), 7.11 (m, 2H), 5.0 (s, 2H), 2.92 (m, 1H), 2.56 (m, 4H), 2.09 (m, 8H), 1.81 (m, 2H) |
| 82 | ![methyl imidazolidinone] | 358.1 | 180-181 | (CDCl3) δ 7.31 (d, J = 2.7 Hz, 1H), 7.11 (dd, J = 3, 8.7 Hz, 1H), 6.79 (d, J = 9 Hz, 1H), 4.80 (s, 2H), 3.71 (m, 2H), 3.42 (m, 2H), 2.85 (s, 3H), 2.76 (m, 1H), 2.39 (m, 4H), 2.05-1.62 (m, 10H) |

Example 83

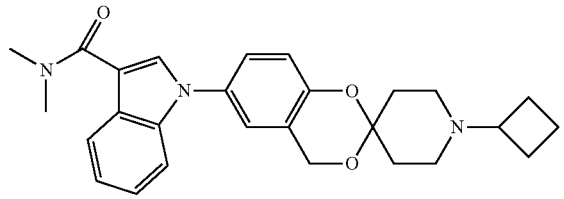 [SMILES: CN(C)C(=O)c1cn(-c2ccc3c(c2)COC2(CCN(C4CCC4)CC2)O3)c2ccccc12]

Example 83 was prepared according to Scheme 3 and the procedures described below:

Scheme 3

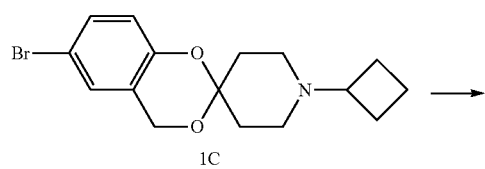

1C

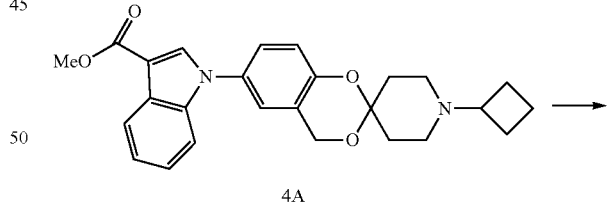

4A

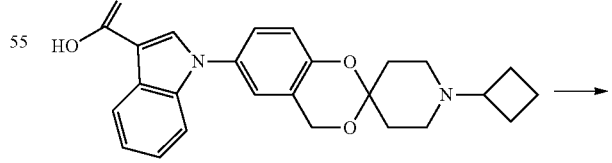

4B

Example 83

4a) To a Pyrex tube was added copper iodide (0.01 g, 0.05 mmol), potassium phosphate (0.233 g, 1.1 mmol), dioxane (3 mL), trans-1,2-cyclohexanediamine 0.02 mL, 0.053 mmol), compound 1C (0.179 g, 0.53 mmol) and methyl-3-indole carboxylate (0.111 g, 0.63 mmol). The resulting solution was heated at 100° C. for 24 h in a rotating oven. After cooling to room temperature, the solution was diluted with DCM (3 mL) and filtered through a syringe filter. The solvent was removed in vacuo and the residue purified by column chromatography (DCM, 5% MeOH/DCM) to provide intermediate 4A (0.170 g, 75%), $^1$H-NMR (CDCl$_3$) δ 8.33 (m, 1H), 8.04 (m, 1H), 7.5 (m, 1H), 7.38 (m, 2H), 7.19 (m, 1H), 7.12 (m, 1H), 5.4 (s, 1H), 5.0 (s, 2H), 4.04 (s, 3H), 2.95 (m, 1H), 2.59 (m, 4H), 2.12 (m, 8H), 1.83 (m, 2H); LC/MS (ESI+): 433.1 (M+H).

4b) Compound 4A (0.085 g, 0.2 mmol) was dissolved in MeOH (1 mL) and H$_2$O (1 mL). Lithium hydroxide (0.010 g, 0.39 mmol) was added and the solution was stirred at room temperature for 72 h. NaOH (0.5 mL of 2M solution) was added and the solution was stirred for 72 h. The solvent was removed in vacuo. The residue was taken up in H$_2$O and washed with DCM. The aqueous phase was acidified with 1N HCl and washed with DCM (2×) and EtOAc (2×). The combined organics were dried (Na$_2$SO$_4$), filtered and concentrated in vacuo go afford compound 4B (0.06 g, 75%, LC/MS (ESI+): 419.1 (M+H)) which was used without purification.

4c) Compound 4B (0.06 g, 0.14 mmol) was treated with N-(3-dimethylaminopropyl)-N'-ethylcarbodiimide (0.04 g, 0.21 mmol), 1-hydroxybenzotriazole hydrate (0.28 g, 0.21 mmol) and diisopropylethylamine (0.098 mL, 0.56 mmol) in DMF (4 mL) and stirred at room temperature for 2 h. Dimethylamine hydrochloride (0.023 g, 0.28 mmol) was added and the solution was stirred at room temperature overnight. The solvent was removed in vacuo. The residue was dissolved in DCM and washed with 1N HCl, brine and saturated sodium bicarbonate. The organics were dried (Na$_2$SO$_4$), filtered and dried in vacuo. The crude product was purified by column chromatography (DCM, 1%, 2% and 3% MeOH/DCM) to provide an oil. Adding 1M HCl in diethyl ether (2 mL, 3×) and removing solvent in vacuo afford Example 83 (0.0289 g, 43%). MP=100-110° C. $^1$H-NMR (CDCl$_3$) δ 7.8 (m, 1H), 7.51 (s, 1H), 7.37 (m, 1H), 7.24 (m, 3H), 7.07 (d, J=2.1 Hz, 1H), 6.99 (d, J=8.4 Hz, 1H), 4.88 (s, 2H), 3.18 (s, 6H), 2.81 (m, 1H), 2.46 (m, 4H), 1.95 (m, 8H), 1.7 (m, 2H); LC/MS (ESI+): 446.2 (M+H).

Example 84

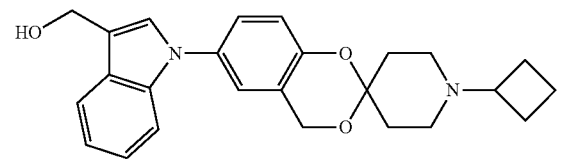 [SMILES: OCc1cn(-c2ccc3c(c2)COC2(CCN(C4CCC4)CC2)O3)c2ccccc12]

Example 84 was prepared from compound 4A using procedures described below:

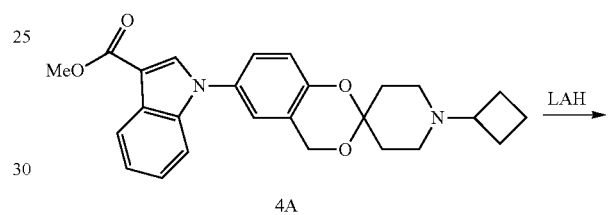

4A

Example 84

Compound 4A (0.117 g, 0.27 mmol) was dissolved in THF (5 mL). To this solution was added Lithium aluminum hydride (1.08 mL, 1.08 mmol, 1M solution in THF) dropwise via syringe. The solution was stirred at room temperature for 2 h. The reaction was carefully quenched with water (0.04 mL), 10% aq. NaOH (0.04 mL), and water (0.12 mL). After stirring for 3 h, the solution was filtered and the solids washed with EtOAc and DCM. The combined organics were filtered and concentrated in vacuo. The crude product was purified by preparative TLC (10% MeOH/DCM) to give Example 84 (0.03 g, 27.5%). MP=138-141° C. $^1$H-NMR (CDCl$_3$) δ 7.75 (m, 1H), 7.41 (m, 1H), 7.2 (m, 4H), 7.03 (d, J=2.1 Hz, 1H), 6.7 (d, J=9 Hz, 1H), 4.91 (s, 2H), 4.86 (s, 2H), 2.81 (m, 1H), 2.46 (m, 4H), 1.97 (m, 8H), 1.69 (m, 2H); LC/MS (ESI+): 405.2 (M+H).

Employing similar procedure as described in Example 83, Examples 85 and 86 in Table 5 can be prepared. Example 87 can be prepared using both procedure as described in Examples 83 and 84.

TABLE 5

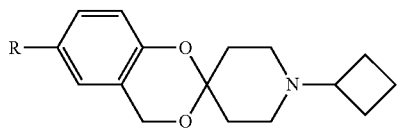

| Ex. | R | MS (MH+) | MP (° C.) | ¹H NMR |
|---|---|---|---|---|
| 85 | (indole with N,N-dimethylcarboxamide) | 446.3 | 76-80 | (CDCl₃) δ 7.42 (d, J = 7.5 Hz, 1H), 7.2 (m, 4H), 7.05 (s, 1H), 6.97 (d, J = 8.7 Hz, 1H), 6.59 (d, J = 3.3 Hz, 1H), 4.88 (s, 2H), 3.19 (s, 3H), 2.96 (s, 3H), 2.81 (m, 1H), 2.45 (m, 4H), 1.96 (m, 8H), 1.69 (m, 2H) |
| 86 | (pyrrole with N-methylcarboxamide, methyl) | 396.2 | 149-153 | (CDCl₃) δ 7.35 (d, J = 2.4 Hz, 1H), 7.13 (dd, J = 2.7, 8.7 Hz, 1H), 7.93 (d, J = 2.7 Hz, 1H), 6.88 (d, J = 8.7 Hz, 1H), 6.69 (m, 1H), 5.73 (d, J = 4.2 Hz, 1H), 4.83 (s, 2H), 2.94 (d, J = 4.8 Hz, 3H), 2.9 (m, 1H), 2.54 (m, 4H), 2.3 (s, 3H), 2.04 (m, 8H), 1.7 (m, 2H) |
| 87 | (pyrrole with hydroxymethyl, methyl) | 369.2 | 133-135 | (CDCl₃) δ 7.10 (dd, J = 2.7, 7.5 Hz, 1H), 6.88 (m, 3H), 6.72 (m, 1H), 4.83 (s, 2H), 4.56 (s, 2H), 2.78 (m, 1H), 2.42 (m, 4H), 2.14 (s, 3H), 1.95 (m, 8H), 1.69 (m, 2H) |

Example 88

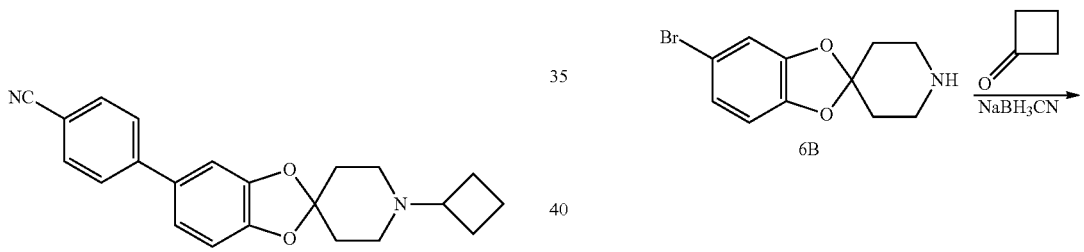

Example 88 was prepared from 4-bromo-2-hydroxyphenol according to Scheme 4 and similar procedures as described in Example 1. Example 88: ¹H NMR (CDCl₃) δ 7.65 (d, J=6.6 Hz, 2H), 7.55 (d, J=6.6 Hz, 2H), 7.00 (m, 2H), 6.82 (d, J=8.1 Hz, 1H), 2.78-2.85 (m, 1H), 2.52 (bs, 4H), 2.00-2.18 (m, 6H), 1.85-1.95 (m, 2H), 1.60-1.80 (m, 2H); LC/MS (ESI+): 347.1 (M+H⁺).

Scheme 4

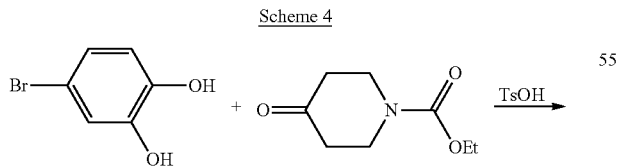

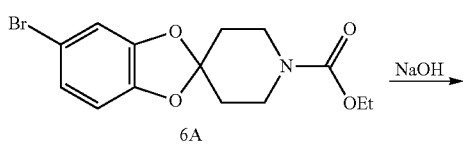

Employing similar procedure as described in Example 1, step 1d, compounds in Table 6 can be prepared by coupling 6C and the appropriate R-boronic acid or R-boronic ester, followed by ISCO purification. Some examples require HPLC purification at the final stage.

TABLE 6

[Structure: benzodioxole-spiro-piperidine-N-cyclobutyl with R substituent]

| Ex. | R | MS (MH+) | MP (° C.) | ¹H NMR |
|---|---|---|---|---|
| 89 | [morpholine-carbonyl-phenyl] | 435.1 | 192-913 | (CDCl₃) δ 7.55 (d, J = 9 Hz, 2H), 7.45 (d, J = 9 Hz, 2H), 7.00 (d, J = 6 Hz, 2H), 6.80 (d, J = 7.8 Hz, 1H), 3.65 (bs, 8H), 2.82 (m, 1H), 2.48 (s, 4H), 2.02-2.12 (m, 6H), 1.82-2.00 (m, 2H), 1.60-1.75 (m, 2H) |
| 90 | [pyrrolidine-carbonyl-phenyl] | 419.1 | 176.8-177.3 | (CDCl₃) δ 7.51 (dd, J1 = 9 Hz, J2 = 2.4 Hz, 4H), 7.00 (d, J = 6 Hz, 2H), 6.80 (d, J = 7.8 Hz, 1H), 3.65 (t, J = 6 Hz, 2H), 3.48 (t, J = 6 Hz, 2H), 2.82 (m, 1H), 2.02-2.12 (m, 6H), 1.82-2.00 (m, 6H), 1.60-1.75 (m, 2H) |
| 91 | [morpholine-carbonyl-phenyl meta] | | | (CDCl₃) δ 7.51 (d, J = 9 Hz, 1H), 7.49 (s, 1H), 7.39 (t, J = 7.5 Hz, 1H), 7.26 (t, J = 7.5 Hz, 1H), 6.97 (d, J = 9 Hz, 2H), 6.78 (d, J = 7.8 Hz, 1H), 3.30-3.82 (m, 8H), 2.79 (m, 2H), 2.49 (bs, 4H), 1.98-2.12 (m, 6H), 1.80-1.95 (m, 2H), 1.60-1.70 (m, 2H) |
| 92 | [NC-phenyl] | | | (CDCl₃) δ 7.75 (s, 1H), 7.69 (d, J = 7.8 Hz, 1H), 7.44-7.57 (m, 2H), 6.94-6.98 (m, 2H), 6.81 (d, J = 8.4 Hz, 1H), 2.82 (m, 2H), 2.52 (bs, 4H), 2.07 (t, J = 5.4 Hz, 6H), 1.80-1.95 (m, 2H), 1.60-1.70 (m, 2H) |

Example 93

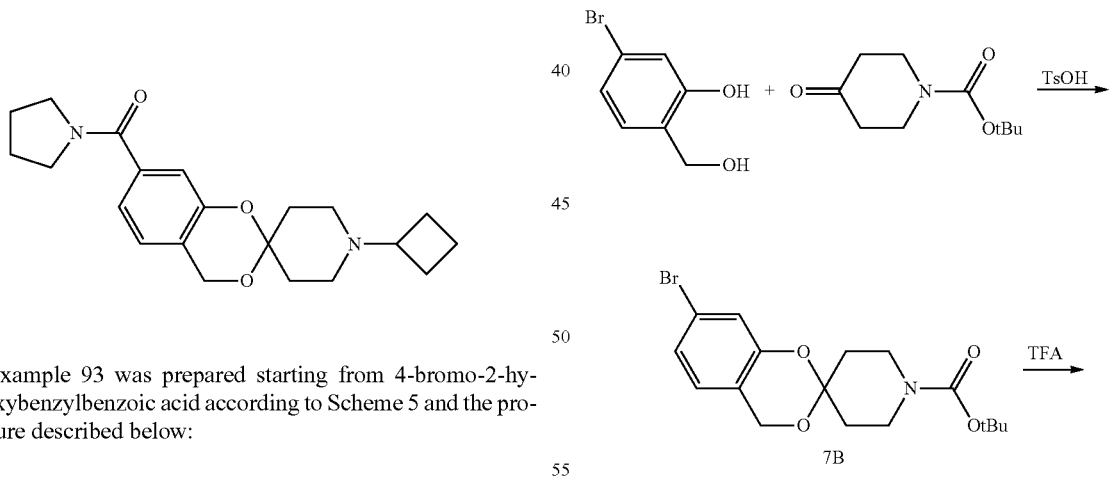

Example 93 was prepared starting from 4-bromo-2-hydroxybenzylbenzoic acid according to Scheme 5 and the procedure described below:

Scheme 5

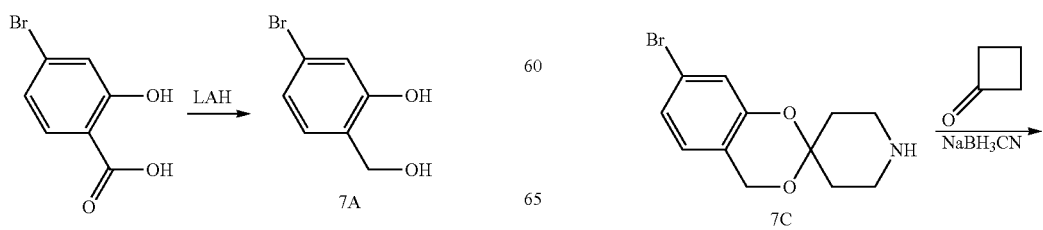

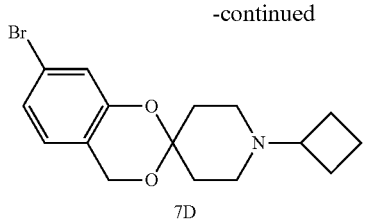

7a) To a suspension of LAH (2.27 g, 60 mmol) in Et$_2$O (40 mL) was added a suspension of 4-bromo-2-hydroxybenzoic acid (8.68 g, 60 mmol) in Et$_2$O (80 mL) dropwise in such a rate that the ether refluxed gently. After completion of the addition, the reaction mixture was stirred at room temperature overnight. The mixture was cooled to 0° C., saturated NH$_4$Cl solution (30 mL) was added dropwise to quench the reaction. The mixture was then treated with 2 N HCl solution carefully until the mixture turn acidic. The mixture was diluted with EtOAc and the supernatant liquid was filtered through a pad of celite. The remaining precipitates were washed with EtOAc (200 mL) and the supernatant again filtered through celite. Repeat the wash two more times. The filtrate were combined and the organic layer was separated. The EtOAc layer was washed thoroughly with 1N HCl three times. The organic layer was dried (Na$_2$SO$_4$), filtered and concentrated to give compound 7A as a yellowish solid (6.54 g, 81%). $^1$H-NMR (CD$_3$OD) δ 7.31 (d, J=7.8 Hz, 1H), 7.10-7.06 (m, 2H), 5.02 (s, 2H, OH+OH), 4.72 (s, 2H).

7b) To a solution of compound 7A (2.83 g, 13.9 mmol) in CHCl$_3$ (anhydrous, no ethanol stabilizer, 33 mL) was added 4-t-butoxycarbonylpiperidone (3.9 g, 19.5 mmol) and p-toluenesulfonic acid (0.28 g, 1.4 mmol). The reaction was equipped with a Dean Stark trap and refluxed for 18 h. The mixture cooled to room temperature. Solvent was removed in vacuo and the residue was purified by ISCO chromatography (120 gram column, SiO$_2$, gradient 5% to 20% EtOAc in hexane) to give compound 7B (2.93 g, 54%). $^1$H-NMR (CDCl$_3$) δ 7.04-7.01 (m, 2H), 6.81 (d, J=8.4 Hz, 1H), 4.78 (s, 2H), 3.63-3.55 (m, 2H), 3.49-3.40 (m, 2H), 1.92-1.76 (m, 4H), 1.45 (s, 9H)

7c) To a stirred solution of compound 7B (2.93 g, 7.65 mmol) in DCM (54 mL) was added TFA (23 mL). The reaction mixture was stirred at room temperature for 1 h. Solvent was removed in vacuo. The residue was dissolved in EtOAc (300 mL) and washed with 1N NaOH (150 mL×2), water and brine. The organic layer was dried (Na$_2$SO$_4$), filtered and concentrated to give compound 7C. LC/MS (ESI+): 284 (M+H).

7d) Compound 7C was converted to compound 7D using reductive alkylation procedure as shown in step 1c. Compound 7D $^1$H-NMR (CDCl$_3$) δ 7.15 (s, 1H), 7.14 (d, J=9 Hz, 1H), 6.92 (d, J=9 Hz, 1H), 4.88 (s, 2H), 2.93 (quint, J=9 Hz, 1H), 2.66-2.44 (m, 4H), 2.24-2.10 (m, 2H), 2.10-1.96 (m, 6H), 1.91-1.70 (m, 2H); LC/MS (ESI+): 338 (M+H).

7e) Compound 7D was converted to Example 93 using Suzuki Coupling procedure as shown in step 1d. Compound 7 $^1$H-NMR (CDCl$_3$) δ 7.73-7.67 (m, 4H), 7.26 (dd, J=7.8, 1.5 Hz, 1H), 7.22 (d, J=1.5 Hz, 1H), 7.14 (1H, J=7.8 Hz, 1H), 4.99 (s, 2H), 3.78 (t, J=6.6 Hz, 2H), 3.59 (t, J=6.3 Hz, 2H), 2.92 (quint, J=7.8 Hz, 1H), 2.56 (br s, 4H), 2.18-1.98 (m, 12H), 1.86-1.76 (m, 2H); LC/MS (ESI+): 433 (M+H).

Employing similar procedure as described for Example 93, compounds in Table 7 can be prepared by coupling 7D and the appropriate R-boronic acid or R-boronic ester, followed by ISCO purification. Some examples require HPLC purification at the final stage.

TABLE 7

| Ex. | R | MS (MH$^+$) | MP (° C.) | $^1$H NMR |
|---|---|---|---|---|
| 94 | pyrrolidine-carbonyl-phenyl | 433 | | (CDCl3) δ 7.83-7.82 (m, 1H), 7.72 (dt, J = 6.9, 1.8 Hz, 1H), 7.60-7.52 (m, 2H), 7.25 (dd, J = 7.8, 1.5 Hz, 1H), 7.22 (d, J = 1.5 Hz, 1H), 7.13 (d, J = 7.8 Hz, 1H), 4.99 (s, 2H), 3.78 (t, J = 6.6 Hz, 2H), 3.57 (t, J = 6.0 Hz, 2H), 2.92 (quint, J = 7.8 Hz, 1H), 2.55 (br s, 4H), 2.18-1.97 (m, 12H), 1.86-1.77 (m, 2H) |
| 95 | 6-ethoxypyridin-3-yl | 381 | 54 | (CDCl3) δ 8.32 (d, J = 2.7 Hz, 1H), 7.73 (dd, J = 8.7, 2.4 Hz, 1H), 7.08 (dd, J = 7.8, 2.1 Hz, 1H), 7.04 (s, 1H), 7.01 (s, 1H), 6.76 (d, J = 8.7 Hz, 1H), 4.87 (s, 2H), 4.37 (q, J = 6 Hz, 2H), 3.2-3.0 (m, 1H), 3.0-2.6 (m, 4H), 2.44 -2.26 (m, 2H), 2.26-2.08 (m, 6H), 1.92-1.65 (m, 2H), 1.40 (t, J = 6.9 Hz, 3H) |
| 96 | morpholine-carbonyl-phenyl | 449 | 61 | (CDCl3) δ 7.63-7.58 (m, 2H), 7.44 (t, J = 9 Hz, 1H), 7.34 (dt, J = 9.0, 1.2 Hz, 1H), 7.12 (dd, J = 7.8, 1.5 Hz, 1H), 7.08 (d, J =1.5 Hz, 1H), 7.03 (d, J = 7.8 Hz, 1H), 4.87 (s, 2H), 3.86-3.3 (m, 8H), 2.8 (quint, J = 6 Hz, 1H), 2.54-2.34 (m, 4H), 2.1-1.82 (m, 8H), 1.74-1.6 (m, 2H) |

TABLE 7-continued

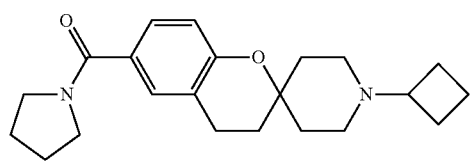 [SMILES: O=C(c1ccc2c(c1)CCC1(CCN(C3CCC3)CC1)O2)N1CCCC1]

| Ex. | R | MS (MH+) | MP (° C.) | 1H NMR |
|---|---|---|---|---|
| 97 | ![structure] | 449 | 55 | (CDCl3) δ 7.58 (dt, J = 9.0, 1.2 Hz, 2H), 7.45 (dt, J = 9.0, 1.2 Hz, 2H), 7.14 (dd, J = 8.1, 2.1 Hz, 1H), 7.08 (d, J = 1.5 Hz, 1H), 7.02 (d, J = 7.8 Hz, 1H), 4.87 (s, 2H), 3.8-3.45 (m, 8H), 2.91 (quint, J = 9 Hz, 1H), 2.68-2.48 (m, 4H), 2.14-1.96 (m, 8H), 1.8-1.6 (m, 2H) |

Example 98

Example 98 was prepared according to Scheme 6 and the procedures described below:

Scheme 6

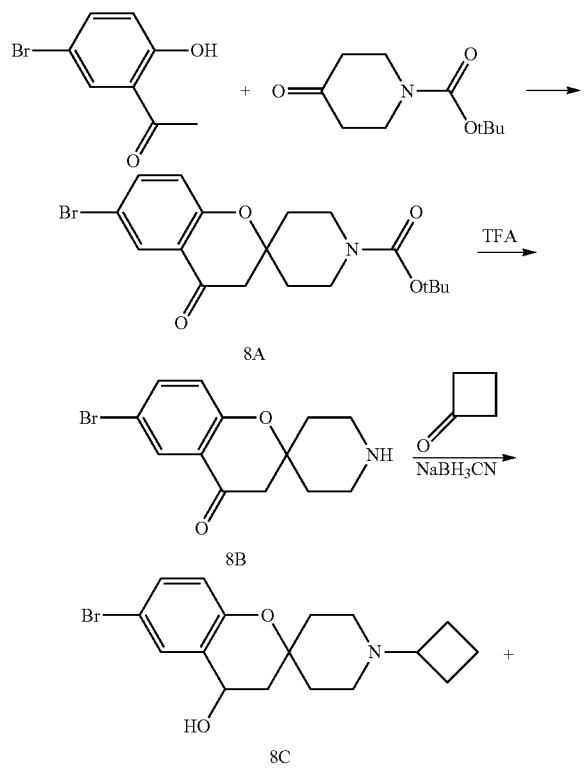

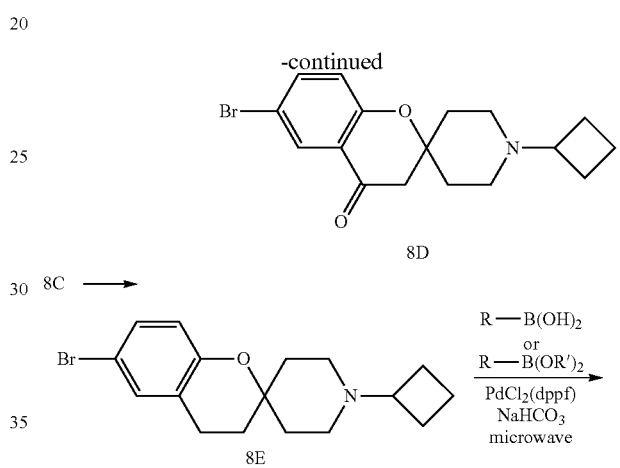

Example 98

8a) To a stirred solution of pyrrolidine (1.07 g, 15 mmol) in MeOH (150 mL) was added 5-bromo-2-hydroxy acetophenone (6.45 g, 30 mmol) (solution turned yellow). Then 4-t-butoxycarbonyl-piperidone (5.98 g, 30 mmol) was added (solution turned brown). The reaction was heated at 80° C. overnight. The reaction mixture was concentrated and the residue was dissolved in EtOAc (300 mL). The mixture was washed with 1 N HCl (150 mL), 1N NaOH (150 mL×2), water and brine. The organic layer was dried ($Na_2SO_4$), filtered and concentrated to give compound 8A (11.7 g, 99%). $^1$H-NMR (CDCl$_3$) δ 7.95 (d, J=2.7 Hz, 1H), 7.55 (dd, J=8.7, 2.7 Hz, 1H), 6.88 (d, J=8.7 Hz, 1H), 3.84 (br s, 2H), 3.21-3.13 (m, 2H), 2.03-1.95 (m, 2H), 1.64-1.55 (m, 2H), 1.44 (s, 9H).

8b) Compound 8A (11.7 g, 29.6 mmol) was dissolved in DCM (210 mL), TFA (90 mL) was added. The mixture was stirred at room temperature for 1 h. The mixture was concentrated and the residue was dissolved in EtOAc (300 mL) and washed with 1N NaOH (150 mL×2), water and brine. The organic layer was dried ($Na_2SO_4$), filtered and concentrated to give compound 8B (8.67 g, 99%) which was used directly in the next reaction.

8c) To a stirred solution of compound 8B (1.48 g, 5 mmol) in THF/H$_2$O (20 mL/0.2 mL) was added cyclobutanone (0.52 g, 7.5 mmol) and acetic acid (2 mL). The mixture was refluxed overnight. The mixture was cooled to room temperature and concentrated. To the residue was added saturated NaHCO$_3$ solution. The mixture was extracted with EtOAc three times. The organic layer was dried (Na$_2$SO$_4$), filtered and concentrated. The residue was purified by ISCO chromatography (40 gram column, SiO$_2$), first eluting with MeOH in DCM (1/20) to give compound 8D (0.47 g, 27%). $^1$H-NMR (CDCl$_3$) δ 8.00 (d, J=2.1 Hz, 1H), 7.60 (dd, J=8.7, 2.1 Hz, 1H), 6.94 (d, J=8.7 Hz, 1H), 2.85 (quint, J=7.8 Hz, 1H), 2.75 (s, 2H), 2.68-2.64 (m, 2H), 2.31-2.23 (m, 2H), 2.12-2.07 (m, 4H), 2.00-1.87 (m, 2H), 1.83-1.71 (m, 4H); LC/MS (ESI+): 350 (M+H). Continue eluting the ISCO column with MeOH/DCM (1/10) give compound 8C (0.84 g, 48%). $^1$H-NMR (CDCl$_3$) δ 7.68 (d, J=2.4 Hz, 1H), 7.41 (dd, J=9.0, 2.4 Hz, 1H), 6.84 (d, J=9.0 Hz, 1H), 4.94 (t, J=7.2 Hz, 1H), 2.88 (quint, J=7.8 Hz, 1H), 2.75-2.68 (m, 2H), 2.37-1.77 (m, 15H); LC/MS (ESI+): 352 (M+H).

8d) To a stirred suspension of compound 8C (1.5 g, 4.26 mmol) in DCM (43 mL) was added TFA (0.66 mL) at 0° C. The mixture was stirred for 15 min and triethylsilane (5.44 mL, 34 mmol) was added, followed by borontrifluoride etherate (0.96 mL, 7.67 mmol). The mixture was stirred at 0° C. for 3 h, room temperature for 1 h, and then placed in the refrigerator over the weekend. The reaction was quenched with saturated Na$_2$CO$_3$ solution and diluted with DCM. The organic layer was washed with saturated Na$_2$CO$_3$ and brine, then dried (Na2SO4), filtered and concentrated. The residue was purified by column chromatography (0-40% Acetone in DCM) to give compound 8E (0.83 g, 58%). MP=78° C. $^1$H-NMR (CDCl$_3$) δ 7.17-7.13 (m, 2H), 6.69-6.66 (m, 1H), 2.85 (quint, J=7.5 Hz, 1H), 2.75-2.68 (m, 4H), 2.30-2.23 (m, 2H), 2.08-1.96 (m, 4H), 1.84-1.62 (m, 8H); LC/MS (ESI+): 336 (M+H).

8e) Compound 8E was converted to Example 98 using Suzuki Coupling procedure as shown in step 1d. Example 98: MP=73° C. $^1$H-NMR (CDCl$_3$) δ 7.69-7.63 (m, 4H), 7.45 (dd, J=8.4, 2.1 Hz, 1H), 7.41 (d, J=2.1 Hz, 1H), 7.04-6.95 (d, J=8.4 Hz, 1H), 3.77 (t, J=6.9 Hz, 2H), 3.59 (t, J=6.5 Hz, 2H), 3.09-2.92 (m, 5H), 2.56-2.48 (m, 2H), 2.24-2.19 (m, 4H), 2.10-1.76 (m, 12H); LC/MS (ESI+): 431 (M+H).

Employing similar procedure as described for Example 98, compounds in Table 8 can be prepared by coupling 8E and the appropriate R-boronic acid or R-boronic ester, followed by ISCO purification. Some examples require HPLC purification at the final stage.

TABLE 8

| ex | R | MS (MH+) | MP (° C.) | $^1$H NMR |
|---|---|---|---|---|
| 99 | morpholine-C(=O)-phenyl-* | 447 | 80 | (CDCl3) δ 7.67 (d, J = 8.1 Hz, 2H), 7.55 (d, J = 8.4 Hz, 2H), 7.44 (dd, J = 8.4, 2.1 Hz, 1H), 7.40 (d, J = 2.1 Hz, 1H), 7.00 (d, J = 8.4 Hz, 1H), 3.82 (br s, 8H), 3.10-2.93 (m, 5H), 2.57-2.48 (m, 2H), 2.24-2.19 (m, 4H), 2.02-1.77 (m, 8H) |
| 100 | EtO-pyridyl-* | 379 | 83 | (CDCl3) δ 8.39 (d, J = 2.4 Hz, 1H), 7.82 (dd, J = 8.7, 2.7 Hz, 1H), 7.37-7.32 (m, 2H), 6.98 (d, J = 8.4 Hz, 1H), 6.86 (d, J = 8.7 Hz, 1H), 4.48 (q, J = 6.9 Hz, 2H), 3.17-2.92 (m, 5H), 2.66-2.58 (m, 2H), 2.38 (br s, 2H), 2.28-2.20 (m, 2H), 2.10-1.78 (m, 8H), 1.52 (t, J = 6.9 Hz, 3H) |
| 101 | MeSO$_2$-phenyl-* | 412 | 94 | (CDCl3) δ 8.06 (d, J = 8.4 Hz, 2H), 7.81 (d, J = 8.4 Hz, 2H), 7.49-7.45 (m, 2H), 7.02 (d, J = 8.1 Hz, 1H), 3.23-3.09 (m, 6H), 2.97 (t, J = 6.6 Hz, 2H), 2.72-2.64 (m, 2H), 2.45 (br s, 2H), 2.30-2.22 (m, 4H), 2.07-1.79 (m, 6H) |
| 102 | phenyl-* | 334 | 115 | (CDCl3) δ 7.65-7.62 (m, 2H), 7.53-7.39 (m, 5H), 6.99 (d, J = 8.4 Hz, 1H), 3.06-2.93 (m, 5H), 2.53 (br s, 2H), 2.26-2.18 (m, 4H), 2.01-1.77 (m, 8H) |
| 103 | pyrrolidinyl-SO$_2$-phenyl-* | 467 | 143 | (CDCl3) δ 7.95 (d, J = 8.4 Hz, 2H), 7.76 (d, J = 8.4 Hz, 2H), 7.49-7.44 (m, 2H), 7.02 (d, J = 8.1 Hz, 1H), 3.38 (t, J = 6.9 Hz, 4H), 3.17-3.02 (m, 3H), 2.96 (t, J = 6.9 Hz, 2H), 2.66 (br s, 2H), 2.41 (br s, 2H), 2.30-2.22 (m, 2H), 2.06-1.80 (m, 12H) |
| 104 | MeO-pyrimidinyl-* | 366.2 | 168-169 | (CDCl3) δ 8.64 (s, 2H), 7.24 (s, 1H), 7.20 (d, J = 6.6 Hz, 1H), 6.91 (d, J = 8.4 Hz, 1H), 4.04 (s, 3H), 2.82 (t, J = 6.8 Hz, 2H), 2.70-2.57 (m, 2H), 2.31-2.12 (m, 2H), 2.14-2.00 (m, 2H), 2.00-1.79 (m, 7H) 1.79-1.60 (m, 4H) |

TABLE 8-continued

| ex | R | MS (MH+) | MP (° C.) | ¹H NMR |
|---|---|---|---|---|
| 105 | CF₃O-C₆H₄-* (4-trifluoromethoxyphenyl) | 418 | 106 | (CDCl3) δ 7.68-7.58 (m, 2H), 7.42-7.33 (m, 4H), 7.05-6.95 (m, 1H), 3.06-2.89 (m, 5H), 2.52-2.45 (m, 2H), 2.24-2.17 (m, 4H), 1.99 (m, 8H) |
| 106 | 4-(N-methylcarbamoyl)phenyl-* | 391.1 | 215-216.5 | (CD3OD) δ 7.98 (d, J = 8.7 Hz, 2H), 7.79 (d, J = 8.5 Hz, 2H), 7.54-7.52 (m, 2H), 7.00 (d, J = 9.3 Hz, 1H), 3.08 (s, 3H), 3.04-2.98 (m, 3H), 2.80-2.79 (m, 2H), 2.46 (t, J = 10.0 HZ, 2H), 2.30-2.16 (m, 2H), 2.15-1.95 (m, 6H), 1.95-1.75 (m, 5H) |
| 107 | pyrimidin-5-yl-* | 336.2 | 148-150 | (CDCl3) δ 9.12 (s, 1H), 8.87 (s, 2H), 7.32 (d, J = 9.0 Hz, 1H), 7.27 (s, 1H), 6.95 (d, J = 8.1 Hz, 1H), 2.84 (t, J = 6.7 Hz, 2H), 2.70-2.60 (m, 2H), 2.30-2.15 (m, 2H), 2.10-1.96 (m, 2H), 2.00-1.80 (m, 7H), 1.80-1.60 (m, 4H) |
| 108 | 2-(dimethylamino)pyrimidin-5-yl-* | 379.1 | 162-164 | (CDCl3) δ 8.47 (s, 2H), 7.20 (d, J = 5.7 Hz, 1H), 7.12 (s, 1H), 6.88 (d, J = 8.1 Hz, 1H), 3.2 (s, 6H), 2.8 (m, 3H), 2.70-2.56 (m, 2H), 2.32-2.15 (m, 2H), 2.15-2.0 (m, 2H), 1.9-1.75 (m, 6H), 1.75-1.6 (m, 4H) |
| 109 | 4-(N-cyclopropylcarbamoyl)phenyl-* | 417.2 | 162-164 | (CDCl3) δ 7.75 (d, J = 8.7 Hz, 2H), 7.56 (d, J = 9.0 Hz, 2H), 7.35 (d, J = 9.0 Hz, 1H), 7.30 (s, 1H), 6.9 (d, J = 8.4 Hz, 1H), 6.25 (s, 1H), 2.92-2.90 (m, 1H), 2.80-2.75 (t, J = 6.9 Hz, 2H) 2.75-2.55 (m, 2H), 2.34-2.11 (m, 2H), 2.11-2.00 (m, 2H), 2.00-1.76 (m, 6H), 1.76-1.6 (m, 5H), 0.90-0.80 (m, 2H), 0.65-0.59 (m, 2H) |
| 110 | 4-cyanophenyl-* | 359 | 170-172 | (CDCl3) δ 7.80-7.71 (m, 4H), 7.47-7.41 (m, 2H), 7.02 (d, J = 8.4 Hz, 1H), 3.09-2.91 (m, 5H), 2.55-2.46 (m, 2H), 2.24-2.18 (m, 4H), 2.00-1.73 (m, 8H) |
| 111 | 1-methyl-1H-pyrazol-4-yl-* | 338 | 110-112 | (CDCl3) δ 7.77 (s, 1H), 7.61 (s, 1H), 7.32-7.26 (m, 2H), 6.92 (d, J = 8.1 Hz, 1H), 4.03 (s, 3H), 3.06-2.82 (m, 5H), 2.52-2.38 (m, 2H), 2.24-2.14 (m, 4H), 2.02-1.76 (m, 8H) |
| 112 | benzo[c][1,2,5]oxadiazol-5-yl-* | 376 | 210-212 | (CDCl3) δ 7.99-7.95 (m, 2H), 7.79 (dd, J = 9.3, 1.8 Hz, 1H), 7.54-7.49 (m, 2H), 7.05 (d, J = 8.4 Hz, 1H), 3.18-2.96 (m, 5H), 2.68-2.58 (m, 2H), 2.44-1.75 (m, 12H) |
| 113 | 4-carbamoylphenyl-* | 377 | 202-204 | (CDCl3) δ 7.96 (d, J = 8.1 Hz, 2H), 7.71 (d, J = 8.4 Hz, 2H), 7.50-7.45 (m, 2H), 7.00 (d, J = 8.4 Hz, 1H), 6.29-5.91 (br s, 2H), 3.36-3.25 (m, 3H), 2.97 (t, J = 6.9 Hz, 2H), 2.86-2.78 (m, 2H), 2.67-2.58 (m, 2H), 2.33-2.24 (m, 4H), 2.09-1.80 (m, 6H) |
| 114 | 1H-pyrazol-4-yl-* | 324 | 194-196 | (CDCl3) δ 7.75 (s, 2H), 7.24-7.18 (m, 3H), 6.82 (d, J = 8.4 Hz, 1H), 2.86-2.76 (m, 3H), 2.69-2.65 (m, 2H), 2.30-2.22 (m, 2H), 2.10-1.65 (m, 12H) |

TABLE 8-continued

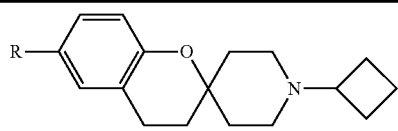

| ex | R | MS (MH+) | MP (°C.) | ¹H NMR |
|---|---|---|---|---|
| 115 | 2-fluoro-N-methylbenzamide | 409 | 230-232 | (CDCl3) δ 8.24 (t, J = 8.1 Hz, 1H), 7.53 (dd, J = 8.1, 1.5 Hz, 1H), 7.48-7.44 (m, 2H), 7.37 (dd, J = 13.5, 1.5 Hz, 1H), 7.00 (d, J = 8.4 Hz, 1H), 6.90-6.84 (m, 1H), 3.24-3.02 (m, 3H + 3H), 2.96 (t, J = 6.9 Hz, 2H), 2.74-2.65 (m, 2H), 2.56-2.42 (m, 2H), 2.30-2.18 (m, 4H), 2.07-1.78 (m, 6H) |
| 116 | 4-sulfamoylphenyl | 413 | 224-226 | (CD3OD/CDCl3) δ 7.71 (d, J = 8.7 Hz, 2H), 7.45 (d, J = 8.4 Hz, 2H), 7.18-7.15 (m, 2H), 6.71 (d, J = 8.1 Hz, 1H), 4.22 (s, 2H), 3.08 (br s, 1H), 2.87 (br s, 2H), 2.67 (t, J = 6.6 Hz, 2H), 2.54 (br s, 2H), 2.08-1.98 (m, 4H), 1.82-1.53 (m, 8H) |
| 117 | 4-(hydroxymethyl)phenyl | 364 | 183-185 | (CD3OD) δ 7.66 (d, J = 8.4 Hz, 2H), 7.53-7.48 (m, 4H), 7.04 (d, J = 8.7 Hz, 1H), 5.02 (s, 1H), 4.76 (s, 2H), 3.63 (br s, 1H), 3.29-3.25 (m, 2H), 3.05-3.00 (m, 4H), 2.45-2.35 (m, 2H), 2.33-2.16 (m, 4H), 2.08-1.92 (m, 6H) |
| 118 | 2-fluoropyridin-3-yl | 353 | 108-110 | (CDCl3) δ 8.13-8.10 (m, 1H), 7.83-7.77 (m, 1H), 7.32-7.28 (m, 2H), 7.26-7.19 (m, 1H), 6.89 (d, J = 8.7 Hz, 1H), 2.96-2.78 (m, 5H), 2.43-2.33 (m, 2H), 2.13-2.05 (m, 4H), 1.92-1.64 (m, 8H) |

Example 119

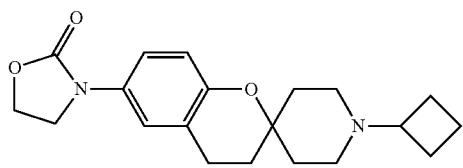 [SMILES: O=C1OCCN1c1ccc2c(c1)CCC1(CCN(C3CCC3)CC1)O2]

Example 119 was prepared from compound 8E using the same procedure as described in Example 77. Example 119: MP=186-188° C. ¹H-NMR (CDCl₃) δ 7.24-7.17 (m, 2H), 6.80 (d, J=8.7 Hz, 1H), 4.47-4.41 (m, 2H), 4.01-3.96 (m, 2H), 3.00-2.75 (m, 5H), 2.39 (br s, 2H), 2.14-2.04 (m, 4H), 1.86-1.64 (m, 8H); LC/MS (ESI+): 343 (M+H).

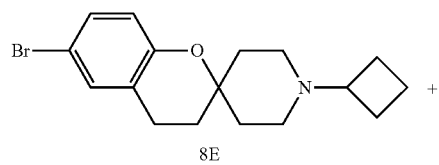

8E

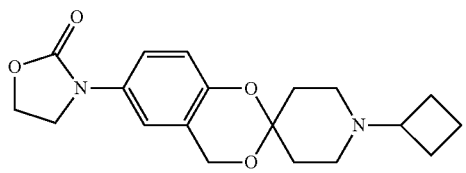

Example 119

Employing similar procedure as described in Example 119, compounds in Table 9 can be prepared by coupling 8E and R—H, followed by ISCO purification. Some examples require HPLC purification at the final stage.

TABLE 9

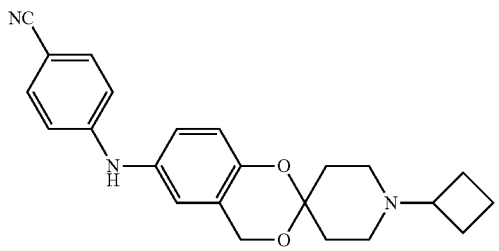 [SMILES: N#Cc1ccc(Nc2ccc3c(c2)COC2(CCN(C4CCC4)CC2)O3)cc1]

| ex | R | MS (MH+) | MP (° C.) | ¹H NMR |
|---|---|---|---|---|
| 120 | (azetidinone) | 327 | 195-197 | (CDCl3) δ 7.11-7.05 (m, 2H), 6.76 (d, J = 8.7 Hz, 1H), 3.55 (t, J = 4.5 Hz, 2H), 3.06 (t, J = 4.5 Hz, 2H), 3.00-2.95 (m, 1H), 2.87-2.82 (m, 2H), 2.75 (t, J = 6.9 Hz, 2H), 2.45-2.37 (m, 2H), 2.24-2.05 (m, 4H), 1.91-1.64 (m, 8H) |
| 121 | (methylimidazolidinone) | 356 | 228-230 | (CDCl3) δ 7.36-7.29 (m, 2H), 6.88 (d, J = 8.4 Hz, 1H), 3.87-3.82 (m, 2H), 3.56-3.51 (m, 2H), 3.10-2.85 (m, 5H + 3H), 2.51 (br s, 2H), 2.28-2.16 (m, 4H), 1.98-1.73 (m, 8H) |

Example 122

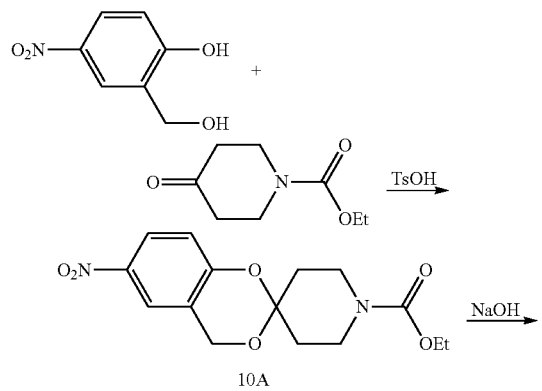

Example 122 was prepared starting from 5-nitro-2-hydroxybenzylalcohol according to Scheme 7 and the procedures described below:

Scheme 7

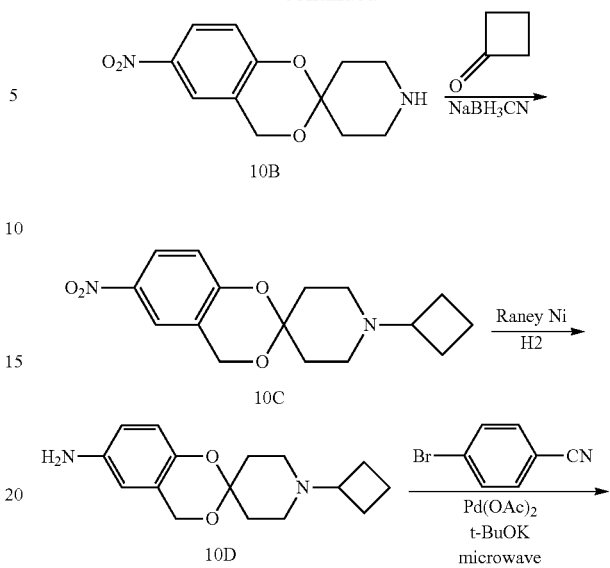

Example 122

10a) Using similar procedure as described in Example 1, steps 1a, 1b and 1c, 5-nitro-2-hydroxybenzylalcohol was converted to compound 10C. ¹H-NMR (CDCl₃) δ 8.05 (d, J=9.0 Hz, 1H), 7.9 (s, 1H), 6.9 (d, J=9.0 Hz, 1H), 4.85 (s, 2H), 2.80 (quintet, J=7.5 Hz, 1H), 2.41 (m, 4H), 2.10-1.80 (m, 7H), 1.8-1.6 (m, 3H). LC/MS (ESI+): 305.0 (M+H).

10b) To a stirred solution of compound 10C (2 g, 6.57 mmol) in EtOAc (80 mL) was added a Raney Ni suspension (2 g) in H₂O. The mixture was stirred under a ballon of hydrogen for 2.5 h. The supernatant was separated from the solid by decantation. The solution was dried (Na₂SO₄), filtered and concentrated to give compound 10D (1.7 g, 94%). ¹H-NMR (CDCl₃) δ 6.65 (d, J=9.0 Hz, 1H), 6.55 (d, J=9.0 Hz, 1H), 6.3 (s, 1H), 4.75 (s, 2H), 3.4 (m, 2H), 2.4 (m, 4H), 2.1-1.8 (m, 8H), 1.6-1.8 (m, 2H); LC/MS (ESI+): 275.1 (M+H).

10c) Compound 10D (0.15 g, 0.54 mmol), 4-bromobenzonitrile (0.11 g, 0.6 mmol), potassium t-butoxide (0.06 g, 0.54 mmol), palladium acetate (0.02 g, 0.09 mmol) and BINAP (0.036 g, 0.05 mmol) was added into a microwave vial, then DMF (2.1 mL) was added. Argon was bubbled through the mixture and the sealed vial was microwaved at 140° C. for 20 min. (Ermy's Optimizer). LC-MS showed 50% conversion. 50% of the original quantity of 4-bromobenzonitrile, KOtBu, Pd(OAc)2, and BINAP was added and the mixture was microwaved again for 10 min. The mixture was poured into water and extracted with EtOAc. The organic layer solution was filtered through celite and concentrated. The residue was purified by column chromatography (7 g SiO₂, gradient 0-20% acetone in DCM) to afford Example 122 (65 mg, 31%). MP=55-60° C. ¹H-NMR (CDCl₃) δ 7.44 (d, J=9 Hz, 2H), 6.99 (d, J=8.4 Hz, 1H), 6.86 (d, J=8.4 Hz, 1H), 6.78 (m, 4H), 5.84 (s, 1H), 4.80 (s, 2H), 2.80 (quintet, J=7.5 Hz, 1H), 2.44 (m, 4H), 2.06-1.91 (m, 7H), 1.74-1.62 (m, 2H), LC/MS (ESI+): 376.1 (M+H).

Employing similar procedure as described in Example 122, compounds in Table 10 can be prepared by coupling intermediate 10D and R-bromide, followed by column chromatography.

TABLE 10

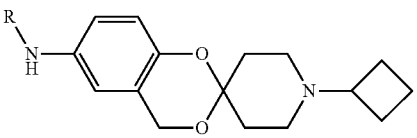

| ex | R | MS (MH+) | MP (° C.) | 1H NMR |
|---|---|---|---|---|
| 123 | NC-phenyl-* (3-cyano) | 376.1 | 55-60 | (CDCl3) δ 7.26-7.21 (m, 2H), 7.05-6.92 (m, 3H), 6.86 (d, J = 8.7 Hz, 1H), 6.76 (s, 1H), 5.59 (s, 1H), 4.80 (s, 2H), 2.81 (quintet, J = 6.9 Hz, 1H), 2.44 (m, 4H), 2.06-1.92 (m, 7H), 1.74-1.64 (m, 3H) |
| 124 | phenyl-* | 351.2 | 52-57 | (CDCl3) δ 7.24-7.17 (m, 3H), 6.94-6.77 (m, 4H), 6.74 (d, J = 2.4 Hz, 1H), 5.45 (s, 1H), 4.78 (s, 2H), 2.80 (quintet, J = 7.2 Hz, 1H), 2.43 (m, 4H), 2.08-1.84 (m, 7H), 1.76-1.64 (m, 3H) |
| 125 | CN-phenyl-* (2-cyano) | 376.3 | 54-58 | (CDCl3) δ 7.46 (d, J = 9.0 Hz, 1H), 7.32-7.22 (m, 2H), 7.03 (d, J = 8.4 Hz, 1H), 6.91-6.81(m, 2H), 6.75 (t, J = 7.5 Hz, 1H), 6.14(s, 1H), 4.81 (s, 2H) 2.81(quintet, J = 7.2 Hz, 1H), 2.43 (m, 4H), 2.09-1.91 (m, 7H), 1.74-1.62 (m, 3H) |

Example 126

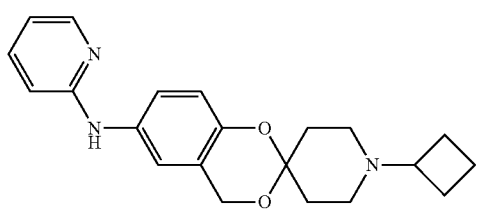 [SMILES: c1ccc(Nc2ccc3c(c2)COC2(CCN(C4CCC4)CC2)O3)nc1]

Example 126 was prepared from compound 10D according to the following procedure:

To a stirred solution of compound 10D (0.1 g, 0.36 mmol) in THF (1 mL) in a small vial was added NaH (0.016 g, 0.4 mmol). When gas evolution ceased, 2-chloropyridine (0.1 g, 0.8 mmol) was added. The vial was capped and the mixture was heated at 90° C. for 32 h. Cooled to room temperature. The reaction cycle was repeated twice by adding fresh NaH and 2-chloropyridine. The reaction mixture was diluted with H$_2$O and extracted with EtOAc. The organic layer was washed with brine, dried (Na$_2$SO$_4$), filtered and concentrated. The residue was purified by column chromatography (6 g SiO$_2$, gradient 0-20% acetone in DCM) to afford Example 126 (55 mg, 43%). MP=159-161° C. $^1$H-NMR (CDCl$_3$) δ 8.14 (d, J=4.5 Hz, 1H), 7.45 (t, J=7.2 Hz, 1H), 7.07 (d, J=8.7 Hz, 1H), 6.99 (s, 1H), 6.84 (d, J=9 Hz, 1H), 6.68 (m, 2H), 6.30 (s, 1H), 4.81 (s, 2H), 2.80 (quintet, J=7.5 Hz, 1H), 2.44 (m, 4H), 2.06-1.88 (m, 7H), 1.73-1.61 (m, 3H), LC/MS (ESI+): 352.2 (M+H).

Example 127

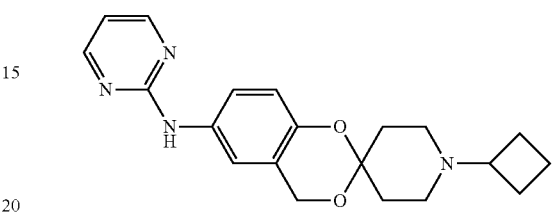

Example 127 was prepared from compound 10D according to the following procedure:

To a stirred solution of compound 10D (0.15 g, 0.54 mmol) in 1,4-dioxane (1.2 mL) in a small vial was added 2-chloropyrimidine (94 mg, 0.82 mmol). The vial was capped and heated at 130° C. for 3 h. 10% conversion identified by LC-MS. An additional equivalent of 2-chloropyrimidine was added and the mixture was heated at 138° C. for 16 h. The reaction was diluted with EtOAc and washed with saturated Na$_2$CO$_3$ and brine. The organic layer was dried (Na$_2$SO$_4$), filtered and concentrated. The residue was purified by column chromatography (7 g SiO$_2$, gradient 0-20% Acetone in DCM) to give Example 127 (70 mg, 37%). MP=55-58° C. $^1$H-NMR (CDCl$_3$) δ 8.36 (d, J=4.8 Hz, 2H), 7.32 (s, 1H), 7.24 (d, J=9 Hz, 1H), 6.96 (s, 1H), 6.84 (d, J=8.7 Hz, 1H), 6.68 (t, J=4.8 Hz, 1H), 4.84 (s, 2H), 2.81 (m, 1H), 2.43 (m, 4H), 2.03-1.8 (m, 7H), 1.73-1.64 (m, 3H), LC/MS (ESI+): 353.1 (M+H).

Example 128

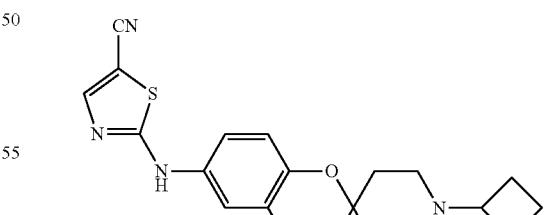

Example 128 was prepared from compound 10D and 2-chloro-5-cyanothiazole using similar procedure as described in Example 127, except the reaction was heated at 112° C. for 25 h. MP=217-218° C. $^1$H-NMR (DMSO) δ 10.96 (s, 1H), 8.20 (s, 1H), 7.52 (s, 1H), 7.43 (d, J=9 Hz, 1H), 6.98 (d, J=9 Hz, 1H), 4.94 (s, 2H), 2.89 (quintet, J=7.5 Hz, 1H), 2.44 (m, 4H), 2.08 (m, 2H), 1.90 (m, 6H), 1.75 (m, 2H), LC/MS (ESI+): 383.0 (M+H).

Example 129

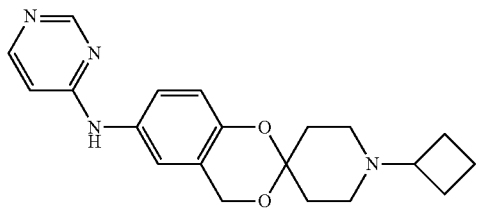 [SMILES: c1cc(Nc2ccc3c(c2)COC2(CCN(C4CCC4)CC2)O3)ncn1]

Example 129 was prepared from compound 10D according to the following procedure:

To a stirred solution of compound 10D (0.15 g, 0.54 mmol) in EtOH (1.8 mL) in a small vial was added diisopropylethylamine (0.19 mL, 1.09 mmol) and 4-chloropyrimidine hydrochloride salt (165 mg, 1.09 mmol). The vial was capped and heated at 45° C. for 16 h. The mixture was concentrated and DCM was added. The mixture was washed with 10% Na$_2$CO$_3$ solution. The organic layer was dried (Na$_2$SO$_4$), filtered and concentrated. The residue was purified by column chromatography (5 g SiO$_2$, gradient 0-50% Aceton in DCM) to give Example 129 (59 mg, 31%). MP=170-171° C. $^1$H-NMR (CDCl$_3$) δ 8.61 (s, 1H), 8.22 (d, J=6.0 Hz, 1H), 7.09 (d, J=9.0 Hz, 1H), 6.97 (s, 1H), 6.88-6.84 (m, 2H), 6.53 (d, J=5.7 Hz, 1H), 4.82 (s, 2H), 2.80 (quintet, J=7.5 Hz, 1H), 2.43 (m, 4H), 2.08-1.85 (m, 7H), 1.79-1.60 (m, 3H), LC/MS (ESI+): 353.2 (M+H).

Example 130

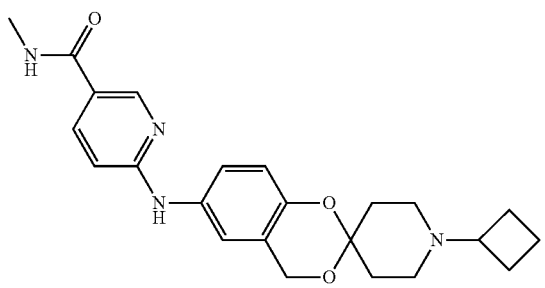 [SMILES: CNC(=O)c1ccc(Nc2ccc3c(c2)COC2(CCN(C4CCC4)CC2)O3)nc1]

Example 130 was prepared starting from compound 10D according to Scheme 8 and the procedures described below:

Scheme 8

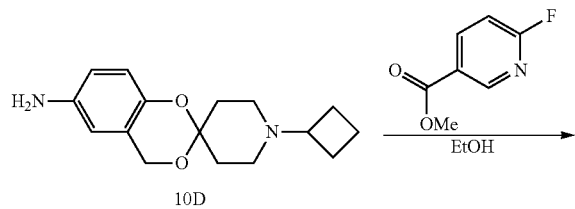

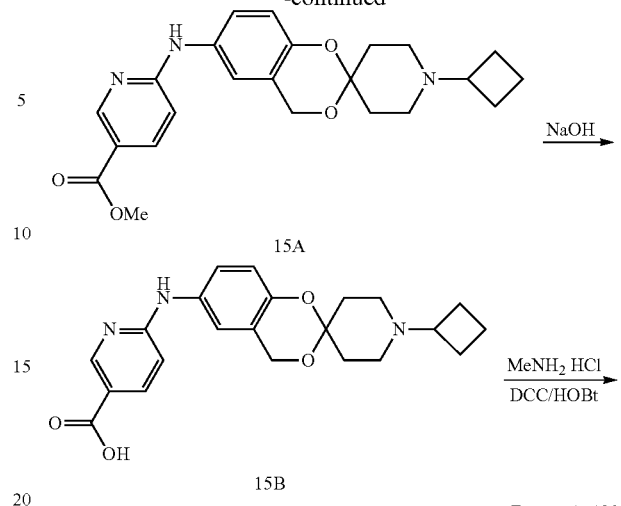

Example 130

15a) To a stirred solution of compound 10D (0.5 g, 1.82 mmol) in EtOH (3 mL) in a small vial was added 6-fluoro-nicotinic acid methyl ester (0.34 g, 2.19 mmol). The vial was capped and heated at 100° C. over the weekend. Additional 6-fluoro-nicotinic acid methyl ester (0.2 g, 1.28 mmol) was added and the reaction heated at 105° C. overnight. The mixture was concentrated and EtOAc was added. The mixture was washed with 15% Na$_2$CO$_3$ solution and brine. The organic layer was dried (Na$_2$SO$_4$), filtered and concentrated. The residue was purified by column chromatography (25 g SiO$_2$, gradient 0-20% Aceton in DCM) to give compound 15A (0.23 g, 31%). $^1$H-NMR (CDCl$_3$) δ 8.77 (s, 1H), 8.01 (d, J=9 Hz, 1H), 7.09 (d, J=9 Hz, 1H), 7.00 (s, 1H), 6.88-6.81 (m, 2H), 6.61 (d, J=9 Hz, 1H), 4.82 (s, 2H), 3.86 (s, 3H), 2.80 (quintet, J=7.8 Hz, 1H), 2.44 (m, 4H), 2.03-1.85 (m, 7H), 1.75-1.6 (m, 3H), LC/MS (ESI+): 410.1 (M+H).

15b) To a stirred solution of compound 15A (0.23 g, 0.56 mmol) in THF (0.56 mL) and MeOH (0.4 mL) in a small vial was added a solution of sodium hydroxide (25 mg) in water (0.26 mL). Additional MeOH (0.9 mL) was added. The vial was capped and stirred at room temperature overnight. Reaction not completed. Additional MeOH (1 mL) was added and the mixture heated at 47° C. overnight. MeOH and THF was removed and the aqueous layer was cooled at 0° C. and neutralized with conc. HCl. The mixture was extracted with EtOAc. The organic layer was dried (Na$_2$SO$_4$), filtered and concentrated to give compound 15B (0.19 g, 87%). LC/MS (ES+): 396.2 (M+H).

15c) To a stirred solution of compound 15B (0.19 g, 0.48 mmol) in THF (1.5 mL) in a small vial was added triethylamine (0.2 mL, 1.44 mmol). The mixture was stirred for 5 min, then DCC (99 mg, 0.48 mmol), HOBt (65 mg, 0.48 mmol) and methylamine hydrochloride salt (80 mg, 1.18 mmol) was added. The vial was capped and stirred at room temperature overnight. The mixture was filtered to remove the precipitate. The filtrate was concentrated and EtOAc was added. The mixture was washed with 10% Na$_2$CO$_3$ solution twice and brine once. The organic layer was dried (Na$_2$SO$_4$), filtered and concentrated. The residue was purified by column chromatography (5 g SiO$_2$, gradient 0-20% Aceton in DCM) to give Example 130 (55 mg, 28%). Mp=211-213° C. $^1$H-NMR (CDCl$_3$) δ 8.51 (s, 1H), 7.87 (d, J=8.7 Hz, 1H), 7.09 (d, J=8.7 Hz, 1H), 6.99 (s, 1H), 6.86 (d, J=9.0 Hz, 1H), 6.63-6.60 (m, 2H), 5.97-5.95 (m, 1H), 4.81 (s, 2H), 2.98 (d, J=4.8 Hz, 3H), 2.80 (quintet, J=8.4 Hz, 1H), 2.43 (m, 4H), 2.08-1.88 (m, 7H), 1.73-1.61 (m, 3H), LC/MS (ESI+): 409.1 (M+H).

Example 131

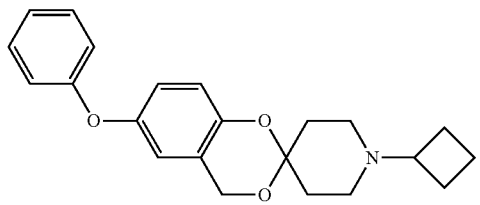 [SMILES: c1ccc(Oc2ccc3c(c2)COC2(CCN(C4CCC4)CC2)O3)cc1]

Example 131 was prepared starting from compound 1C according to the procedures described below:

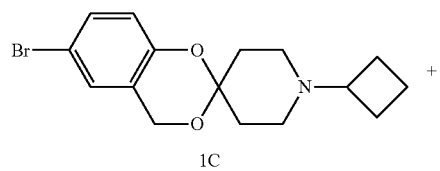

1C

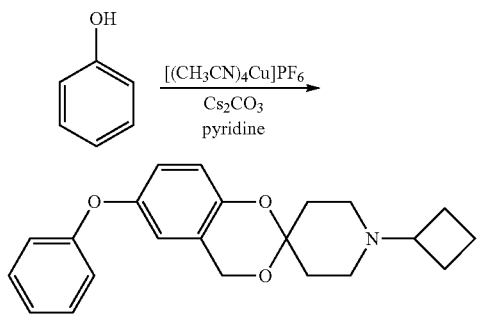

To a stirred solution of compound 1C (0.05 g, 0.15 mmol) in pyridine (2 mL) was added phenol (0.028 g, 0.3 mmol), Cs₂CO₃ (0.146 g, 0.45 mmol), and tetrakis(acetonitrile)-copper(I) hexafluorophosphate (6 mg, 0.015 mmol). The mixture was degassed by argon for about 2 min., then refluxed for 72 h. Two identical reactions were set up and combined for the following work up. The mixture was concentrated to remove pyridine. The residue was dissolved in DCM containing 5% MeOH and filtered. The filtrated was concentrated and the residue was purified by preparative HPLC. The resulting salt was neutralized with MP-carbonate (150 mg) in DCM (5 mL) overnight. The solution was filtered and solvent removed in vacuo to provide Example 131 as an oil (41 mg, 40%). Treating the oil with 4M HCl in dioxane gave the corresponding HCl salt. MP=240-245° C. ¹H-NMR (CDCl₃) δ 7.28 (t, J=8.0 Hz, 2H), 7.04 (t, J=7.36 Hz, 1H), 6.93 (d, J=7.8 Hz, 2H), 6.85 (m, 2H) 6.64 (s, 1H), 4.79 (s, 2H), 2.81 (m, 1H), 2.44 (m, 4H), 1.96 (m, 8H), 1.71 (m, 2H); LC/MS (ESI+): 352 (M+H).

Employing similar procedure as described in Example 131, compounds in Table 11 can be prepared by coupling compound 1C and R—OH, followed by prep. HPLC purification.

Table 11

TABLE 11

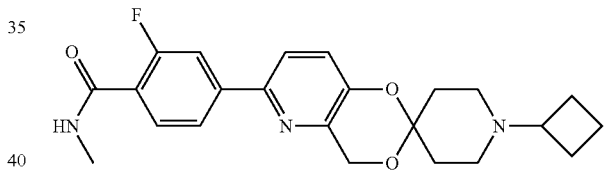

| ex | R | MS (MH⁺) | MP (° C.) | ¹H NMR |
|---|---|---|---|---|
| 132 | NC—⟨phenyl⟩—* | 377 | | (CDCl3) δ 7.57 (d, J = 8.88 Hz, 2H), 6.95 (d, J = 8.88 Hz, 2H), 6.89 (m, 2H), 6.70 (d, J = 1.81 Hz, 1H), 4.82 (s, 2H), 2.80 (m, 1H), 2.42 (m, 3H), 1.96 (m, 8H), 1.69 (m, 3H) |

Example 133

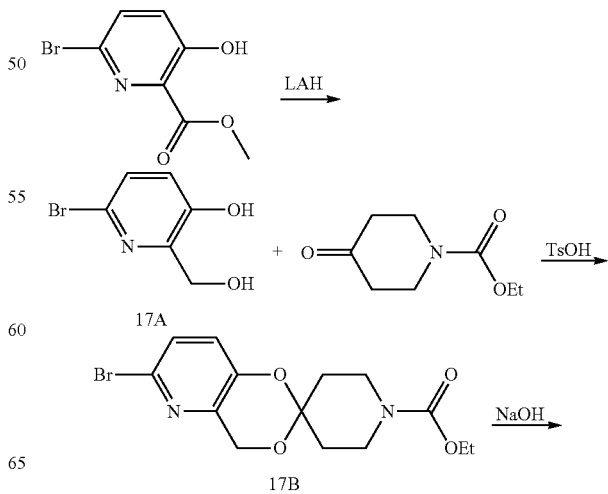

Example 133 was prepared according to Scheme 9 and the procedures described below:

Scheme 9

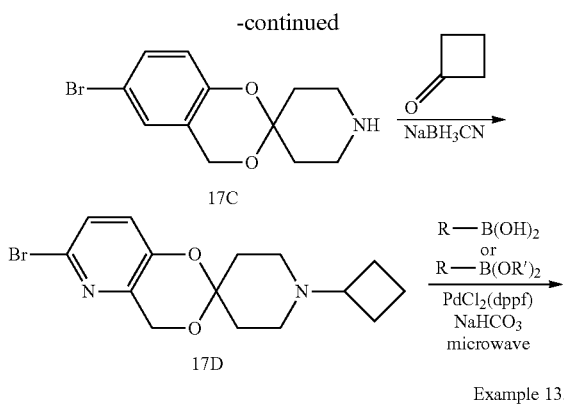

Example 133

17a) To a solution of methyl 6-bromo-3-hydroxypyridine-2-carboxylate (2 g, 8.6 mmol, prepared according to procedures in WO2005009962) in THF (30 mL), was added LAH (34 mL, 34.4 mmol, 1 M in THF). The solution was stirred at rt for 2 h. To the solution was then added water (1.3 mL), 10% aqueous NaOH (1.3 mL), and water (3.9 mL). After stirring for 1 h, the solution was filtered and the solids washed with EtOAc. The organics were then washed with 1N HCl and brine, dried over sodium sulfate, filtered and concentrated in vacuo to yield intermediate 17A (0.99 g, 56%). $^1$H-NMR (CD$_3$OD) δ 7.3 (d, J=8.4 Hz, 1H), 7.09 (d, J=8.4 Hz, 1H), 4.67 (s, 2 H); MS (ESI+): 204.1 (M+H).

17b) To a solution of 17A (0.33 g, 1.62 mmol) in CHCl$_3$ (10 mL) was added 4-ethylcarboxypiperidone (0.332 g, 1.94 mmol) and p-toluenesulfonic acid (0.03 g, 0.16 mmol). The reaction was equipped with a Dean Stark trap and refluxed for 18 h. The mixture cooled to room temperature. The mixture was washed with saturated aqueous sodium bicarbonate and brine, then dried (Na$_2$SO$_4$), filtered and concentrated. Purification by ISCO chromatography (12 gram column, SiO$_2$, gradient DCM to 5% MeOH in DCM) gave compound 17B (0.371 g, 64%). $^1$H-NMR (CDCl$_3$) δ 7.38 (d, J=8.7 Hz, 1H), 7.15 (d, J=8.7 Hz, 1H), 4.95 (s, 2H), 4.24 (m, 2H), 3.68 (m, 4H), 1.99 (m, 4H), 1.36 (m, 3H); MS (ESI+): 357.3 (M+H).

17c) A solution of 17B (0.371 g, 1.04 mmol) in EtOH (5 mL) was treated with 6N NaOH (1.5 mL), and refluxed overnight. After cooling to room temperature, solvent was removed and the residue was washed with DCM and MeOH and filtered. The solution was concentrated to give 17C (0.29 g, 98%). $^1$H-NMR (CDCl$_3$) δ 7.38 (m, 1H), 7.15 (m, 1H), 4.95 (m, 2H), 3.04 (bs, 4H), 1.97 (bs, 4H), 1.45 (bs, 1H); LC/MS (ESI+): 285 (M+H).

17d) Compound 17C (0.29 g, 1.02 mmol) was dissolved in THF (4 mL). Water (0.04 mL), acetic acid (0.18 mL) and cyclobutanone (0.112 mL, 1.5 mmol) was added, followed by sodium cyanoborohydride (0.095 g, 1.5 mmol). The reaction was heated at 60° C. overnight. The mixture was cooled to room temperature, and the residue was treated with saturated NaHCO$_3$ solution and DCM. The organic layer was dried (Na$_2$SO$_4$), filtered and concentrated in vacuo. The product was purified by preparative TLC (SiO$_2$, 10% MeOH in DCM) to give compound 17D (0.20 g, 57%); $^1$H-NMR (CDCl$_3$) δ 7.38 (d, J=8.1 Hz, 1H), 7.15 (d, J=8.1 Hz, 1H), 4.95 (s, 2H), 2.90 (m, 1H), 2.53 (m, 4H), 2.18-1.78 (m, 10H); MS (ESI+): 339.4 (M+H).

17e) Compound 17D (0.10 g, 0.29 mmol) was dissolved in 80% EtOH (3 mL) in a 20 mL microwave vial, sodium bicarbonate (0.037 g, 0.44 mmol), 3-fluoro-4-(methylcarbamoyl) phenylboronic acid (0.070 g, 0.35 mmol), and PdCl$_2$(dppf) (11 mg, 0.015 mmol) was added. The vial was capped and microwaved at 100° C. for 25 min. (Ermy's Optimizer). The reaction mixture was filtered through a syringe filter. The solvent was removed in vacuo. Purification by reverse phase HPLC (Sunfire column C$_{18}$ OBD™ 5 μm, 19×100 mm, gradient 10% to 90% CH$_3$CN in H$_2$O with 0.01% TFA) was carried out. The pure fraction from HPLC was concentrated and stirred with MP-carbonate resin (3 eq.) overnight in DCM to remove TFA salt and give pure Example 133 (27.9 mg, 23%). MP 172-173° C.; $^1$H NMR (CDCl$_3$) δ 8.15 (t, J=8.7 Hz, 1H), 7.73 (m, 2H), 7.58 (d, J=8.7 Hz, 1H), 7.23 (d, J=8.7 Hz, 1H), 6.78 (m, 1H), 4.92 (s, 2H), 3.03 (m, 3H), 2.79 (m, 1H), 2.43 (m, 4H), 2.07-1.66 (m, 10H); LC/MS (ESI+): 412.3 (M+H$^+$).

The compounds of the present invention wherein Y$^1$, Y$^2$, Y$^3$ or Y$^4$ are nitrogen may be prepared in a number of methods well known to those skilled in the art, including, but not limited to those described herein, or through modifications of these methods by applying standard techniques known to those skilled in the art of organic synthesis. The general route to prepare examples wherein Y$^1$ is nitrogen is shown herein in the general Scheme 9. The reagents and starting materials are commercially available, or readily synthesized by well-known techniques by one of ordinary skill in the arts.

Example 134

1'-Cyclobutyl-spirobenzofuran-2(3H)-4'-piperidine-(5-(4-methylaminocarbamoylphenyl))

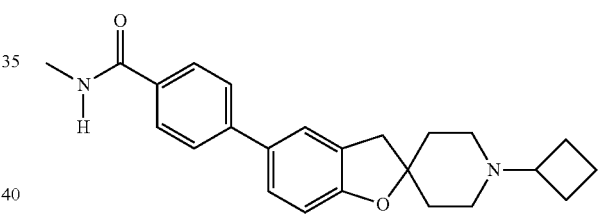

Step 18A: Compound 18A.

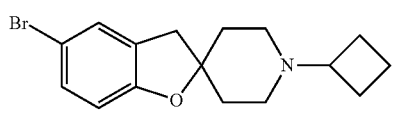

To a solution of 5-bromo-spiro[benzofuran-2-(3H)-4'-piperidine] (260.0 mg, 0.97 mmol) in methanol (5.0 mL, 120 mmol) was added 100 μl (1.75 mmol) of AcOH followed by cyclobutanone (679.6 mg, 9.7 mmol;) at rt. To this mixture was added sodium cyanoborohydride (200 mg, 3.18 mmol) in small portions over 5 min. After 5 min. HPLC indicated about 10% of starting material. Added another 100 μl of AcOH followed by another 200 mg of NaCNBH$_3$. After stirring for 15 min, LCMS indicated total disappearance of the starting material. The mixture was concentrated and extracted with CH$_2$Cl$_2$/sat. NaHCO$_3$. After evaporation and drying (Na$_2$SO$_4$), a pale yellow oil was obtained which was purified by ISCO chromatography using CH$_2$Cl$_2$ and 0-10% MeOH containing 1% aq. NH$_4$OH to afford the title compound as a waxy white solid (250 mg, 74%). Mp 79-80° C., MS: m/z 322/324 (M+1, Br isotopic peaks). $^1$H NMR (400 MHz, CDCl₃): δ 7.28 (d, J=0.75 Hz, 1H), 7.20 (d, J=8.4 Hz, 1H), 6.64 (d, J=8.4 Hz, 1H), 2.98 (s, 2H), 2.80 (m, 1H), 2.1-2.6 (br.s, 4H), 1.6-2.1 (m, 10H).

Step 18B: Example 134.

To a mixture of the product from step 1 (1'-cyclobutyl-5-bromo-spiro[benzofuran-2(3H)-4'-piperidine]) (322 mg, 1.00 mmol), 4-(N-methylaminocarbonyl)phenylboronic acid (179 mg, 1.00 mmol), tetrakis(triphenylphosphine)palladium (0) (0.12 g, 0.10 mmol) in ethanol (10.00 mL, 171.3 mmol) was added saturated aq. NaHCO₃ solution (2 mL) and heated to reflux for 15 h under N₂. The reaction was concentrated, then extracted with DCM and purified by ISCO chromatography (DCM/MeOH/NH4OH) to give a tan solid (0.21 g, 55%). Mp 197-198° C., MS: m/z 377 (M+1). ¹H NMR (CDCl₃) δ 7.8 (d, J=8.1 Hz, 2H), 7.6 (d, J=8.1 Hz, 2H), 7.4 (m, 2H), 6.85 (d, J=8.1 Hz, 1H), 6.15 (m, 1H), 3.07 (s, 3H), 3.05 (s, 2H), 2.85, m, 1H), 2.4-2.6 (br.s, 4H), 1.65-2.15 (m, 10H).

Example 135

1'-Cyclobutyl-spirobenzofuran-2(3H)-4'-piperidine-(5-(4-methylsulfonylphenyl))

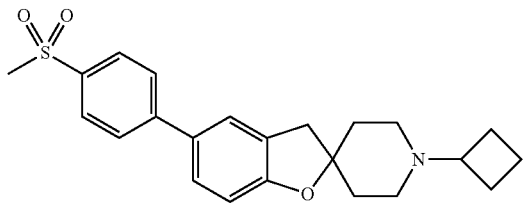 [SMILES: CS(=O)(=O)c1ccc(-c2ccc3c(c2)CC2(CCN(C4CCC4)CC2)O3)cc1]

This compound was made by the same general method as Example 134.

Mp>25° C.; MS: m/z 398 (M+1). ¹H NMR (CDCl₃) δ 7.95 (d, 2H), 7.7 (d, 2H), 7.4 (m, 2H), 6.85 (d, 1H), 3.07 (s, 3H), 3.05 (s, 2H), 2.85, m, 1H), 2.4-2.6 (br.s, 4H), 1.65-2.15 (m, 10H).

Compounds of the invention of Formula (I) may contain a spiro-pyrrolidine ring when k+m=1. Spiro-pyrrolidine containing compounds may be synthesized using methods outlined in Scheme 1, Scheme 4 or Scheme 6 disclosed herein starting with N-Boc-3-pyaolidinone or an appropriate ketone. Compounds of the invention of Formula (I) may contain a spiro-azepine ring when k+m=3. Spiro-azepine containing compounds may be synthesized using methods outlined in Scheme 1, Scheme 4 or Scheme 6 disclosed herein starting with N-Boc-hexahydro-1H-azepin-4-one or an appropriate ketone. Compounds of the invention of Formula (I) may contain a spiro-3-piperidine ring when k+m=2. Spiro-3-piperidine containing compounds may be synthesized using methods outlined in Scheme 1, Scheme 4 or Scheme 6 disclosed herein starting with N-Boc-3-piperidone or an appropriate ketone.

Compounds of the invention wherein X=NR²⁹COR², NR²⁹CO(C₁-C₃-alkyl)-R² or NR²⁹CONHR² may be synthesized from aniline intermediates, for example aniline 10D, using standard methods know to those in the art. Additional aniline intermediates may be synthesized using Scheme 7 starting with 1,2-dihydroxy-4-nitrobenzene for W=O, or 2-(2-hydroxyethyl)-4-nitrophenol for W=CH₂CH₂O. Using Scheme 6 and replacing 2-hydroxy-5-nitroacetophenone for 5-bromo-2-hydroxy-acetophenone, aniline intermediates wherein W=CH₂CH₂, COCH₂, CHOHCH₂ may be synthesized. The corresponding phenol intermediates may be synthesized starting with 2,5-dihydroxyacetophenone, 2-(2-hydroxy-ethyl)-benzene-1,4-diol or trihydroxybenzene and used in the synthesis of examples where X=OR² or O—(C¹-C³-alkyl)-R² using standard methods.

Bromo intermediates, for example 1C, 8C, 8D, 8E, in the preparation of compounds of the invention may be coupled with piperidine, pyrrolidine or piperazine derivatives using Buchwald conditions (phosphine ligand (BINAP, or nBu₃P; Pd(OAc)2, Cs₂CO₃, o-xylene, 120° C.) to give N-pyrrolidine, piperidine or piperazine examples of the invention.

Utility

The compounds of the present invention are useful, inter alia, as therapeutic agents. Particularly, the compounds are useful for interacting with the H₃ receptor. In one embodiment, the present invention provides a method for treating or preventing diseases and disorders, such as those disclosed herein, which comprises administering to a subject in need of such treatment or prevention a therapeutically effective amount of a compound of the present invention.

In an additional embodiment, the present invention provides a method for inhibiting H₃ activity comprising providing a compound of the present invention in an amount sufficient to result in effective inhibition. Particularly, the compounds of the present invention can be administered to treat such diseases and disorders such as narcolepsy or other sleep/wake disorders, such as obstructive sleep apnea/hypopnea syndrome, and shift work sleep disorder; feeding behavior, eating disorders, obesity, cognition, arousal, memory, mood disorders, mood attention alteration, attention deficit hyperactivity disorder (ADHD), Alzheimer's disease/dementia, schizophrenia, pain, stress, migraine, motion sickness, depression, psychiatric disorders, epilepsy, gastrointestinal disorders, respiratory disorders (such as asthma), inflammation, and myocardial infarction. In certain embodiments, the compounds can be administered to treat narcolepsy or other sleep/wake disorders, such as obstructive sleep apnea/hypopnea syndrome, and shift work sleep disorder; obesity, cognition, attention deficit hyperactivity disorder (ADHD), and dementia. In other embodiments, the compounds can be administered to treat narcolepsy or other sleep/wake disorders, such as obstructive sleep apnea/hypopnea syndrome, and shift work sleep disorder; or they can used to treat obesity, or they can used to treat cognition, or they can used to treat attention deficit hyperactivity disorder (ADHD), or they can used to treat dementia.

Compounds of the invention either have demonstrated or are expected to demonstrate inhibition of H₃ and thereby for utility for treatment of the indications described herein. Such utilities can be determined using, for example, the following assays as set forth below. They are not intended, nor are they to be construed, as limiting the scope of the disclosure.

Rat H₃ Assays:

Cell line development and membrane preparation. The rat H₃ receptor cDNA was PCR amplified from reverse-transcribed RNA pooled from rat thalamus, hypothalamus, striatum and prefrontal cortex with a sequence corresponding to by #338-1672 of Genbank file #NM_053506, encoding the entire 445-amino-acid rat histamine H₃ receptor. This was engineered into the pIRES-neo3 mammalian expression vector, which was stably transfected into the CHO-A3 cell line (Euroscreen, Belgium), followed by clonal selection by limiting dilution. Cells were harvested and cell pellets were frozen (−80° C.). Cell pellets were resuspended in 5 mM Tris-HCl, pH 7.5 with 5 nM EDTA and a cocktail of protease inhibitors (Complete Protease Inhibitior Tablets, Roche Diagnostics). Cells were disrupted using a polytron cell homogenizer and the suspension was centrifuged at 1000×g for 10 minutes at 4° C. The pellet was discarded and the supernatant centrifuged at 40,000×g for 30 min at 4° C. This membrane pellet was washed in membrane buffer containing 50 mM Tris-HCl, pH 7.5 with 0.6 mM EDTA, 5 mM $MgCl_2$ and protease inhibitors, recentrifuged as above and the final pellet resuspended in membrane buffer plus 250 mM sucrose and frozen at −80° C.

Radioligand Binding. Membranes were resuspended in 50 mM Tris HCl (pH 7.4), 5 mM $MgCl_2$, 0.1% BSA. The membrane suspensions (10 µg protein per well) were incubated in a 96 well microtiter plate with [$^3$H]-N-alpha-methylhistamine (approximately 1 nM final concentration), test compounds at various concentrations (0.01 nM-30 µM) and scintillation proximity beads (Perkin Elmer, FlashBlueGPCR Scintillating Beads) in a final volume of 80 µl for 4 hours at room temperature, protected from light. Non-specific binding was determined in the presence of 10 µM clobenpropit. Radioligand bound to receptor, and therefore in proximity to the scintillation beads, was measured using a MicroBeta scintillation counter.

GTPγS Binding. Membranes were resuspended in 20 mM HEPES pH 7.4 containing 1 mM EDTA, 0.17 mg/ml dithiothreitol, 100 mM NaCl, 30 µg/ml saponin and 5 mM $MgCl_2$. For measurement of inverse agonist activity, increasing concentrations of test compounds were incubated in a 96 well microtiter plate with 10 µg/well membrane protein, 5 µM GDP, scintillation proximity beads (Perkin Elmer, FlashBlue-GPCR Scintillating Beads) and [$^{35}$S]-GTPγS (0.1 nM final concentration). Following incubation for 45 minutes in the dark at room temperature, the microtiter plate was centrifuged at 1000×g for 5 minutes and radioactivity bound to the membranes was counted using a MicroBeta scintillation counter. Non-specific binding was measured in the presence of 10 µM GTP. A decrease in bound [$^{35}$S]-GTPγS is indicative of $H_3$ receptor inverse agonist activity in this assay. Antagonist activity of test compounds was determined in a similar experiment under the following conditions. Membranes were resuspended in 20 mM HEPES pH 7.4 containing: 1 mM EDTA, 0.17 mg/ml dithiothreitol, 200 mM NaCl, 30 µg/ml saponin and 20 mM $MgCl_2$. The membranes were incubated at 10 µg/well membrane protein in a microtiter plate with increasing concentrations of test compounds, 20 µM GDP, scintillation proximity beads and [$^{35}$S]-GTPγS (0.1 nM final concentration) plus 30 nM R-alpha-methylhistamine. The microtiter plates were incubated and processed as described above. A decrease in R-alpha-methylhistamine stimulated [$^{35}$S]-GTPγS binding is indicative of $H_3$ receptor antagonist activity in this assay.

Human $H_3$ Assays:

Methods: CHO cells stably expressing the human $H_3$ receptor (GenBank: NM_007232) were harvested and cell pellets were frozen (−80° C.). Cell pellets were resuspended in 5 mM Tris-HCl, pH 7.5 with 5 nM EDTA and a cocktail of protease inhibitors (Complete Protease Inhibitior Tablets, Roche Diagnostics). Cells were disrupted using a polytron cell homogenizer and the suspension was centrifuged at 1000×g for 10 minutes at 4° C. The pellet was discarded and the supernatant centrifuged at 40,000×g for 30 min at 4° C. This membrane pellet was washed in membrane buffer containing 50 mM Tris-HCl, pH 7.5 with 0.6 mM EDTA, 5 mM $MgCl_2$ and protease inhibitors, recentrifuged as above and the final pellet resuspended in membrane buffer plus 250 mM sucrose and frozen at −80° C.

Radioligand Binding. Membranes were resuspended in 50 mM Tris HCl (pH 7.4), 5 mM $MgCl_2$, 0.1% BSA. The membrane suspensions (10 µg protein per well) were incubated in a 96 well microtiter plate with [$^3$H]-N-alpha-methylhistamine (approximately 1 nM final concentration), test compounds at various concentrations (0.01 nM-30 µM) and scintillation proximity beads (Perkin Elmer, FlashBlueGPCR Scintillating Beads) in a final volume of 80 µl for 4 hours at room temperature, protected from light. Non-specific binding was determined in the presence of 10 µM clobenpropit. Radioligand bound to receptor, and therefore in proximity to the scintillation beads, was measured using a MicroBeta scintillation counter.

GTPγS Binding. Membranes were resuspended in 20 mM HEPES pH 7.4 containing 1 mM EDTA, 0.17 mg/ml dithiothreitol, 100 mM NaCl, 30 µg/ml saponin and 5 mM $MgCl_2$. For measurement of inverse agonist activity, increasing concentrations of test compounds were incubated in a 96 well microtiter plate with 10 µg/well membrane protein, 5 µM GDP, scintillation proximity beads (Perkin Elmer, FlashBlue-GPCR Scintillating Beads) and [$^{35}$S]-GTPγS (0.1 nM final concentration). Following incubation for 45 minutes in the dark at room temperature, the microtiter plate was centrifuged at 1000×g for 5 minutes and radioactivity bound to the membranes was counted using a MicroBeta scintillation counter. Non-specific binding was measured in the presence of 10 µM GTP. A decrease in bound [$^{35}$S]-GTPγS is indicative of $H_3$ receptor inverse agonist activity in this assay. Antagonist activity of test compounds was determined in a similar experiment under the following conditions. Membranes were resuspended in 20 mM HEPES pH 7.4 containing: 1 mM EDTA, 0.17 mg/ml dithiothreitol, 200 mM NaCl, 30 µg/ml saponin and 20 mM $MgCl_2$. The membranes were incubated at 10 µg/well membrane protein in a microtiter plate with increasing concentrations of test compounds, 20 µM GDP, scintillation proximity beads and [$^{35}$S]-GTPγS (0.1 nM final concentration) plus 30 nM R-alpha-methylhistamine. The microtiter plates were incubated and processed as described above. A decrease in R-alpha-methylhistamine stimulated [$^{35}$S]-GTPγS binding is indicative of $H_3$ receptor antagonist activity in this assay.

Other assays that may be used in connection with the present invention are set forth below. Examples of the present invention can be tested in the following in vivo models:

Evaluation of Wake Promoting Activity in Rats

The methodology utilized for evaluating wake promoting activity of test compounds is based on that described by Edgar and Seidel, *Journal of Pharmacology and Experimental Therapeutics*, 283:757-769, 1997, and incorporated herein in its entirety by reference.

Compounds of the invention either have demonstrated or are expected to demonstrate utility for wake promoting activity.

Dipsogenia Model: Inhibition of histamine agonist-induced water drinking in the rat. Histamine, and the $H_3$-selective agonist (R)-α-methylhistamine (RAMH) induce water drinking behavior in the rat when administered either peripherally or centrally (Kraly, F. S., June, K. R. 1982 *Physiol. Behav.* 28: 841. Leibowitz, S. F. 1973 *Brain Res.* 63:440; Ligneau X., Lin, J-S., Vanni-Mercier G., Jouvet M., Muir J. L., Ganellin C. R., Stark H., Elz S., Schunack W., Schwartz, J-C. 1998 *J Pharmcol. Exp. Ther.* 287:658-66. Clapham, J. and Kilpatrick G. J. 1993 *Eur. J. Pharmacol.* 232:99-103) an effect which is blocked by $H_3$ receptor antagonists thioperamide and ciproxifan. Compounds of the invention either have demonstrated or are expected to block RAMH induce water drinking behavior.

Novel object discrimination: Novel object discrimination (NOD; also referred to as novel object recognition) is an assay for short-term visual recognition memory that was first described by Ennaceur and Delacour (Ennaceur, A. and Delacour, J. (1988) *Behav Brain Res* 31: 47-59).

Social recognition: Social recognition (SR) is an assay for short-term social (olfactory) memory that was first described by Thor and Holloway (1982). Thor, D. and Holloway, W. (1982) *J Comp Physiolog Psychcol* 96: 1000-1006.

Compounds of the invention either have demonstrated or are expected to demonstrate inhibition of $H_3$ and thereby utility for treatment of the indications described herein.

Table A lists the Human and Rat $H_3$ binding data for Examples 1-133 of the present invention. Binding constants ($K_i$) for Examples 1-133 in the Human $H_3$ and Rat $H_3$ methods described herein are expressed by letter descriptor to indicate the following ranges: "+++" is less than 200 nM; "++" is 200-1000 nM; "+" is >1000 nM.

TABLE A

| Example | Human Ki (nM) | Rat Ki (nM) |
|---|---|---|
| 1 | +++ | +++ |
| 2 | +++ | +++ |
| 3 | +++ | +++ |
| 4 | +++ | +++ |
| 5 | +++ | +++ |
| 6 | ++ | |
| 7 | +++ | +++ |
| 8 | +++ | +++ |
| 9 | +++ | +++ |
| 10 | +++ | +++ |
| 11 | +++ | +++ |
| 12 | +++ | +++ |
| 13 | +++ | +++ |
| 14 | +++ | +++ |
| 15 | +++ | +++ |
| 16 | +++ | +++ |
| 17 | +++ | +++ |
| 18 | +++ | +++ |
| 19 | +++ | +++ |
| 20 | +++ | +++ |
| 21 | +++ | +++ |
| 22 | +++ | +++ |
| 23 | +++ | +++ |
| 24 | +++ | +++ |
| 25 | +++ | +++ |
| 26 | +++ | +++ |
| 27 | +++ | +++ |
| 28 | +++ | +++ |
| 29 | +++ | +++ |
| 30 | +++ | +++ |
| 31 | +++ | +++ |
| 32 | +++ | +++ |
| 33 | +++ | +++ |
| 34 | +++ | +++ |
| 35 | +++ | +++ |
| 36 | +++ | +++ |
| 37 | +++ | +++ |
| 38 | +++ | +++ |
| 39 | +++ | +++ |
| 40 | +++ | +++ |
| 41 | +++ | +++ |
| 42 | +++ | +++ |
| 43 | +++ | +++ |
| 44 | +++ | +++ |
| 45 | +++ | +++ |
| 46 | +++ | +++ |
| 47 | +++ | +++ |
| 48 | +++ | +++ |
| 49 | +++ | +++ |
| 50 | +++ | +++ |
| 51 | +++ | +++ |
| 52 | +++ | +++ |
| 53 | +++ | +++ |
| 54 | +++ | +++ |
| 55 | +++ | +++ |
| 56 | +++ | +++ |
| 57 | +++ | +++ |
| 58 | +++ | +++ |
| 59 | +++ | +++ |
| 60 | +++ | |
| 61 | +++ | |
| 62 | +++ | |
| 63 | +++ | |
| 64 | +++ | |
| 65 | +++ | +++ |
| 66 | +++ | +++ |
| 67 | +++ | +++ |
| 68 | +++ | +++ |
| 69 | +++ | +++ |
| 70 | +++ | +++ |
| 71 | +++ | +++ |
| 72 | +++ | +++ |
| 73 | +++ | +++ |
| 74 | +++ | +++ |
| 75 | +++ | +++ |
| 76 | +++ | +++ |
| 77 | +++ | +++ |
| 78 | +++ | ++ |
| 79 | ++ | ++ |
| 80 | +++ | ++ |
| 81 | +++ | +++ |
| 82 | +++ | +++ |
| 83 | +++ | +++ |
| 84 | +++ | +++ |
| 85 | +++ | +++ |
| 86 | +++ | +++ |
| 87 | +++ | +++ |
| 88 | ++ | +++ |
| 89 | +++ | +++ |
| 90 | +++ | ++ |
| 91 | +++ | +++ |
| 92 | ++ | + |
| 93 | ++ | + |
| 94 | ++ | ++ |
| 95 | + | + |
| 96 | ++ | ++ |
| 97 | + | ++ |
| 98 | +++ | +++ |
| 99 | +++ | +++ |
| 100 | +++ | +++ |
| 101 | +++ | +++ |
| 102 | +++ | +++ |
| 103 | +++ | +++ |
| 104 | +++ | +++ |
| 105 | +++ | ++ |
| 106 | +++ | +++ |
| 107 | +++ | +++ |
| 108 | +++ | +++ |
| 109 | +++ | +++ |
| 110 | +++ | +++ |
| 111 | +++ | +++ |
| 112 | +++ | +++ |
| 113 | +++ | +++ |
| 114 | +++ | +++ |
| 115 | +++ | +++ |
| 116 | +++ | +++ |
| 117 | +++ | +++ |
| 118 | +++ | +++ |
| 119 | +++ | +++ |
| 120 | +++ | +++ |
| 121 | +++ | +++ |
| 122 | +++ | +++ |
| 123 | +++ | +++ |
| 124 | +++ | +++ |
| 125 | +++ | +++ |
| 126 | +++ | +++ |
| 127 | +++ | +++ |
| 128 | +++ | +++ |
| 129 | +++ | +++ |
| 130 | +++ | +++ |
| 131 | ++ | +++ |
| 132 | +++ | +++ |
| 133 | +++ | +++ |
| 134 | +++ | +++ |
| 135 | +++ | +++ |

Table B lists the Human and Rat H₃ binding data for Examples 136-362 of the present invention. Binding constants (K$_i$) for Examples 136-362 in the Human H₃ and Rat H₃ methods described herein are expressed by letter descriptor to indicate the following ranges: "+++" is less than 200 nM; "++" is 200-1000 nM; "+" is >1000 nM.

The compounds of Table B were prepared by methods well known to those skilled in the art, including, but not limited to those described herein, or through modifications of these methods by applying standard techniques known to those skilled in the art of organic synthesis. General routes of synthesis to prepare Examples of Table B are shown in the Schemes herein. The reagents and starting materials are commercially available, or readily synthesized by well-known techniques by one of ordinary skill in the arts.

TABLE B

| Example | Structure | MP (°C.) | MS (ESI+) (M + H) | hum H3 binding Ki (nM) | rat H3 binding Ki (nM) |
|---|---|---|---|---|---|
| 136 | 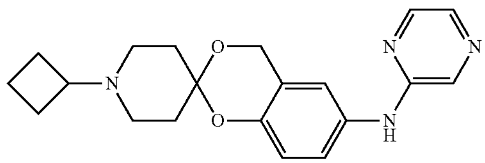 [SMILES: c1cnc(Nc2ccc3c(c2)COC2(CCN(C4CCC4)CC2)O3)cn1] | 57-61 | 352 | +++ | +++ |
| 137 | 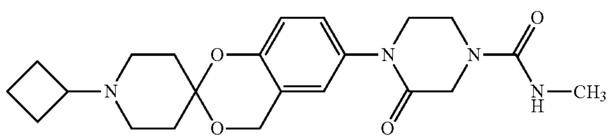 | 145-149 | 415 | +++ | ++ |
| 138 | 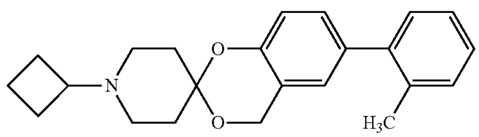 [SMILES: Cc1ccccc1-c1ccc2c(c1)COC1(CCN(C3CCC3)CC1)O2] | 241-243 | 350 | +++ | +++ |
| 139 | Chiral | 120-122 | 359 | +++ | +++ |
| 140 | 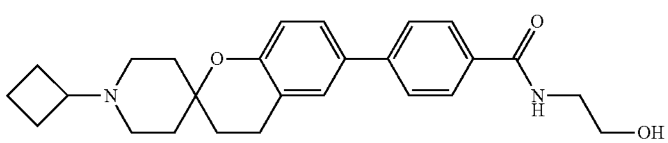 [SMILES: O=C(NCCO)c1ccc(-c2ccc3c(c2)CCC2(CCN(C4CCC4)CC2)O3)cc1] | 145-147 | 421 | +++ | +++ |
| 141 | 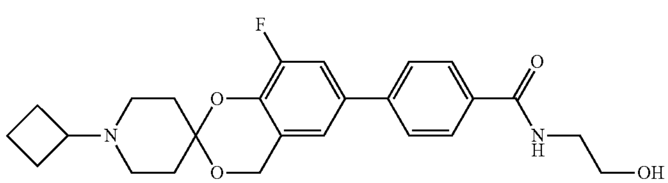 [SMILES: O=C(NCCO)c1ccc(-c2cc(F)c3c(c2)COC2(CCN(C4CCC4)CC2)O3)cc1] | 145-147 | 441 | +++ | +++ |
| 142 | 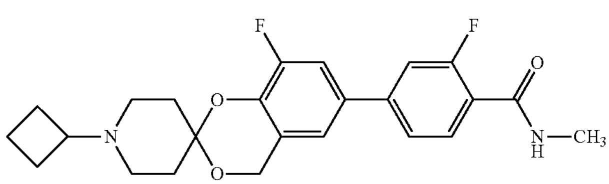 [SMILES: CNC(=O)c1ccc(-c2cc(F)c3c(c2)COC2(CCN(C4CCC4)CC2)O3)cc1F] | 156-158 | 430 | +++ | +++ |
| 143 | 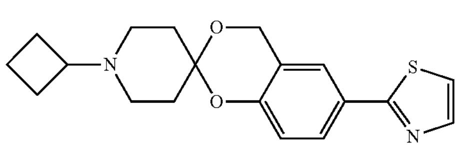 [SMILES: c1csc(-c2ccc3c(c2)COC2(CCN(C4CCC4)CC2)O3)n1] | 181-183 | 343 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 144 | 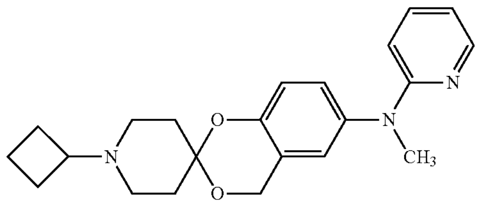 [SMILES: CN(c1ccc2c(c1)COC1(CCN(C3CCC3)CC1)O2)c1ccccn1] | 216-220 | 366 | +++ | +++ |
| 145 | 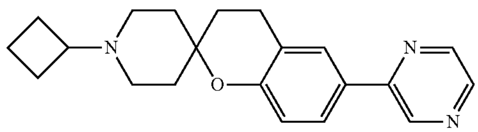 [SMILES: c1cnc(-c2ccc3c(c2)CCC2(CCN(C4CCC4)CC2)O3)cn1] | NA | 336 | +++ | +++ |
| 146 | 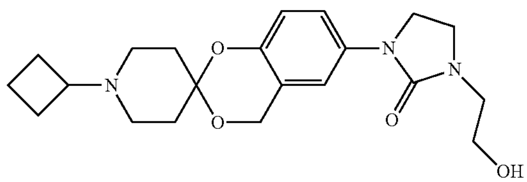 [SMILES: O=C1N(CCO)CCN1c1ccc2c(c1)COC1(CCN(C3CCC3)CC1)O2] | 152-155 | 388 | +++ | +++ |
| 147 | 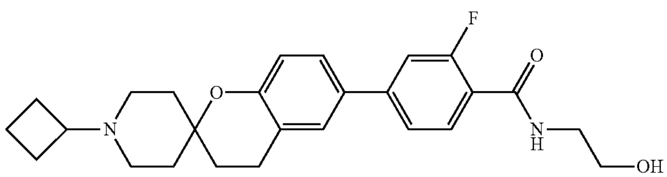 [SMILES: O=C(NCCO)c1ccc(-c2ccc3c(c2)CCC2(CCN(C4CCC4)CC2)O3)cc1F] | 215-217 | 439 | +++ | +++ |
| 148 | 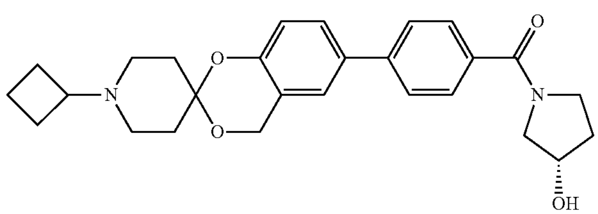 [SMILES: O=C(c1ccc(-c2ccc3c(c2)COC2(CCN(C4CCC4)CC2)O3)cc1)N1CC[C@H](O)C1] | 178-181 | 449 | +++ | +++ |
| 149 | 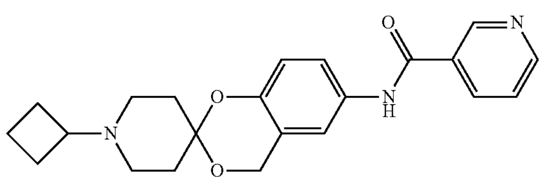 [SMILES: O=C(Nc1ccc2c(c1)COC1(CCN(C3CCC3)CC1)O2)c1cccnc1] | 215-217 | 380 | +++ | +++ |
| 150 | 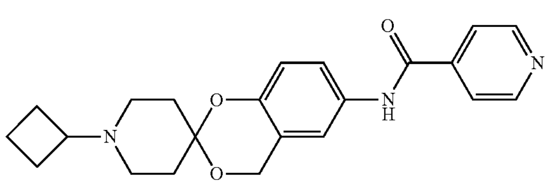 [SMILES: O=C(Nc1ccc2c(c1)COC1(CCN(C3CCC3)CC1)O2)c1ccncc1] | 180-182 | 380 | +++ | +++ |
| 151 | 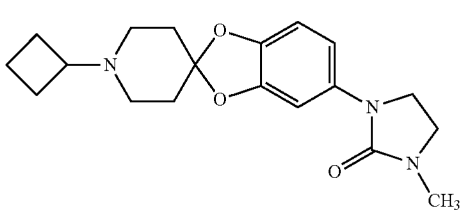 [SMILES: CN1CCN(c2ccc3c(c2)OC2(CCN(C4CCC4)CC2)O3)C1=O] | 186-187 | 344 | +++ | >300 nM |

TABLE B-continued
| Example | Structure | MP (°C.) | MS (ESI+) (M + H) | hum H3 binding Ki (nM) | rat H3 binding Ki (nM) |
|---|---|---|---|---|---|
| 152 | 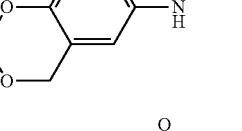 | 172-174 | 380 | +++ | +++ |
| 153 | 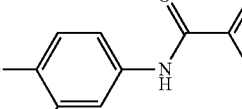 | 212-215 | 404 | +++ | +++ |
| 154 | 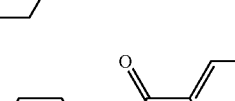 | 206-208 | 404 | +++ | +++ |
| 155 | 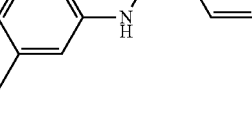 | 156-158 | 451 | +++ | +++ |
| 156 | 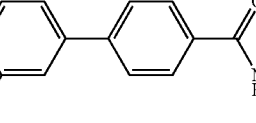 | 67-69 | 392 | +++ | +++ |
| 157 | 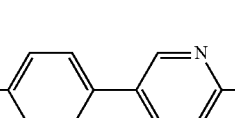 | 170-172 | 419 | +++ | +++ |
| 158 | 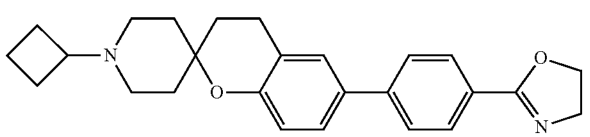 [SMILES: c1cc(-c2ccc3c(c2)CCC2(CCN(C4CCC4)CC2)O3)ccc1C1=NCCO1] | 213-215 | 403 | +++ | +++ |
| 159 | 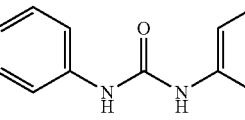 | 60-63 | 464 | +++ | ++ |
| 160 | 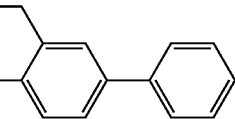 | 208-210 | 394 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 161 | 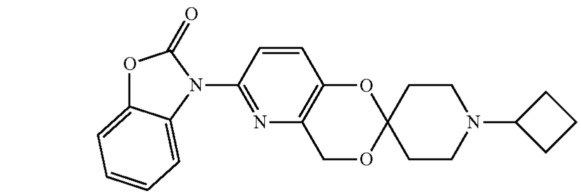 [SMILES: O=c1oc2ccccc2n1-c1ccc2c(n1)COC1(CCN(C3CCC3)CC1)O2] | 67-70 | 394 | +++ | ++ |
| 162 | 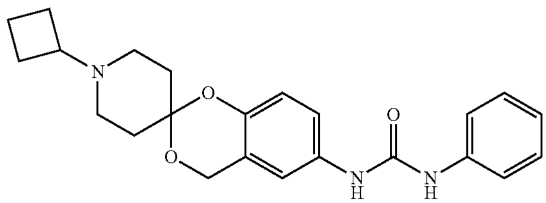 [SMILES: O=C(Nc1ccccc1)Nc1ccc2c(c1)COC1(CCN(C3CCC3)CC1)O2] | 229-231 | 394 | +++ | +++ |
| 163 | 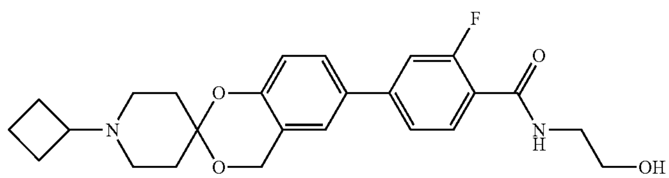 | 166-168 | 441 | +++ | +++ |
| 164 | 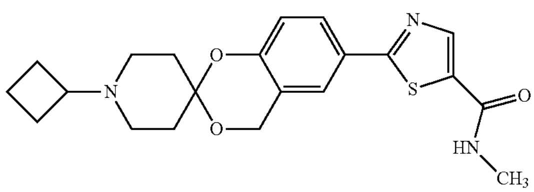 | 200-203 | 400 | +++ | +++ |
| 165 | 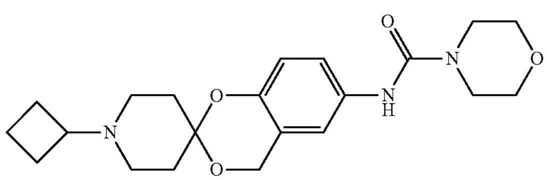 [SMILES: O=C(Nc1ccc2c(c1)COC1(CCN(C3CCC3)CC1)O2)N1CCOCC1] | 238-240 | 388 | +++ | ++ |
| 166 | 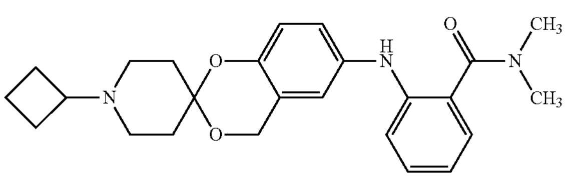 [SMILES: CN(C)C(=O)c1ccccc1Nc1ccc2c(c1)COC1(CCN(C3CCC3)CC1)O2] | 50-53 | 422 | +++ | +++ |
| 167 | 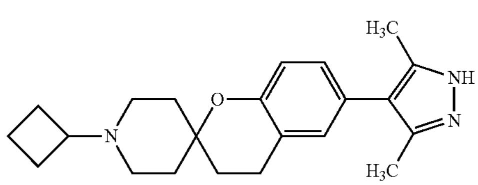 [SMILES: Cc1n[nH]c(C)c1-c1ccc2c(c1)CCC1(CCN(C3CCC3)CC1)O2] | 86-88 | 352 | +++ | +++ |
| 168 | 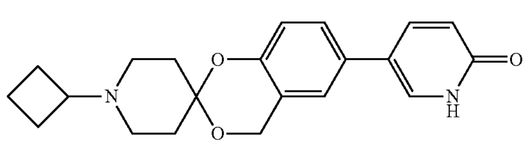 [SMILES: O=c1ccc(-c2ccc3c(c2)COC2(CCN(C4CCC4)CC2)O3)c[nH]1] | 145-147 | 353 | +++ | +++ |

TABLE B-continued

| Example | Structure | MP (°C.) | MS (ESI+) (M + H) | hum H3 binding Ki (nM) | rat H3 binding Ki (nM) |
|---|---|---|---|---|---|
| 169 | 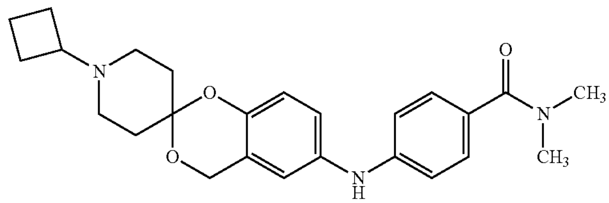 [SMILES: CN(C)C(=O)c1ccc(Nc2ccc3c(c2)COC2(CCN(C4CCC4)CC2)O3)cc1] | 66-74 | 422 | +++ | +++ |
| 170 | 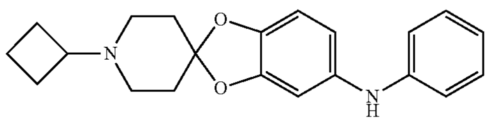 [SMILES: c1ccc(Nc2ccc3c(c2)OC2(CCN(C4CCC4)CC2)O3)cc1] | 238-240 | 337 | +++ | +++ |
| 171 | 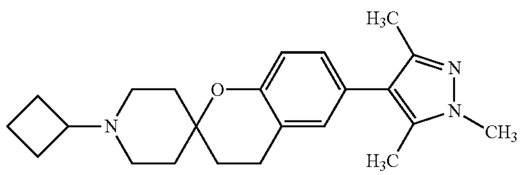 [SMILES: Cc1nn(C)c(C)c1-c1ccc2c(c1)CCC1(CCN(C3CCC3)CC1)O2] | 47-49 | 366 | +++ | +++ |
| 172 | 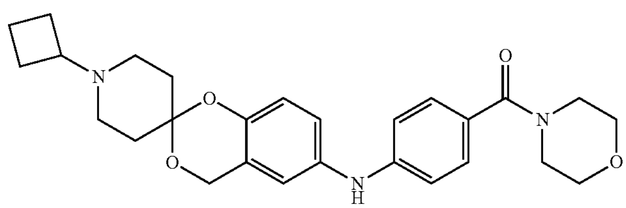 [SMILES: O=C(c1ccc(Nc2ccc3c(c2)COC2(CCN(C4CCC4)CC2)O3)cc1)N1CCOCC1] | 79-84 | 464 | +++ | +++ |
| 173 | Chiral | 100-101 | 450 | +++ | +++ |
| 174 | 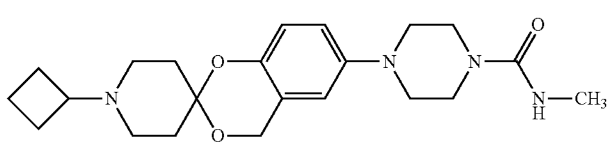 [SMILES: CNC(=O)N1CCN(c2ccc3c(c2)COC2(CCN(C4CCC4)CC2)O3)CC1] | 59-62 | 401 | +++ | +++ |
| 175 | 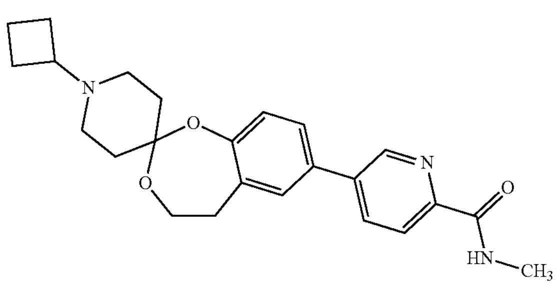 [SMILES: CNC(=O)c1ccc(-c2ccc3c(c2)CCOC2(CCN(C4CCC4)CC2)O3)cn1] | 141.0-142.2 | 408 | ++ | + |

TABLE B-continued

| Example | Structure | MP (° C.) | MS (ESI+) (M + H) | hum H3 binding Ki (nM) | rat H3 binding Ki (nM) |
|---|---|---|---|---|---|
| 176 | 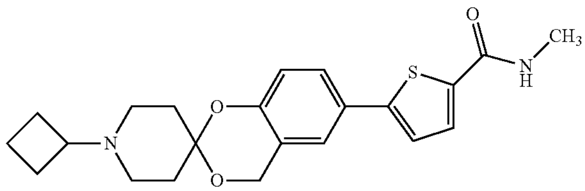 [SMILES: CNC(=O)c1ccc(-c2ccc3c(c2)COC2(CCN(C4CCC4)CC2)O3)s1] | 215-219 | 399 | +++ | +++ |
| 177 | 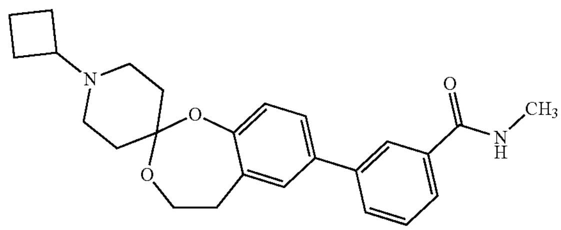 [SMILES: CNC(=O)c1cccc(-c2ccc3c(c2)CCOC2(CCN(C4CCC4)CC2)O3)c1] | 100.2-102.5 | 407 | ++ | + |
| 178 | 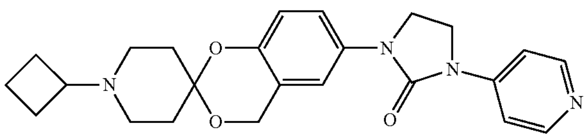 [SMILES: O=C1N(c2ccncc2)CCN1c1ccc2c(c1)COC1(CCN(C3CCC3)CC1)O2] | 185-189 | 421 | +++ | +++ |
| 179 | 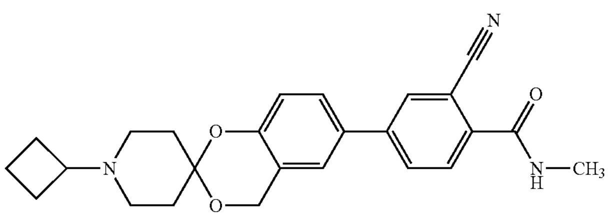 [SMILES: CNC(=O)c1ccc(-c2ccc3c(c2)COC2(CCN(C4CCC4)CC2)O3)cc1C#N] | NA | 418 | +++ | +++ |
| 180 | 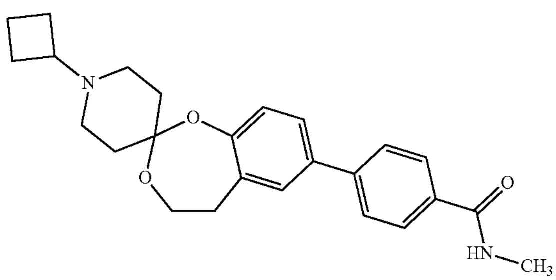 [SMILES: CNC(=O)c1ccc(-c2ccc3c(c2)CCOC2(CCN(C4CCC4)CC2)O3)cc1] | 155.6-157.3 | 407 | ++ | + |
| 181 | 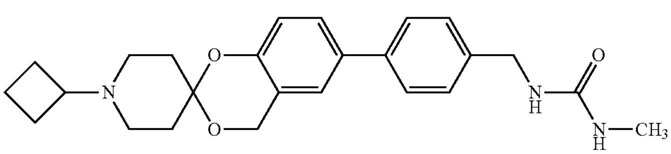 [SMILES: CNC(=O)NCc1ccc(-c2ccc3c(c2)COC2(CCN(C4CCC4)CC2)O3)cc1] | 205-206.5 | 422 | +++ | +++ |
| 182 | 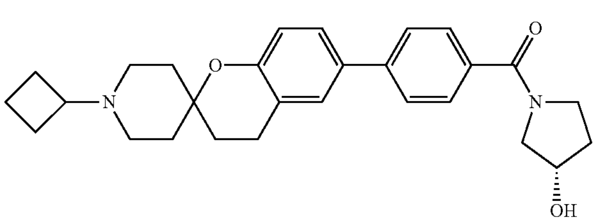 | 193-195 | 447 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 183 | 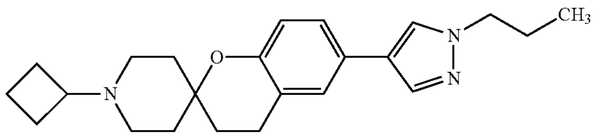 [SMILES: CCCn1cc(-c2ccc3c(c2)CCC2(CCN(C4CCC4)CC2)O3)cn1] | 97-99 | 366 | +++ | +++ |
| 184 | 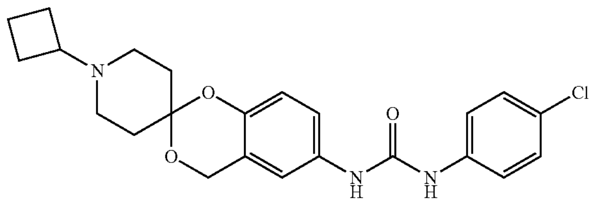 [SMILES: O=C(Nc1ccc(Cl)cc1)Nc1ccc2c(c1)COC1(CCN(C3CCC3)CC1)O2] | 201-203 | 428 | +++ | ++ |
| 185 | 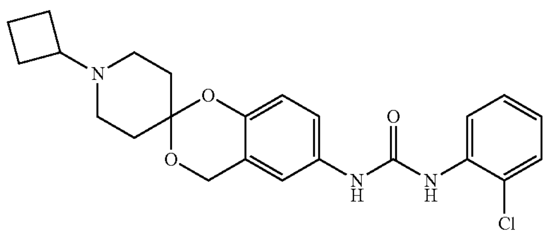 [SMILES: O=C(Nc1ccc2c(c1)COC1(CCN(C3CCC3)CC1)O2)Nc1ccccc1Cl] | 220.222 | 428 | +++ | +++ |
| 186 | 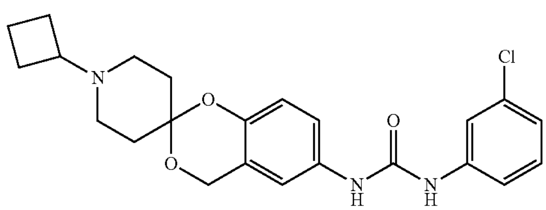 | 216-217 | 428 | +++ | +++ |
| 187 | 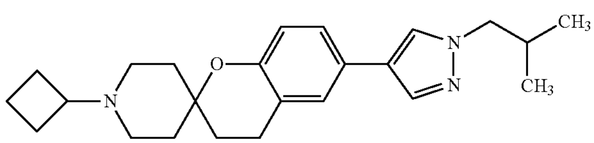 [SMILES: CC(C)Cn1cc(-c2ccc3c(c2)CCC2(CCN(C4CCC4)CC2)O3)cn1] | 106-108 | 380 | +++ | +++ |
| 188 | 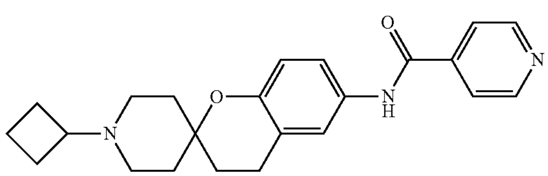 | 65-67 | 378 | +++ | +++ |
| 189 | 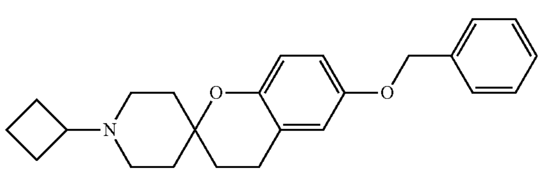 [SMILES: c1ccc(COc2ccc3c(c2)CCC2(CCN(C4CCC4)CC2)O3)cc1] | 102-103 | 364 | +++ | +++ |
| 190 | 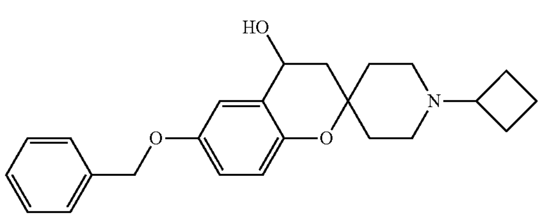 [SMILES: OC1CC2(CCN(C3CCC3)CC2)Oc2ccc(OCc3ccccc3)cc21] | 69-71 | 380 | +++ | ++ |

TABLE B-continued

| Example | Structure | MP (° C.) | MS (ESI+) (M + H) | hum H3 binding Ki (nM) | rat H3 binding Ki (nM) |
| --- | --- | --- | --- | --- | --- |
| 191 | 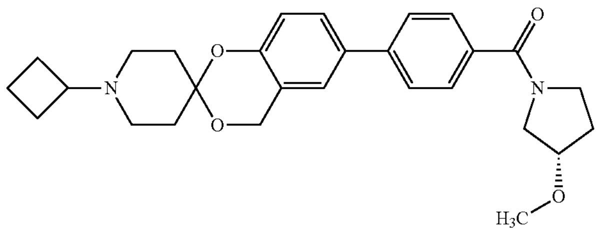 [SMILES: CO[C@H]1CCN(C(=O)c2ccc(-c3ccc4c(c3)COC3(CCN(C5CCC5)CC3)O4)cc2)C1] | 120-121 | 463 | +++ | +++ |
| 192 | 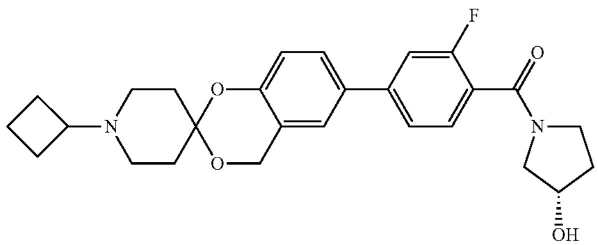 [SMILES: O=C(c1ccc(-c2ccc3c(c2)COC2(CCN(C4CCC4)CC2)O3)cc1F)N1CC[C@H](O)C1] | 99.5-100.5 | 467 | +++ | +++ |
| 193 | 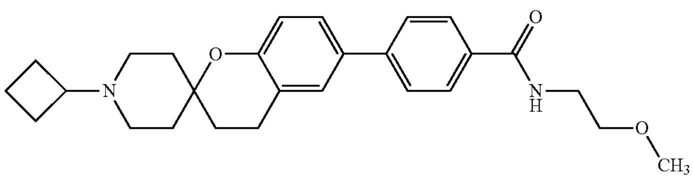 | 158-160 | 435 | +++ | +++ |
| 194 | 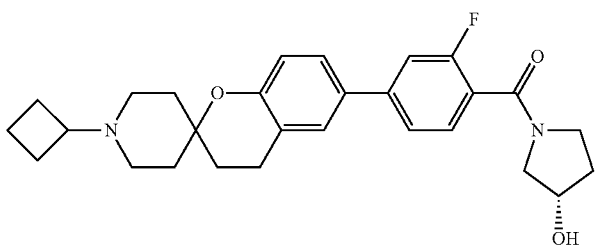 [SMILES: O=C(c1ccc(-c2ccc3c(c2)CCC2(CCN(C4CCC4)CC2)O3)cc1F)N1CC[C@H](O)C1] | 78-80 | 465 | +++ | +++ |
| 195 | 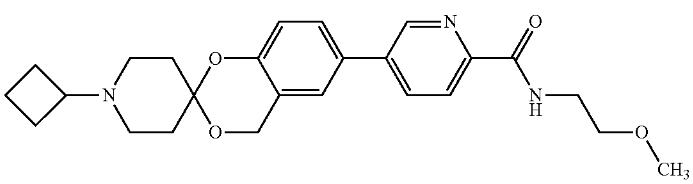 [SMILES: COCCNC(=O)c1ccc(-c2ccc3c(c2)COC2(CCN(C4CCC4)CC2)O3)cn1] | 113-114 | 438 | +++ | +++ |
| 196 | 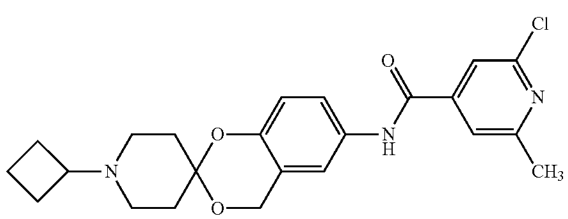 [SMILES: Cc1cc(C(=O)Nc2ccc3c(c2)COC2(CCN(C4CCC4)CC2)O3)cc(Cl)n1] | 179-180 | 428 | +++ | +++ |
| 197 | 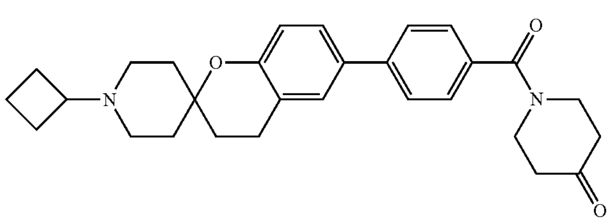 [SMILES: O=C1CCN(C(=O)c2ccc(-c3ccc4c(c3)CCC3(CCN(C5CCC5)CC3)O4)cc2)CC1] | 82.9-84.3 | 459 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 198 | 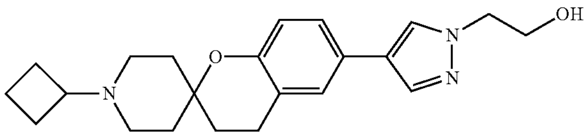 [SMILES: OCCn1cc(-c2ccc3c(c2)CCC2(CCN(C4CCC4)CC2)O3)cn1] | 101-103 | 368 | +++ | +++ |
| 199 | 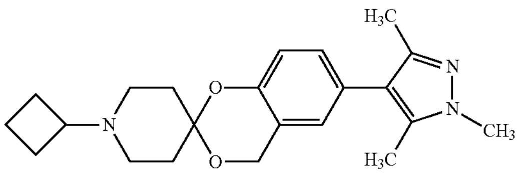 | 140-143 | 368 | +++ | +++ |
| 200 | 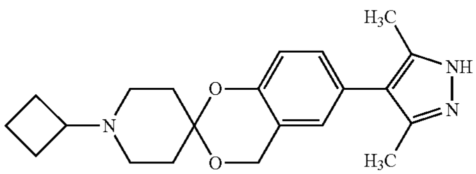 | 110-112 | 354 | +++ | +++ |
| 201 | 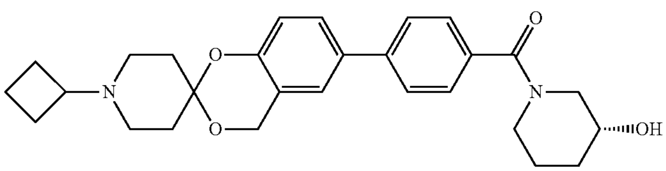 [SMILES: O=C(c1ccc(-c2ccc3c(c2)COC2(CCN(C4CCC4)CC2)O3)cc1)N1CCC[C@@H](O)C1] | 85-87 | 463 | +++ | +++ |
| 202 | 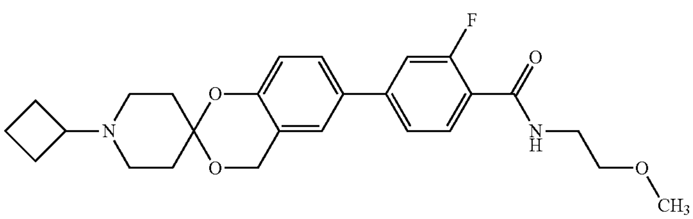 [SMILES: COCCNC(=O)c1ccc(-c2ccc3c(c2)COC2(CCN(C4CCC4)CC2)O3)cc1F] | 107-108.5 | 455 | +++ | +++ |
| 203 | 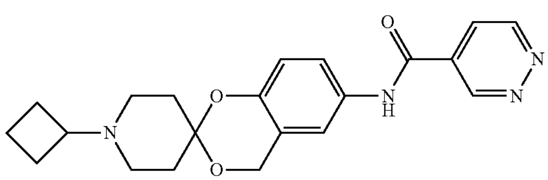 | 206-207 | 381 | +++ | +++ |
| 204 | 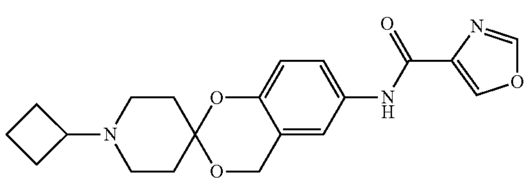 [SMILES: O=C(Nc1ccc2c(c1)COC1(CCN(C3CCC3)CC1)O2)c1cocn1] | 175-177 | 469 | +++ | +++ |
| 205 | 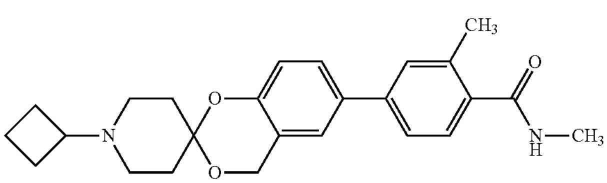 | 174.0-176.2 | 407 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 206 | 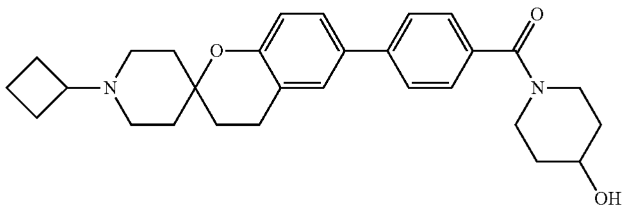 | 90.4-92.6 | 461 | +++ | +++ |
| 207 | 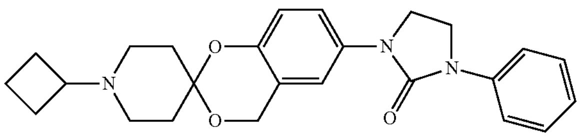 [SMILES: O=C1N(c2ccccc2)CCN1c1ccc2c(c1)COC1(CCN(C3CCC3)CC1)O2] | 195-197 | 420 | +++ | +++ |
| 208 | 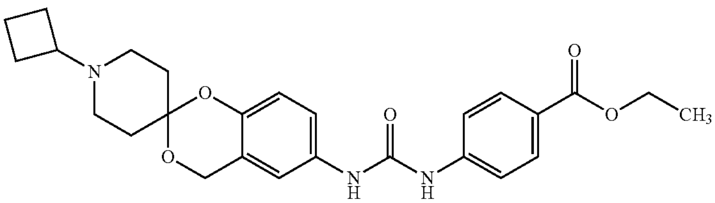 [SMILES: CCOC(=O)c1ccc(NC(=O)Nc2ccc3c(c2)COC2(CCN(C4CCC4)CC2)O3)cc1] | 188-189 | 466 | +++ | ++ |
| 209 | 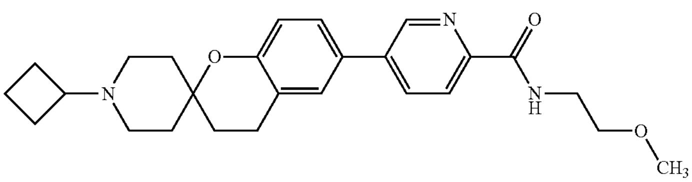 [SMILES: COCCNC(=O)c1ccc(-c2ccc3c(c2)CCC2(CCN(C4CCC4)CC2)O3)cn1] | 218-219 | 436 | +++ | +++ |
| 210 | 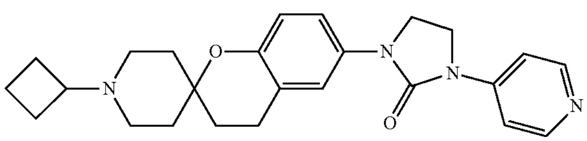 [SMILES: O=C1N(c2ccncc2)CCN1c1ccc2c(c1)CCC1(CCN(C3CCC3)CC1)O2] | 208-210 | 419 | +++ | +++ |
| 211 | Chiral | 70.2-71 | 461 | +++ | +++ |
| 212 | Chiral | 82-83.3 | 461 | +++ | +++ |
| 213 | Chiral | 128.130 | 448 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 214 | 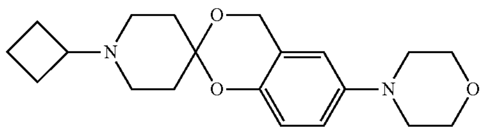 [SMILES: c1cc2c(cc1N1CCOCC1)COC1(CCN(C3CCC3)CC1)O2] | NA | 345 | +++ | +++ |
| 215 | Chiral | 114-116 | 464 | +++ | +++ |
| 216 | 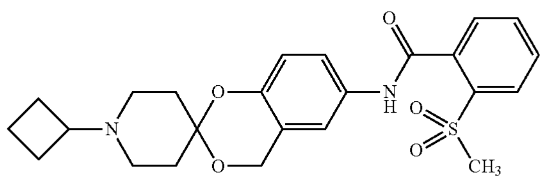 [SMILES: CS(=O)(=O)c1ccccc1C(=O)Nc1ccc2c(c1)COC1(CCN(C3CCC3)CC1)O2] | 143-145 | 457 | ++ | +++ |
| 217 | 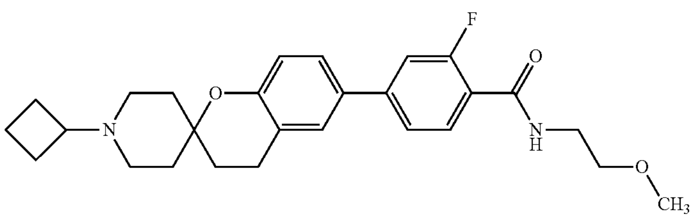 | 190-192 | 453 | +++ | +++ |
| 218 | 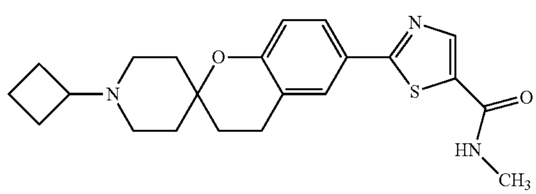 [SMILES: CNC(=O)c1cnc(-c2ccc3c(c2)CCC2(CCN(C4CCC4)CC2)O3)s1] | 201-203 | 398 | +++ | +++ |
| 219 | 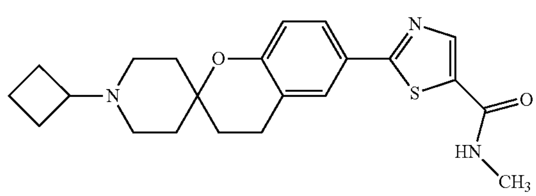 [SMILES: CNC(=O)c1cnc(-c2ccc3c(c2)CCC2(CCN(C4CCC4)CC2)O3)s1] | | | +++ | +++ |
| 220 | 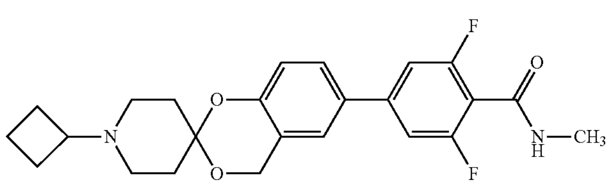 [SMILES: CNC(=O)c1c(F)cc(-c2ccc3c(c2)COC2(CCN(C4CCC4)CC2)O3)cc1F] | 212.6-214.2 | 429 | +++ | +++ |
| 221 | 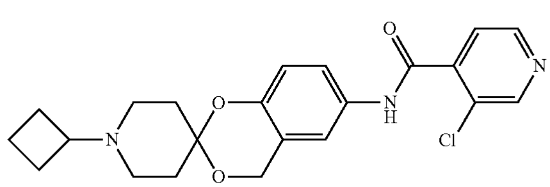 | 192-193 | 414 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 222 | 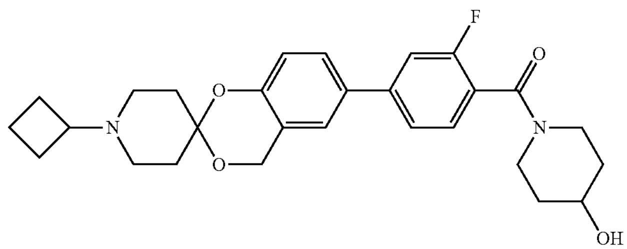 [SMILES: O=C(c1ccc(-c2ccc3c(c2)COC2(CCN(C4CCC4)CC2)O3)cc1F)N1CCC(O)CC1] | 105.2-106.9 | 481 | +++ | +++ |
| 223 | 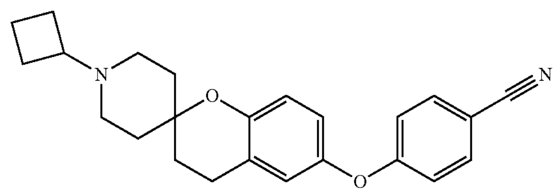 [SMILES: N#Cc1ccc(Oc2ccc3c(c2)CCC2(CCN(C4CCC4)CC2)O3)cc1] | 237-239 | 375 | +++ | +++ |
| 224 | 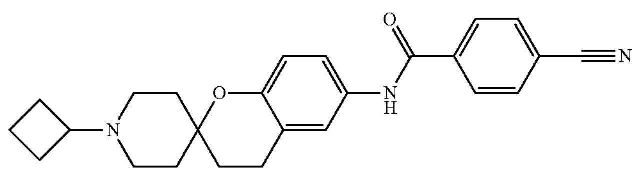 [SMILES: N#Cc1ccc(C(=O)Nc2ccc3c(c2)CCC2(CCN(C4CCC4)CC2)O3)cc1] | 186-188 | 402 | +++ | +++ |
| 225 | 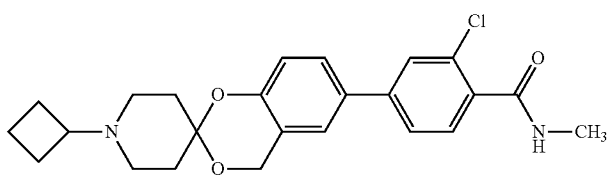 [SMILES: CNC(=O)c1ccc(-c2ccc3c(c2)COC2(CCN(C4CCC4)CC2)O3)cc1Cl] | 276-277 | 427 | +++ | +++ |
| 226 | 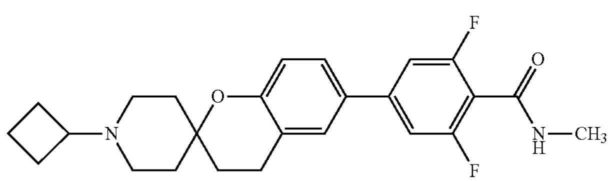 [SMILES: CNC(=O)c1c(F)cc(-c2ccc3c(c2)CCC2(CCN(C4CCC4)CC2)O3)cc1F] | 110-112 | 427 | +++ | +++ |
| 227 | 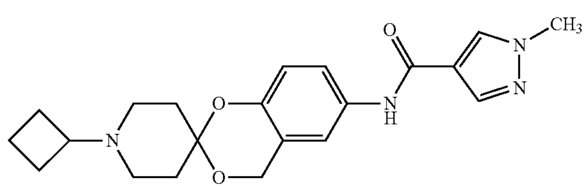 [SMILES: Cn1cc(C(=O)Nc2ccc3c(c2)COC2(CCN(C4CCC4)CC2)O3)cn1] | 227-228 | 382 | +++ | ++ |
| 228 | 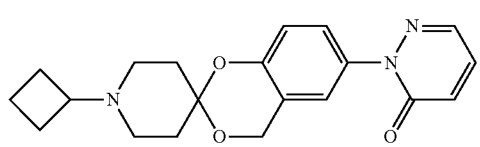 [SMILES: O=c1cccnn1-c1ccc2c(c1)COC1(CCN(C3CCC3)CC1)O2] | 173-174 | 354 | ++ | ++ |
| 229 | 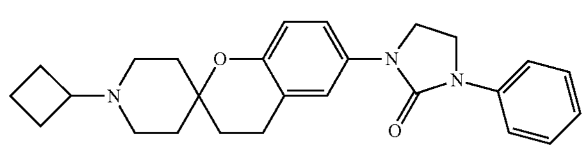 [SMILES: O=C1N(c2ccccc2)CCN1c1ccc2c(c1)CCC1(CCN(C3CCC3)CC1)O2] | 182-185 | 418 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 230 | 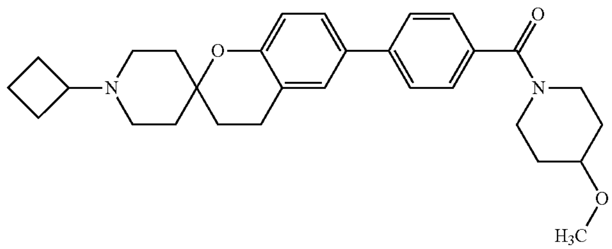 | 66.8-67.5 | 475 | +++ | +++ |
| 231 | 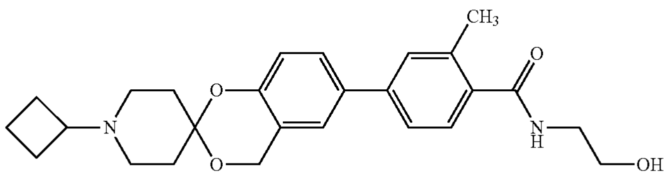 [SMILES: Cc1cc(-c2ccc3c(c2)COC2(CCN(C4CCC4)CC2)O3)ccc1C(=O)NCCO] | 168.5-169.9 | 437 | +++ | +++ |
| 232 | 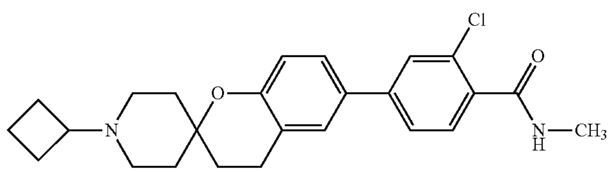 [SMILES: CNC(=O)c1ccc(-c2ccc3c(c2)CCC2(CCN(C4CCC4)CC2)O3)cc1Cl] | 144.2 | 425 | +++ | +++ |
| 233 | 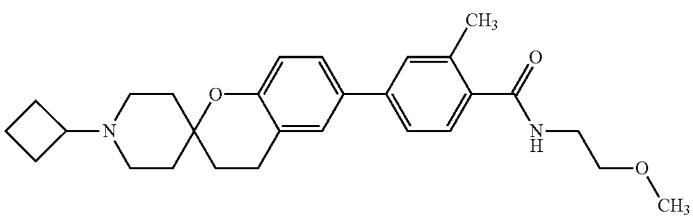 [SMILES: COCCNC(=O)c1ccc(-c2ccc3c(c2)CCC2(CCN(C4CCC4)CC2)O3)cc1C] | 59.8-60.9 | 449 | +++ | +++ |
| 234 | 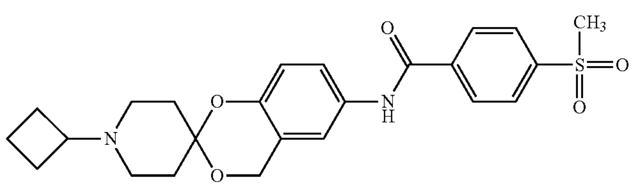 [SMILES: CS(=O)(=O)c1ccc(C(=O)Nc2ccc3c(c2)COC2(CCN(C4CCC4)CC2)O3)cc1] | 280-282 | 494 | +++ | +++ |
| 235 | 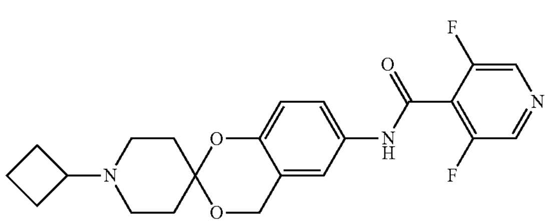 [SMILES: O=C(Nc1ccc2c(c1)COC1(CCN(C3CCC3)CC1)O2)c1c(F)cncc1F] | 192-193 | 415 | +++ | +++ |
| 236 | 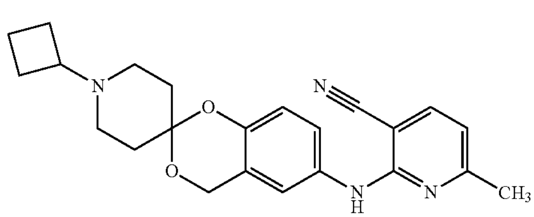 [SMILES: Cc1ccc(C#N)c(Nc2ccc3c(c2)COC2(CCN(C4CCC4)CC2)O3)n1] | 56-58 | 391 | +++ | +++ |

TABLE B-continued

| Example | Structure | MP (°C.) | MS (ESI+) (M + H) | hum H3 binding Ki (nM) | rat H3 binding Ki (nM) |
|---|---|---|---|---|---|
| 237 | 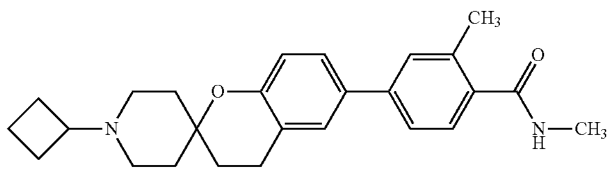 [SMILES: CNC(=O)c1ccc(-c2ccc3c(c2)CCC2(CCN(C4CCC4)CC2)O3)cc1C] | 94.7-95.6 | 405 | +++ | +++ |
| 238 | 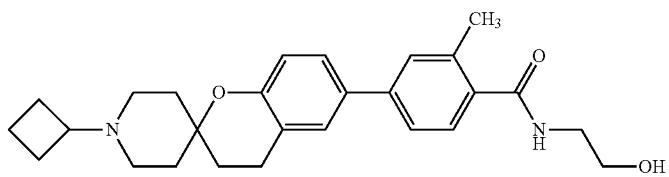 | 78.5-79.8 | 435 | +++ | +++ |
| 239 | 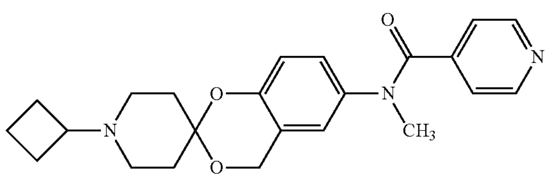 [SMILES: CN(C(=O)c1ccncc1)c1ccc2c(c1)COC1(CCN(C3CCC3)CC1)O2] | 53-55 | 494 | +++ | ++ |
| 240 | 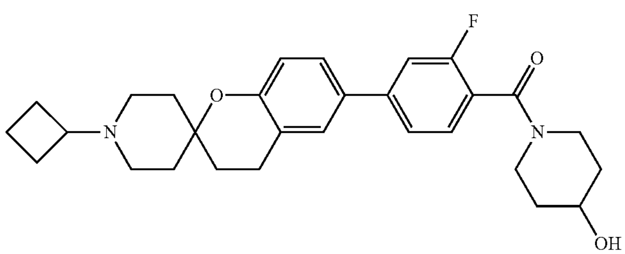 [SMILES: O=C(c1ccc(-c2ccc3c(c2)CCC2(CCN(C4CCC4)CC2)O3)cc1F)N1CCC(O)CC1] | 102.8-104.6 | 479 | +++ | +++ |
| 241 | 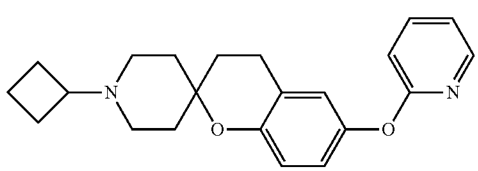 [SMILES: c1ccc(Oc2ccc3c(c2)CCC2(CCN(C4CCC4)CC2)O3)nc1] | 232-234 | 351 | +++ | +++ |
| 242 | 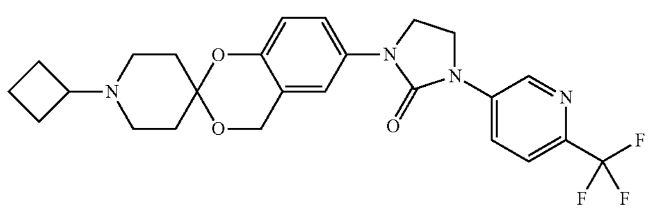 [SMILES: O=C1N(c2ccc(C(F)(F)F)nc2)CCN1c1ccc2c(c1)COC1(CCN(C3CCC3)CC1)O2] | 222-224 | 489 | +++ | +++ |
| 243 | 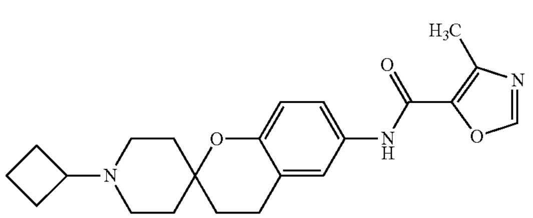 [SMILES: Cc1ncoc1C(=O)Nc1ccc2c(c1)CCC1(CCN(C3CCC3)CC1)O2] | 169-171 | 382 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 244 | 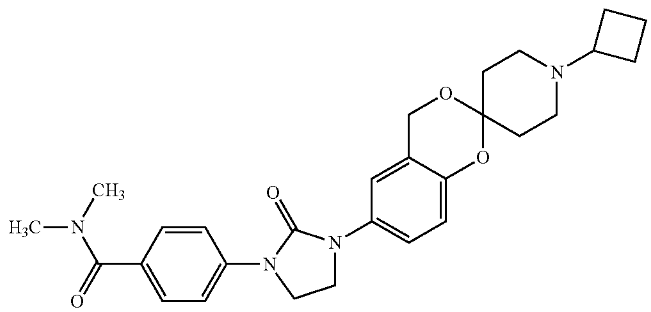 [SMILES: CN(C)C(=O)c1ccc(N2CCN(c3ccc4c(c3)COC3(CCN(C5CCC5)CC3)O4)C2=O)cc1] | 243-245 | 491 | +++ | +++ |
| 245 | 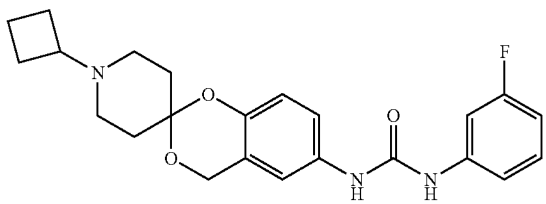 [SMILES: O=C(Nc1cccc(F)c1)Nc1ccc2c(c1)COC1(CCN(C3CCC3)CC1)O2] | 227-228 | 412 | +++ | +++ |
| 246 | 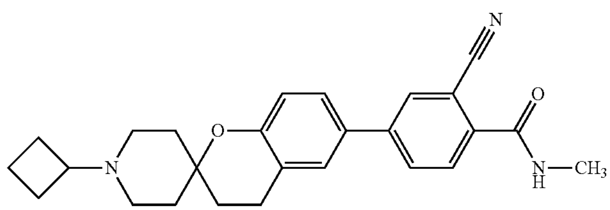 [SMILES: CNC(=O)c1ccc(-c2ccc3c(c2)CCC2(CCN(C4CCC4)CC2)O3)cc1C#N] | 80-82 | 416 | +++ | +++ |
| 247 | 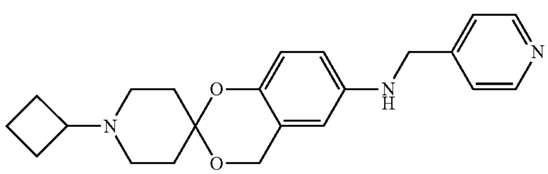 [SMILES: c1cc(CNc2ccc3c(c2)COC2(CCN(C4CCC4)CC2)O3)ccn1] | 45-48 | 366 | +++ | +++ |
| 248 | 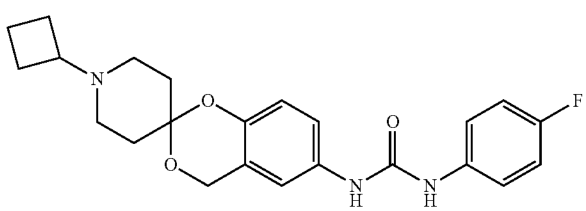 [SMILES: O=C(Nc1ccc(F)cc1)Nc1ccc2c(c1)COC1(CCN(C3CCC3)CC1)O2] | 237-238 | 412 | +++ | +++ |
| 249 | 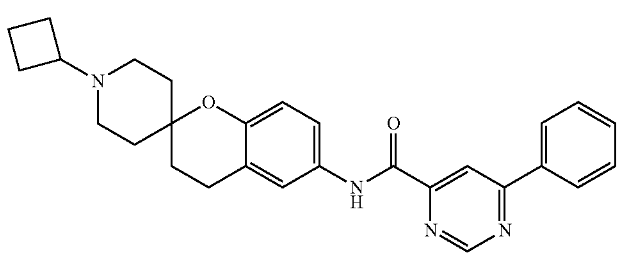 [SMILES: O=C(Nc1ccc2c(c1)CCC1(CCN(C3CCC3)CC1)O2)c1cc(-c2ccccc2)ncn1] | 153-155 | 455 | +++ | +++ |
| 250 | 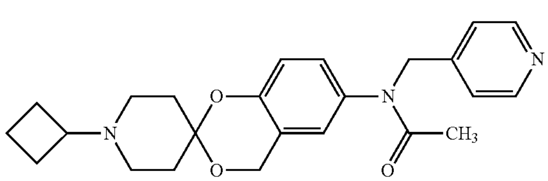 [SMILES: CC(=O)N(Cc1ccncc1)c1ccc2c(c1)COC1(CCN(C3CCC3)CC1)O2] | 63-65 | 408 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 251 | 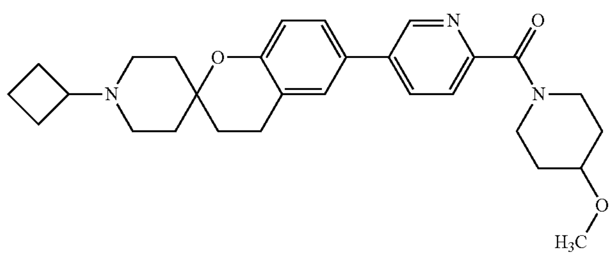 [SMILES: COC1CCN(C(=O)c2ccc(-c3ccc4c(c3)CCC3(CCN(C5CCC5)CC3)O4)cn2)CC1] | 150-152 | 476 | +++ | +++ |
| 252 | Chiral | 249-251 | 462 | +++ | +++ |
| 253 | 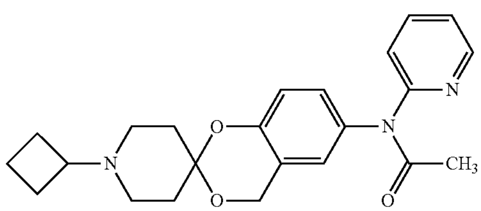 [SMILES: CC(=O)N(c1ccc2c(c1)COC1(CCN(C3CCC3)CC1)O2)c1ccccn1] | 53-55 | 394 | +++ | +++ |
| 254 | 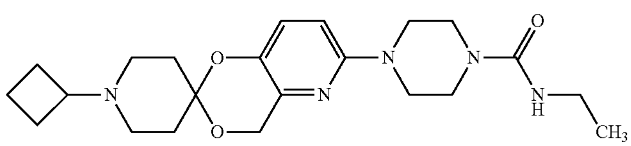 [SMILES: CCNC(=O)N1CCN(c2ccc3c(n2)COC2(CCN(C4CCC4)CC2)O3)CC1] | 122-124 | 416 | +++ | +++ |
| 255 | 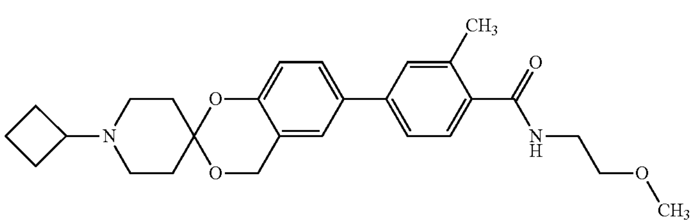 | 124.6-126.4 | 451 | +++ | +++ |
| 256 | 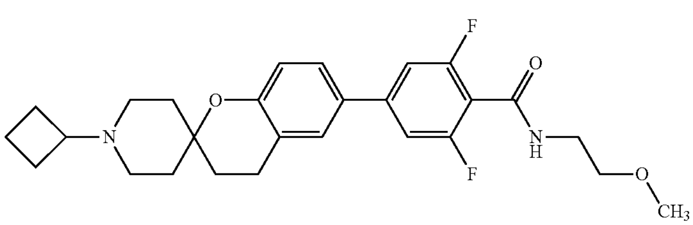 [SMILES: COCCNC(=O)c1c(F)cc(-c2ccc3c(c2)CCC2(CCN(C4CCC4)CC2)O3)cc1F] | 64.9-65.4 | 471 | +++ | +++ |
| 257 | 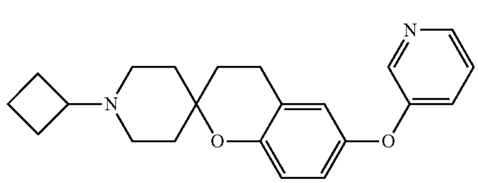 [SMILES: c1cncc(Oc2ccc3c(c2)CCC2(CCN(C4CCC4)CC2)O3)c1] | 255-257 | 351 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 258 | 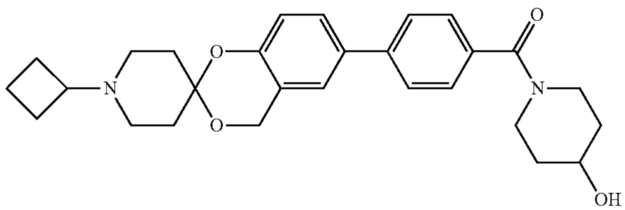 [SMILES: O=C(c1ccc(-c2ccc3c(c2)COC2(CCN(C4CCC4)CC2)O3)cc1)N1CCC(O)CC1] | 100.4-102.2 | 463 | +++ | +++ |
| 259 | 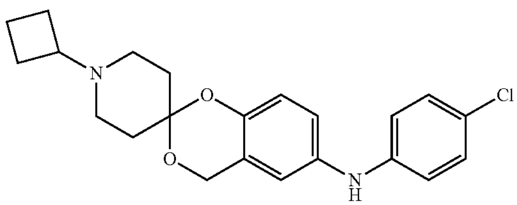 [SMILES: Clc1ccc(Nc2ccc3c(c2)COC2(CCN(C4CCC4)CC2)O3)cc1] | 234-235 | 385 | +++ | +++ |
| 260 | 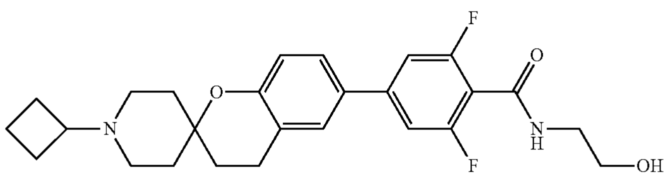 [SMILES: O=C(NCCO)c1c(F)cc(-c2ccc3c(c2)CCC2(CCN(C4CCC4)CC2)O3)cc1F] | 76.3-78.2 | 457 | +++ | +++ |
| 261 | 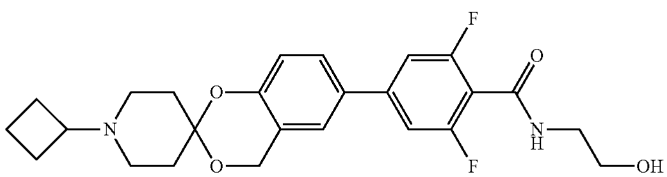 | 78.6-80.4 | 459 | +++ | +++ |
| 262 | 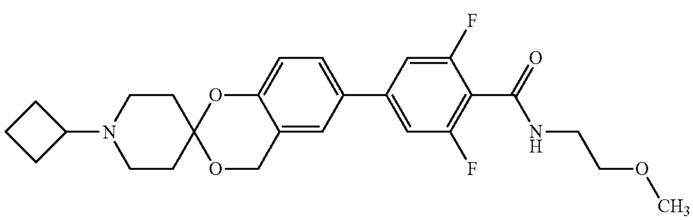 | 125.0-126.3 | 473 | +++ | +++ |
| 263 | 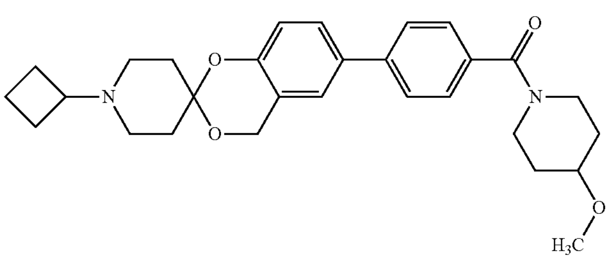 [SMILES: COC1CCN(C(=O)c2ccc(-c3ccc4c(c3)COC3(CCN(C5CCC5)CC3)O4)cc2)CC1] | 94-96 | 477 | +++ | +++ |
| 264 | 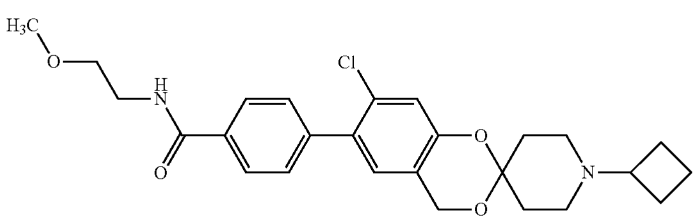 [SMILES: COCCNC(=O)c1ccc(-c2cc3c(cc2Cl)OC2(CCN(C4CCC4)CC2)OC3)cc1] | 49-51 | 471 | +++ | ++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 265 | 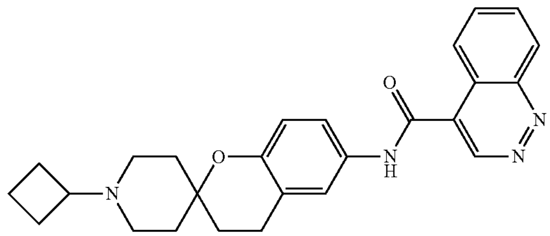 [SMILES: O=C(Nc1ccc2c(c1)CCC1(CCN(C3CCC3)CC1)O2)c1cnnc2ccccc12] | 233-235 | 429 | +++ | +++ |
| 266 | 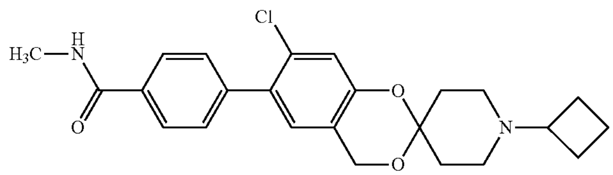 [SMILES: CNC(=O)c1ccc(-c2cc3c(cc2Cl)OC2(CCN(C4CCC4)CC2)OC3)cc1] | 95-97 | 427 | +++ | +++ |
| 267 | 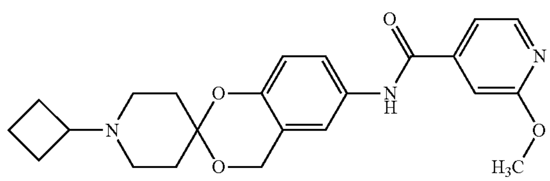 [SMILES: COc1cc(C(=O)Nc2ccc3c(c2)COC2(CCN(C4CCC4)CC2)O3)ccn1] | 175-176 | 410 | +++ | +++ |
| 268 | 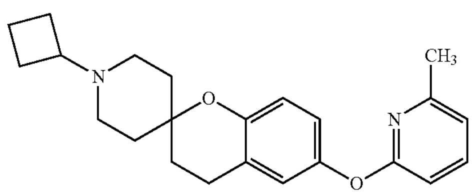 [SMILES: Cc1cccc(Oc2ccc3c(c2)CCC2(CCN(C4CCC4)CC2)O3)n1] | 213-215 | 365 | +++ | +++ |
| 269 | 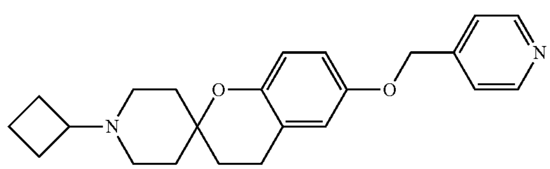 [SMILES: c1cc(COc2ccc3c(c2)CCC2(CCN(C4CCC4)CC2)O3)ccn1] | 233-235 | 365 | +++ | +++ |
| 270 | 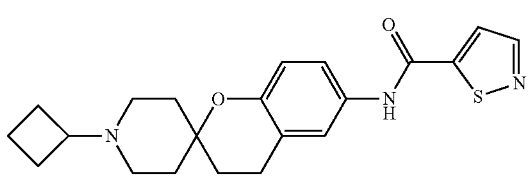 [SMILES: O=C(Nc1ccc2c(c1)CCC1(CCN(C3CCC3)CC1)O2)c1ccns1] | 109-111 | 384 | +++ | +++ |
| 271 | 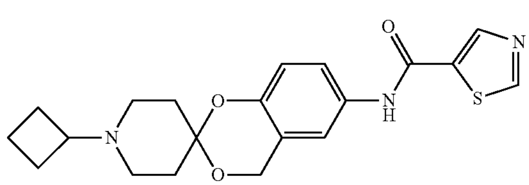 | 222-224 | 386 | +++ | +++ |
| 272 | 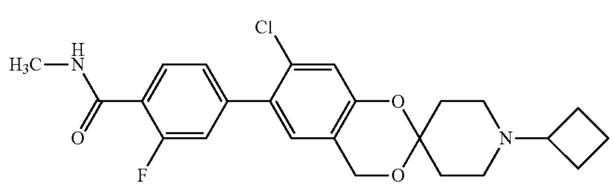 [SMILES: CNC(=O)c1ccc(-c2cc3c(cc2Cl)OC2(CCN(C4CCC4)CC2)OC3)cc1F] | 70-72 | 445 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 273 | 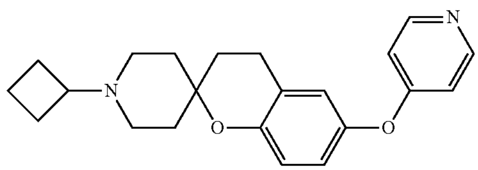 [SMILES: c1cc(Oc2ccc3c(c2)CCC2(CCN(C4CCC4)CC2)O3)ccn1] | 266-268 | 351 | +++ | +++ |
| 274 | 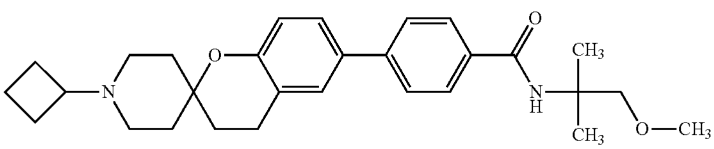 | 264-266 | 463 | +++ | +++ |
| 275 | 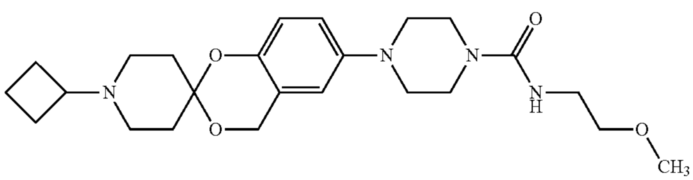 | 66.8-68.4 | 445 | +++ | +++ |
| 276 | 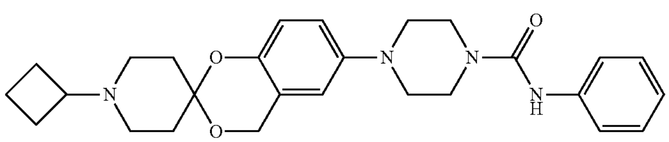 [SMILES: O=C(Nc1ccccc1)N1CCN(c2ccc3c(c2)COC2(CCN(C4CCC4)CC2)O3)CC1] | 194.6-195.8 | 463 | +++ | +++ |
| 277 | 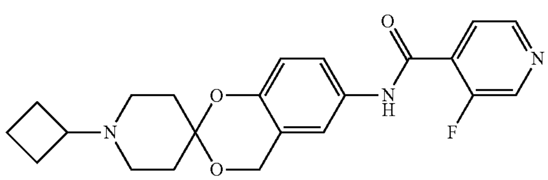 [SMILES: O=C(Nc1ccc2c(c1)COC1(CCN(C3CCC3)CC1)O2)c1ccncc1F] | 168-169 | 397 | +++ | +++ |
| 278 | 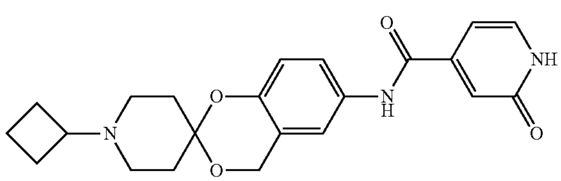 [SMILES: O=C(Nc1ccc2c(c1)COC1(CCN(C3CCC3)CC1)O2)c1cc[nH]c(=O)c1] | 260-262 | 396 | +++ | +++ |
| 279 | 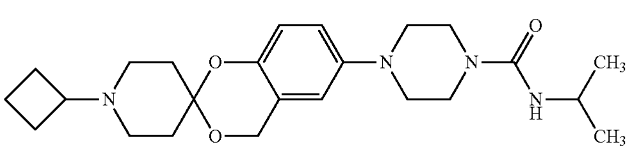 [SMILES: CC(C)NC(=O)N1CCN(c2ccc3c(c2)COC2(CCN(C4CCC4)CC2)O3)CC1] | 206.5-207.5 | 429 | +++ | +++ |
| 280 | 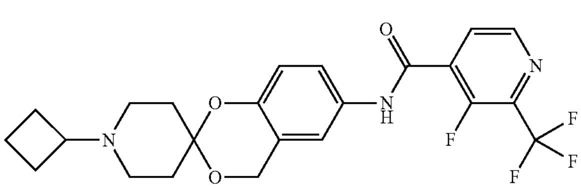 [SMILES: O=C(Nc1ccc2c(c1)COC1(CCN(C3CCC3)CC1)O2)c1ccnc(C(F)(F)F)c1F] | 186-188 | 365 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 281 | 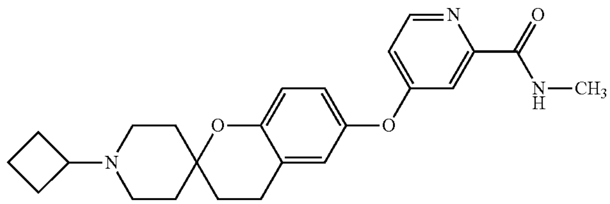 [SMILES: CNC(=O)c1cc(Oc2ccc3c(c2)CCC2(CCN(C4CCC4)CC2)O3)ccn1] | 255-257 | 408 | +++ | +++ |
| 282 | 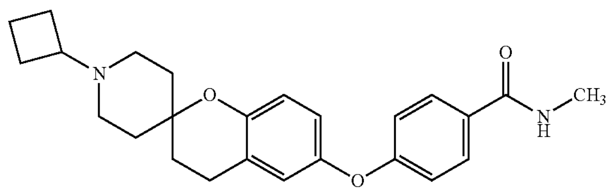 [SMILES: CNC(=O)c1ccc(Oc2ccc3c(c2)CCC2(CCN(C4CCC4)CC2)O3)cc1] | 179-181 | 407 | +++ | +++ |
| 283 | 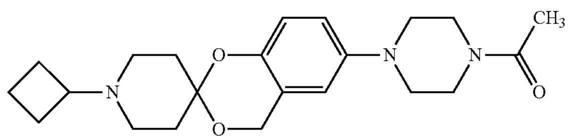 [SMILES: CC(=O)N1CCN(c2ccc3c(c2)COC2(CCN(C4CCC4)CC2)O3)CC1] | 60.8-62.3 | 386 | +++ | +++ |
| 284 | 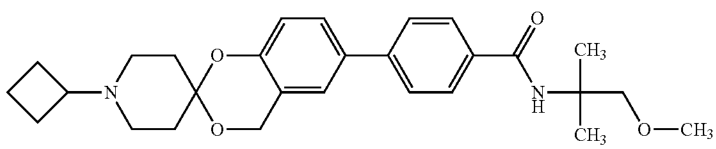 [SMILES: COCC(C)(C)NC(=O)c1ccc(-c2ccc3c(c2)COC2(CCN(C4CCC4)CC2)O3)cc1] | 138-140 | 465 | +++ | +++ |
| 285 | 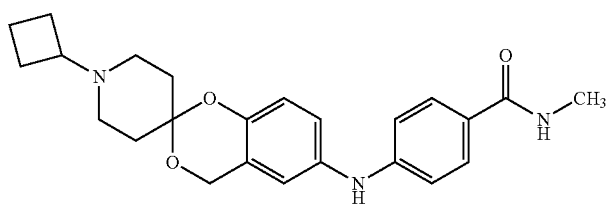 [SMILES: CNC(=O)c1ccc(Nc2ccc3c(c2)COC2(CCN(C4CCC4)CC2)O3)cc1] | 206-208 | 408 | +++ | +++ |
| 286 | 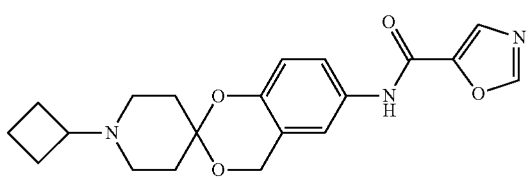 [SMILES: O=C(Nc1ccc2c(c1)COC1(CCN(C3CCC3)CC1)O2)c1cnco1] | 175-177 | 370 | +++ | +++ |
| 287 | 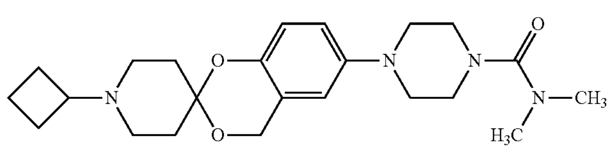 [SMILES: CN(C)C(=O)N1CCN(c2ccc3c(c2)COC2(CCN(C4CCC4)CC2)O3)CC1] | 153-155 | 415 | +++ | +++ |
| 288 | 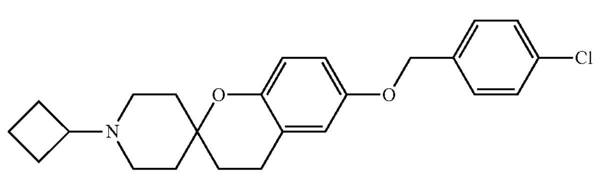 [SMILES: Clc1ccc(COc2ccc3c(c2)CCC2(CCN(C4CCC4)CC2)O3)cc1] | 115-116 | 398 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 289 | 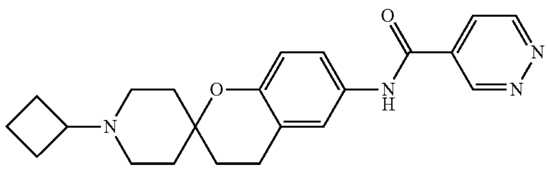 | 213-215 | 379 | +++ | +++ |
| 290 | 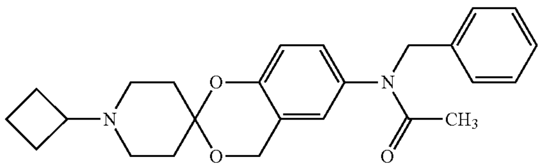 [SMILES: CC(=O)N(Cc1ccccc1)c1ccc2c(c1)COC1(CCN(C3CCC3)CC1)O2] | 115-117 | 407 | +++ | +++ |
| 291 | 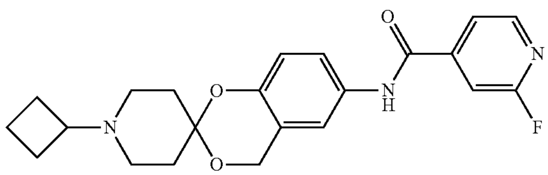 [SMILES: O=C(Nc1ccc2c(c1)COC1(CCN(C3CCC3)CC1)O2)c1ccnc(F)c1] | 187-188 | 397 | +++ | +++ |
| 292 | 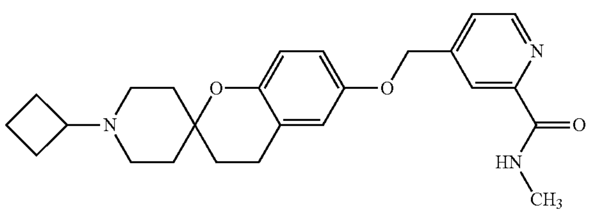 [SMILES: CNC(=O)c1cc(COc2ccc3c(c2)CCC2(CCN(C4CCC4)CC2)O3)ccn1] | 141-143 | 422 | +++ | +++ |
| 293 | 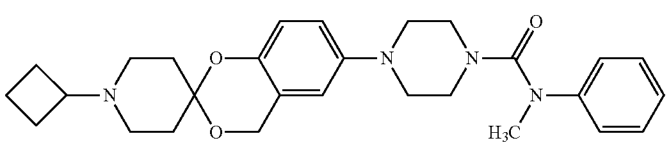 [SMILES: CN(C(=O)N1CCN(c2ccc3c(c2)COC2(CCN(C4CCC4)CC2)O3)CC1)c1ccccc1] | 107-110 | 477 | +++ | +++ |
| 294 | 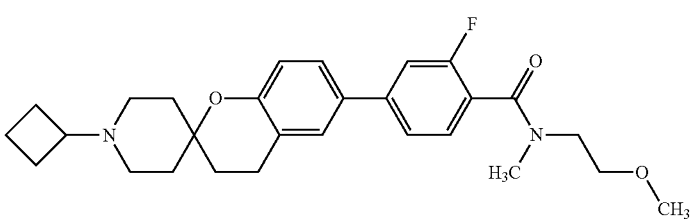 [SMILES: COCCN(C)C(=O)c1ccc(-c2ccc3c(c2)CCC2(CCN(C4CCC4)CC2)O3)cc1F] | NA | 467 | +++ | +++ |
| 295 | 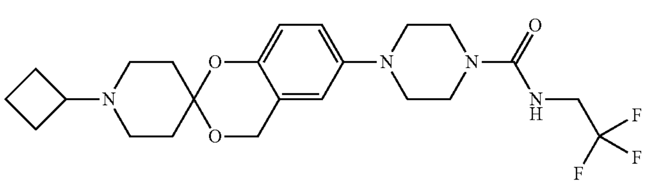 [SMILES: O=C(NCC(F)(F)F)N1CCN(c2ccc3c(c2)COC2(CCN(C4CCC4)CC2)O3)CC1] | 182.5-183.5 | 469 | +++ | +++ |
| 296 | 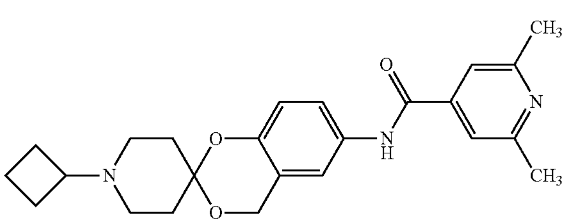 [SMILES: Cc1cc(C(=O)Nc2ccc3c(c2)COC2(CCN(C4CCC4)CC2)O3)cc(C)n1] | 191-193 | 408 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 297 | 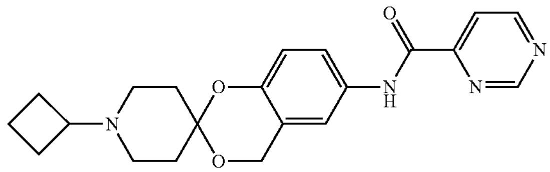 [SMILES: O=C(Nc1ccc2c(c1)COC1(CCN(C3CCC3)CC1)O2)c1ccncn1] | 198-199 | 381 | +++ | +++ |
| 298 | 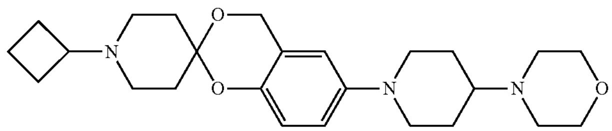 [SMILES: c1cc2c(cc1N1CCC(N3CCOCC3)CC1)COC1(CCN(C3CCC3)CC1)O2] | 142.4-144.3 | 428 | +++ | +++ |
| 299 | 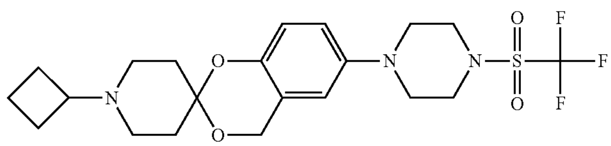 [SMILES: O=S(=O)(N1CCN(c2ccc3c(c2)COC2(CCN(C4CCC4)CC2)O3)CC1)C(F)(F)F] | 154.6-156.4 | 476 | +++ | +++ |
| 300 | 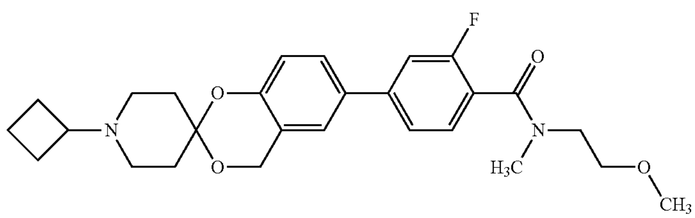 [SMILES: COCCN(C)C(=O)c1ccc(-c2ccc3c(c2)COC2(CCN(C4CCC4)CC2)O3)cc1F] | NA | 469 | +++ | +++ |
| 301 | 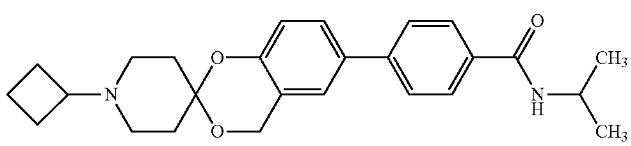 [SMILES: CC(C)NC(=O)c1ccc(-c2ccc3c(c2)COC2(CCN(C4CCC4)CC2)O3)cc1] | 221-222 | 421 | +++ | +++ |
| 302 | 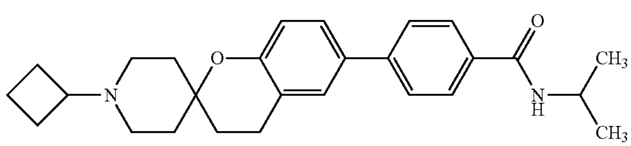 | 191-192 | 419 | +++ | +++ |
| 303 | 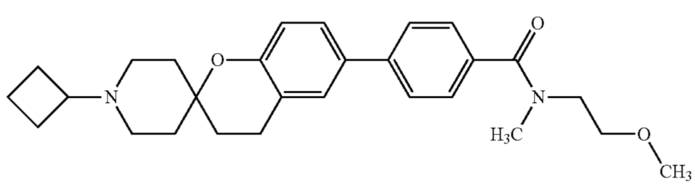 | 225-227 | 449 | +++ | +++ |
| 304 | 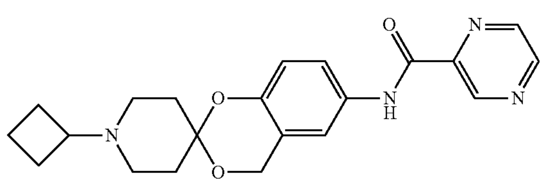 | 173-175 | 381 | +++ | +++ |
| 305 | 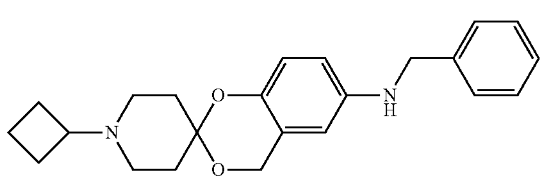 [SMILES: c1ccc(CNc2ccc3c(c2)COC2(CCN(C4CCC4)CC2)O3)cc1] | 85-87 | 365 | +++ | +++ |

TABLE B-continued

| Example | Structure | MP (°C.) | MS (ESI+) (M + H) | hum H3 binding Ki (nM) | rat H3 binding Ki (nM) |
|---|---|---|---|---|---|
| 306 | 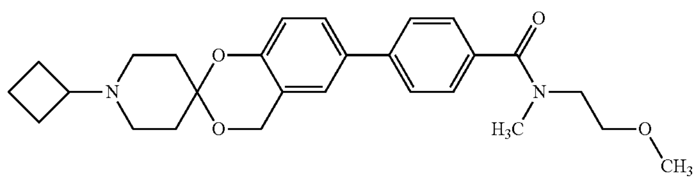 | 232-234 | 451 | +++ | +++ |
| 307 | 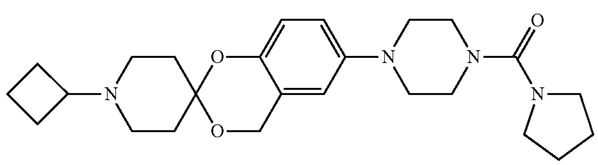 [SMILES: O=C(N1CCCC1)N1CCN(c2ccc3c(c2)COC2(CCN(C4CCC4)CC2)O3)CC1] | 132-135 | 441 | +++ | +++ |
| 308 | 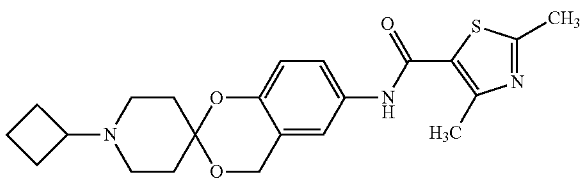 [SMILES: Cc1nc(C)c(C(=O)Nc2ccc3c(c2)COC2(CCN(C4CCC4)CC2)O3)s1] | 174-175 | 414 | +++ | +++ |
| 309 | 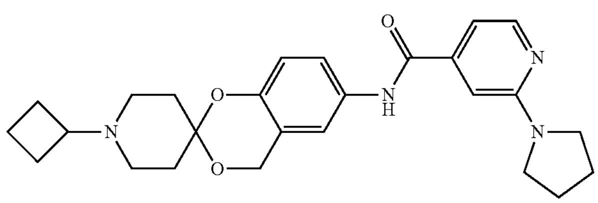 [SMILES: O=C(Nc1ccc2c(c1)COC1(CCN(C3CCC3)CC1)O2)c1ccnc(N2CCCC2)c1] | 234-236 | 449 | +++ | +++ |
| 310 | 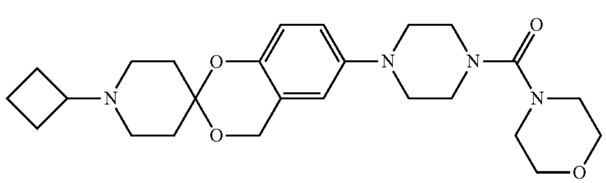 [SMILES: O=C(N1CCOCC1)N1CCN(c2ccc3c(c2)COC2(CCN(C4CCC4)CC2)O3)CC1] | 174-176 | 457 | +++ | +++ |
| 311 | 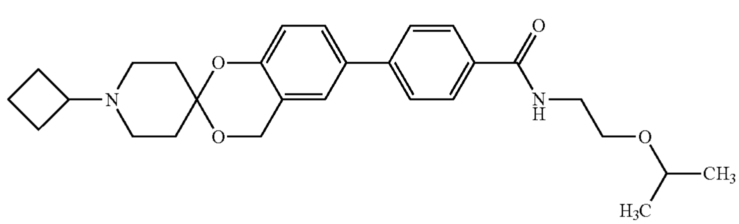 | 155.5-157.3 | 465 | +++ | +++ |
| 312 | 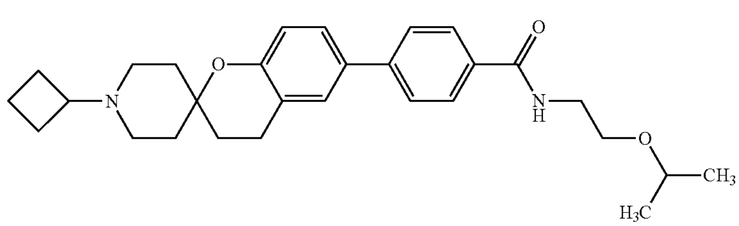 [SMILES: CC(C)OCCNC(=O)c1ccc(-c2ccc3c(c2)CCC2(CCN(C4CCC4)CC2)O3)cc1] | 135-137 | 463 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 313 | 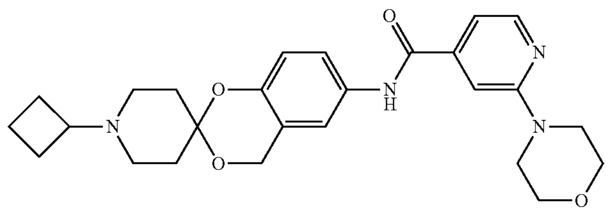 [SMILES: O=C(Nc1ccc2c(c1)COC1(CCN(C3CCC3)CC1)O2)c1ccnc(N2CCOCC2)c1] | 205-207 | 465 | +++ | +++ |
| 314 | 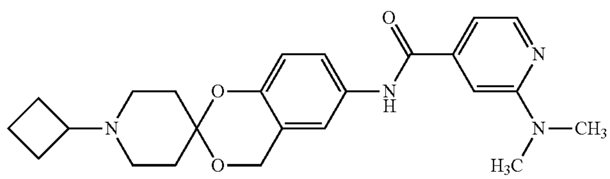 [SMILES: CN(C)c1cc(C(=O)Nc2ccc3c(c2)COC2(CCN(C4CCC4)CC2)O3)ccn1] | 213-215 | 423 | +++ | +++ |
| 315 | 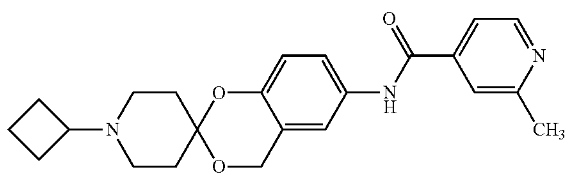 [SMILES: Cc1cc(C(=O)Nc2ccc3c(c2)COC2(CCN(C4CCC4)CC2)O3)ccn1] | 184-185 | 394 | +++ | +++ |
| 316 | 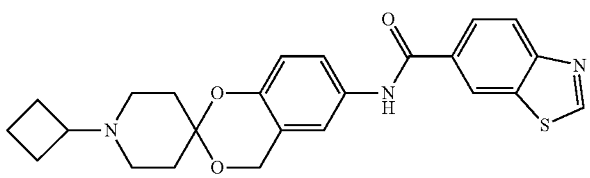 [SMILES: O=C(Nc1ccc2c(c1)COC1(CCN(C3CCC3)CC1)O2)c1ccc2ncsc2c1] | 232-234 | 436 | +++ | +++ |
| 317 | 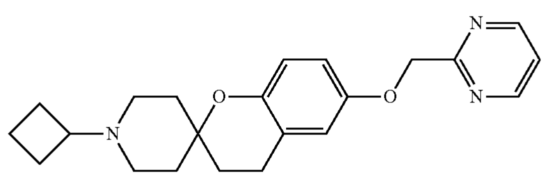 [SMILES: c1cnc(COc2ccc3c(c2)CCC2(CCN(C4CCC4)CC2)O3)nc1] | NA | 366 | +++ | +++ |
| 318 | 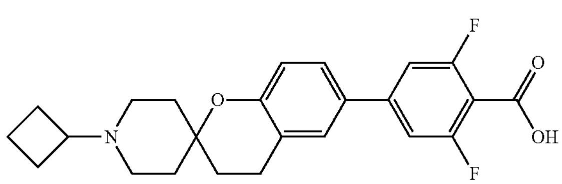 [SMILES: O=C(O)c1c(F)cc(-c2ccc3c(c2)CCC2(CCN(C4CCC4)CC2)O3)cc1F] | NA | 414 | +++ | +++ |
| 319 | 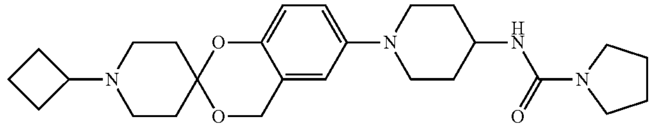 [SMILES: O=C(NC1CCN(c2ccc3c(c2)COC2(CCN(C4CCC4)CC2)O3)CC1)N1CCCC1] | 210.2-212.6 | 455 | +++ | +++ |
| 320 | 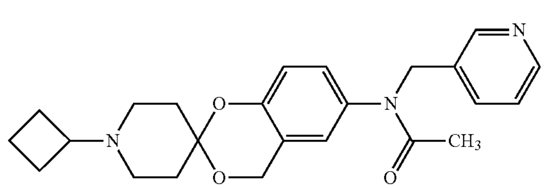 [SMILES: CC(=O)N(Cc1cccnc1)c1ccc2c(c1)COC1(CCN(C3CCC3)CC1)O2] | 57-59 | 408 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 321 | 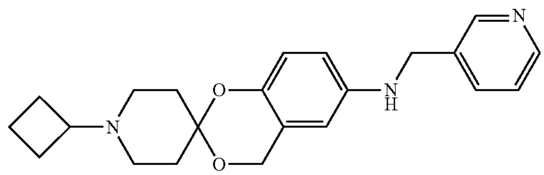 [SMILES: c1cncc(CNc2ccc3c(c2)COC2(CCN(C4CCC4)CC2)O3)c1] | 117-118 | 366 | +++ | +++ |
| 322 | 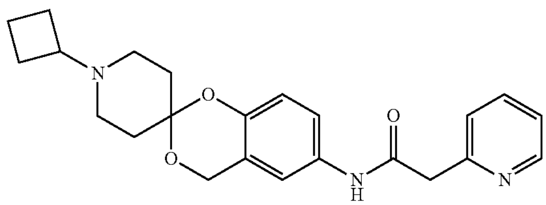 [SMILES: O=C(Cc1ccccn1)Nc1ccc2c(c1)COC1(CCN(C3CCC3)CC1)O2] | 166-168 | 394 | +++ | +++ |
| 323 | 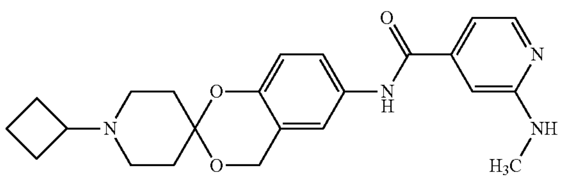 [SMILES: CNc1cc(C(=O)Nc2ccc3c(c2)COC2(CCN(C4CCC4)CC2)O3)ccn1] | 207-208 | 409 | +++ | +++ |
| 324 | 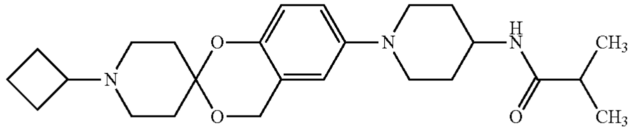 | 208.4-210.6 | 428 | +++ | +++ |
| 325 | 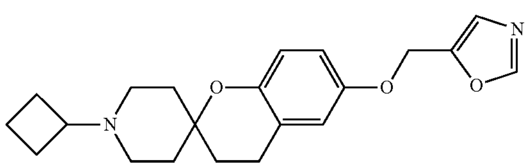 [SMILES: c1ncc(COc2ccc3c(c2)CCC2(CCN(C4CCC4)CC2)O3)o1] | 45-47 | 355 | +++ | +++ |
| 326 | 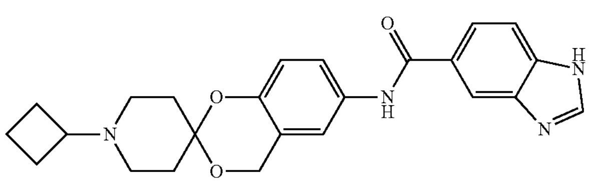 [SMILES: O=C(Nc1ccc2c(c1)COC1(CCN(C3CCC3)CC1)O2)c1ccc2[nH]cnc2c1] | 235-237 | 419 | +++ | +++ |
| 327 | 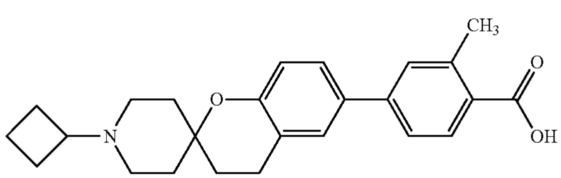 [SMILES: Cc1cc(-c2ccc3c(c2)CCC2(CCN(C4CCC4)CC2)O3)ccc1C(=O)O] | NA | 392 | +++ | ++ |
| 328 | 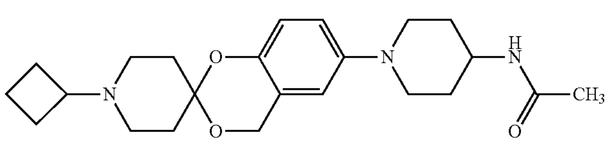 [SMILES: CC(=O)NC1CCN(c2ccc3c(c2)COC2(CCN(C4CCC4)CC2)O3)CC1] | 190.8-192.0 | 400 | +++ | +++ |
| 329 | 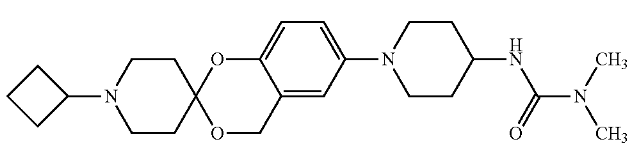 | 193.0-195.2 | 429 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 330 | 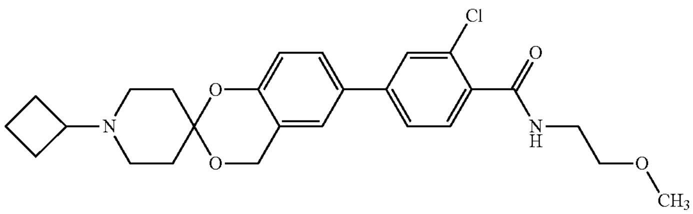 [SMILES: COCCNC(=O)c1ccc(-c2ccc3c(c2)COC2(CCN(C4CCC4)CC2)O3)cc1Cl] | 234-235 | 472 | +++ | +++ |
| 331 | 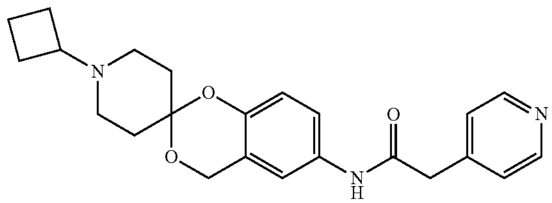 [SMILES: O=C(Cc1ccncc1)Nc1ccc2c(c1)COC1(CCN(C3CCC3)CC1)O2] | 170-172 | 394 | +++ | +++ |
| 332 | 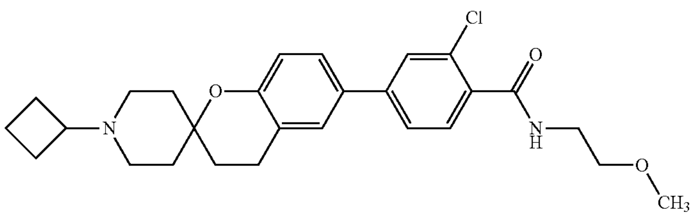 | 231-232 | 470 | +++ | +++ |
| 333 | 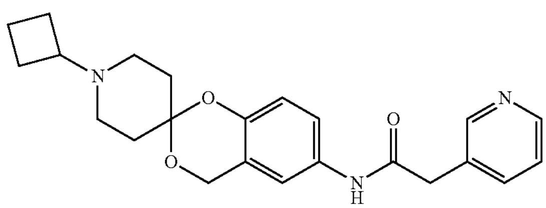 [SMILES: O=C(Cc1cccnc1)Nc1ccc2c(c1)COC1(CCN(C3CCC3)CC1)O2] | 167-169 | 394 | +++ | +++ |
| 334 | 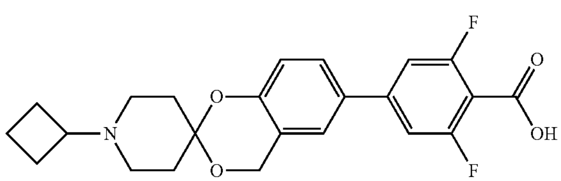 | NA | 416 | ++ | >300 nM |
| 335 | 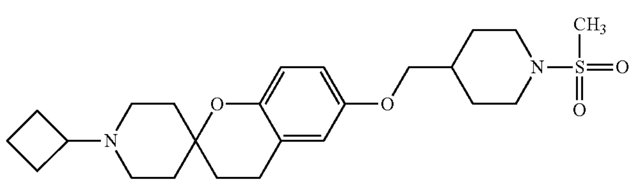 [SMILES: CS(=O)(=O)N1CCC(COc2ccc3c(c2)CCC2(CCN(C4CCC4)CC2)O3)CC1] | 159-161 | 449 | +++ | +++ |
| 336 | 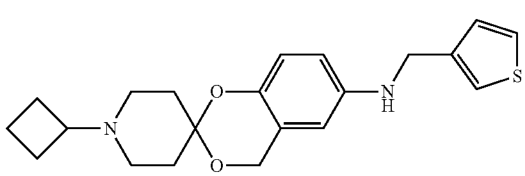 [SMILES: c1cc(CNc2ccc3c(c2)COC2(CCN(C4CCC4)CC2)O3)cs1] | 101-102 | 371 | +++ | +++ |

TABLE B-continued
| Example | Structure | MP (° C.) | MS (ESI+) (M + H) | hum H3 binding Ki (nM) | rat H3 binding Ki (nM) |
|---|---|---|---|---|---|
| 337 | 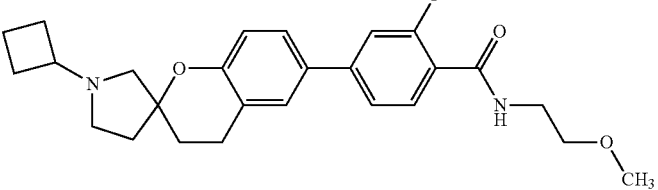 | 58-60 | 439 | +++ | +++ |
| 338 | 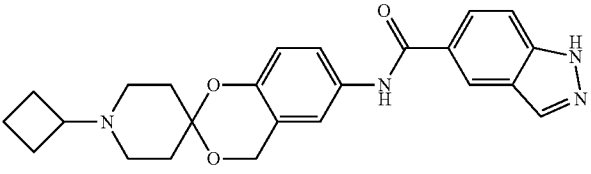 [SMILES: O=C(Nc1ccc2c(c1)COC1(CCN(C3CCC3)CC1)O2)c1ccc2[nH]ncc2c1] | 249-250 | 419 | +++ | +++ |
| 339 | 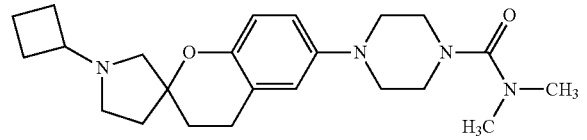 [SMILES: CN(C)C(=O)N1CCN(c2ccc3c(c2)CCC2(CCN(C4CCC4)C2)O3)CC1] | 231-233 | 399 | +++ | +++ |
| 340 | 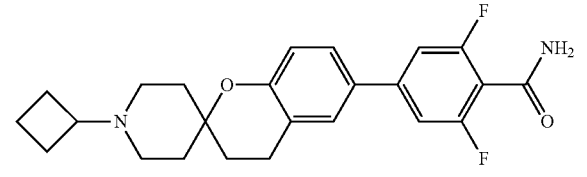 | NA | 413 | +++ | +++ |
| 341 | 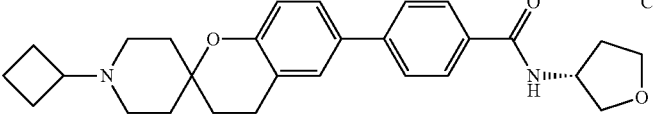 Chiral | 194-195 | 447 | +++ | +++ |
| 342 | 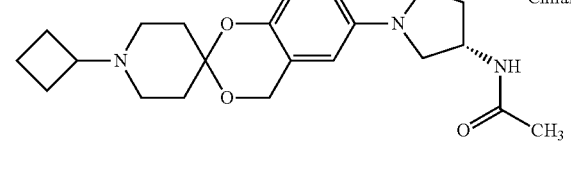 Chiral | 77.9-80.0 | 386 | +++ | +++ |
| 343 | 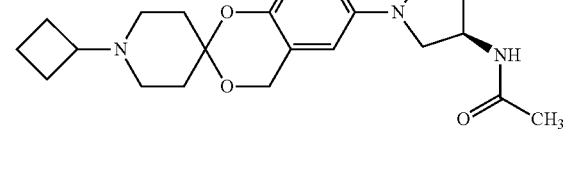 Chiral | 77.9-79.9 | 386 | +++ | +++ |
| 344 | 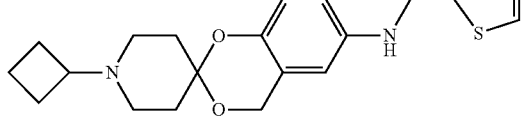 | 112-113 | 371 | +++ | +++ |

TABLE B-continued
| Example | Structure | | MP (° C.) | MS (ESI+) (M + H) | hum H3 binding Ki (nM) | rat H3 binding Ki (nM) |
|---|---|---|---|---|---|---|
| 345 | 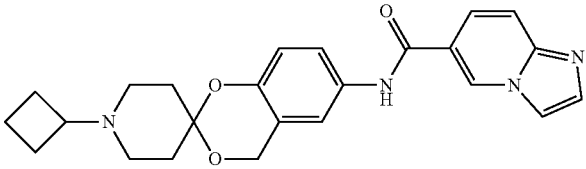 [SMILES: O=C(Nc1ccc2c(c1)COC1(CCN(C3CCC3)CC1)O2)c1ccc2nccn2c1] | | 254-255 | 419 | +++ | +++ |
| 346 | 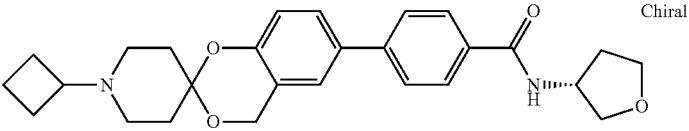 [SMILES: O=C(N[C@@H]1CCOC1)c1ccc(-c2ccc3c(c2)COC2(CCN(C4CCC4)CC2)O3)cc1] | Chiral | 198-199 | 449 | +++ | +++ |
| 347 | 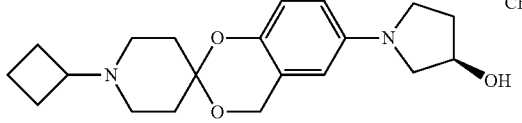 | Chiral | 70.2-72.2 | 345 | +++ | +++ |
| 348 | 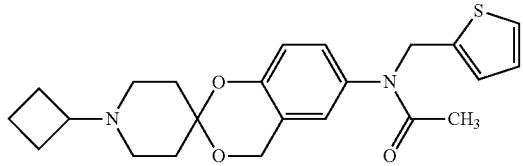 [SMILES: CC(=O)N(Cc1cccs1)c1ccc2c(c1)COC1(CCN(C3CCC3)CC1)O2] | | 119-120 | 413 | +++ | +++ |
| 349 | 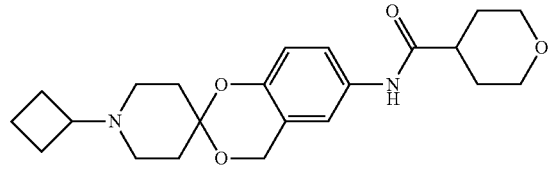 | | 228-229 | 387 | +++ | +++ |
| 350 | 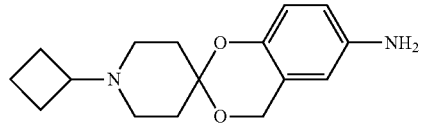 [SMILES: Nc1ccc2c(c1)COC1(CCN(C3CCC3)CC1)O2] | | 160-162 | 275 | ++ | ++ |
| 351 | 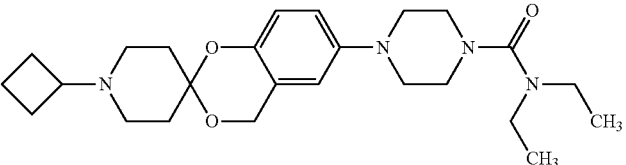 | | 113.0-116.1 | 443 | +++ | +++ |
| 352 | 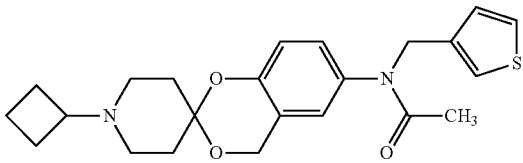 [SMILES: CC(=O)N(Cc1ccsc1)c1ccc2c(c1)COC1(CCN(C3CCC3)CC1)O2] | | 101-102 | 413 | +++ | +++ |
| 353 | 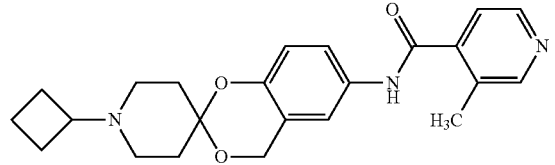 | | 209-210 | 394 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 354 | Chiral | 72.6-74.9 | 345 | +++ | +++ |
| 355 | 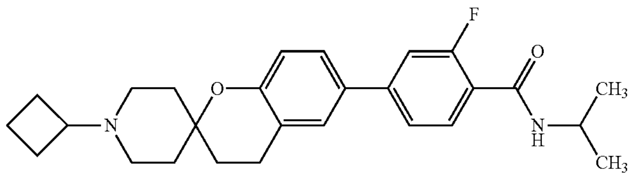 | 131-132 | 437 | +++ | +++ |
| 356 | 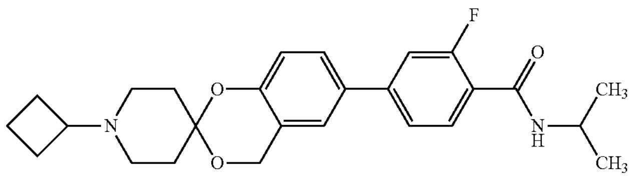 [SMILES: CC(C)NC(=O)c1ccc(-c2ccc3c(c2)COC2(CCN(C4CCC4)CC2)O3)cc1F] | 146.5-148 | 439 | +++ | +++ |
| 357 | 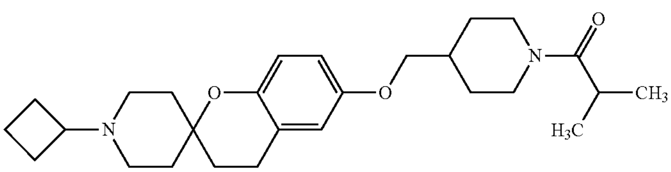 | 130-132 | 441 | +++ | +++ |
| 358 | 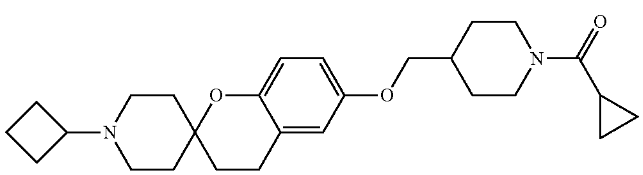 [SMILES: O=C(C1CC1)N1CCC(COc2ccc3c(c2)CCC2(CCN(C4CCC4)CC2)O3)CC1] | 128-130 | 439 | +++ | +++ |
| 359 | 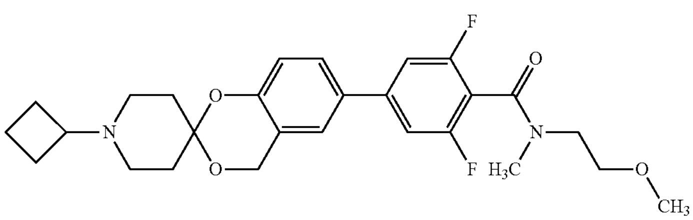 | 78-80 | 487 | +++ | +++ |
| 360 | 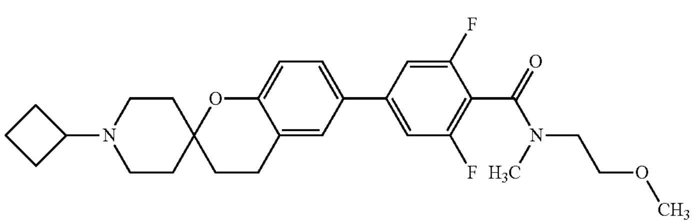 [SMILES: COCCN(C)C(=O)c1c(F)cc(-c2ccc3c(c2)CCC2(CCN(C4CCC4)CC2)O3)cc1F] | 100-102 | 485 | +++ | +++ |
| 361 | 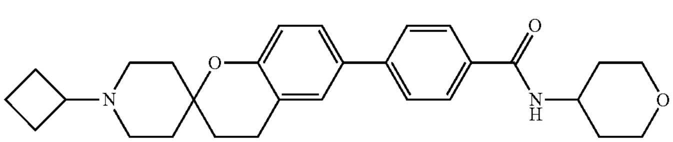 [SMILES: O=C(NC1CCOCC1)c1ccc(-c2ccc3c(c2)CCC2(CCN(C4CCC4)CC2)O3)cc1] | 205-207 | 461 | +++ | +++ |

TABLE B-continued

| Example | Structure | MP (° C.) | MS (ESI+) (M + H) | hum H3 binding Ki (nM) | rat H3 binding Ki (nM) |
|---|---|---|---|---|---|
| 362 | 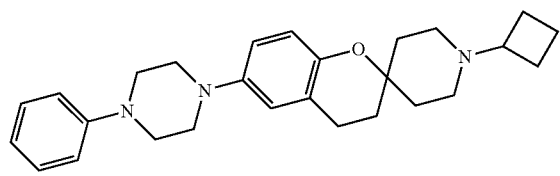 [SMILES: c1ccc(N2CCN(c3ccc4c(c3)CCC3(CCN(C5CCC5)CC3)O4)CC2)cc1] | 216-218 | 463 | +++ | +++ |

General coupling procedure for R2 heterocycloalkyl amines.

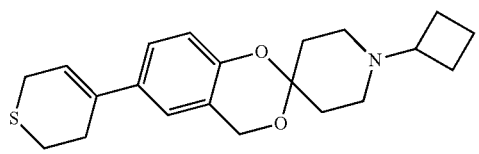

Example 363

Method A: A mixture of 8E (1'-cyclobutyl-6-bromo-3,4-dihydrospiro(chromene-2,4'-piperidine) (0.34 g, 1.0 mmol), Cs₂CO₃ (0.49 g, 1.5 eq.), Pd(OAc)₂ (0.02 g, 0.1 eq.) and 1-phenylpiperazine (0.49 g, 3.0 eq.) in o-xylene (8.0 mL) was degassed with N₂ for 2 min. Then 10% tributylphosphine in hexane (0.30 g, 0.15 eq.) was added. The reaction was heated to 120° C. for 12 h under N₂ (HPLC was used to monitor the reaction). The reaction mixture was cooled to rt, filtered through celite, washed with CH₂Cl₂, and concentrated. The crude material was diluted with CH₂Cl₂, washed with NaHCO₃ solution, NaCl solution, dried over Na₂SO4, and concentrated. Prep. TLC using 10% MeOH in CH₂Cl₂ with 0.5% iPrNH₂ followed by crystallization with MeOH-ether gave Example 363 (0.060 g): MS m/z 418 (M+H), mp: 173-5° C.

Method B: A mixture of 8E (0.34 g, 1.0 mmol), Cs₂CO₃ (0.49 g, 1.5 eq.), Pd(OAc)₂ (0.02 g, 0.1 eq.) and 1-phenylpiperazine (0.49 g, 3.0 eq.) 10% tributylphosphine in hexane (0.30 g, 0.15 eq.) in o-xylene (8.0 mL).

General procedure for R2 heterocycloalkyl

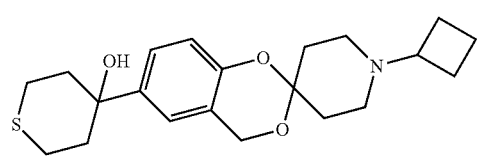 [SMILES: OC1(c2ccc3c(c2)COC2(CCN(C4CCC4)CC2)O3)CCSCC1]

Example 465

To 1C (1.00 g, 2.96 mmol) in ether (10 mL)/THF (40 mL) under N₂ at −78° C. was added 2.5 M n-BuLi (2.36 mL, 5.91 mmol) dropwise. After stirring for 45 min, tetrahydrothiopyran-4-one (0.687 g, 5.91 mmol) in THF (5 mL) was added, stirred for 1 h at −78° C., and quenched with water. The reaction was partitioned between DCM/water, washed with brine, dried over sodium sulfate, and concentrated. The product was purified using a single step column (3-5% methanol/DCM) and concentrated to give example 465 0.847 g (76%); mp: 174-176° C.; MS m/z 376 (M+H).

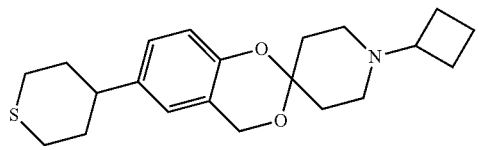 [SMILES: c1cc2c(cc1C1CCSCC1)COC1(CCN(C3CCC3)CC1)O2]

Example 466

To Example 465 in DCM (20 mL) was added TFA (3 mL) dropwise. After stirring 30 min at r.t., the mixture was concentrated. The product was partitioned between DCM/1N sodium carbonate, washed with water/brine, dried over sodium sulfate, and concentrated to give Example 466 0.770 g (95%); mp: 162-163° C.; MS m/z 358 (M+H).

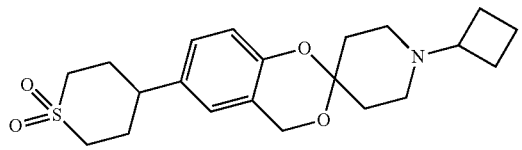 [SMILES: O=S1(=O)CCC(c2ccc3c(c2)COC2(CCN(C4CCC4)CC2)O3)CC1]

Example 480

To Example 466 (0.770 mg, 2.15 mmol) in methanol (5 mL)/DCM (10 mL) under an atomsphere of nitrogen was added 20% Pd(OH)₂/C, 50% wet (10:40:50, palladium hydroxide, carbon black, water) (0.302 g) and the reaction was hydrogenated on a Parr apparatus at 40 psi for 1 h and filtered through celite. The product was purified using a single step column (5% methanol/DCM) and recrystallized from DCM/ether to give Example 466 0.674 g (87%); mp: 153-155° C.; MS m/z 360 (M+H).

Example 489

To Example 480 (0.235 g, 0.654 mmol) in acetic acid (6 mL) at 0° C. was added 50% aq. hydrogen peroxide (1:1 hydrogen peroxide: water) (6.5 mL), warmed at r.t. overnight, and concentrated. The reaction was partitioned between dichloromethane/1N sodium carbonate, washed with water/brine, dried over sodium sulfate, and concentrated. The product was purified using Prep TLC plates (10% methanol/dichloromethane) and recrystallized from methanol/ether to obtain 0.049 g (19%); mp: 210-211° C.; MS m/z 392 (M+H).

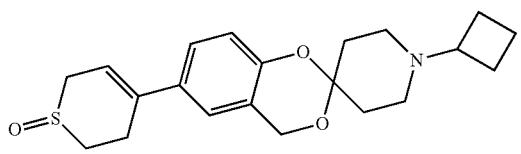 [SMILES: O=S1CC=C(c2ccc3c(c2)COC2(CCN(C4CCC4)CC2)O3)CC1]

Example 461

To Example 466 (0.473 g, 1.32 mmol) in DCM (10 mL) was added m-chlorobenzoic acid (0.52 g, 3.0 mmol) at 0° C. and warmed to r.t. for 1 h. The reaction was washed with 1N sodium carbonate/water/brine, dried over sodium sulfate, and concentrated. The product was purified using Prep TLC plates (10% methanol/DCM) and concentrated to obtain 0.065 g (13%); mp: 155-158° C.; MS m/z 374 (M+H).

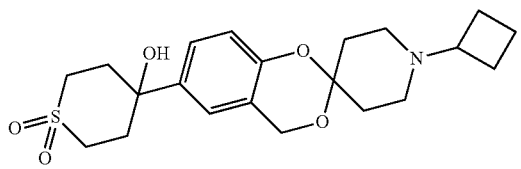 [SMILES: O=S1(=O)CCC(O)(c2ccc3c(c2)COC2(CCN(C4CCC4)CC2)O3)CC1]

Example 517

This compound was synthesized from Example 465 using conditions for Example 489. mp: 240-241° C.; MS m/z 408 (M+H).

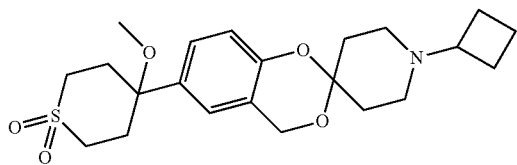 [SMILES: COC1(c2ccc3c(c2)COC2(CCN(C4CCC4)CC2)O3)CCS(=O)(=O)CC1]

Example 542

To Example 517 in DMF (2 mL) was added sodium hydride (60% dispersion mineral oil) (0.00842 g, 0.210 mmol), followed by methyl iodide (0.0179 mL, 0.287 mmol) and the reaction was heated at 65° C. for 1 h. The reaction was diluted with water, extracted with dichloromethane, washed with brine, dried over sodium sulfate, and concentrated. The product was purified using Prep TLC plates (5% methanol/DCM), concentrated, and triturated with ether/hexanes to obtain 0.041 g (51%); mp: 199-201° C.; MS m/z 422 (M+H).

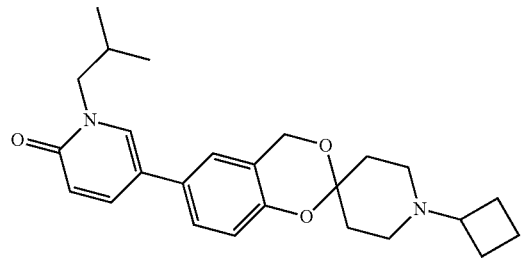 [SMILES: CC(C)Cn1cc(-c2ccc3c(c2)COC2(CCN(C4CCC4)CC2)O3)ccc1=O]

Example 562

To a round-bottom flask was added 5-bromo-1-isobutyl-1H-pyridin-2-one (266 mg, 1.16 mmol), 4-[6-(1'-cyclobutyl-4H-spiro(1,3-benzodioxine-2,4'-piperidinyl)]-4,4,5,5-tetramethyl-1,3,2-dioxaborolane (468 mg, 1.21 mmol), tetrakis (triphenyl-phosphine)palladium(0) (70 mg, 0.06 mmol), potassium carbonate (479 mg, 3.47 mmol), 1,2-dimethoxyethane (8 mL), and water (8 mL). The reaction mixture was heated at reflux for 18 h, cooled to rt and diluted with $CH_2Cl_2$ (100 mL). It was washed with water (20 mL), brined, dried ($Na_2SO_4$), filtered, and the filtrate was concentrated. The residue was purified by prep-HPLC to give 250 mg (53%) of Example 562. mp=182-190 (HCl salt); MS: m/z 409 (M+1).

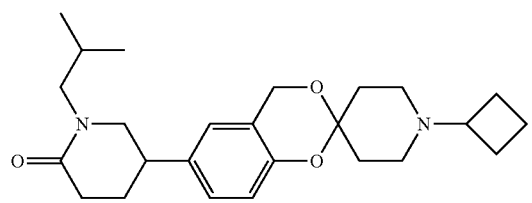 [SMILES: CC(C)CN1CC(c2ccc3c(c2)COC2(CCN(C4CCC4)CC2)O3)CCC1=O]

Example 564

To a Parr bottle was added example 562 (230 mg, 0.563 mmol), 5% rhodium on alumina powder (5% $Rh/Al_2O_3$, 159 mg, 0.0772 mmol), and MeOH (15 mL). The reaction mixture was hydrogenated at 50 psi for 16 h, filtered through a pad of Celite and eluted with MeOH. The filtrate was concentrated and the residue was purified by prep-TLC (5% MeOH in $CH_2Cl_2$) to give 220 mg (95%) of example 564. mp=98-103 (HCl salt)° C.; MS: m/z 413 (M+1).

General procedures for $X=OR^2$.

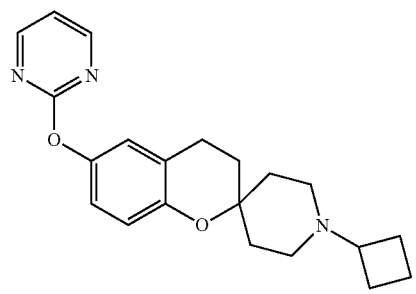 [SMILES: c1cnc(Oc2ccc3c(c2)CCC2(CCN(C4CCC4)CC2)O3)nc1]

Example 400

A solution of 1'-cyclobutyl-6-hydroxy-3,4-dihydro spiro-[2H-benzopyran-2,4'-piperidine] (250 mg, 0.91 mmol) in dimethyl sulfoxide (10 mL) was added NaH (44 mg, 1.8 mmol) at rt. After stirring for 30 min at rt 2-chloropyrimidine (209 mg, 1.83 mmol) was added and the reaction mixture was heated to 60° C. for 1 h and poured into a mixture of aqueous saturated sodium bicarbonate and brine solutions (1:1 ratio, 200 mL). The aqueous layer was extracted 3× with DCM and the combined organics was washed with brine, dried (Na$_2$SO$_4$), filtered, and concentrated to afford a crude product. The crude product was purified by ISCO (40 g) chromatography using 4 to 11.6% methanol in methylene chloride to obtain a pure product. The pure product was redissolved in methylene chloride and washed with aqueous saturated sodium bicarbonate solution, brine, dried (Na$_2$SO$_4$), filtered and concentrated to give an oily product. The oily product was dissolved in ethyl acetate and treated with 2M HCl in ether (2.5 mL) and evaporated under vacuum and fresh ethyl acetate was added twice and evaporated. The white solid was triturated from a mixture of ether and hexane (1:1 ratio, 25 mL) and dried at 87° C. in a ChemDry for overnight to produce Example 400 as an off-white solid (273 mg, 80%, 94% purity), mp 258-260° C. (ether-hexane), MS m/z=352 (M+H).

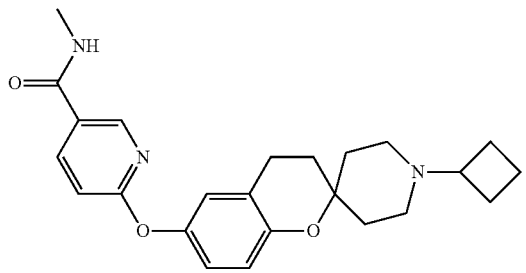 [SMILES: CNC(=O)c1ccc(Oc2ccc3c(c2)CCC2(CCN(C4CCC4)CC2)O3)nc1]

Example 401 was synthesized from 1'-cyclobutyl-6-hydroxy-3,4-dihydro spiro-[2H-benzopyran-2,4'-piperidine] (250 mg, 0.91 mmol) and 2-chloro-N-methyl-nicotinamide (312 mg, 1.83 mmol) using similar conditions as Example 400. mp 245-247° C. (methylene chloride, ether, and hexane), MS m/z=408 (M+H).

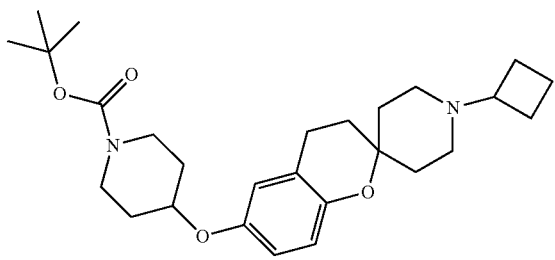 [SMILES: CC(C)(C)OC(=O)N1CCC(Oc2ccc3c(c2)CCC2(CCN(C4CCC4)CC2)O3)CC1]

Example 417

A solution of 1'-cyclobutyl-6-hydroxy-3,4-dihydro spiro-[2H-benzopyran-2,4'-piperidine] (3.00 g, 11 mmol) and 4-hydroxy-piperidine-1-carboxylic acid tert-butyl ester (2.65 g, 13.2 mmol) in THF (30 mL) was cooled to 5° C. and triphenylphosphine (3.45 g, 13.2 mmol) and di-tert-butyl azodicarboxylate (3.03 g, 13.2 mmol) were added and further stirred at room temperature for 3.5 days. Additional quantities of 4-hydroxy-piperidine-1-carboxylic acid tert-butyl ester (420 mg), di-tert-butyl azodicarboxylate (1.5 g) and triphenylphosine (1.5 g) were added during the course of the reaction. The reaction mixture was evaporated under vacuum and purified by ISCO (120 g) chromatography using 5 to 10% methanol in methylene chloride to produce 1'-cyclobutyl-6-(piperidine-1-carboxylic acid tert-butyl ester-4-yloxy)-3,4-dihydro spiro-[2H-benzopyran-2,4'-piperidine], (4.2 g, 74%). mp 118-120° C. (methylene chloride, ether, and hexane), MS m/z=457 (M+H).

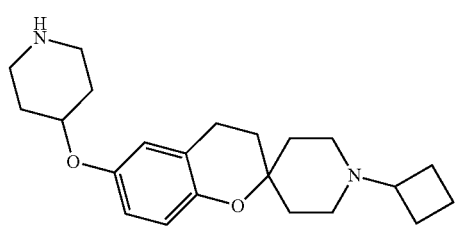 [SMILES: c1cc2c(cc1OC1CCNCC1)CCC1(CCN(C3CCC3)CC1)O2]

Example 425

A solution of example 417 (4.2 g, 9.2 mmol) in methylene chloride (45 mL) was treated with trifluoroacetic acid (12 mL, 156 mmol) at rt and further stirred at rt for 1.5 h. The reaction mixture was concentrated under vacuum and fresh ethyl acetate was added and evaporated to give an oily crude product, 7.73 g, which upon standing at room temperature formed a solid. A small amount of the above crude product was dissolved in methylene chloride and washed with aqueous saturated sodium bicarbonate solution, brine, dried (Na$_2$SO$_4$), filtered and concentrated to afford the free base of product. The free base of product was dissolved in ethyl acetate (3 mL) and treated with 2M HCl in ether (1.5 mL) and evaporated under vacuum. Fresh ethyl acetate was added twice and concentrated then crystallized from a mixture of ethanol, ether, and hexane to produce a tan solid as Example 425 2-HCl salt mp>320° C. (ethanol, ether, and hexane), MS m/z=357 (M+H).

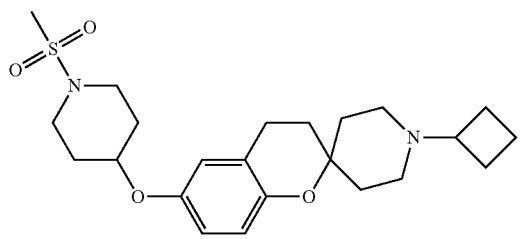 [SMILES: CS(=O)(=O)N1CCC(Oc2ccc3c(c2)CCC2(CCN(C4CCC4)CC2)O3)CC1]

Example 408

A solution of Example 425 (0.35 g, 0.99 mmol) in DDCM (3 mL) was added TEA (0.20 ml, 1.44 mmol) and methanesulfonyl chloride (0.03 mL, 0.40 mmol) at 0° C. then stirred at rt for 1 h. The reaction mixture was quenched with aqueous saturated sodium bicarbonate solution and the aqueous layer was extracted twice with methylene chloride. The combined organics was washed with brine, dried (Na$_2$SO$_4$), filtered and concentrated to obtain a pure material. The pure material was dissolved in ethyl acetate and treated with 2M HCl in ether (1.5 mL) then concentrated under vacuum. Fresh ethyl acetate was added twice and concentrated under vacuum then crystallized from a mixture of ethanol, ether, and hexane to produce Example 408HCl (130 mg, 28%), mp 252-254° C. (ethanol, ether, and hexane), MS m/z=435 (M+H).

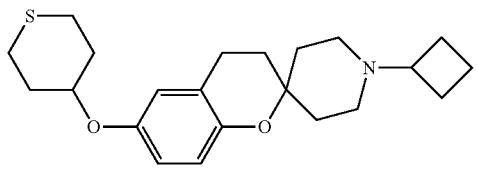 [SMILES: c1cc2c(cc1OC1CCSCC1)CCC1(CCN(C3CCC3)CC1)O2]

Example 457

A solution of 1'-cyclobutyl-6-hydroxy-3,4-dihydro spiro-[2H-benzopyran-2,4'-piperidine] (0.80 g, 2.93 mmol) and tetrahydro-thiopyran-4-ol (0.39 g, 3.3 mmol) in tetrahydrofuran (30 mL) was cooled to 0° C. and triphenylphosphine (3.45 g, 13.2 mmol) and di-tert-butyl azodicarboxylate (3.03 g, 13.2 mmol) were added and further stirred at room temperature for 4 days. The reaction mixture was evaporated under vacuum and purified by ISCO chromatography using a mixture of methanol and methylene chloride to produce Example 457 (0.6 g, 55%), mp 252-254° C. (methylene chloride and methanol), MS m/z=374 (M+H).

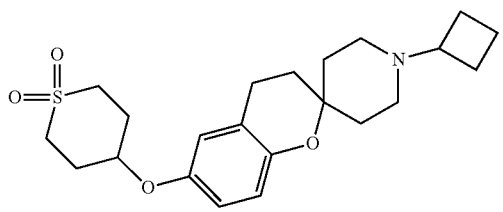 [SMILES: O=S1(=O)CCC(Oc2ccc3c(c2)CCC2(CCN(C4CCC4)CC2)O3)CC1]

Example 467

A solution of Example 457 (0.3 g, 0.80 mmol) in acetic acid (7 mL) was cooled to 0° C. and hydrogen peroxide (50% in water) was added then stirred at rt for 6 h. The reaction mixture was evaporated under vacuum and partitioned between methylene chloride and aqueous saturated sodium bicarbonate solution. The aqueous layer was extracted twice with DCM and the combined organics was washed with brine, dried (Na$_2$SO$_4$), filtered and concentrated to obtain a crude product. The crude product was purified by ISCO (40 g) chromatography using 5 to 10% methanol in DCM to afford a pure product. The pure product was dissolved in ethyl acetate and treated with 2M HCl in ether and evaporated under vacuum. Fresh ethyl acetate was added and concentrated then crystallized from a mixture of ethyl acetate, ether, and hexane and dried to give example 467 (270 mg, 83%), mp 239-240° C. (ethyl acetate, ether, and hexane), MS m/z=406 (M+H).

General Procedure for Amides.

Employing similar procedure as described in example 196, or using DIC in place of DCC, amide compounds of the invention can be prepared by coupling intermediate 10D and acid, followed by column chromatography.

Example 196

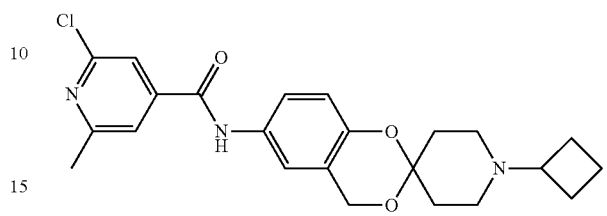

Compound 196 was prepared from compound 10D according to the following procedure.

To a solution containing 2-chloro-6-methyl-isonicotinic acid (75 mg, 0.44 mmol) in THF (2 mL) was added DCC (90 mg, 0.44 mmol), HOBt (59 mg, 0.44 mmol) and Et$_3$N (102 uL, 0.73 mmol). The mixture was stirred for 5 min then compound 10D (0.1 g, 0.36 mmol) was added. The mixture was stirred at room temperature for 16 h then concentrated. The residue was partitioned between DCM and sat. NaHCO$_3$ (aq.). The organic layer was dried (Na$_2$SO$_4$), filtered and concentrated. The residue was purified by normal phase column chromatography with a gradient elution of DCM to 30% acetone in DCM to afford compound 196 (34 mg, 22%): MP=179-180° C. $^1$H NMR (CD3OD) 7.72(d, J=7.5 Hz, 2H), 7.44(m, 2H), 6.87(d, J=9.0 Hz, 1H), 4.91(s, 2H), 2.87(m, 1H), 2.63(s, 3H), 2.50(m, 4H), 2.12(m, 2H), 1.99(m, 6H), 1.77(m, 2H); LC/MS (ESI+): 428 (M+H).

General Procedure for Anilines

Example 285

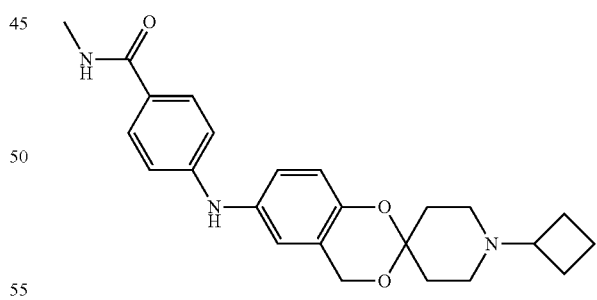

Example 285 was prepared from compound 10D according to the following procedure:

Compound 10D (110 mg, 0.4 mmol), 4-N-methylcaroxyamide phenylboronic acid (215 mg, 1.2 mmol) and Cu(OAc)$_2$ was mixed in DCM (4 mL) and then to the above blue mixture was added TEA (121 mg, 1.2 mmol). The resulting green mixture was stirred under ambient pressure at rt for 2 days. The resulting mixture was placed on the top of a silica gel-filled column and the column was eluted with mixed solvents of DCM and MeOH to give example 285: mp=206-208° C. ¹H-NMR (CDCl₃) 7.62-7.58 (m, 2H), 6.96 (dd, J=8.7, 2.7 Hz, 1H), 6.84-6.77 (m, 4H), 5.97 (quasi t, J=4.8 Hz, 1H), 5.71 (s, 1H), 4.79 (s, 2H), 2.97 (d, J=5.1 Hz, 3H), 2.84-2.73 (m, 1H), 2.42 (m, 4H), 2.09-1.61 (m, 10H); LC/MS (ESI+): 408 (M+H).

General Procedure for X=(C₁-C₃alkyl) Optionally Substituted with OH or OCH3

Example 664

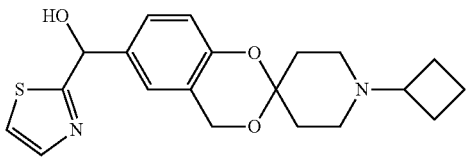 [SMILES: OC(c1ccc2c(c1)COC1(CCN(C3CCC3)CC1)O2)c1nccs1]

To a stirred solution of compound 1C (0.6 g, 1.77 mmol) in THF (6 mL) at −78° C. was added n-BuLi (2.5 M in hexane, 0.78 mL, 1.95 mmol) dropwise. The solution turned light yellow. The mixture was stirred at −78° C. for 5 min, followed by addition of 2-thiazole carboxaldehyde (0.22 g, 1.95 mmol). The stirring was continued at −78° C. for 10 min and then quenched with sat. NH₄Cl at −78° C. The mixture was extracted with EtOAc (20 mL×3). The organic layer was washed with brine, dried (Na₂SO₄), filtered and concentrated. The residue was purified by column chromatography (SiO₂, gradient 0-3% MeOH in DCM) to give example 664: mp=70-72° C. ¹H NMR (CDCl₃) 7.67(d, J=3.4 Hz, 1H), 7.24(d, J=3.4 Hz, 1H), 7.17(d, J=2.0 Hz, 1H), 7.01(d, J=2.0 Hz, 1H), 6.80 (d, J=8.4 Hz, 1H), 5.91(s, 1H), 4.76(s, 2H), 3.56(br s, 1H), 2.73(quint, J=7.8 Hz, 1H), 2.45-2.26(br s, 4H), 2.03-1.77 (m, 8H), 1.63(m, 2H); LC/MS (ESI+): 373 (M+H).

Example 724

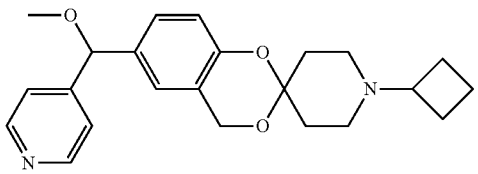 [SMILES: COC(c1ccncc1)c1ccc2c(c1)COC1(CCN(C3CCC3)CC1)O2]

To a stirred solution of example 683 (0.256 g, 0.7 mmol) in THF (3 mL) was added NaH (30%, 33 mg, 0.84 mmol). After gas evolution ceased the mixture was cooled to −75° C. and methyl iodide (0.1 g, 0.7 mmol) was added. The mixture was stirred at room temperature for 2 h. The reaction was cooled to −50° C. and treated by 10% NaOH in H₂O then extracted with EtOAc (2×). The organic layer was dried (Na₂SO₄), filtered and concentrated. The residue was purified by column chromatography (SiO₂, gradient 1-4% MeOH in DCM) to give example 724: ¹H NMR (CDCl₃) 8.47(d, J=5.6 Hz, 2H), 7.18(d, J=5.6 Hz, 2H), 7.02(d, J=7.4 Hz, 1H), 6.84(s, 1H), 6.74 (d, J=7.4 Hz, 1H), 5.03(s, 1H), 4.75(s, 2H), 3.28(s, 3H), 2.71(q, J=7.4 Hz, 1H), 2.33(m, 4H), 2.00-1.73 (m, 8H), 1.67-1.55(m, 2H); LC/MS (ESI+): 381 (M+H).

Example 696

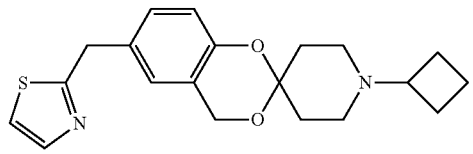 [SMILES: c1csc(Cc2ccc3c(c2)COC2(CCN(C4CCC4)CC2)O3)n1]

To a stirred solution of example 664 (0.2 g, 0.52 mmol) in DCM (3 mL) was added TFA (0.15 mL, 2 mmol) followed by triethylsilane (0.38 mL, 2.4 mmol). The mixture was stirred at 45° C. for 16 h, followed by addition of more TFA (0.15 mL, 2 mmol) and triethylsilane (0.38 mL, 2.4 mmol). The reaction was continued at 45° C. for 4 days. The mixture was poured into 10% Na₂CO₃ and extracted with DCM. The organic layer was washed with brine, dried (Na₂SO₄), filtered and concentrated. The residue was purified by column chromatography (SiO₂, gradient 0-3% MeOH in DCM) to give example 696 (126 mg): ¹H NMR (CDCl₃) 7.63(d, J=3.2 Hz, 1H), 7.13(d, J=3.2 Hz, 1H), 7.04(d, J=7.8 Hz, 1H), 6.84(s, 1H), 6.76(d, J=8.7 Hz, 1H), 4.74(s, 2H), 4.19(s, 2H), 2.73(q, J=7.8 Hz, 1H), 2.46-2.26(br s, 4H), 2.04-1.76 (m, 8H), 1.63(m, 2H); LC/MS (ESI+): 357 (M+H).

Example 528

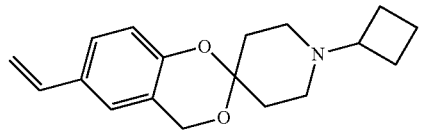 [SMILES: C=Cc1ccc2c(c1)COC1(CCN(C3CCC3)CC1)O2]

Step 1. A mixture of 1C (2.0 g, 5.0 mmol), (2-ethenyl)tri-n-butyltin (2.0 g, 6.4 mmol), Pd₂(dba)₃ (0.50 g, 0.5 mmol), Cs₂CO₃ (2.40 g, 16 mmol), and Pd(tBu)₃ (0.40 mL, 2.0 mmol) in toluene (10.0 mL) was degassed with N₂ for 3 min, then heated to 80° C. overnight. The reaction was cooled to rt, filtered through celite, washed with CH₂Cl₂, and concentrated. The residue was diluted with 10 mL of CH₂Cl₂ and 10 mL of 2.5 M KF solution and stirred for 1 hr, and the organic layer was separated. The aqueous layer was extracted with CH₂Cl₂ (3×10 mL), then the combined organic layers were washed with NaHCO₃ solution, NaCl solution, dried over Na₂SO₄, and concentrated. Prep. TLC with 5% MeOH in CH₂Cl₂ gave the desired product (1.1 g, 70%). MS m/z 286 (M+H), mp: 108-110° C.,

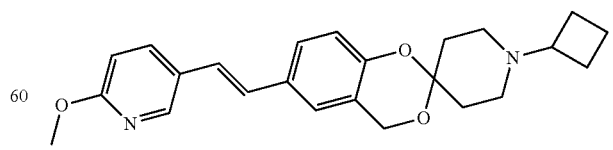

Step 2. A mixture of the product from step 1 (0.30 g, 1.0 mmol), D-μ-chlorobis[5-chloro-2-[(4-chlorophenyl)(hydroxylimino-kN)methyl]phenyl-kC] palladium dimmer (40.0 mg, 0.05 mmol), 5-bromo-2-methoxy-pyridine (0.20 g, 1.0 mmol), K$_2$CO$_3$ (0.40 g, 3.0 mmol), and tetra-N-butylammonium bromide (0.17 g, 0.52 mmol) in DMF (2.0 mL) was heated to 130° C. for 4 h. The reaction was cooled to rt, filtered through celite, washed with DCM. The DCM solution was washed with water, NaCl solution, dried over Na$_2$SO$_4$, and concentrated. Prep. TLC with 5% MeOH in CH$_2$Cl$_2$ gave the desired product (0.21 g, 48%): MS m/z 393 (M+H). mp: 144-6° C.

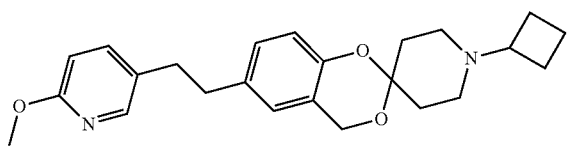 [SMILES: COc1ccc(CCc2ccc3c(c2)COC2(CCN(C4CCC4)CC2)O3)cn1]

Step 3. Example 522. A suspension of the product from step 2 (0.10 g, 0.20 mmol) and 80 mg of 20% Pd(OH)$_2$/C in 2.0 mL of ethanol and 2.0 mL of 10% aqueous HCl solution was hydrogenated at 50 psi under H$_2$ on a Parr Apparatus for 2 h. The solution was filtered through celite under N$_2$, washed with CH$_2$Cl$_2$, and the solvent was concentrated. The crude was added NH$_4$OH solution to pH ~10, extracted with CH$_2$Cl$_2$. The combined CH$_2$Cl$_2$ layers were washed with NaCl solution, dried, and concentrated. Prep. TLC with 5% MeOH in CH$_2$Cl$_2$ gave Example 522 (0.055 g, 50%): MS m/z 395 (M+H), mp: 202-4° C.

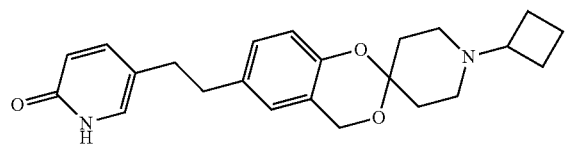 [SMILES: O=c1ccc(CCc2ccc3c(c2)COC2(CCN(C4CCC4)CC2)O3)c[nH]1]

Step 4. Example 528. A Example 522 (80 mg, 0.20 mmol) and sodium iodide (60 mg, 0.40 mmol) in acetic acid (5.0 mL, 88 mmol) was heated to 100° C. for 3 hr. HPLC indicated no starting material reamined. The reaction was cooled to rt, and the solvent was evaporated. The crude material was dissolved CH$_2$Cl$_2$, washed with 5% of sodium thiosulfate solution, NaCl solution, dried over Na$_2$SO$_4$, and concentrated. Prep. TLC with 8% of MeOH in CH$_2$Cl$_2$ and 0.5% iPrNH$_2$ gave Example 528 (35 mg, 45%): MS m/z 381 (M+H), mp: 183-5° C.

General Procedures for R2 Cycloalkyl

Example 482

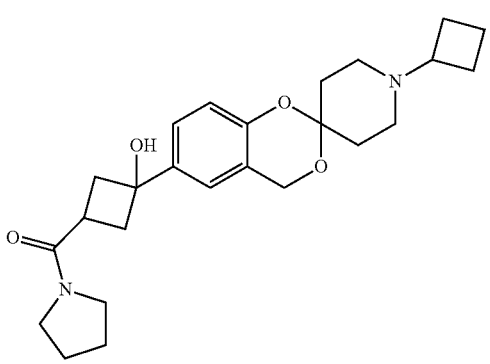 [SMILES: O=C(C1CC(O)(c2ccc3c(c2)COC2(CCN(C4CCC4)CC2)O3)C1)N1CCCC1]

A solution of 1C (0.99 g, 2.93 mmol) in 10 mL of anhydrous THF under N$_2$ was stirred at −78° C. as n-BuLi (1.6 M in hexane, 2.2 eq.) was added dropwise. After 30 min stirring at −78° C. under N$_2$, a solution of 3-oxo-cyclobutanecarboxylic acid (0.168 g, 1.47 mmol) in 4.0 mL of anhydrous THF was added dropwise. After 5 min at −78° C., the reaction was warmed to 0° C. and stirred for 2 h. The reaction was then warmed to rt, the solvent was evaporated, and the residue was diluted with DMF (8.0 mL). To this solution was added benzotriazol-1-yloxytris(dimethylamino)phosphonium hexafluorophosphate (0.78 g, 1.8 mmol) and pyrrolidine hydrochloride (2.0 eq.) at 0° C. under N$_2$ with stirring. After 16 h at rt, the solvent was evaporated, and the residue was added CH$_2$Cl$_2$ (20 mL) and saturated K$_2$CO$_3$ solution (10 mL). The organic layer was washed with NaHCO$_3$ solution, NaCl solution, dried over Na$_2$SO4, and concentrated. Prep. TLC with 10% MeOH in CH$_2$Cl$_2$ Example 482 (89 mg, 46%): MS m/z 427 (M+H), mp 157-9° C.

Example 540

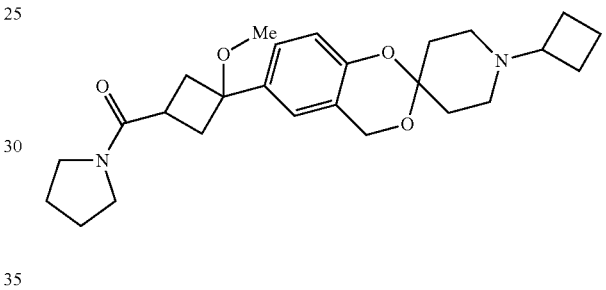

A suspension of sodium hydride (0.119 g, 2.98 mmol) in 2.0 mL of DMF was stirred under N$_2$ as Example 482 (0.424 g, 0.994 mmol) in 5.0 mL of DMF was added dropwise. After 30 min at rt, a solution of methyl iodide (0.14 g, 1.0 eq.) in 1.0 mL of DMF was added. The reaction was heated to 60° C. for 1 h, and HPLC indicated no starting material remain. The reaction was cooled to rt, quenched with saturated NaCl solution, and extracted with CH$_2$Cl$_2$ (3×20 mL). The combined CH$_2$Cl$_2$ solution was washed with NaHCO$_3$ solution, water, NaCl solution, dried over MgSO$_4$, and concentrated. Flash chromatography with 5% MeOH in CH$_2$Cl$_2$ gave Example 540: MS m/z 441 (M+H), mp: 65-7° C.

Table C lists the Human and Rat H$_3$ binding data for Examples 363-569 of the present invention. Binding constants (K$_i$) for Examples 363-569 in the Human H$_3$ and Rat H$_3$ methods described herein are expressed by letter descriptor to indicate the following ranges: "+++" is less than 200 nM; "++" is 200-1000 nM; "+" is >1000 nM.

The compounds of Table C were prepared by methods well known to those skilled in the art, including, but not limited to those described herein, or through modifications of these methods by applying standard techniques known to those skilled in the art of organic synthesis. General routes of synthesis to prepare Examples of Table C are shown in the Schemes herein. The reagents and starting materials are commercially available, or readily synthesized by well-known techniques by one of ordinary skill in the art.

TABLE C
| Ex. No. | Structure | Human H3 Ki (nM) | Rat H3 Ki (nM) | MP (° C.) | MS (m/z) |
|---|---|---|---|---|---|
| 363 | 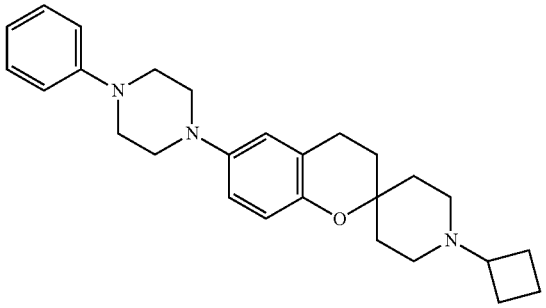 [SMILES: c1ccc(N2CCN(c3ccc4c(c3)CCC3(CCN(C5CCC5)CC3)O4)CC2)cc1] | +++ | +++ | 173-175 | 418 (M + H) |
| 364 | 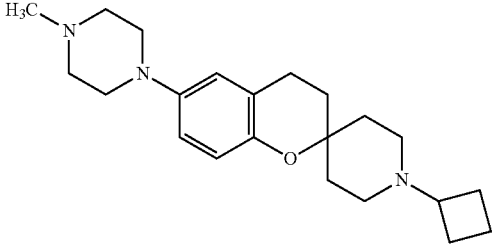 [SMILES: CN1CCN(c2ccc3c(c2)CCC2(CCN(C4CCC4)CC2)O3)CC1] | +++ | +++ | 125-6 | 356 (M + H) |
| 365 | 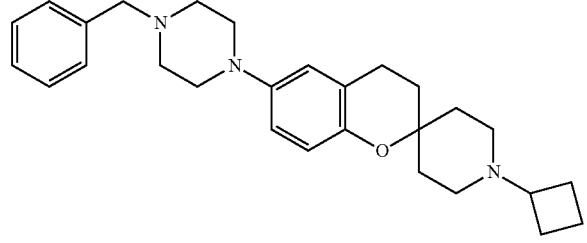 [SMILES: c1ccc(CN2CCN(c3ccc4c(c3)CCC3(CCN(C5CCC5)CC3)O4)CC2)cc1] | +++ | +++ | 292-3 | 432 (M + H) |
| 366 | 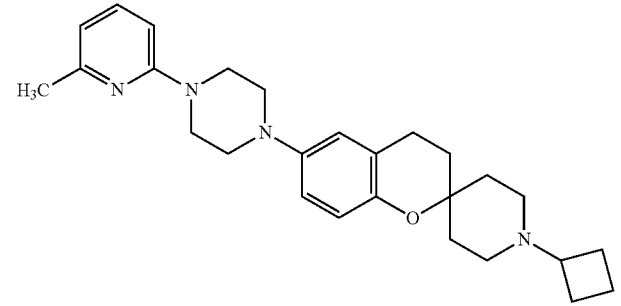 [SMILES: Cc1cccc(N2CCN(c3ccc4c(c3)CCC3(CCN(C5CCC5)CC3)O4)CC2)n1] | +++ | +++ | 159-161 | 433 (M + H) |
| 367 | 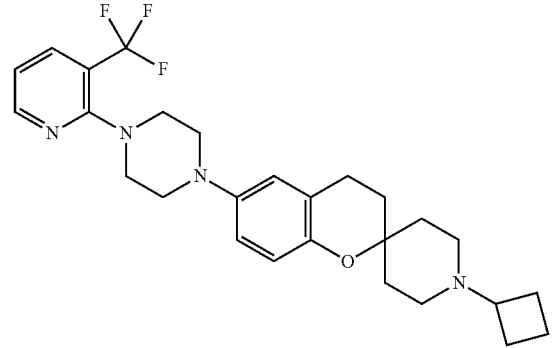 [SMILES: FC(F)(F)c1cccnc1N1CCN(c2ccc3c(c2)CCC2(CCN(C4CCC4)CC2)O3)CC1] | +++ | +++ | 138-9 | 487 (M + H) |

TABLE C-continued
| Ex. No. | Structure | Human H3 Ki (nM) | Rat H3 Ki (nM) | MP (° C.) | MS (m/z) |
|---|---|---|---|---|---|
| 368 | 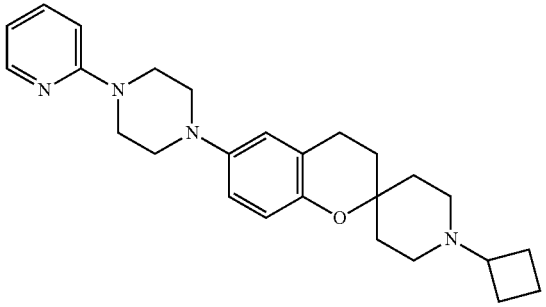 [SMILES: c1ccc(N2CCN(c3ccc4c(c3)CCC3(CCN(C5CCC5)CC3)O4)CC2)nc1] | +++ | +++ | 171-2 | 419 (M + H) |
| 369 | 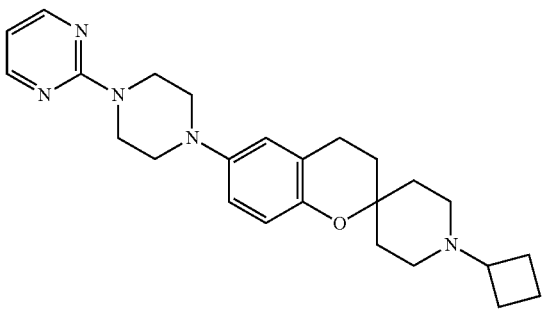 [SMILES: c1cnc(N2CCN(c3ccc4c(c3)CCC3(CCN(C5CCC5)CC3)O4)CC2)nc1] | +++ | +++ | 156-7 | 420 (M + H) |
| 370 | 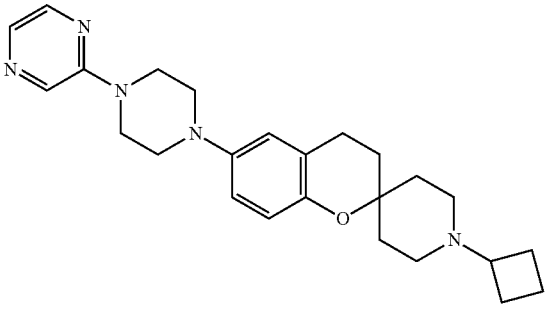 [SMILES: c1cnc(N2CCN(c3ccc4c(c3)CCC3(CCN(C5CCC5)CC3)O4)CC2)cn1] | +++ | +++ | 168-9 | 420 (M + H) |
| 371 | 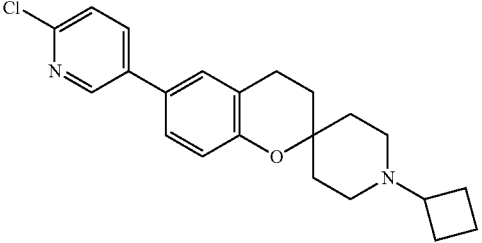 [SMILES: Clc1ccc(-c2ccc3c(c2)CCC2(CCN(C4CCC4)CC2)O3)cn1] | +++ | +++ | 168-9 | 369 (M + H) |

TABLE C-continued

| Ex. No. | Structure | Human H3 Ki (nM) | Rat H3 Ki (nM) | MP (° C.) | MS (m/z) |
| --- | --- | --- | --- | --- | --- |
| 372 | 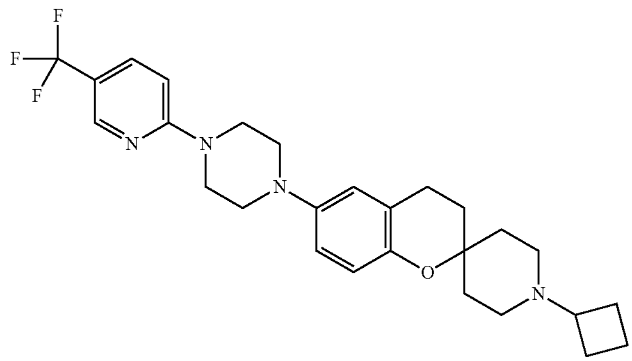 [SMILES: FC(F)(F)c1ccc(N2CCN(c3ccc4c(c3)CCC3(CCN(C5CCC5)CC3)O4)CC2)nc1] | +++ | +++ | 212-3 | 487 (M + H) |
| 373 | 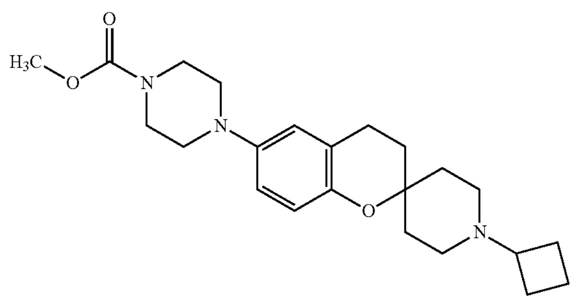 | +++ | +++ | 157-8 | 400 (M + H) |
| 374 | 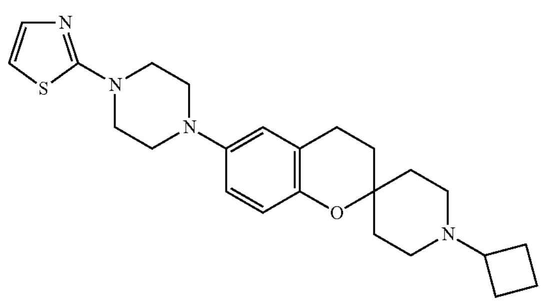 [SMILES: c1csc(N2CCN(c3ccc4c(c3)CCC3(CCN(C5CCC5)CC3)O4)CC2)n1] | +++ | +++ | 182-4 | 425 (M + H) |
| 375 | 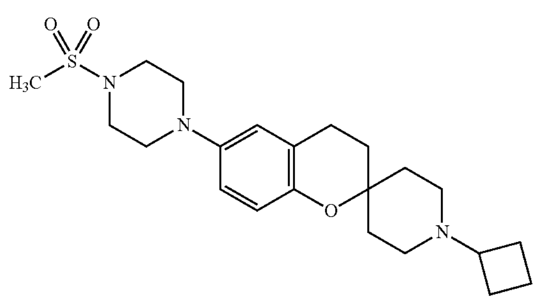 [SMILES: CS(=O)(=O)N1CCN(c2ccc3c(c2)CCC2(CCN(C4CCC4)CC2)O3)CC1] | +++ | +++ | 240-242 | 420 (M + H) |
| 376 | 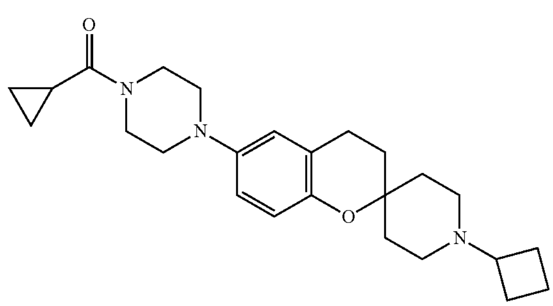 [SMILES: O=C(C1CC1)N1CCN(c2ccc3c(c2)CCC2(CCN(C4CCC4)CC2)O3)CC1] | +++ | +++ | 169-171 | 410 (M + H) |

TABLE C-continued

| Ex. No. | Structure | Human H3 Ki (nM) | Rat H3 Ki (nM) | MP (° C.) | MS (m/z) |
|---|---|---|---|---|---|
| 377 | 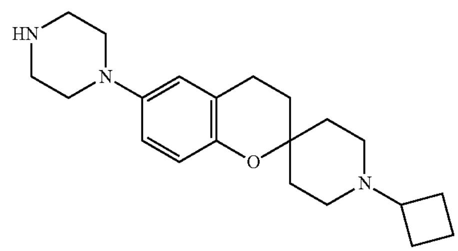 [SMILES: c1cc2c(cc1N1CCNCC1)CCC1(CCN(C3CCC3)CC1)O2] | +++ | +++ | 116-8 | 342 (M + H) |
| 378 | 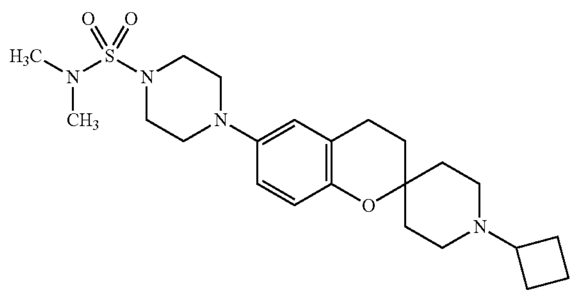 | +++ | +++ | 194-196 | 462 (M + H) |
| 379 | 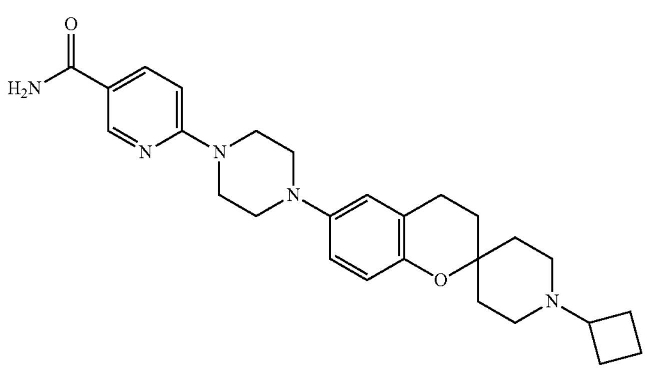 [SMILES: NC(=O)c1ccc(N2CCN(c3ccc4c(c3)CCC3(CCN(C5CCC5)CC3)O4)CC2)nc1] | +++ | +++ | dec @ 281 | 462 (M + H) |
| 380 | 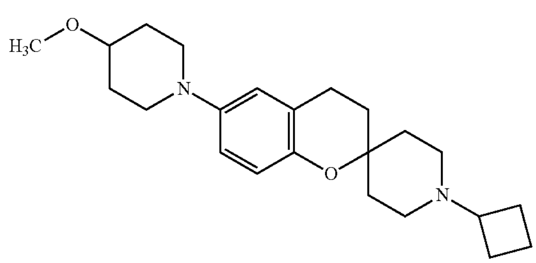 [SMILES: COC1CCN(c2ccc3c(c2)CCC2(CCN(C4CCC4)CC2)O3)CC1] | +++ | +++ | 285-72 | 371 (M + H) |
| 381 | 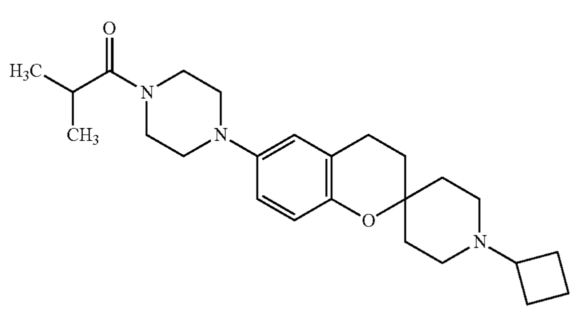 [SMILES: CC(C)C(=O)N1CCN(c2ccc3c(c2)CCC2(CCN(C4CCC4)CC2)O3)CC1] | +++ | +++ | 173-5 | 412 (M + H) |

TABLE C-continued

| Ex. No. | Structure | Human H3 Ki (nM) | Rat H3 Ki (nM) | MP (° C.) | MS (m/z) |
|---|---|---|---|---|---|
| 382 | 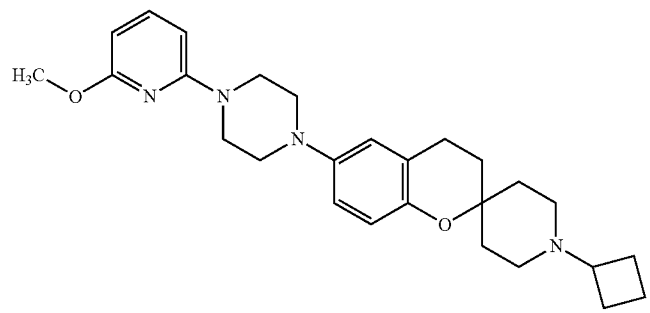 [SMILES: COc1cccc(N2CCN(c3ccc4c(c3)CCC3(CCN(C5CCC5)CC3)O4)CC2)n1] | +++ | +++ | 243-5 | 449 (M + H) |
| 383 | 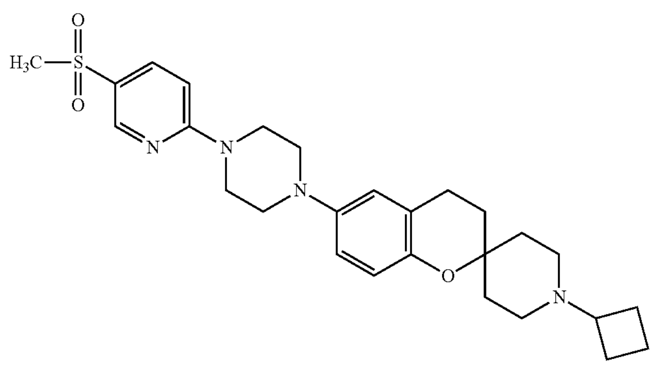 [SMILES: CS(=O)(=O)c1ccc(N2CCN(c3ccc4c(c3)CCC3(CCN(C5CCC5)CC3)O4)CC2)nc1] | +++ | +++ | 258-260 | 497 (M + H) |
| 384 | 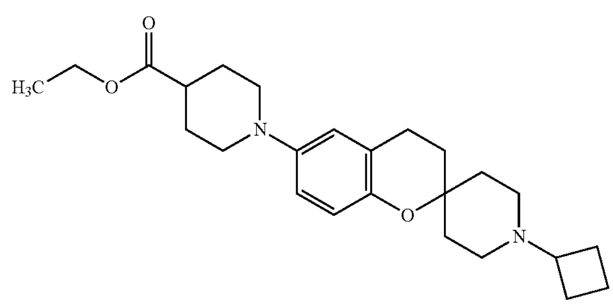 [SMILES: CCOC(=O)C1CCN(c2ccc3c(c2)CCC2(CCN(C4CCC4)CC2)O3)CC1] | +++ | +++ | 256-8 | 413 (M + H) |
| 385 | 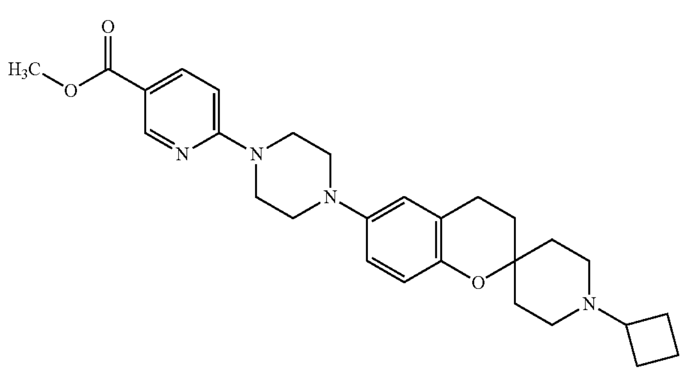 [SMILES: COC(=O)c1ccc(N2CCN(c3ccc4c(c3)CCC3(CCN(C5CCC5)CC3)O4)CC2)nc1] | +++ | +++ | 202-3 | 477 (M + H) |

TABLE C-continued

| Ex. No. | Structure | Human H3 Ki (nM) | Rat H3 Ki (nM) | MP (° C.) | MS (m/z) |
|---|---|---|---|---|---|
| 386 | 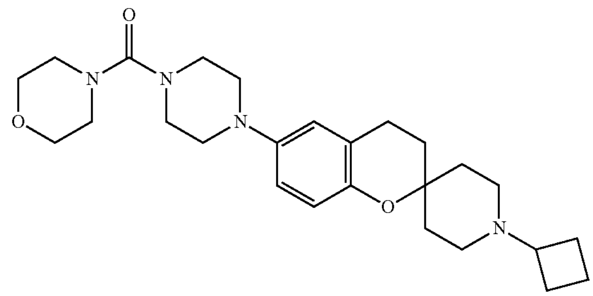 [SMILES: O=C(N1CCOCC1)N1CCN(c2ccc3c(c2)CCC2(CCN(C4CCC4)CC2)O3)CC1] | +++ | +++ | 292-4 | 455 (M + H) |
| 387 | 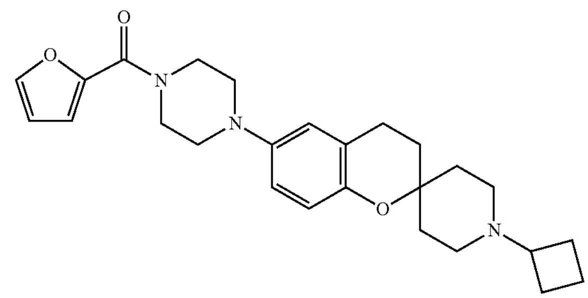 [SMILES: O=C(c1ccco1)N1CCN(c2ccc3c(c2)CCC2(CCN(C4CCC4)CC2)O3)CC1] | +++ | +++ | 133-5 | 436 (M + H) |
| 388 | 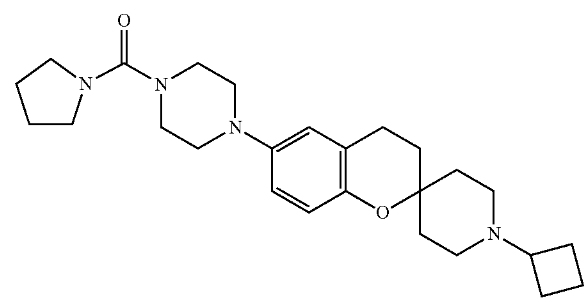 [SMILES: O=C(N1CCCC1)N1CCN(c2ccc3c(c2)CCC2(CCN(C4CCC4)CC2)O3)CC1] | +++ | +++ | 165-7 | 439 (M + H) |
| 389 | 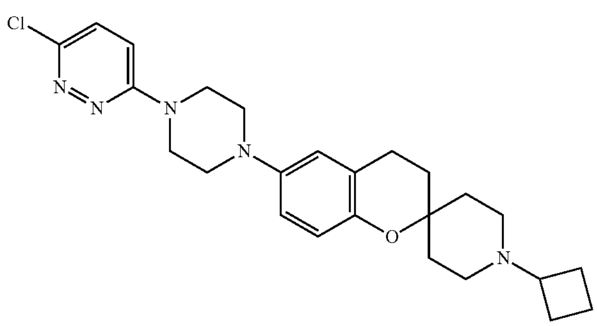 [SMILES: Clc1ccc(N2CCN(c3ccc4c(c3)CCC3(CCN(C5CCC5)CC3)O4)CC2)nn1] | +++ | +++ | 229-231 | 454 (M + H) |
| 390 | 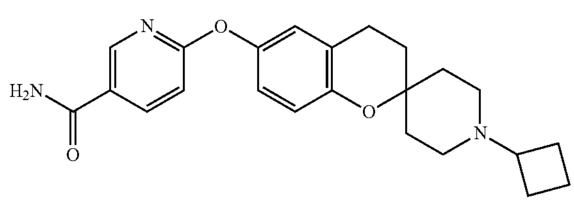 [SMILES: NC(=O)c1ccc(Oc2ccc3c(c2)CCC2(CCN(C4CCC4)CC2)O3)nc1] | +++ | +++ | 191-193 | 394 (M + H) |

TABLE C-continued

| Ex. No. | Structure | Human H3 Ki (nM) | Rat H3 Ki (nM) | MP (° C.) | MS (m/z) |
|---|---|---|---|---|---|
| 391 | 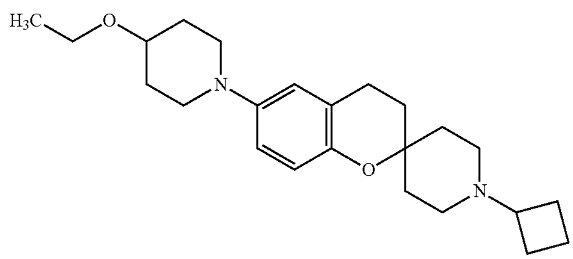 | +++ | +++ | 285-290 | 385 (M + H) |
| 392 | 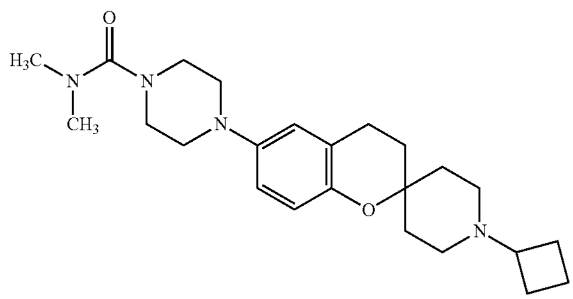 | +++ | +++ | 272-4 | 413 (M + H) |
| 393 | 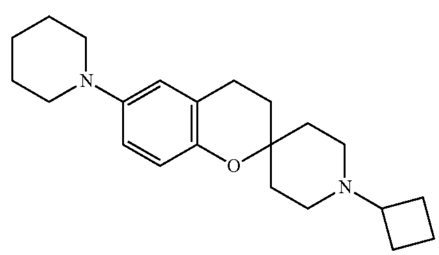 [SMILES: c1cc2c(cc1N1CCCCC1)CCC1(CCN(C3CCC3)CC1)O2] | +++ | +++ | dec. >280 | 341 (M + H) |
| 394 | 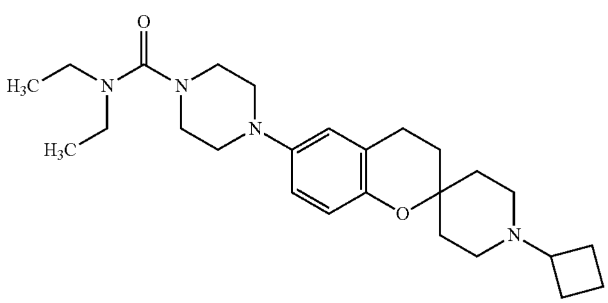 [SMILES: CCN(CC)C(=O)N1CCN(c2ccc3c(c2)CCC2(CCN(C4CCC4)CC2)O3)CC1] | +++ | +++ | 272-4 | 441 (M + H) |
| 395 | 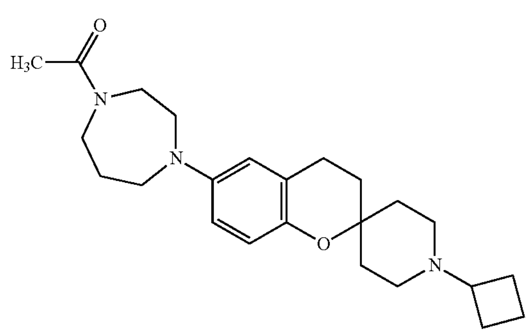 [SMILES: CC(=O)N1CCCN(c2ccc3c(c2)CCC2(CCN(C4CCC4)CC2)O3)CC1] | +++ | +++ | 276-8 | 398 (M + H) |

TABLE C-continued

| Ex. No. | Structure | Human H3 Ki (nM) | Rat H3 Ki (nM) | MP (° C.) | MS (m/z) |
|---|---|---|---|---|---|
| 396 | 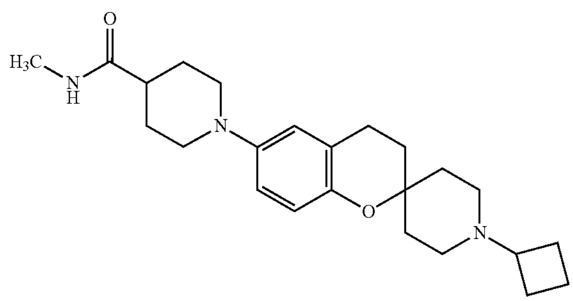 [SMILES: CNC(=O)C1CCN(c2ccc3c(c2)CCC2(CCN(C4CCC4)CC2)O3)CC1] | +++ | +++ | 264-267 | 398 (M + H) |
| 397 | 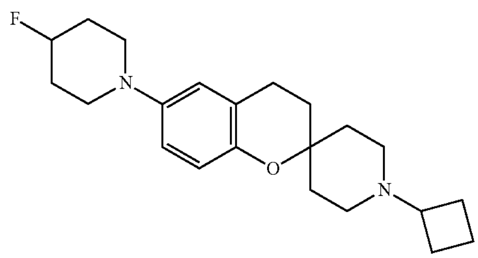 [SMILES: FC1CCN(c2ccc3c(c2)CCC2(CCN(C4CCC4)CC2)O3)CC1] | +++ | +++ | dec. >265 | 359 (M + H) |
| 398 | 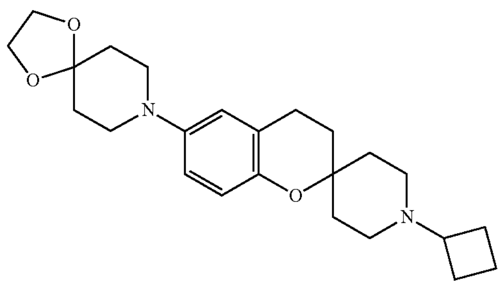 [SMILES: c1cc2c(cc1N1CCC3(CC1)OCCO3)CCC1(CCN(C3CCC3)CC1)O2] | +++ | +++ | 135-137 | 399 (M + H) |
| 399 | 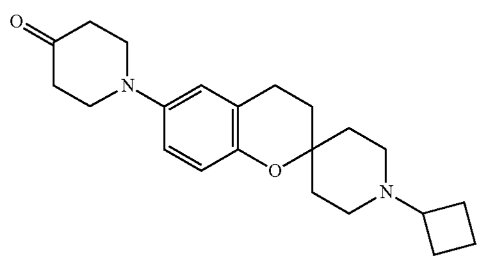 [SMILES: O=C1CCN(c2ccc3c(c2)CCC2(CCN(C4CCC4)CC2)O3)CC1] | +++ | +++ | dec. >247 | 355 (M + H) |
| 400 | 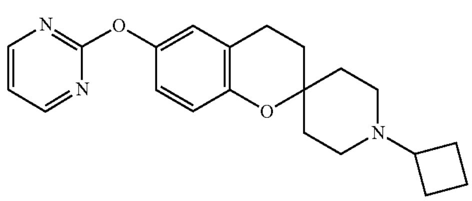 [SMILES: c1cnc(Oc2ccc3c(c2)CCC2(CCN(C4CCC4)CC2)O3)nc1] | ++ | >300 nM | 258-260 C. | 352 (M + H) |
| 401 | 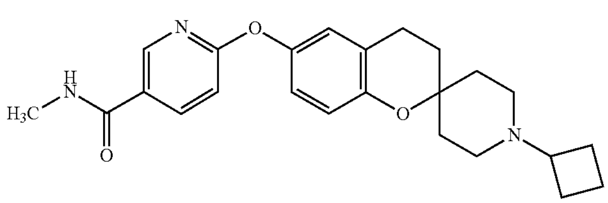 [SMILES: CNC(=O)c1ccc(Oc2ccc3c(c2)CCC2(CCN(C4CCC4)CC2)O3)nc1] | +++ | +++ | 245-247 | 408 (M + H) |

TABLE C-continued

| Ex. No. | Structure | Human H3 Ki (nM) | Rat H3 Ki (nM) | MP (° C.) | MS (m/z) |
|---|---|---|---|---|---|
| 402 | 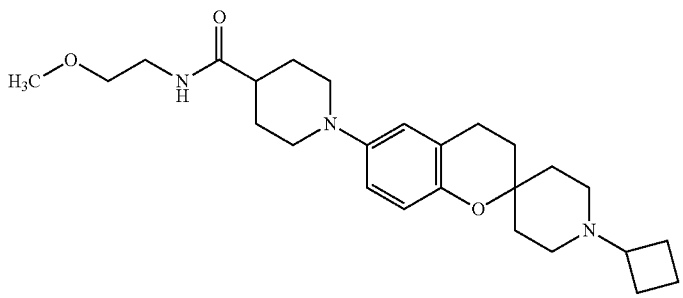 | +++ | +++ | 273-5 | 422 (M + H) |
| 403 | 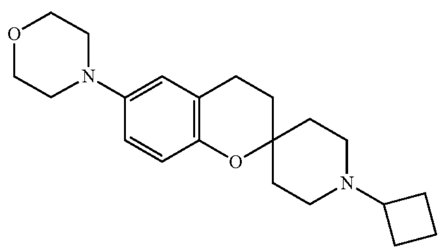 [SMILES: c1cc2c(cc1N1CCOCC1)CCC1(CCN(C3CCC3)CC1)O2] | +++ | +++ | dec. >285 | 343 (M + H) |
| 404 | 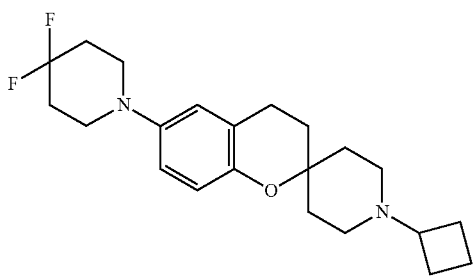 [SMILES: FC1(F)CCN(c2ccc3c(c2)CCC2(CCN(C4CCC4)CC2)O3)CC1] | +++ | +++ | dec. >283 | 377 (M + H) |
| 405 | 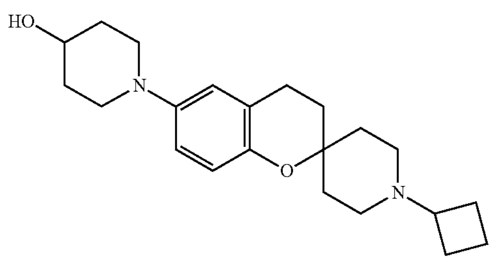 [SMILES: OC1CCN(c2ccc3c(c2)CCC2(CCN(C4CCC4)CC2)O3)CC1] | +++ | +++ | dec. >265 | 357 (M + H) |
| 406 | 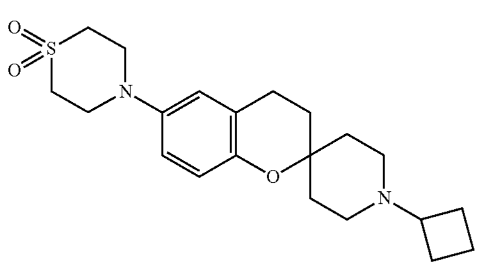 [SMILES: O=S1(=O)CCN(c2ccc3c(c2)CCC2(CCN(C4CCC4)CC2)O3)CC1] | +++ | +++ | dec. >285 | 391 (M + H) |
| 407 | 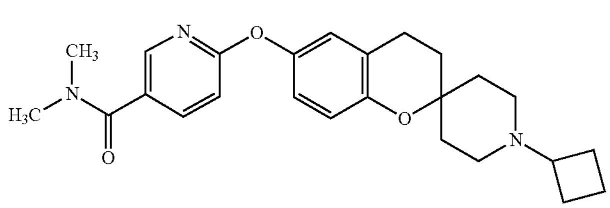 [SMILES: CN(C)C(=O)c1ccc(Oc2ccc3c(c2)CCC2(CCN(C4CCC4)CC2)O3)nc1] | +++ | ++ | 267-269 | 422 (M + H) |

TABLE C-continued

| Ex. No. | Structure | Human H3 Ki (nM) | Rat H3 Ki (nM) | MP (° C.) | MS (m/z) |
|---|---|---|---|---|---|
| 408 | 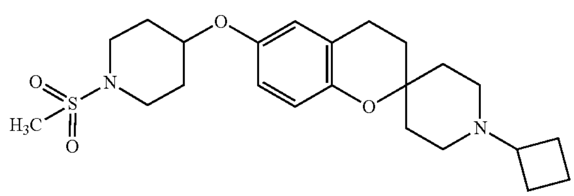 [SMILES: CS(=O)(=O)N1CCC(Oc2ccc3c(c2)CCC2(CCN(C4CCC4)CC2)O3)CC1] | +++ | +++ | 252-254 | 435 (M + H) |
| 409 | 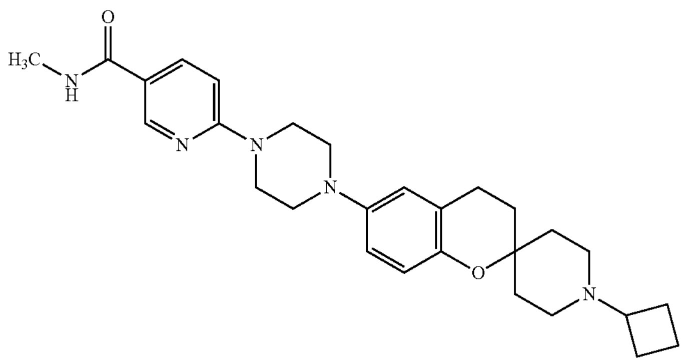 [SMILES: CNC(=O)c1ccc(N2CCN(c3ccc4c(c3)CCC3(CCN(C5CCC5)CC3)O4)CC2)nc1] | +++ | +++ | 297-9 | 476 (M + H) |
| 410 | 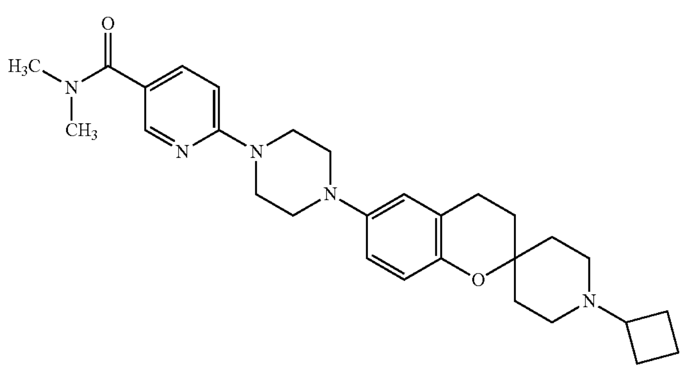 [SMILES: CN(C)C(=O)c1ccc(N2CCN(c3ccc4c(c3)CCC3(CCN(C5CCC5)CC3)O4)CC2)nc1] | +++ | +++ | dec @ 220 | 490 (M + H) |
| 411 | 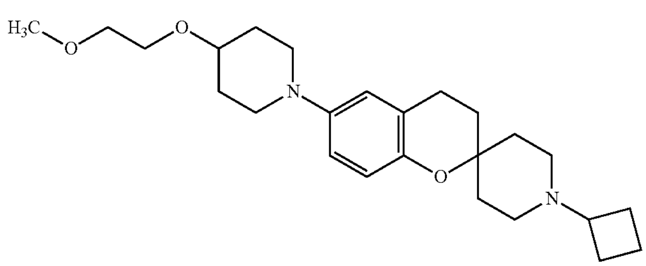 | +++ | +++ | 268-270 | 332 (M + H) |
| 412 | 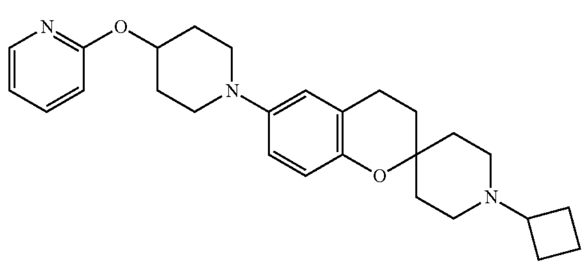 [SMILES: c1ccc(OC2CCN(c3ccc4c(c3)CCC3(CCN(C5CCC5)CC3)O4)CC2)nc1] | +++ | +++ | 240-245 | 434 (M + H) |

TABLE C-continued

| Ex. No. | Structure | Human H3 Ki (nM) | Rat H3 Ki (nM) | MP (° C.) | MS (m/z) |
|---|---|---|---|---|---|
| 413 | 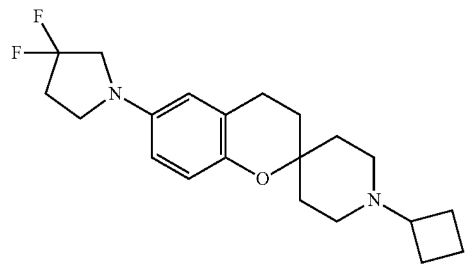 [SMILES: FC1(F)CCN(c2ccc3c(c2)CCC2(CCN(C4CCC4)CC2)O3)C1] | +++ | +++ | dec. >275 | 363 (M + H) |
| 414 | Chiral | +++ | +++ | 275-280 | 345 (M + H) |
| 415 | 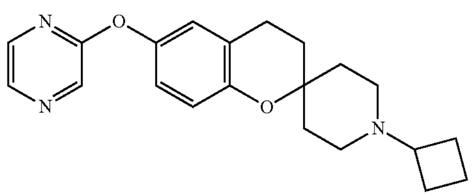 [SMILES: c1cnc(Oc2ccc3c(c2)CCC2(CCN(C4CCC4)CC2)O3)cn1] | +++ | +++ | 256-258 | 352 (M + H) |
| 416 | 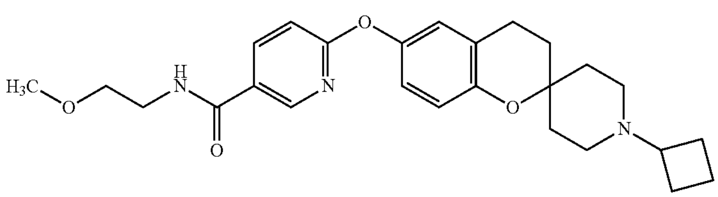 [SMILES: COCCNC(=O)c1ccc(Oc2ccc3c(c2)CCC2(CCN(C4CCC4)CC2)O3)nc1] | +++ | +++ | 235-237 | 452 (M + H) |
| 417 | 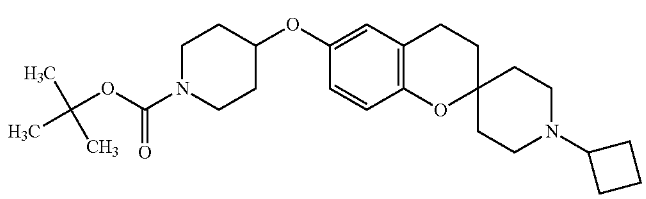 [SMILES: CC(C)(C)OC(=O)N1CCC(Oc2ccc3c(c2)CCC2(CCN(C4CCC4)CC2)O3)CC1] | +++ | +++ | 118-120 | 457 (M + H) |
| 418 | 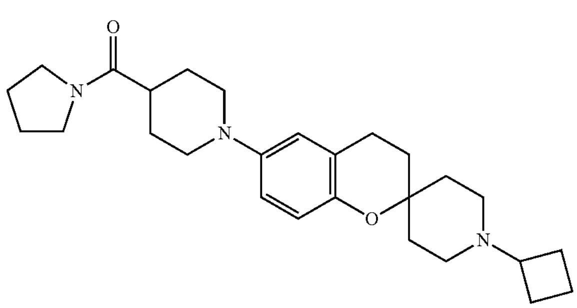 [SMILES: O=C(C1CCN(c2ccc3c(c2)CCC2(CCN(C4CCC4)CC2)O3)CC1)N1CCCC1] | +++ | +++ | 290-2 | 438 (M + H) |

TABLE C-continued

| Ex. No. | Structure | Human H3 Ki (nM) | Rat H3 Ki (nM) | MP (° C.) | MS (m/z) |
| --- | --- | --- | --- | --- | --- |
| 419 | 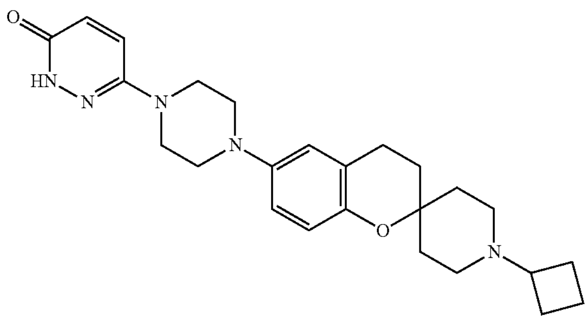 [SMILES: O=c1ccc(N2CCN(c3ccc4c(c3)CCC3(CCN(C5CCC5)CC3)O4)CC2)n[nH]1] | +++ | +++ | 278-280 | 436 (M + H) |
| 420 | 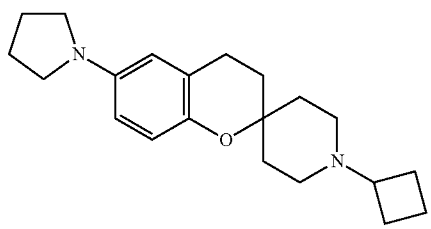 [SMILES: c1cc2c(cc1N1CCCC1)CCC1(CCN(C3CCC3)CC1)O2] | +++ | +++ | dec. >275 | 327 (M + H) |
| 421 | 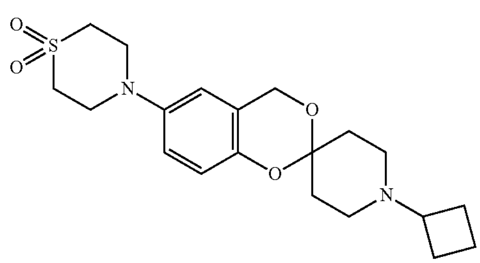 [SMILES: O=S1(=O)CCN(c2ccc3c(c2)COC2(CCN(C4CCC4)CC2)O3)CC1] | +++ | +++ | 157-158 | 393 (M + H) |
| 422 | 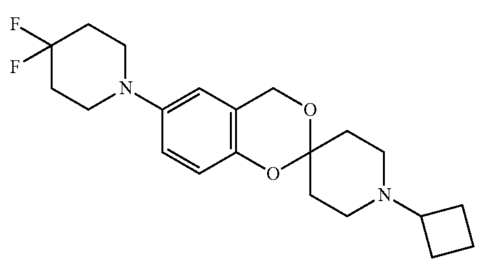 [SMILES: FC1(F)CCN(c2ccc3c(c2)COC2(CCN(C4CCC4)CC2)O3)CC1] | +++ | ++ | dec. >250 | 379 (M + H) |
| 423 | 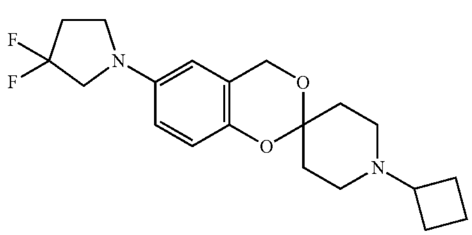 [SMILES: FC1(F)CCN(c2ccc3c(c2)COC2(CCN(C4CCC4)CC2)O3)C1] | +++ | +++ | 217-221 | 365 (M + H) |

TABLE C-continued

| Ex. No. | Structure | Human H3 Ki (nM) | Rat H3 Ki (nM) | MP (° C.) | MS (m/z) |
|---|---|---|---|---|---|
| 424 | 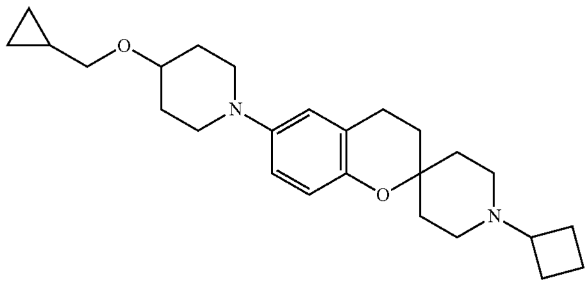 [SMILES: c1cc2c(cc1N1CCC(OCC3CC3)CC1)CCC1(CCN(C3CCC3)CC1)O2] | +++ | +++ | 280-283 | 411 (M + H) |
| 425 | 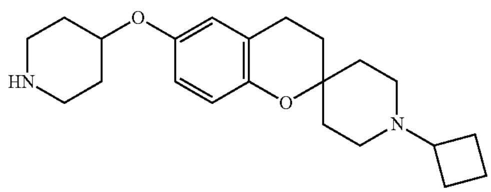 [SMILES: c1cc2c(cc1OC1CCNCC1)CCC1(CCN(C3CCC3)CC1)O2] | +++ | +++ | >320 | 357 (M + H) |
| 426 | 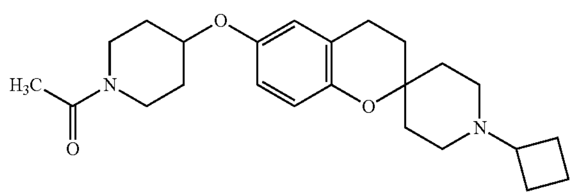 [SMILES: CC(=O)N1CCC(Oc2ccc3c(c2)CCC2(CCN(C4CCC4)CC2)O3)CC1] | +++ | +++ | 227-229 | 399 (M + H) |
| 427 | 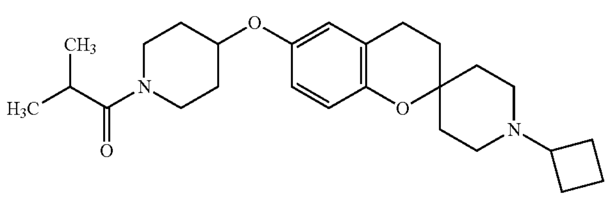 [SMILES: CC(C)C(=O)N1CCC(Oc2ccc3c(c2)CCC2(CCN(C4CCC4)CC2)O3)CC1] | +++ | +++ | 239-241 | 427 (M + H) |
| 428 | 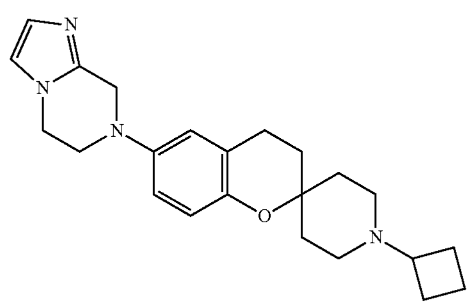 [SMILES: c1cn2c(n1)CN(c1ccc3c(c1)CCC1(CCN(C4CCC4)CC1)O3)CC2] | +++ | +++ | dec @ 190 | 379 (M + H) |
| 429 | 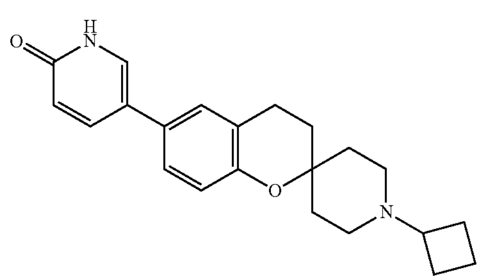 [SMILES: O=c1ccc(-c2ccc3c(c2)CCC2(CCN(C4CCC4)CC2)O3)c[nH]1] | +++ | +++ | 260-2 | 351 (M + H) |

TABLE C-continued

| Ex. No. | Structure | Human H3 Ki (nM) | Rat H3 Ki (nM) | MP (° C.) | MS (m/z) |
| --- | --- | --- | --- | --- | --- |
| 430 | 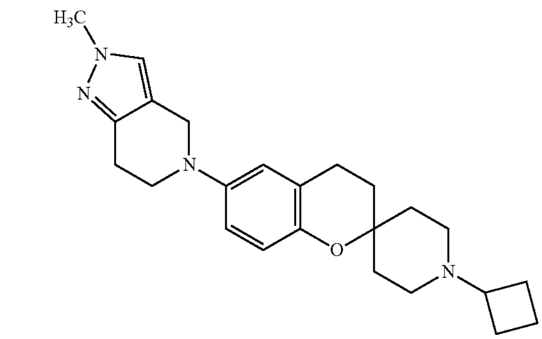 [SMILES: Cn1cc2c(n1)CCN(c1ccc3c(c1)CCC1(CCN(C4CCC4)CC1)O3)C2] | +++ | +++ | 132-4 | 393 (M + H) |
| 431 | 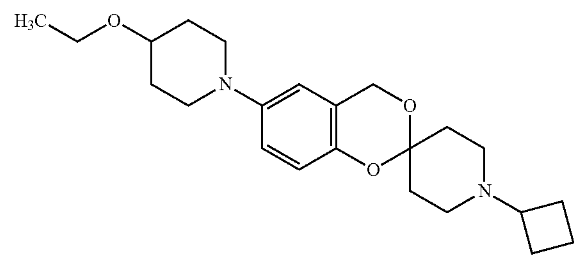 [SMILES: CCOC1CCN(c2ccc3c(c2)COC2(CCN(C4CCC4)CC2)O3)CC1] | +++ | +++ | 266-269 | 387 (M + H) |
| 432 | 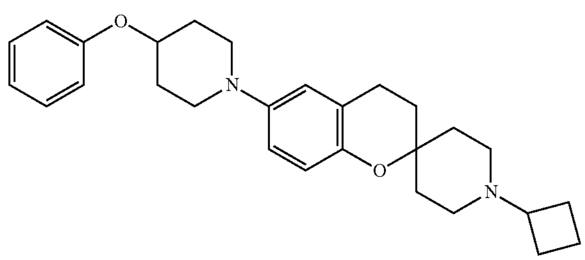 [SMILES: c1ccc(OC2CCN(c3ccc4c(c3)CCC3(CCN(C5CCC5)CC3)O4)CC2)cc1] | +++ | +++ | dec. >265 | 433 (M + H) |
| 433 | 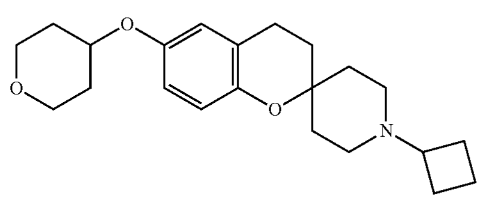 [SMILES: c1cc2c(cc1OC1CCOCC1)CCC1(CCN(C3CCC3)CC1)O2] | +++ | +++ | 252-254 | 358 (M + H) |
| 434 | 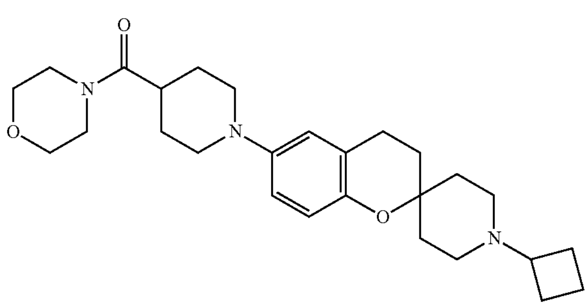 [SMILES: O=C(C1CCN(c2ccc3c(c2)CCC2(CCN(C4CCC4)CC2)O3)CC1)N1CCOCC1] | +++ | +++ | 165-7 | 454 (M + H) |
| 435 | 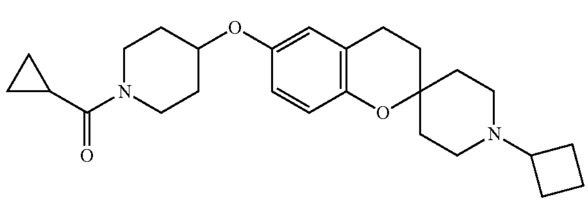 [SMILES: O=C(C1CC1)N1CCC(Oc2ccc3c(c2)CCC2(CCN(C4CCC4)CC2)O3)CC1] | +++ | +++ | 243-245 | 425 (M + H) |

TABLE C-continued
| Ex. No. | Structure | Human H3 Ki (nM) | Rat H3 Ki (nM) | MP (° C.) | MS (m/z) |
|---|---|---|---|---|---|
| 436 | 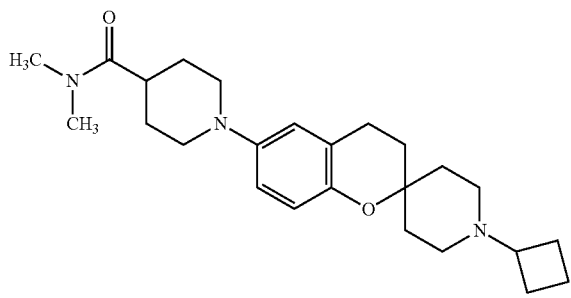 | +++ | +++ | 140-2 | 412 (M + H) |
| 437 | 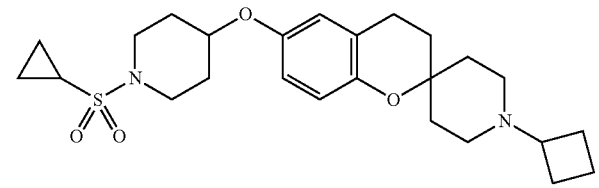 [SMILES: O=S(=O)(C1CC1)N1CCC(Oc2ccc3c(c2)CCC2(CCN(C4CCC4)CC2)O3)CC1] | +++ | +++ | 233-235 | 461 (M + H) |
| 438 | 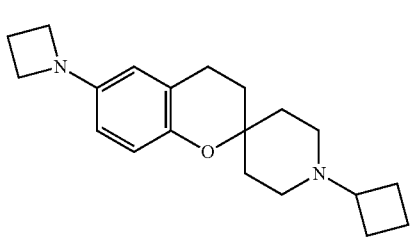 [SMILES: c1cc2c(cc1N1CCC1)CCC1(CCN(C3CCC3)CC1)O2] | +++ | +++ | 118-120 | 313 (M + H) |
| 439 | 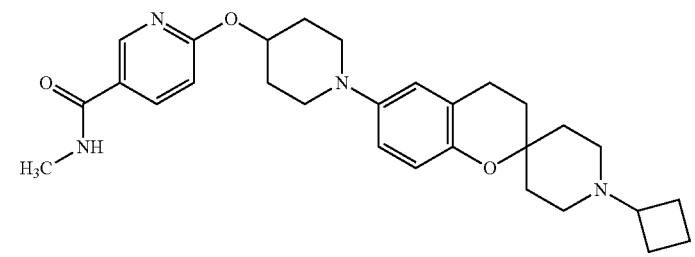 [SMILES: CNC(=O)c1ccc(OC2CCN(c3ccc4c(c3)CCC3(CCN(C5CCC5)CC3)O4)CC2)nc1] | +++ | +++ | 214-216 | 491 (M + H) |
| 440 | 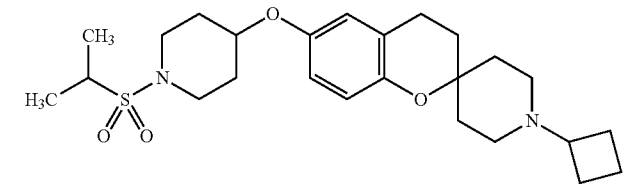 [SMILES: CC(C)S(=O)(=O)N1CCC(Oc2ccc3c(c2)CCC2(CCN(C4CCC4)CC2)O3)CC1] | +++ | +++ | 233-235 | 463 (M + H) |
| 441 | 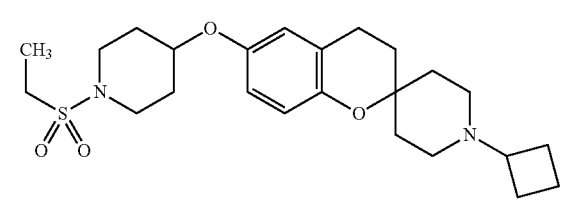 [SMILES: CCS(=O)(=O)N1CCC(Oc2ccc3c(c2)CCC2(CCN(C4CCC4)CC2)O3)CC1] | +++ | +++ | 226-229 | 449 (M + H) |

TABLE C-continued

| Ex. No. | Structure | | Human H3 Ki (nM) | Rat H3 Ki (nM) | MP (° C.) | MS (m/z) |
|---|---|---|---|---|---|---|
| 442 | 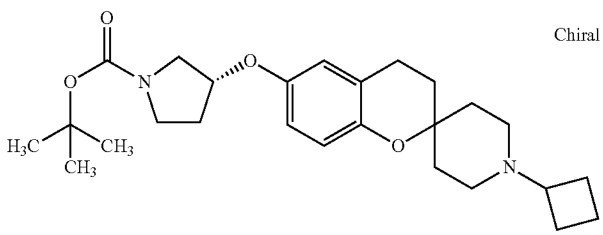 [SMILES: CC(C)(C)OC(=O)N1CC[C@@H](Oc2ccc3c(c2)CCC2(CCN(C4CCC4)CC2)O3)C1] | Chiral | +++ | +++ | 280-283 | 443 (M − C5H8O2) |
| 443 | 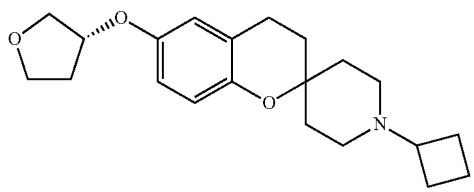 | Chiral | +++ | ++ | 261-263 | 344 (M + H) |
| 444 | 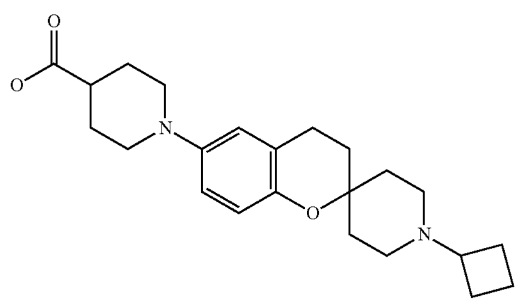 [SMILES: O=C(O)C1CCN(c2ccc3c(c2)CCC2(CCN(C4CCC4)CC2)O3)CC1] | | +++ | >100 nM | dec @ 295 | 383 (M + H) |

TABLE D

| Ex. No. | Structure | MP (° C.) | MS (m/z) | Human H3 Ki (nM) | Rat H3 kI (nM) |
|---|---|---|---|---|---|
| 445 | 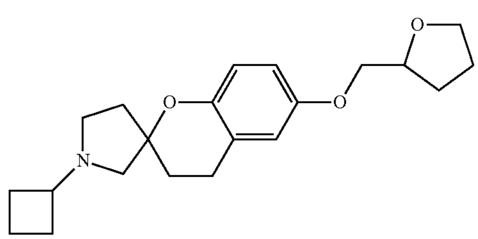 [SMILES: c1cc2c(cc1OCC1CCCO1)CCC1(CCN(C3CCC3)C1)O2] | oil | 344 (M + H) | ++ | ++ |
| 446 | 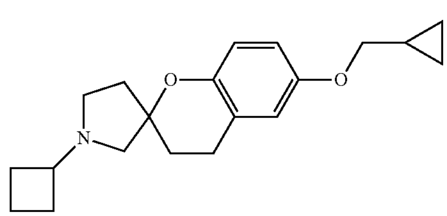 [SMILES: c1cc2c(cc1OCC1CC1)CCC1(CCN(C3CCC3)C1)O2] | 177-178 | 314 (M + H) | ++ | ++ |

TABLE D-continued

| Ex. No. | Structure | MP (° C.) | MS (m/z) | Human H3 Ki (nM) | Rat H3 kI (nM) |
|---|---|---|---|---|---|
| 447 | 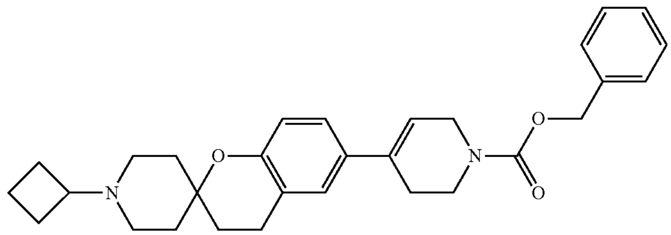 [SMILES: O=C(OCc1ccccc1)N1CC=C(c2ccc3c(c2)CCC2(CCN(C4CCC4)CC2)O3)CC1] | 237-9 | 473 (M + H) | +++ | +++ |
| 448 | 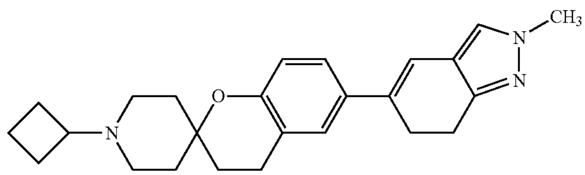 [SMILES: Cn1cc2c(n1)CCC(c1ccc3c(c1)CCC1(CCN(C4CCC4)CC1)O3)=C2] | 205-8 | 390 (M + H) | +++ | +++ |
| 449 | 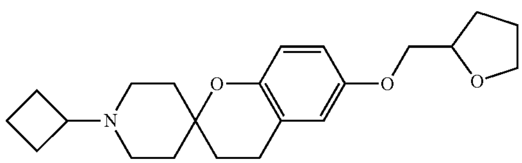 [SMILES: c1cc2c(cc1OCC1CCCO1)CCC1(CCN(C3CCC3)CC1)O2] | 276-278 | 358 (M + H) | +++ | +++ |
| 450 | 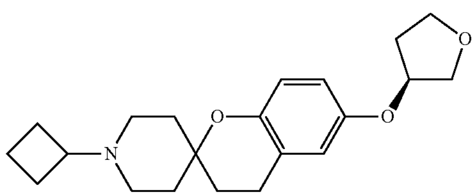 | 259-261 | 344 (M + H) | +++ | +++ |
| 451 | 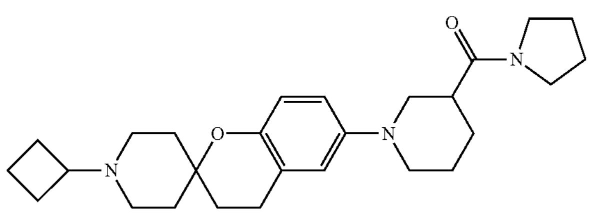 [SMILES: O=C(C1CCCN(c2ccc3c(c2)CCC2(CCN(C4CCC4)CC2)O3)C1)N1CCCC1] | 305-7 | 438 (M + H) | +++ | +++ |
| 452 | 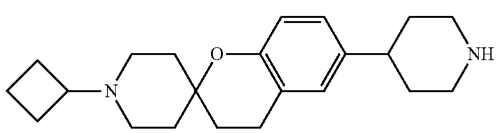 [SMILES: c1cc2c(cc1C1CCNCC1)CCC1(CCN(C3CCC3)CC1)O2] | 88-90 | 341 (M + H) | +++ | +++ |
| 453 | 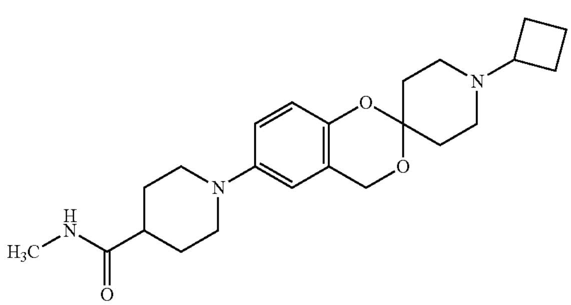 | dec. >245 | 400 (M + H) | +++ | +++ |
| 454 | 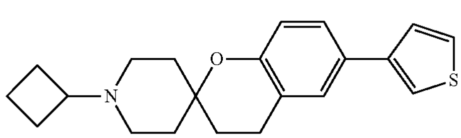 [SMILES: c1cc(-c2ccc3c(c2)CCC2(CCN(C4CCC4)CC2)O3)cs1] | 110-112 | 340 (M + H) | +++ | +++ |

TABLE D-continued

| Ex. No. | Structure | MP (° C.) | MS (m/z) | Human H3 Ki (nM) | Rat H3 kI (nM) |
|---|---|---|---|---|---|
| 455 | 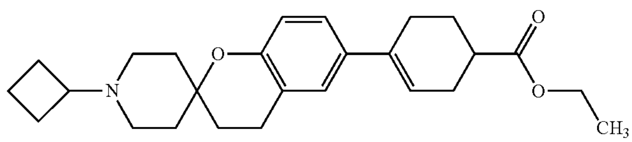 | 137-9 | 410 (M + H) | +++ | +++ |
| 456 | 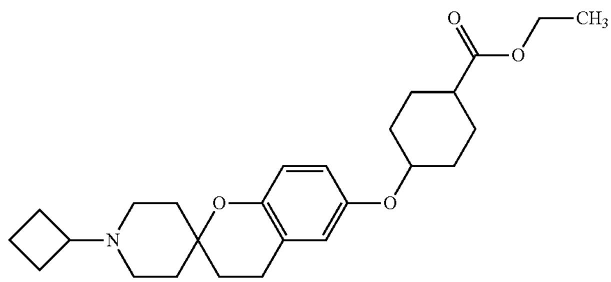 [SMILES: CCOC(=O)C1CCC(Oc2ccc3c(c2)CCC2(CCN(C4CCC4)CC2)O3)CC1] | 236-238 | 428 (M + H) | +++ | +++ |
| 457 | 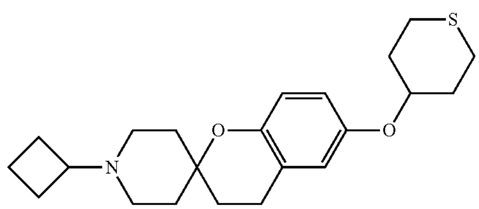 [SMILES: c1cc2c(cc1OC1CCSCC1)CCC1(CCN(C3CCC3)CC1)O2] | 252-254 | 374 (M + H) | +++ | +++ |
| 458 | 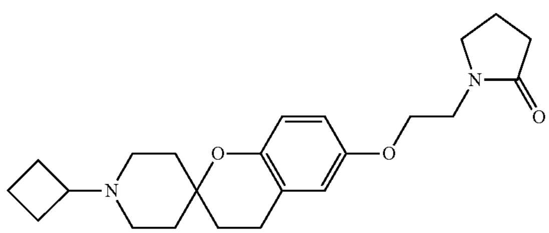 [SMILES: O=C1CCCN1CCOc1ccc2c(c1)CCC1(CCN(C3CCC3)CC1)O2] | 170-172 | 385 (M + H) | +++ | +++ |
| 459 | 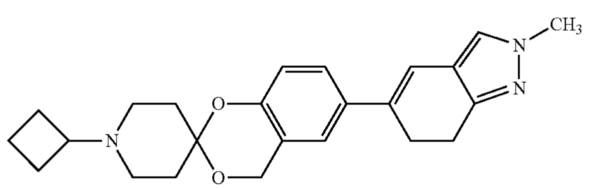 [SMILES: Cn1cc2c(n1)CCC(c1ccc3c(c1)COC1(CCN(C4CCC4)CC1)O3)=C2] | 149-150 | 392 (M + H) | +++ | +++ |
| 460 | 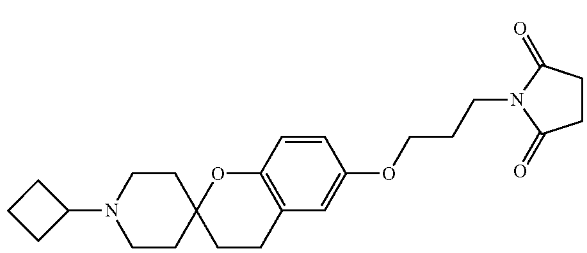 [SMILES: O=C1CCC(=O)N1CCCOc1ccc2c(c1)CCC1(CCN(C3CCC3)CC1)O2] | 235-237 | 413 (M + H) | +++ | +++ |
| 461 | 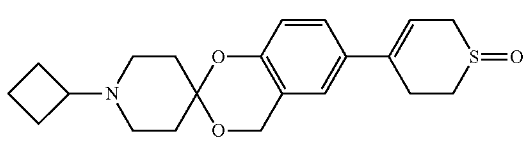 [SMILES: O=S1CC=C(c2ccc3c(c2)COC2(CCN(C4CCC4)CC2)O3)CC1] | 155-158 | 374 (M + H) | +++ | +++ |

TABLE D-continued
| Ex. No. | Structure | MP (° C.) | MS (m/z) | Human H3 Ki (nM) | Rat H3 kI (nM) |
|---|---|---|---|---|---|
| 462 | 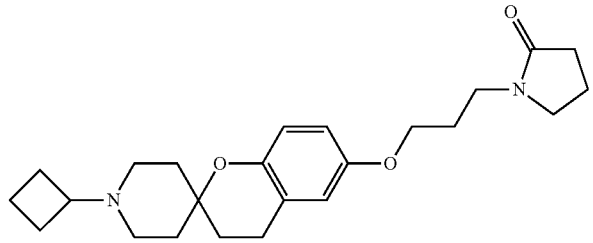 [SMILES: O=C1CCCN1CCCOc1ccc2c(c1)CCC1(CCN(C3CCC3)CC1)O2] | 196-198 | 399 (M + H) | +++ | +++ |
| 463 | 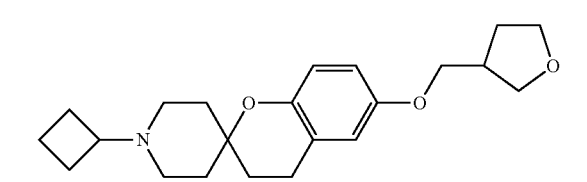 [SMILES: c1cc2c(cc1OCC1CCOC1)CCC1(CCN(C3CCC3)CC1)O2] | 97-99 | 358 (M + H) | +++ | +++ |
| 464 | 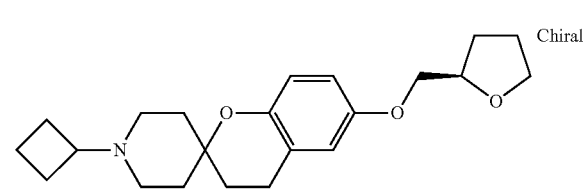 [SMILES: c1cc2c(cc1OC[C@H]1CCCO1)CCC1(CCN(C3CCC3)CC1)O2] Chiral | 253-256 | 358 (M + H) | +++ | +++ |
| 465 | 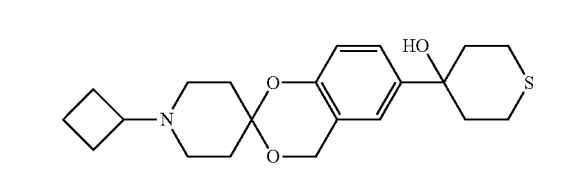 [SMILES: OC1(c2ccc3c(c2)COC2(CCN(C4CCC4)CC2)O3)CCSCC1] | 174-176 | 376 (M + H) | +++ | +++ |
| 466 | 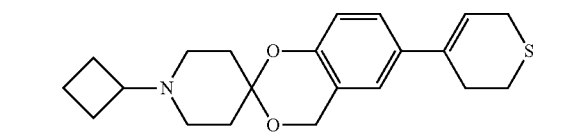 [SMILES: C1=C(c2ccc3c(c2)COC2(CCN(C4CCC4)CC2)O3)CCSC1] | 162-163 | 358 (M + H) | +++ | +++ |
| 467 | 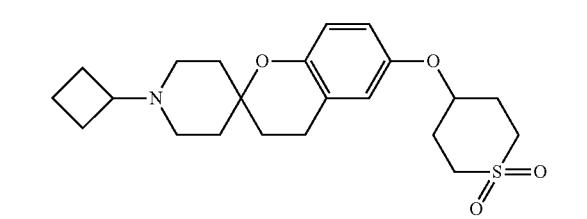 [SMILES: O=S1(=O)CCC(Oc2ccc3c(c2)CCC2(CCN(C4CCC4)CC2)O3)CC1] | 239-241 | 406 (M + H) | +++ | +++ |
| 468 | 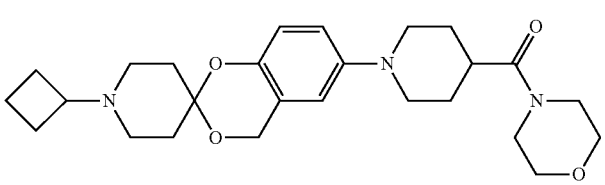 [SMILES: O=C(C1CCN(c2ccc3c(c2)COC2(CCN(C4CCC4)CC2)O3)CC1)N1CCOCC1] | 282-4 | 456 (M + H) | +++ | +++ |
| 469 | 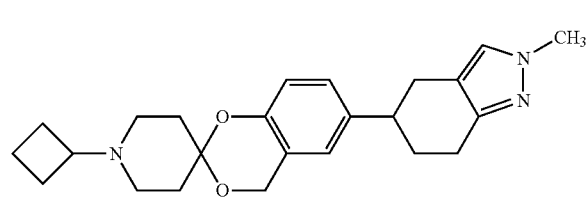 | 138-140 | 394 (M + H) | +++ | +++ |

TABLE D-continued

| Ex. No. | Structure | MP (° C.) | MS (m/z) | Human H3 Ki (nM) | Rat H3 kI (nM) |
|---|---|---|---|---|---|
| 470 | 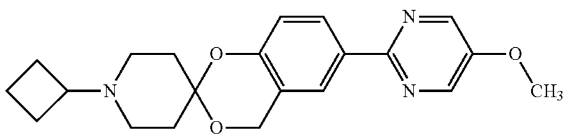 [SMILES: COc1cnc(-c2ccc3c(c2)COC2(CCN(C4CCC4)CC2)O3)nc1] | 113-5 | 368 (M + H) | +++ | +++ |
| 471 | 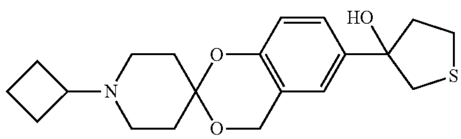 [SMILES: OC1(c2ccc3c(c2)COC2(CCN(C4CCC4)CC2)O3)CCSC1] | 125-126 | 362 (M + H) | +++ | +++ |
| 472 | 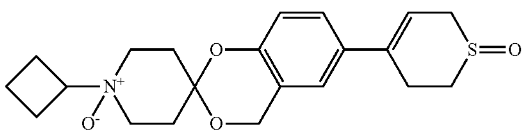 [SMILES: O=S1CC=C(c2ccc3c(c2)COC2(CC[N+]([O-])(C4CCC4)CC2)O3)CC1] | 130-133 | 390 (M + H) | +++ | +++ |
| 473 | 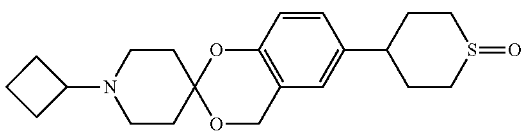 | 187-189 | 376 (M + H) | +++ | +++ |
| 474 | 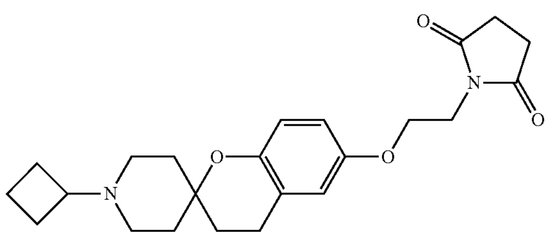 [SMILES: O=C1CCC(=O)N1CCOc1ccc2c(c1)CCC1(CCN(C3CCC3)CC1)O2] | 238-240 | 341 (M + H) | +++ | +++ |
| 475 | 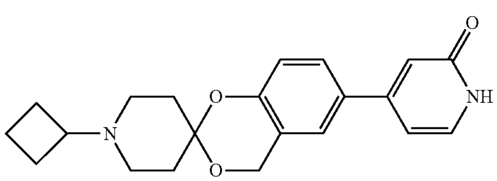 [SMILES: O=c1cc(-c2ccc3c(c2)COC2(CCN(C4CCC4)CC2)O3)cc[nH]1] | 211-3 | 353 (M + H) | +++ | +++ |
| 476 | 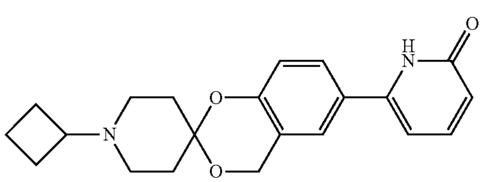 [SMILES: O=c1cccc(-c2ccc3c(c2)COC2(CCN(C4CCC4)CC2)O3)[nH]1] | 207-9 | 353 (M + H) | +++ | +++ |
| 477 | 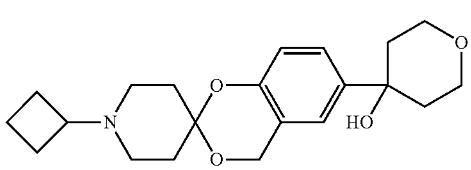 [SMILES: OC1(c2ccc3c(c2)COC2(CCN(C4CCC4)CC2)O3)CCOCC1] | 157-159 | 360 (M + H) | +++ | +++ |
| 478 | 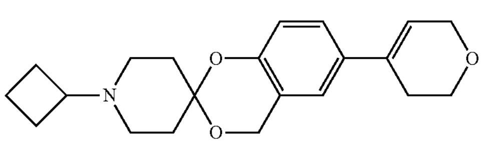 [SMILES: C1=C(c2ccc3c(c2)COC2(CCN(C4CCC4)CC2)O3)CCOC1] | 168-169 | 342 (M + H) | +++ | +++ |

TABLE D-continued

| Ex. No. | Structure | MP (° C.) | MS (m/z) | Human H3 Ki (nM) | Rat H3 kI (nM) |
|---|---|---|---|---|---|
| 479 | 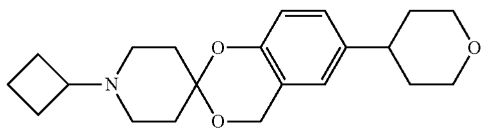 [SMILES: c1cc2c(cc1C1CCOCC1)COC1(CCN(C3CCC3)CC1)O2] | 249-251 | 344 (M + H) | +++ | +++ |
| 480 | 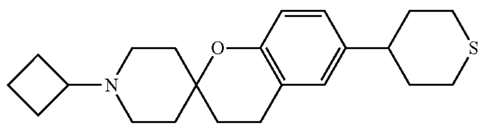 [SMILES: c1cc2c(cc1C1CCSCC1)CCC1(CCN(C3CCC3)CC1)O2] | 153-155 | 360 (M + H) | +++ | +++ |
| 481 | 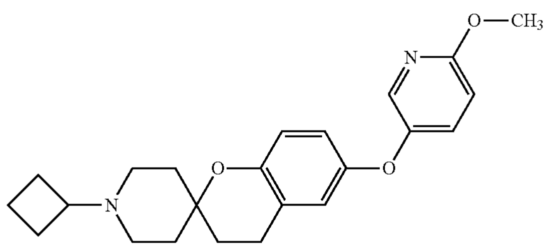 [SMILES: COc1ccc(Oc2ccc3c(c2)CCC2(CCN(C4CCC4)CC2)O3)cn1] | 232-234 | 381 (M + H) | +++ | +++ |
| 482 | 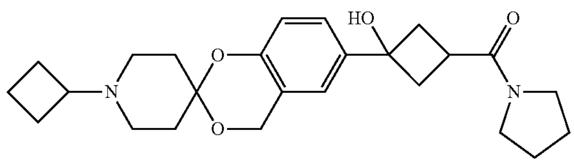 [SMILES: O=C(C1CC(O)(c2ccc3c(c2)COC2(CCN(C4CCC4)CC2)O3)C1)N1CCCC1] | 157-9 | 427 (M + H) | +++ | +++ |
| 483 | 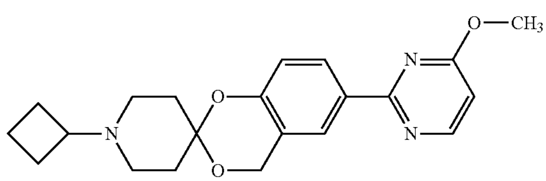 [SMILES: COc1ccnc(-c2ccc3c(c2)COC2(CCN(C4CCC4)CC2)O3)n1] | 100-102 | 368 (M + H) | +++ | +++ |
| 484 | 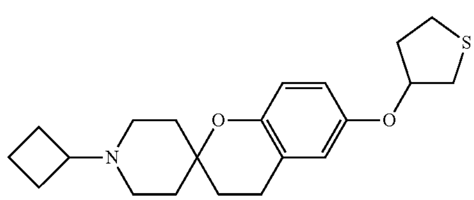 [SMILES: c1cc2c(cc1OC1CCSC1)CCC1(CCN(C3CCC3)CC1)O2] | 96-98 | 360 (M + H) | +++ | +++ |
| 485 | 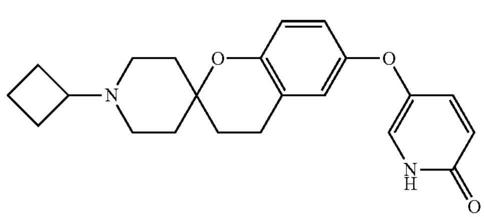 [SMILES: O=c1ccc(Oc2ccc3c(c2)CCC2(CCN(C4CCC4)CC2)O3)c[nH]1] | 284-286 | 367 (M + H) | +++ | +++ |
| 486 | 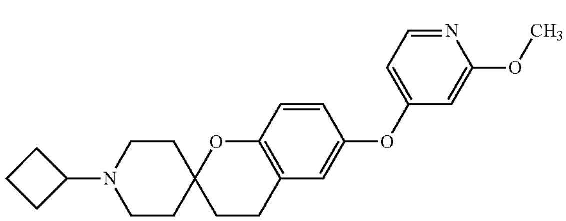 [SMILES: COc1cc(Oc2ccc3c(c2)CCC2(CCN(C4CCC4)CC2)O3)ccn1] | 125-127 | 381 (M + H) | +++ | +++ |

TABLE D-continued

| Ex. No. | Structure | MP (° C.) | MS (m/z) | Human H3 Ki (nM) | Rat H3 kI (nM) |
|---|---|---|---|---|---|
| 487 | 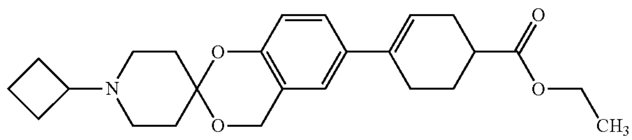 [SMILES: CCOC(=O)C1CC=C(c2ccc3c(c2)COC2(CCN(C4CCC4)CC2)O3)CC1] | 263-5 | 412 (M + H) | +++ | +++ |
| 488 | 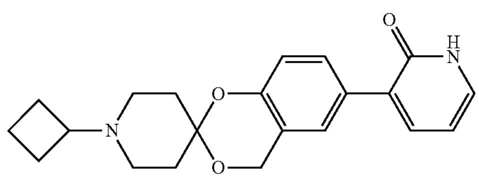 [SMILES: O=c1[nH]cccc1-c1ccc2c(c1)COC1(CCN(C3CCC3)CC1)O2] | 167-9 | 353 (M + H) | +++ | +++ |
| 489 | 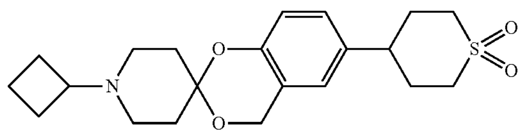 [SMILES: O=S1(=O)CCC(c2ccc3c(c2)COC2(CCN(C4CCC4)CC2)O3)CC1] | 210-211 | 392 (M + H) | +++ | +++ |
| 490 | 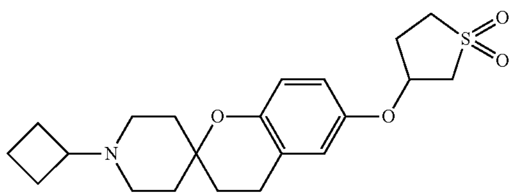 [SMILES: O=S1(=O)CCC(Oc2ccc3c(c2)CCC2(CCN(C4CCC4)CC2)O3)C1] | 252-254 | 392 (M + H) | +++ | +++ |
| 491 | 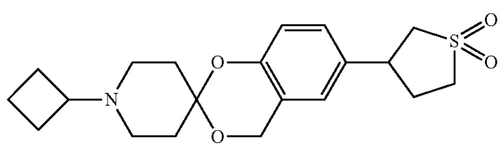 [SMILES: O=S1(=O)CCC(c2ccc3c(c2)COC2(CCN(C4CCC4)CC2)O3)C1] | 151-152 | 378 (M + H) | +++ | +++ |
| 492 | 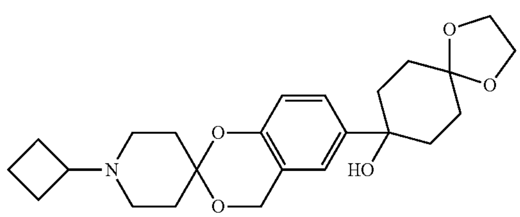 [SMILES: OC1(c2ccc3c(c2)COC2(CCN(C4CCC4)CC2)O3)CCC2(CC1)OCCO2] | 191-192 | 416 (M + H) | +++ | +++ |
| 493 | 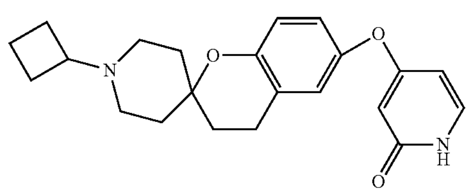 [SMILES: O=c1cc(Oc2ccc3c(c2)CCC2(CCN(C4CCC4)CC2)O3)cc[nH]1] | 186-188 | 367 (M + H) | +++ | +++ |
| 494 | 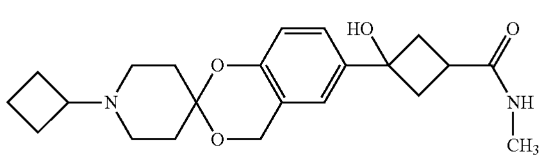 [SMILES: CNC(=O)C1CC(O)(c2ccc3c(c2)COC2(CCN(C4CCC4)CC2)O3)C1] | 246-8 | 387 (M + H) | +++ | +++ |

TABLE D-continued
| Ex. No. | Structure | MP (° C.) | MS (m/z) | Human H3 Ki (nM) | Rat H3 kI (nM) |
|---|---|---|---|---|---|
| 495 | 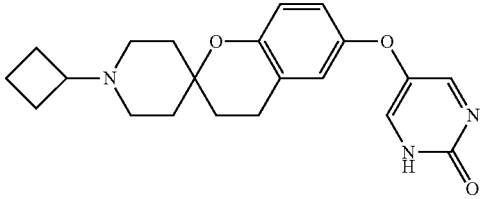 [SMILES: O=c1ncc(Oc2ccc3c(c2)CCC2(CCN(C4CCC4)CC2)O3)c[nH]1] | 259-261 | 368 (M + H) | +++ | +++ |
| 496 | 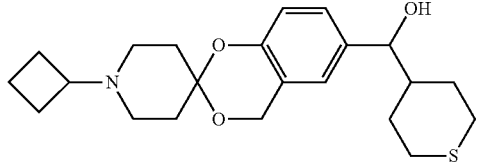 [SMILES: OC(c1ccc2c(c1)COC1(CCN(C3CCC3)CC1)O2)C1CCSCC1] | 85-90 | 390 (M + H) | +++ | +++ |
| 497 | 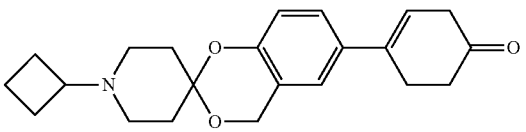 [SMILES: O=C1CC=C(c2ccc3c(c2)COC2(CCN(C4CCC4)CC2)O3)CC1] | 153-155 | 354 (M + H) | +++ | +++ |
| 498 | 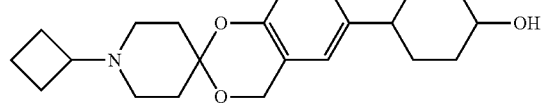 | 150-153 | 358 (M + H) | +++ | +++ |
| 499 | 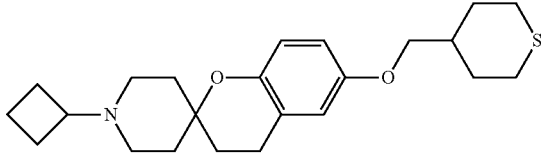 | 117-118 | 388 (M + H) | +++ | +++ |
| 500 | 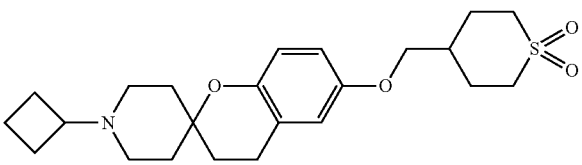 [SMILES: O=S1(=O)CCC(COc2ccc3c(c2)CCC2(CCN(C4CCC4)CC2)O3)CC1] | 175-176 | 420 (M + H) | +++ | +++ |
| 501 | 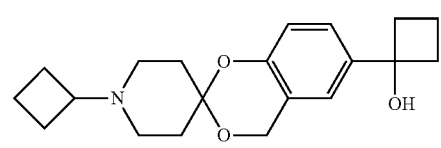 [SMILES: OC1(c2ccc3c(c2)COC2(CCN(C4CCC4)CC2)O3)CCC1] | 64-66 | 330 (M + H) | +++ | +++ |
| 502 | 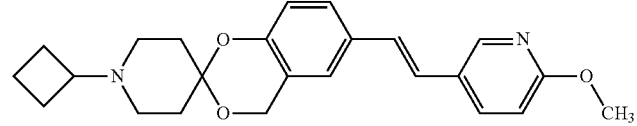 | 144-6 | 393 (M + H) | +++ | +++ |

| Ex. No. | Structure | MP (° C.) | MS (m/z) | Human H3 Ki (nM) | Rat H3 kI (nM) |
|---|---|---|---|---|---|
| 503 | 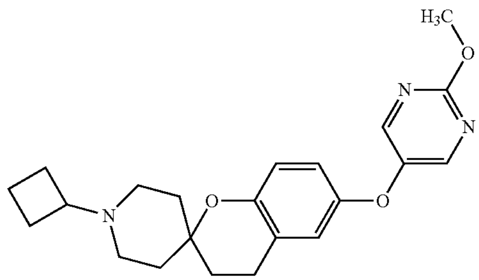 [SMILES: COc1ncc(Oc2ccc3c(c2)CCC2(CCN(C4CCC4)CC2)O3)cn1] | 227-229 | 382 (M + H) | +++ | +++ |
| 504 | 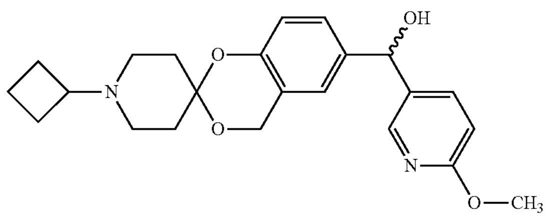 [SMILES: COc1ccc(C(O)c2ccc3c(c2)COC2(CCN(C4CCC4)CC2)O3)cn1] | 78-80 | 397 (M + H) | +++ | +++ |
| 505 | 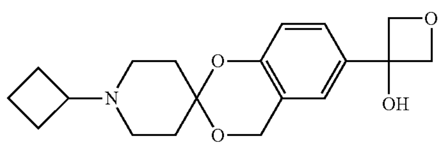 [SMILES: OC1(c2ccc3c(c2)COC2(CCN(C4CCC4)CC2)O3)COC1] | 180-183 | 332 (M + H) | +++ | +++ |
| 506 | 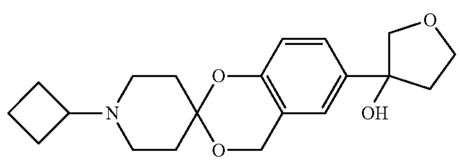 [SMILES: OC1(c2ccc3c(c2)COC2(CCN(C4CCC4)CC2)O3)CCOC1] | 50 | 346 (M + H) | +++ | +++ |
| 507 | 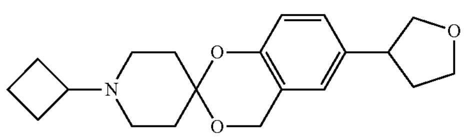 [SMILES: c1cc2c(cc1C1CCOC1)COC1(CCN(C3CCC3)CC1)O2] | 249-250 | 330 (M + H) | +++ | +++ |
| 508 | 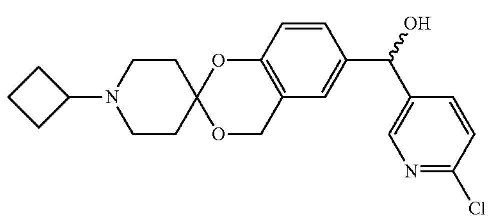 [SMILES: OC(c1ccc(Cl)nc1)c1ccc2c(c1)COC1(CCN(C3CCC3)CC1)O2] | 79-81 | 401 (M + H) | +++ | +++ |
| 509 | 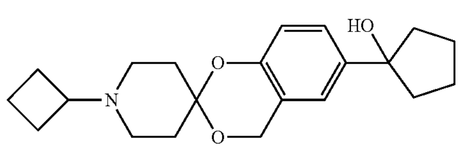 [SMILES: OC1(c2ccc3c(c2)COC2(CCN(C4CCC4)CC2)O3)CCCC1] | 149-151 | 344 (M + H) | +++ | +++ |
| 510 | 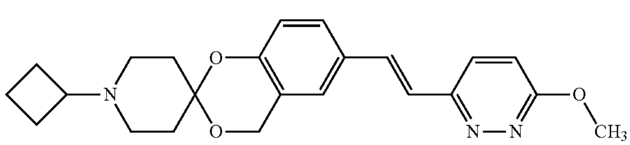 | 168-170 | 394 (M + H) | +++ | +++ |

TABLE D-continued
| Ex. No. | Structure | MP (° C.) | MS (m/z) | Human H3 Ki (nM) | Rat H3 kI (nM) |
|---|---|---|---|---|---|
| 511 | 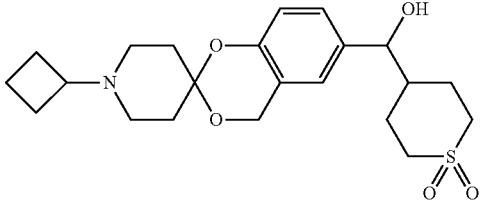 [SMILES: O=S1(=O)CCC(C(O)c2ccc3c(c2)COC2(CCN(C4CCC4)CC2)O3)CC1] | 127-129 | 422 (M + H) | +++ | +++ |
| 512 | 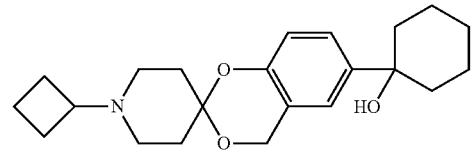 [SMILES: OC1(c2ccc3c(c2)COC2(CCN(C4CCC4)CC2)O3)CCCCC1] | 164-165 | 358 (M + H) | +++ | +++ |
| 513 | 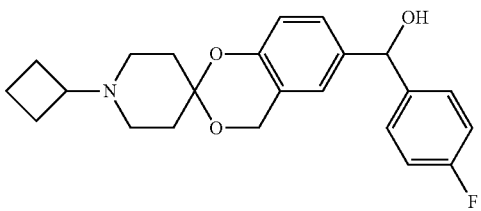 [SMILES: OC(c1ccc(F)cc1)c1ccc2c(c1)COC1(CCN(C3CCC3)CC1)O2] | 58-62 (glass) | 384 (M + H) | +++ | +++ |
| 514 | 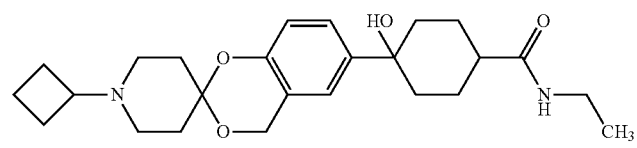 | 195-6 | 429 (M + H) | +++ | +++ |
| 515 | 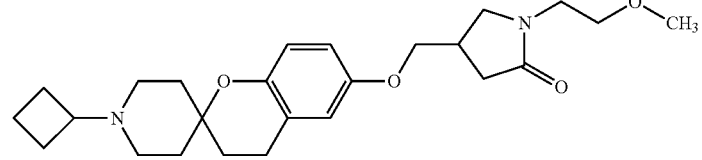 | 194-196 | 429 (M + H) | +++ | +++ |
| 516 | 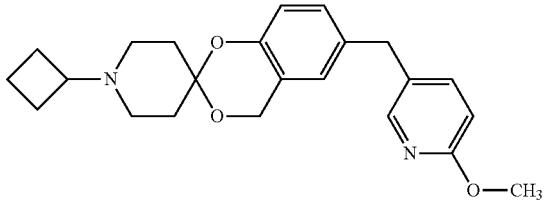 [SMILES: COc1ccc(Cc2ccc3c(c2)COC2(CCN(C4CCC4)CC2)O3)cn1] | 229-231 | 381 (M + H) | +++ | +++ |
| 517 | 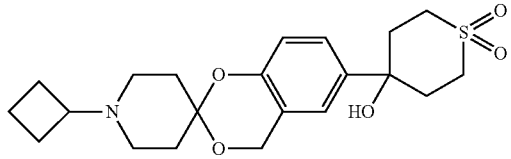 [SMILES: O=S1(=O)CCC(O)(c2ccc3c(c2)COC2(CCN(C4CCC4)CC2)O3)CC1] | 240-241 | 408 (M + H) | +++ | +++ |
| 518 | 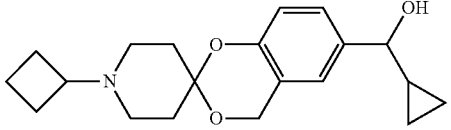 [SMILES: OC(c1ccc2c(c1)COC1(CCN(C3CCC3)CC1)O2)C1CC1] | 94-97 | 329 (M + H) | +++ | +++ |

TABLE D-continued

| Ex. No. | Structure | MP (° C.) | MS (m/z) | Human H3 Ki (nM) | Rat H3 kI (nM) |
|---|---|---|---|---|---|
| 519 | 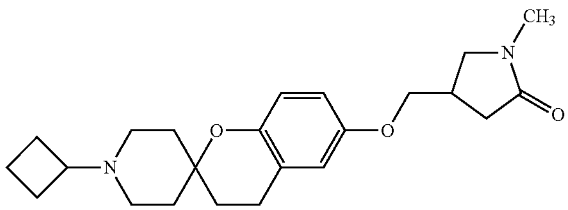 [SMILES: CN1CC(COc2ccc3c(c2)CCC2(CCN(C4CCC4)CC2)O3)CC1=O] | 234-236 | 385 (M + H) | +++ | +++ |
| 520 | 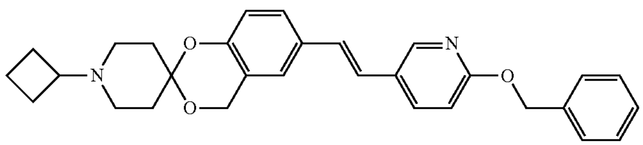 [SMILES: C(=C\c1ccc2c(c1)COC1(CCN(C3CCC3)CC1)O2)/c1ccc(OCc2ccccc2)nc1] | 161-3 | 369 (M + H) | ++ | ++ |
| 521 | 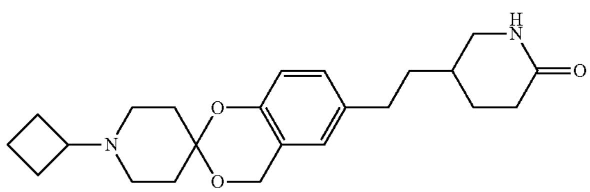 [SMILES: O=C1CCC(CCc2ccc3c(c2)COC2(CCN(C4CCC4)CC2)O3)CN1] | 122-4 | 360 (M + H) | +++ | +++ |
| 522 | 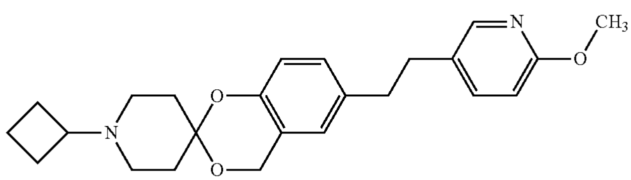 [SMILES: COc1ccc(CCc2ccc3c(c2)COC2(CCN(C4CCC4)CC2)O3)cn1] | | 395 (M + H) | +++ | +++ |
| 523 | 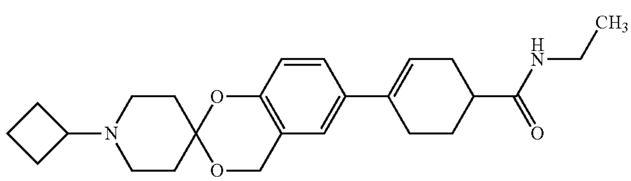 [SMILES: CCNC(=O)C1CC=C(c2ccc3c(c2)COC2(CCN(C4CCC4)CC2)O3)CC1] | Gummy | 411 (M + H) | +++ | +++ |
| 524 | 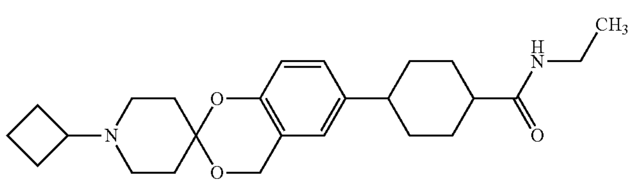 [SMILES: CCNC(=O)C1CCC(c2ccc3c(c2)COC2(CCN(C4CCC4)CC2)O3)CC1] | | 413 (M + H) | +++ | +++ |
| 525 | 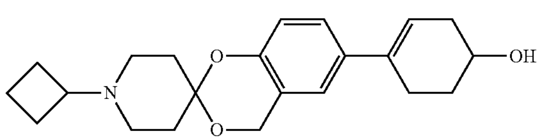 [SMILES: OC1CC=C(c2ccc3c(c2)COC2(CCN(C4CCC4)CC2)O3)CC1] | 128-132 | 356 (M + H) | +++ | +++ |
| 526 | 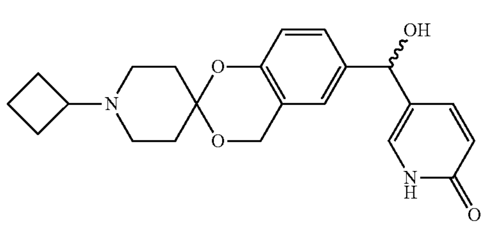 [SMILES: O=c1ccc(C(O)c2ccc3c(c2)COC2(CCN(C4CCC4)CC2)O3)c[nH]1] | 217-219 | 383 (M + H) | +++ | +++ |

TABLE D-continued

| Ex. No. | Structure | MP (° C.) | MS (m/z) | Human H3 Ki (nM) | Rat H3 kI (nM) |
|---|---|---|---|---|---|
| 527 | 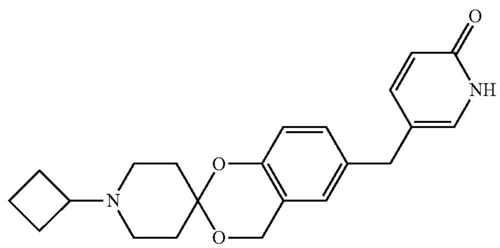 [SMILES: O=c1ccc(Cc2ccc3c(c2)COC2(CCN(C4CCC4)CC2)O3)c[nH]1] | 194-196 | 367 (M + H) | +++ | +++ |
| 528 | 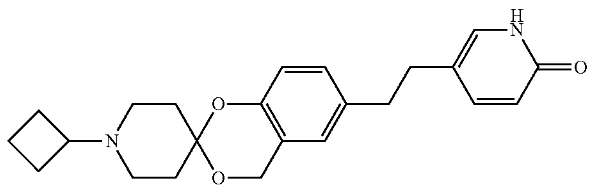 [SMILES: O=c1ccc(CCc2ccc3c(c2)COC2(CCN(C4CCC4)CC2)O3)c[nH]1] | 183-5 | 381 (M + H) | +++ | +++ |
| 529 | 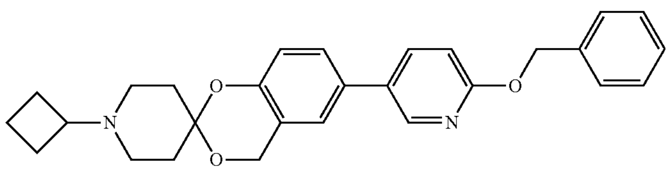 [SMILES: c1ccc(COc2ccc(-c3ccc4c(c3)COC3(CCN(C5CCC5)CC3)O4)cn2)cc1] | 139-141 | 443 (M + H) | +++ | ++ |
| 530 | 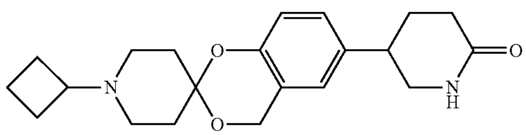 | 233-235 | 357 (M + H) | +++ | +++ |
| 531 | 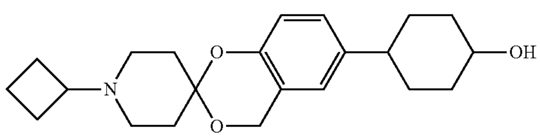 [SMILES: OC1CCC(c2ccc3c(c2)COC2(CCN(C4CCC4)CC2)O3)CC1] | 113-115 | 358 (M + H) | +++ | +++ |
| 532 | 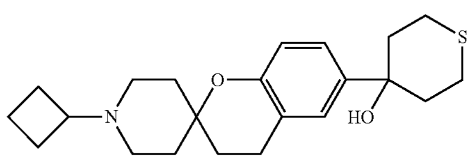 [SMILES: OC1(c2ccc3c(c2)CCC2(CCN(C4CCC4)CC2)O3)CCSCC1] | 146-148 | 374 (M + H) | +++ | +++ |
| 533 | 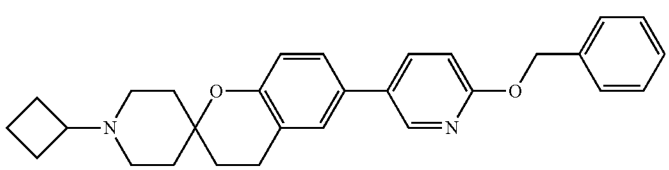 [SMILES: c1ccc(COc2ccc(-c3ccc4c(c3)CCC3(CCN(C5CCC5)CC3)O4)cn2)cc1] | 115-117 | 441 (M + H) | +++ | +++ |
| 534 | 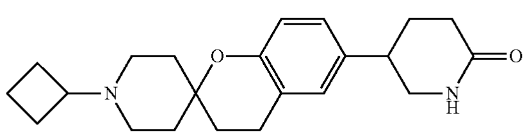 [SMILES: O=C1CCC(c2ccc3c(c2)CCC2(CCN(C4CCC4)CC2)O3)CN1] | 292-294 | 355 (M + H) | +++ | +++ |
| 535 | 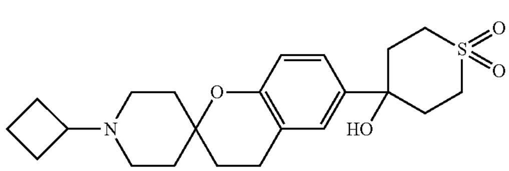 [SMILES: O=S1(=O)CCC(O)(c2ccc3c(c2)CCC2(CCN(C4CCC4)CC2)O3)CC1] | 213-215 | 406 (M + H) | +++ | +++ |

TABLE D-continued

| Ex. No. | Structure | MP (° C.) | MS (m/z) | Human H3 Ki (nM) | Rat H3 kI (nM) |
|---|---|---|---|---|---|
| 536 | 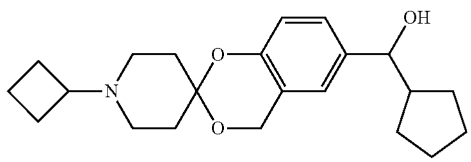 [SMILES: OC(c1ccc2c(c1)COC1(CCN(C3CCC3)CC1)O2)C1CCCC1] | 148-150 | 358 (M + H) | +++ | +++ |
| 537 | 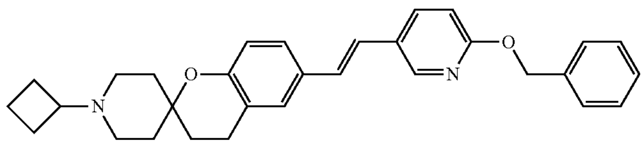 [SMILES: C(=C\c1ccc2c(c1)CCC1(CCN(C3CCC3)CC1)O2)/c1ccc(OCc2ccccc2)nc1] | 236-8 | 467 (M + H) | ++ | + |
| 538 | 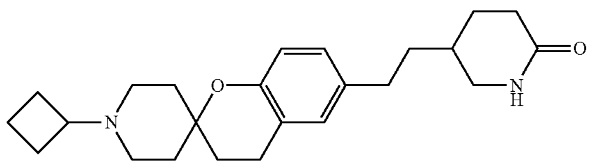 [SMILES: O=C1CCC(CCc2ccc3c(c2)CCC2(CCN(C4CCC4)CC2)O3)CN1] | 253-4 | 338 (M + H) | +++ | +++ |
| 539 | 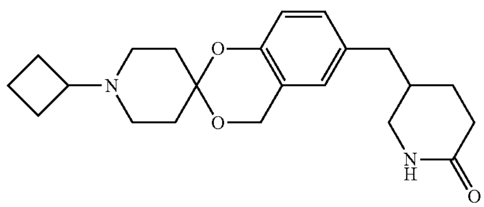 [SMILES: O=C1CCC(Cc2ccc3c(c2)COC2(CCN(C4CCC4)CC2)O3)CN1] | 219-221 | 371 (M + H) | +++ | +++ |
| 540 | 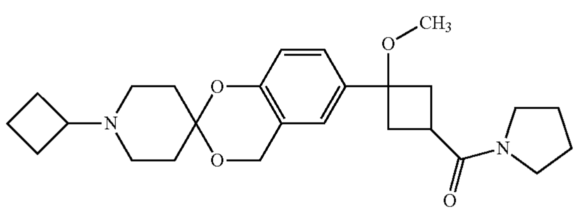 [SMILES: COC1(c2ccc3c(c2)COC2(CCN(C4CCC4)CC2)O3)CC(C(=O)N2CCCC2)C1] | 117-8 | 441 (M + H) | +++ | +++ |
| 541 | 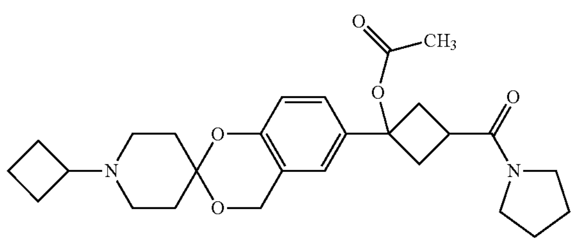 [SMILES: CC(=O)OC1(c2ccc3c(c2)COC2(CCN(C4CCC4)CC2)O3)CC(C(=O)N2CCCC2)C1] | 72-4 | 469 (M + H) | +++ | +++ |
| 542 | 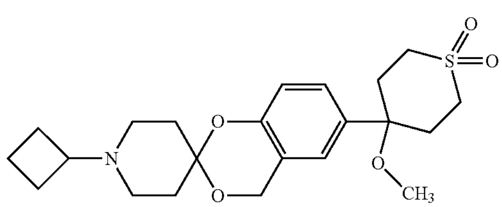 [SMILES: COC1(c2ccc3c(c2)COC2(CCN(C4CCC4)CC2)O3)CCS(=O)(=O)CC1] | 199-201 | 422 (M + H) | +++ | +++ |
| 543 | 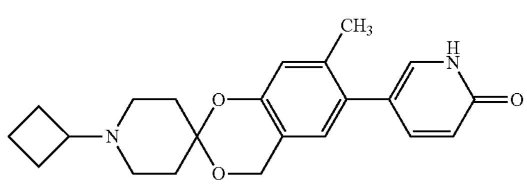 [SMILES: Cc1cc2c(cc1-c1ccc(=O)[nH]c1)COC1(CCN(C3CCC3)CC1)O2] | 239-40 | 367 (M + H) | +++ | ++ |

TABLE D-continued

| Ex. No. | Structure | MP (° C.) | MS (m/z) | Human H3 Ki (nM) | Rat H3 kI (nM) |
|---|---|---|---|---|---|
| 544 | 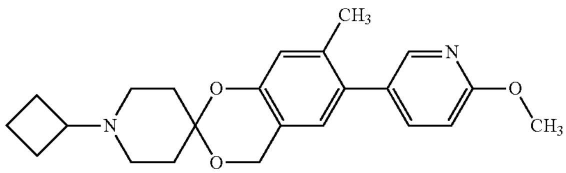 [SMILES: COc1ccc(-c2cc3c(cc2C)OC2(CCN(C4CCC4)CC2)OC3)cn1] | 96-98 | 381 (M + H) | +++ | +++ |
| 545 | 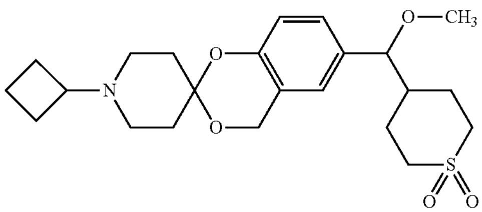 [SMILES: COC(c1ccc2c(c1)COC1(CCN(C3CCC3)CC1)O2)C1CCS(=O)(=O)CC1] | 178-180 | 436 (M + H) | +++ | +++ |
| 546 | 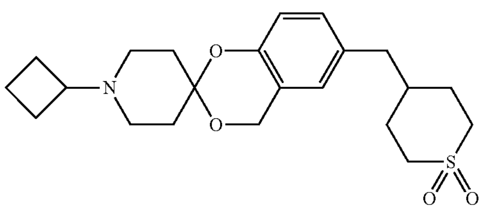 [SMILES: O=S1(=O)CCC(Cc2ccc3c(c2)COC2(CCN(C4CCC4)CC2)O3)CC1] | 150-152 | 360 (M + H) | +++ | +++ |
| 547 | 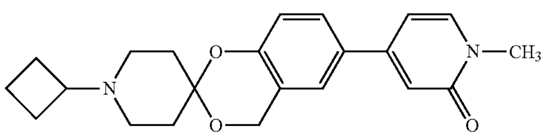 [SMILES: Cn1ccc(-c2ccc3c(c2)COC2(CCN(C4CCC4)CC2)O3)cc1=O] | 208-209 | 367 (M + H) | +++ | +++ |
| 548 | 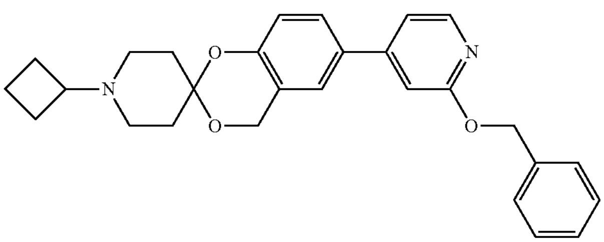 [SMILES: c1ccc(COc2cc(-c3ccc4c(c3)COC3(CCN(C5CCC5)CC3)O4)ccn2)cc1] | 120-125 | 443 (M + H) | +++ | +++ |
| 549 | 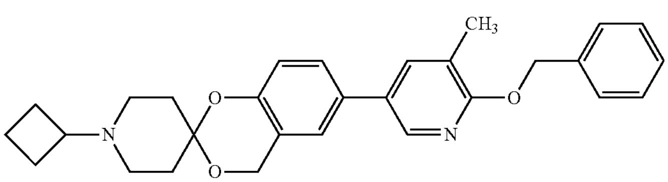 [SMILES: Cc1cc(-c2ccc3c(c2)COC2(CCN(C4CCC4)CC2)O3)cnc1OCc1ccccc1] | Gummy | 457 (M + H) | ++ | + |
| 550 | 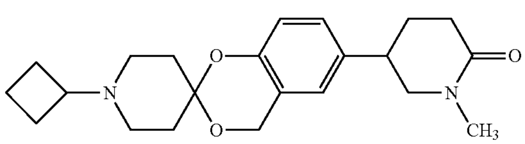 [SMILES: CN1CC(c2ccc3c(c2)COC2(CCN(C4CCC4)CC2)O3)CCC1=O] | 120-125 | 371 (M + H) | +++ | +++ |
| 551 | 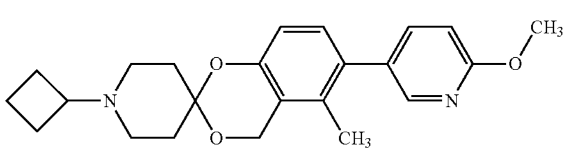 [SMILES: COc1ccc(-c2ccc3c(c2C)COC2(CCN(C4CCC4)CC2)O3)cn1] | 231-232 | 381 (M + H) | +++ | +++ |

TABLE D-continued
| Ex. No. | Structure | MP (° C.) | MS (m/z) | Human H3 Ki (nM) | Rat H3 kI (nM) |
|---|---|---|---|---|---|
| 552 | 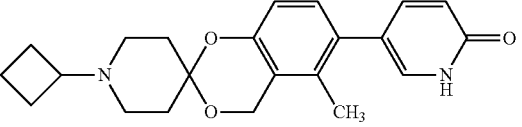 | 246-249 | 367 (M + H) | +++ | +++ |
| 553 | 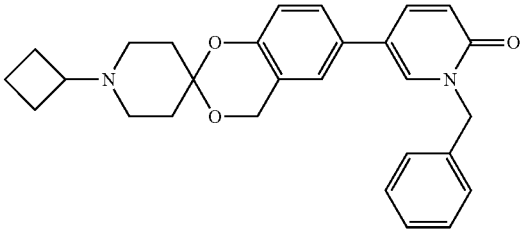 [SMILES: O=c1ccc(-c2ccc3c(c2)COC2(CCN(C4CCC4)CC2)O3)cn1Cc1ccccc1] | 193-196 | 443 (M + H) | +++ | +++ |
| 554 | 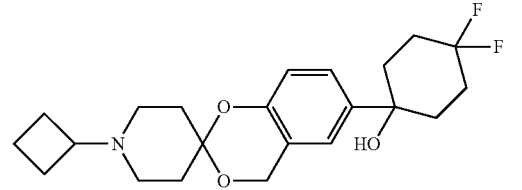 [SMILES: OC1(c2ccc3c(c2)COC2(CCN(C4CCC4)CC2)O3)CCC(F)(F)CC1] | 186-187 | 394 (M + H) | +++ | +++ |
| 555 | 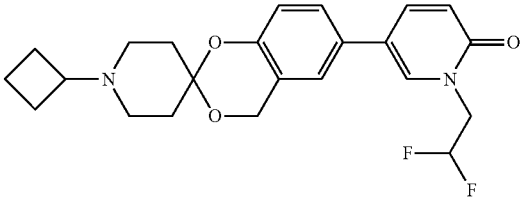 [SMILES: O=c1ccc(-c2ccc3c(c2)COC2(CCN(C4CCC4)CC2)O3)cn1CC(F)F] | 65-70 | 417 (M + H) | +++ | +++ |
| 556 | 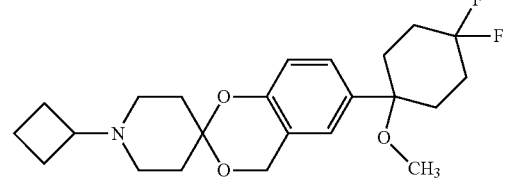 | 116-118 | 408 (M + H) | +++ | +++ |
| 557 | 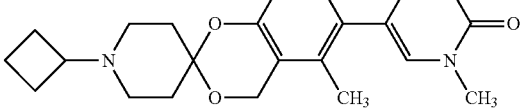 | n/a | 381 (M + H) | +++ | +++ |
| 558 | 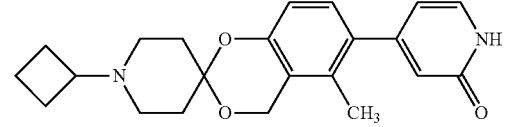 | >300 C. | 367 (M + H) | +++ | +++ |
| 559 | 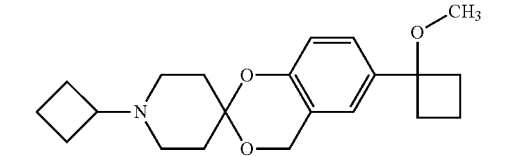 [SMILES: COC1(c2ccc3c(c2)COC2(CCN(C4CCC4)CC2)O3)CCC1] | <50 C. | 344 (M + H) | +++ | +++ |

TABLE D-continued
| Ex. No. | Structure | MP (° C.) | MS (m/z) | Human H3 Ki (nM) | Rat H3 kI (nM) |
|---|---|---|---|---|---|
| 560 | 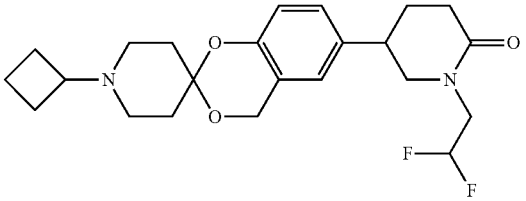 [SMILES: O=C1CCC(c2ccc3c(c2)COC2(CCN(C4CCC4)CC2)O3)CN1CC(F)F] | 120-126 | 421 (M + H) | ++ | ++ |
| 561 | 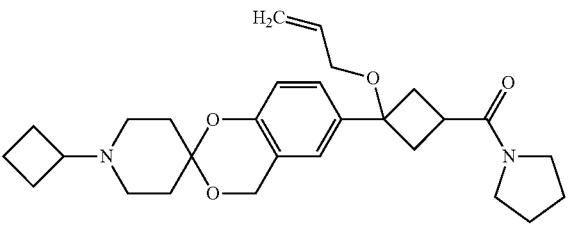 [SMILES: C=CCOC1(c2ccc3c(c2)COC2(CCN(C4CCC4)CC2)O3)CC(C(=O)N2CCCC2)C1] | 49-51 | 467 (M + H) | ++ | ++ |
| 562 | 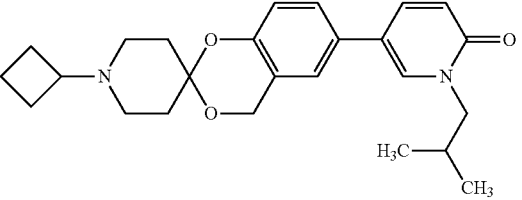 [SMILES: CC(C)Cn1cc(-c2ccc3c(c2)COC2(CCN(C4CCC4)CC2)O3)ccc1=O] | 182-190 | 409 (M + H) | +++ | +++ |
| 563 | 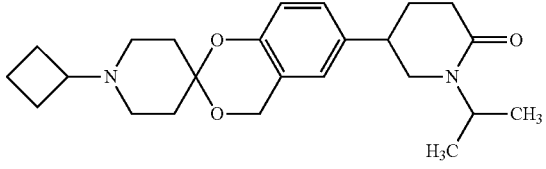 | 129-134 | 399 (M + H) | +++ | +++ |
| 564 | 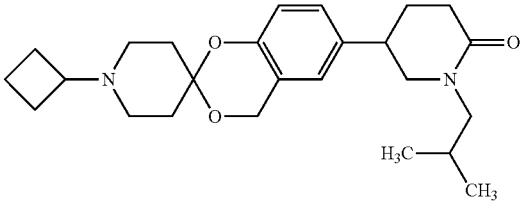 [SMILES: CC(C)CN1CC(c2ccc3c(c2)COC2(CCN(C4CCC4)CC2)O3)CCC1=O] | 98-103 | 413 (M + H) | +++ | +++ |
| 565 | 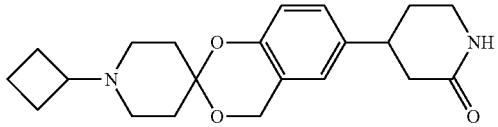 | 182-184 | 357 (M + H) | +++ | +++ |
| 566 | 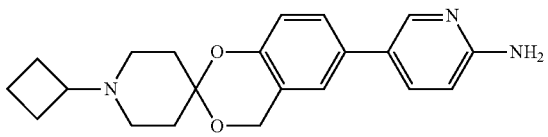 [SMILES: Nc1ccc(-c2ccc3c(c2)COC2(CCN(C4CCC4)CC2)O3)cn1] | 201-203 | 352 (M + H) | +++ | +++ |
| 567 | 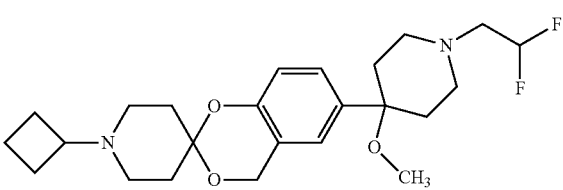 | 247-249 | 434 (M + H) | +++ | +++ |

TABLE D-continued

| Ex. No. | Structure | MP (° C.) | MS (m/z) | Human H3 Ki (nM) | Rat H3 kI (nM) |
|---|---|---|---|---|---|
| 568 | 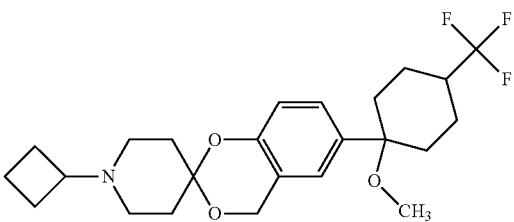 [SMILES: COC1(c2ccc3c(c2)COC2(CCN(C4CCC4)CC2)O3)CCC(C(F)(F)F)CC1] | oil | 440 (M + H) | +++ | +++ |
| 569 | 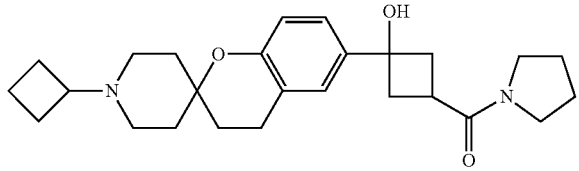 [SMILES: O=C(C1CC(O)(c2ccc3c(c2)CCC2(CCN(C4CCC4)CC2)O3)C1)N1CCCC1] | 180-181 | 425 (M + H) | +++ | +++ |

Table D lists the Human and Rat $H_3$ binding data for Examples 570-808 of the present invention. Binding constants ($K_i$) for Examples 570-808 in the Human $H_3$ and Rat $H_3$ methods described herein are expressed by letter descriptor to indicate the following ranges: "+++" is less than 200 nM; "++" is 200-1000 nM; "+" is >1000 nM.

The compounds of Table D were prepared by methods well known to those skilled in the art, including, but not limited to those described herein, or through modifications of these methods by applying standard techniques known to those skilled in the art of organic synthesis. General routes of synthesis to prepare Examples of Table D are shown in the Schemes herein. The reagents and starting materials are commercially available, or readily synthesized by well-known techniques by one of ordinary skill in the arts.

TABLE D

| Ex. No | Structure | MP (°C.) | (M + H) | Human H3 Ki (nM) | Rat H3 Ki (nM) |
|---|---|---|---|---|---|
| 570 | 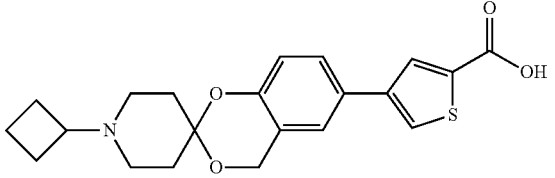 [SMILES: O=C(O)c1cc(-c2ccc3c(c2)COC2(CCN(C4CCC4)CC2)O3)cs1] | dec 230-240 | 386 | +++ | +++ |
| 571 | 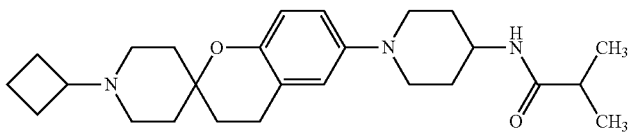 | 199.3-201.2 | 426 | +++ | +++ |
| 572 | 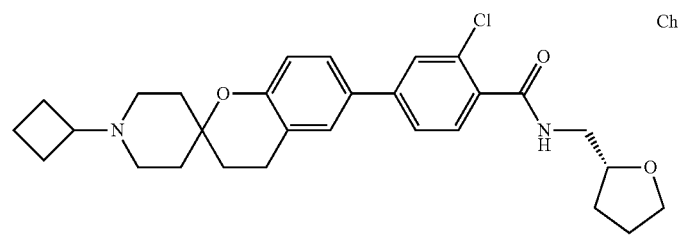 Chiral | 62-64 | 496 | +++ | +++ |
| 573 | 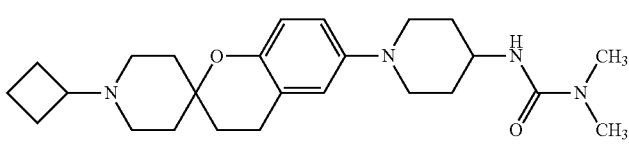 | 204.2-206.4 | 427 | +++ | +++ |

TABLE D-continued
| Ex. No | Structure | MP (°C.) | (M + H) | Human H3 Ki (nM) | Rat H3 Ki (nM) |
|---|---|---|---|---|---|
| 574 | 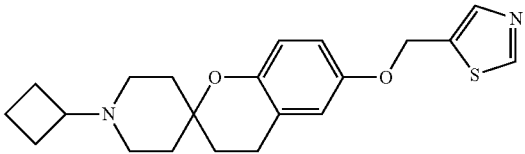 | 85-87 | 371 | +++ | +++ |
| 575 | 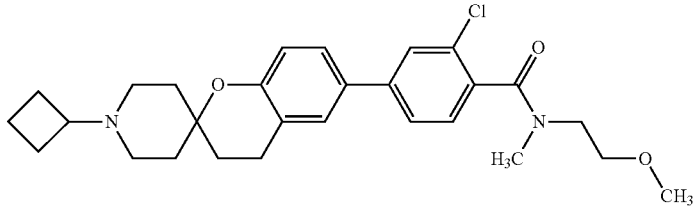 | 101-104 | 484 | +++ | +++ |
| 576 | 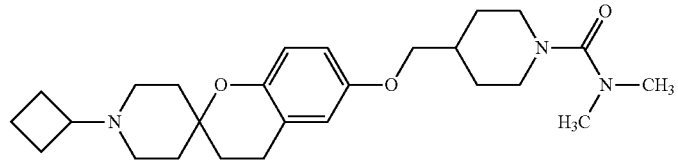 | 230-232 | 442 | +++ | +++ |
| 577 | 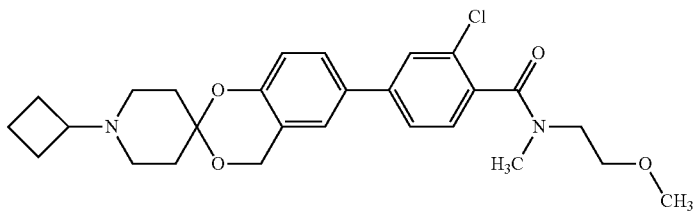 [SMILES: COCCN(C)C(=O)c1ccc(-c2ccc3c(c2)COC2(CCN(C4CCC4)CC2)O3)cc1Cl] | 105-107 | 485 | +++ | +++ |
| 578 | 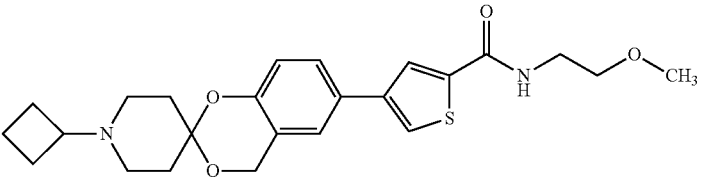 [SMILES: COCCNC(=O)c1cc(-c2ccc3c(c2)COC2(CCN(C4CCC4)CC2)O3)cs1] | 145-146 | 443 | +++ | +++ |
| 579 | 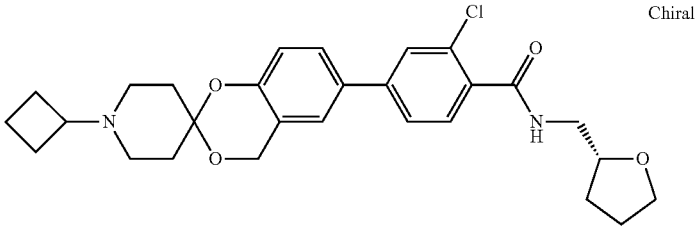 [SMILES: O=C(NC[C@H]1CCCO1)c1ccc(-c2ccc3c(c2)COC2(CCN(C4CCC4)CC2)O3)cc1Cl] Chiral | 155-157 | 498 | +++ | +++ |
| 580 | 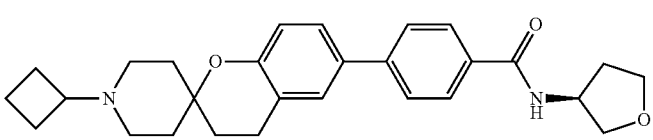 Chiral | 196-198 | 447 | +++ | +++ |

TABLE D-continued

| Ex. No | Structure | MP (°C.) | (M + H) | Human H3 Ki (nM) | Rat H3 Ki (nM) |
|---|---|---|---|---|---|
| 581 | 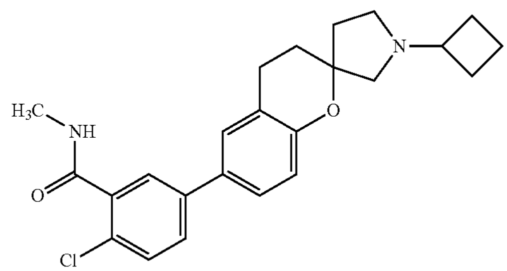 [SMILES: CNC(=O)c1cc(-c2ccc3c(c2)CCC2(CCN(C4CCC4)C2)O3)ccc1Cl] | 100-103 | 411 | +++ | ++ |
| 582 | 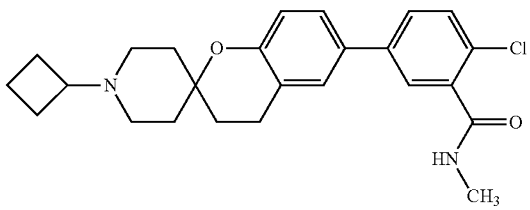 [SMILES: CNC(=O)c1cc(-c2ccc3c(c2)CCC2(CCN(C4CCC4)CC2)O3)ccc1Cl] | 89-91 | 425 | +++ | +++ |
| 583 | 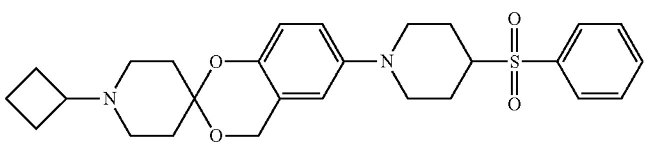 [SMILES: O=S(=O)(c1ccccc1)C1CCN(c2ccc3c(c2)COC2(CCN(C4CCC4)CC2)O3)CC1] | 78.4-80.2 | 483 | +++ | +++ |
| 584 | 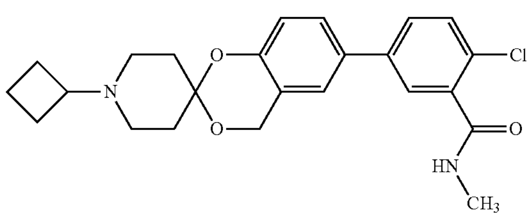 [SMILES: CNC(=O)c1cc(-c2ccc3c(c2)COC2(CCN(C4CCC4)CC2)O3)ccc1Cl] | 198-200 | 427 | +++ | +++ |
| 585 | Chiral | 159-161 | 497 | +++ | +++ |
| 586 | 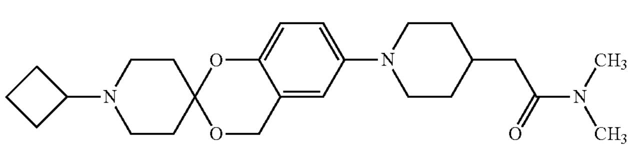 | 68.5-70.2 | 428 | +++ | +++ |
| 587 | 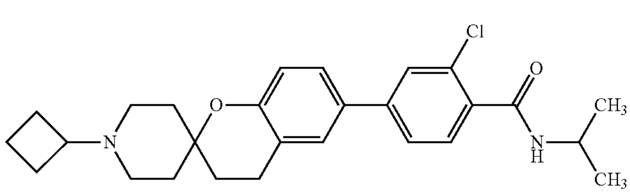 | 155-156 | 454 | +++ | +++ |

TABLE D-continued
| Ex. No | Structure | MP (°C.) | (M + H) | Human H3 Ki (nM) | Rat H3 Ki (nM) |
|---|---|---|---|---|---|
| 588 | 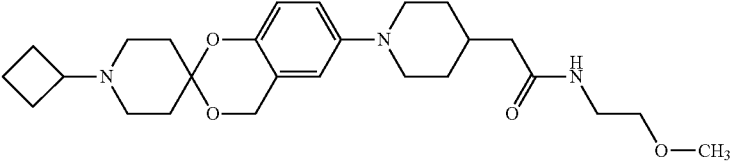 | 150.1-152.2 | 458 | +++ | +++ |
| 589 | 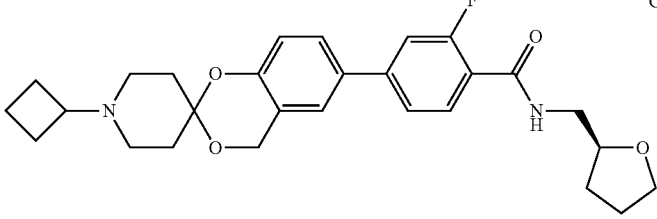 Chiral | 128-130 | 481 | +++ | +++ |
| 590 | 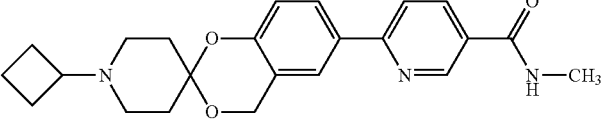 | 175-177 | 394 | +++ | +++ |
| 591 | 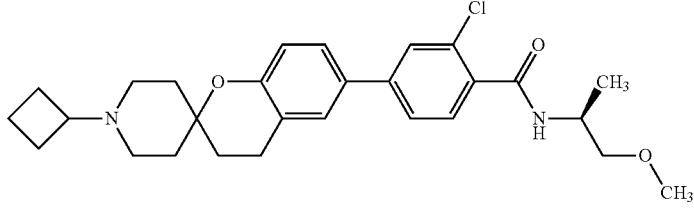 [SMILES: COC[C@H](C)NC(=O)c1ccc(-c2ccc3c(c2)CCC2(CCN(C4CCC4)CC2)O3)cc1Cl] | 120-122 | 483 | +++ | +++ |
| 592 | 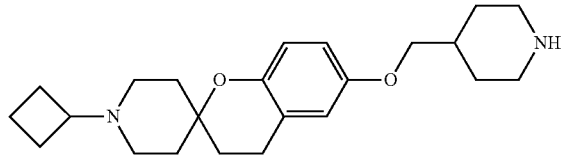 [SMILES: c1cc2c(cc1OCC1CCNCC1)CCC1(CCN(C3CCC3)CC1)O2] | 292-294 | 371 | +++ | +++ |
| 593 | 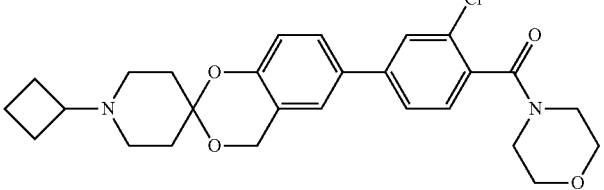 | 80.7-82 | 484 | +++ | +++ |
| 594 | 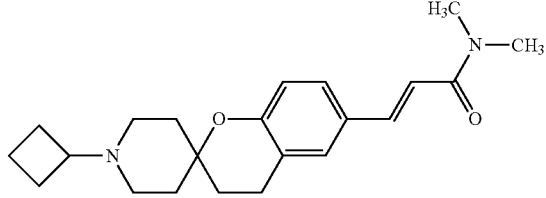 [SMILES: CN(C)C(=O)/C=C/c1ccc2c(c1)CCC1(CCN(C3CCC3)CC1)O2] | 187-189 | 355 | +++ | ++ |
| 595 | 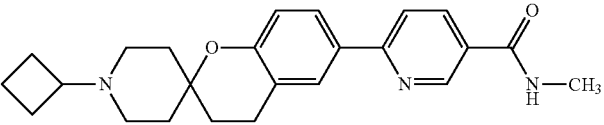 [SMILES: CNC(=O)c1ccc(-c2ccc3c(c2)CCC2(CCN(C4CCC4)CC2)O3)nc1] | 192-194 | 392 | +++ | +++ |

TABLE D-continued
| Ex. No | Structure | | MP (°C.) | (M + H) | Human H3 Ki (nM) | Rat H3 Ki (nM) |
|---|---|---|---|---|---|---|
| 596 | 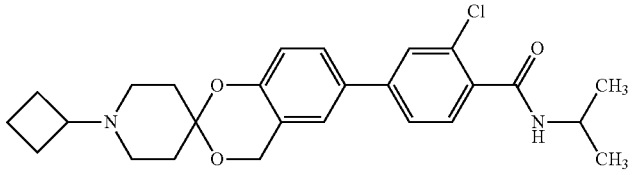 | | 186-187.5 | 456 | +++ | +++ |
| 597 | 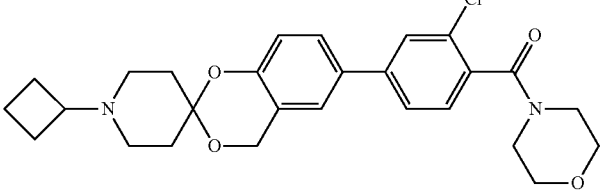 | | 85-87 | 482 | +++ | +++ |
| 598 | 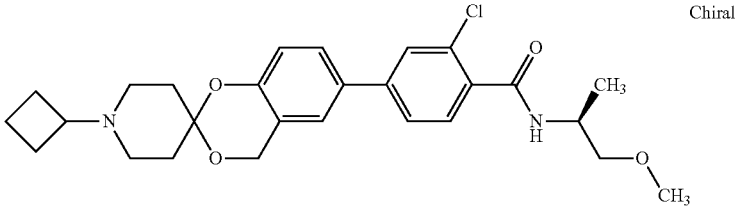 [SMILES: COC[C@H](C)NC(=O)c1ccc(-c2ccc3c(c2)COC2(CCN(C4CCC4)CC2)O3)cc1Cl] | Chiral | 150-152 | 486 | +++ | +++ |
| 599 | 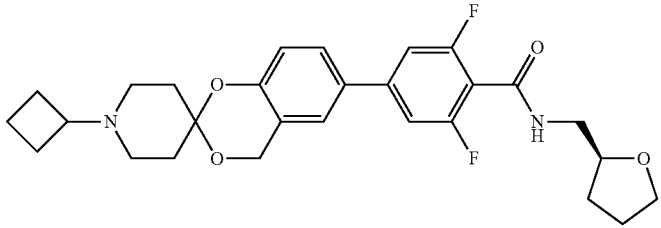 | Chiral | 142-145 | 499 | +++ | +++ |
| 600 | 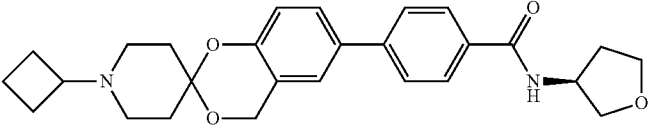 | Chiral | 205-207 | 449 | +++ | +++ |
| 601 | 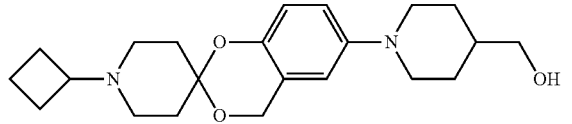 [SMILES: OCC1CCN(c2ccc3c(c2)COC2(CCN(C4CCC4)CC2)O3)CC1] | | 88.9-91.4 | 373 | +++ | +++ |
| 602 | 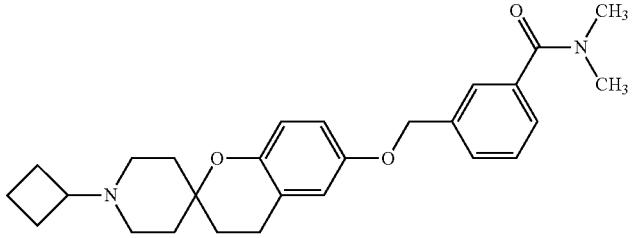 [SMILES: CN(C)C(=O)c1cccc(COc2ccc3c(c2)CCC2(CCN(C4CCC4)CC2)O3)c1] | | 183-185 | 435 | +++ | +++ |

TABLE D-continued

| Ex. No | Structure | MP (°C.) | (M + H) | Human H3 Ki (nM) | Rat H3 Ki (nM) |
|---|---|---|---|---|---|
| 603 | 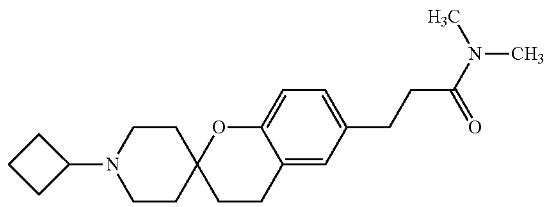 [SMILES: CN(C)C(=O)CCc1ccc2c(c1)CCC1(CCN(C3CCC3)CC1)O2] | 180-182 | 357 | +++ | +++ |
| 604 | 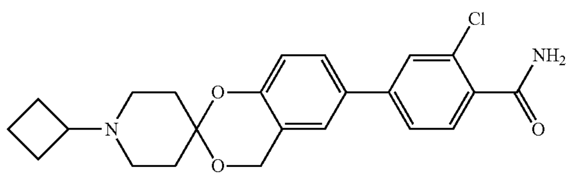 [SMILES: NC(=O)c1ccc(-c2ccc3c(c2)COC2(CCN(C4CCC4)CC2)O3)cc1Cl] | 164-166 | 413 | +++ | +++ |
| 605 | Chiral | 189-191 | 483 | +++ | +++ |
| 606 | 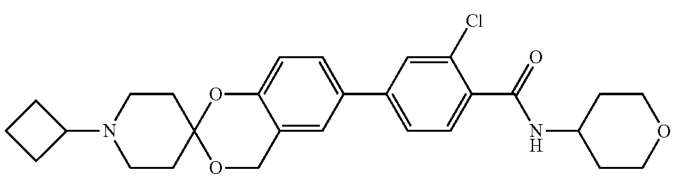 | 209-211 | 497 | +++ | +++ |
| 607 | 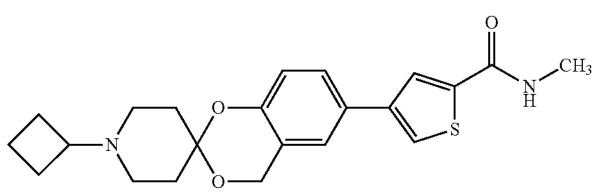 [SMILES: CNC(=O)c1cc(-c2ccc3c(c2)COC2(CCN(C4CCC4)CC2)O3)cs1] | 186-188 | 399 | +++ | +++ |
| 608 | 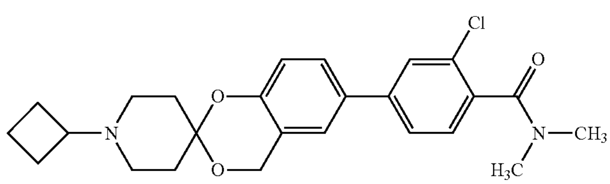 [SMILES: CN(C)C(=O)c1ccc(-c2ccc3c(c2)COC2(CCN(C4CCC4)CC2)O3)cc1Cl] | 80-82 | 441 | +++ | +++ |
| 609 | 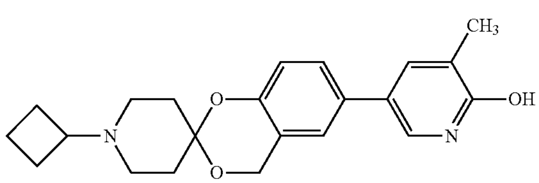 [SMILES: Cc1cc(-c2ccc3c(c2)COC2(CCN(C4CCC4)CC2)O3)cnc1O] | 95.2-97 | 367 | +++ | +++ |
| 610 | 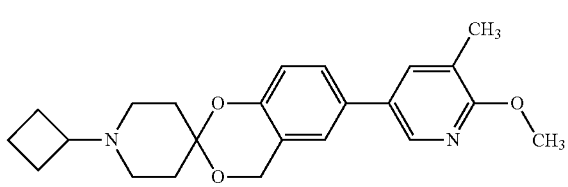 | 142-145 | 381 | +++ | +++ |

TABLE D-continued

| Ex. No | Structure | MP (°C.) | (M + H) | Human H3 Ki (nM) | Rat H3 Ki (nM) |
|---|---|---|---|---|---|
| 611 | 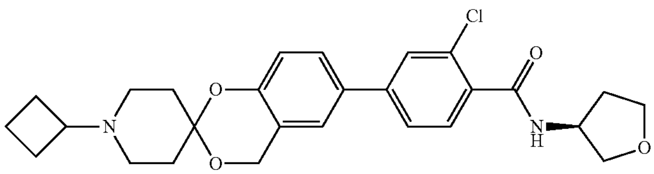 | 185-187 | 483 | +++ | +++ |
| 612 | 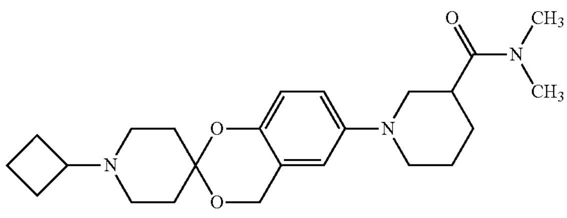 [SMILES: CN(C)C(=O)C1CCCN(c2ccc3c(c2)COC2(CCN(C4CCC4)CC2)O3)C1] | 51.2-54.2 | 414 | +++ | +++ |
| 613 | 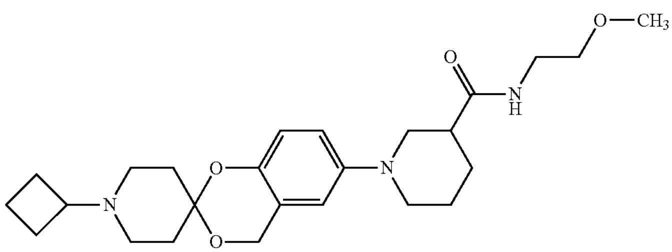 [SMILES: COCCNC(=O)C1CCCN(c2ccc3c(c2)COC2(CCN(C4CCC4)CC2)O3)C1] | 55.4-57.3 | 444 | +++ | +++ |
| 614 | 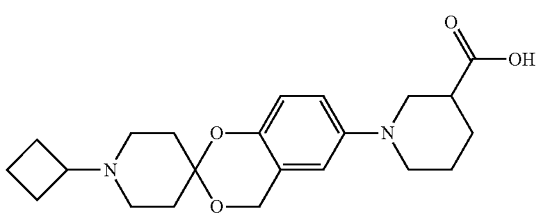 [SMILES: O=C(O)C1CCCN(c2ccc3c(c2)COC2(CCN(C4CCC4)CC2)O3)C1] | 84.0-86.4 | 387 | ++ | ++ |
| 615 | 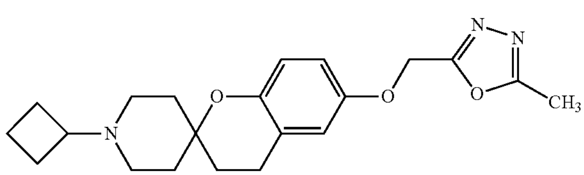 [SMILES: Cc1nnc(COc2ccc3c(c2)CCC2(CCN(C4CCC4)CC2)O3)o1] | 97-98 | 370 | +++ | +++ |
| 616 | 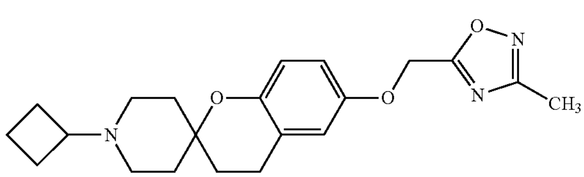 [SMILES: Cc1noc(COc2ccc3c(c2)CCC2(CCN(C4CCC4)CC2)O3)n1] | 95-96 | 370 | +++ | +++ |
| 617 | 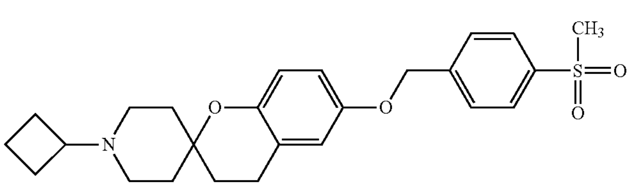 [SMILES: CS(=O)(=O)c1ccc(COc2ccc3c(c2)CCC2(CCN(C4CCC4)CC2)O3)cc1] | 142-146 | 442 | +++ | +++ |

TABLE D-continued

| Ex. No | Structure | MP (°C.) | (M + H) | Human H3 Ki (nM) | Rat H3 Ki (nM) |
|---|---|---|---|---|---|
| 618 | 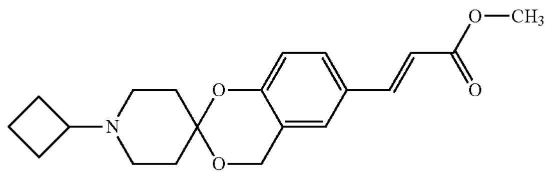 [SMILES: COC(=O)/C=C/c1ccc2c(c1)COC1(CCN(C3CCC3)CC1)O2] | 131-133 | 344 | +++ | +++ |
| 619 | 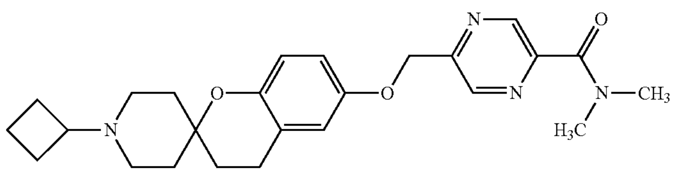 [SMILES: CN(C)C(=O)c1cnc(COc2ccc3c(c2)CCC2(CCN(C4CCC4)CC2)O3)cn1] | 120-123 | 437 | +++ | +++ |
| 620 | 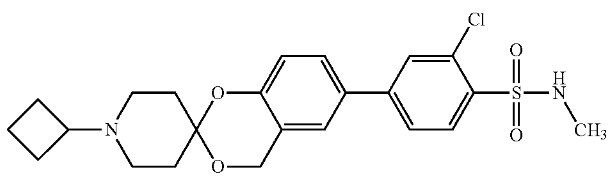 [SMILES: CNS(=O)(=O)c1ccc(-c2ccc3c(c2)COC2(CCN(C4CCC4)CC2)O3)cc1Cl] | 127-129 | 464 | +++ | +++ |
| 621 | 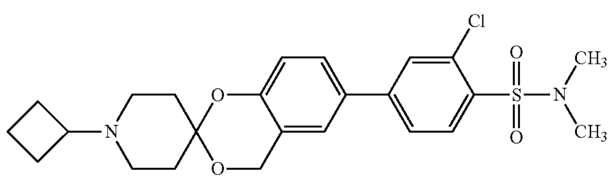 [SMILES: CN(C)S(=O)(=O)c1ccc(-c2ccc3c(c2)COC2(CCN(C4CCC4)CC2)O3)cc1Cl] | 97-99 | 478 | +++ | +++ |
| 622 | 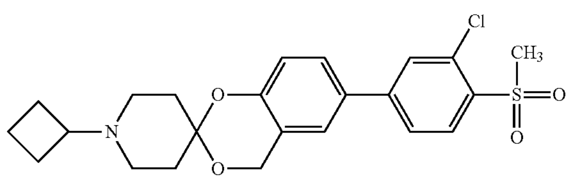 [SMILES: CS(=O)(=O)c1ccc(-c2ccc3c(c2)COC2(CCN(C4CCC4)CC2)O3)cc1Cl] | 198-201 | 448 | +++ | +++ |
| 623 | 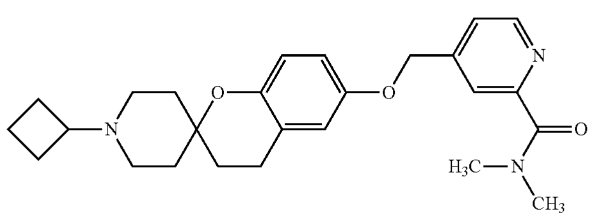 | 165-167 | 436 | +++ | +++ |
| 624 | 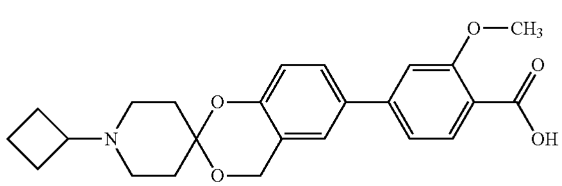 [SMILES: COc1cc(-c2ccc3c(c2)COC2(CCN(C4CCC4)CC2)O3)ccc1C(=O)O] | 173-175 | 410 | +++ | ++ |
| 625 | 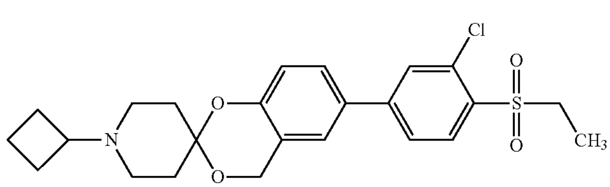 [SMILES: CCS(=O)(=O)c1ccc(-c2ccc3c(c2)COC2(CCN(C4CCC4)CC2)O3)cc1Cl] | 157-159 | 462 | +++ | +++ |

TABLE D-continued

| Ex. No | Structure | MP (°C.) | (M + H) | Human H3 Ki (nM) | Rat H3 Ki (nM) |
|---|---|---|---|---|---|
| 626 | 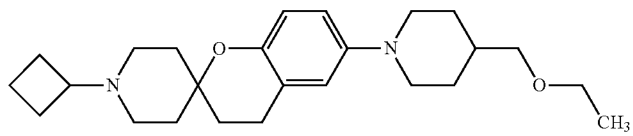 | 101.6-103.2 | 399 | +++ | +++ |
| 627 | 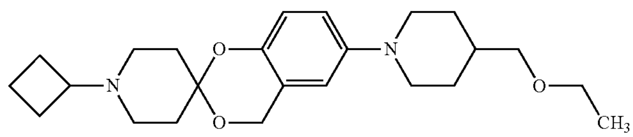 [SMILES: CCOCC1CCN(c2ccc3c(c2)COC2(CCN(C4CCC4)CC2)O3)CC1] | 85.2-86.5 | 401 | +++ | +++ |
| 628 | 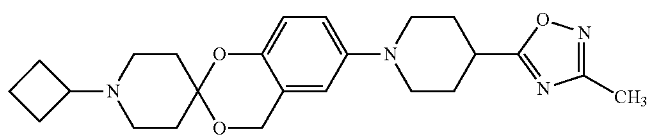 | 125.0-126.2 | 425 | +++ | +++ |
| 629 | 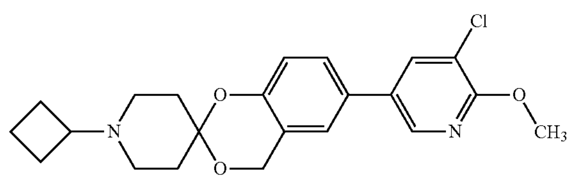 | 174-175 | 401 | +++ | +++ |
| 630 | 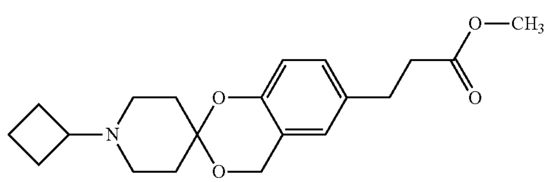 [SMILES: COC(=O)CCc1ccc2c(c1)COC1(CCN(C3CCC3)CC1)O2] | 66-68 | 346 | +++ | +++ |
| 631 | 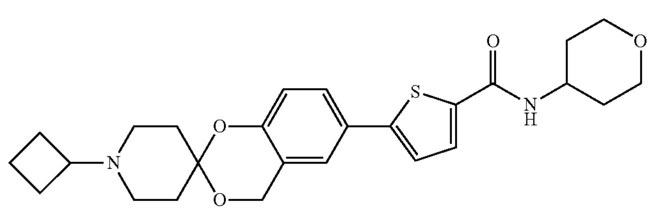 [SMILES: O=C(NC1CCOCC1)c1ccc(-c2ccc3c(c2)COC2(CCN(C4CCC4)CC2)O3)s1] | 209-211 | 469 | +++ | +++ |
| 632 | 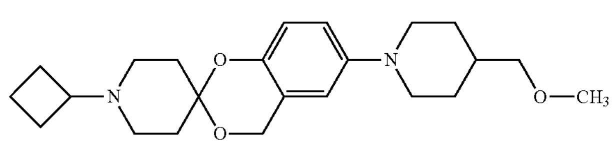 [SMILES: COCC1CCN(c2ccc3c(c2)COC2(CCN(C4CCC4)CC2)O3)CC1] | 92.3-94.2 | 387 | +++ | +++ |
| 633 | 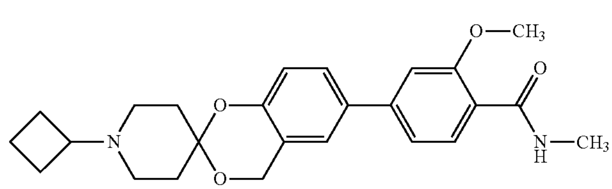 | 175-177 | 423 | +++ | +++ |

TABLE D-continued

| Ex. No | Structure | MP (°C.) | (M + H) | Human H3 Ki (nM) | Rat H3 Ki (nM) |
|---|---|---|---|---|---|
| 634 | 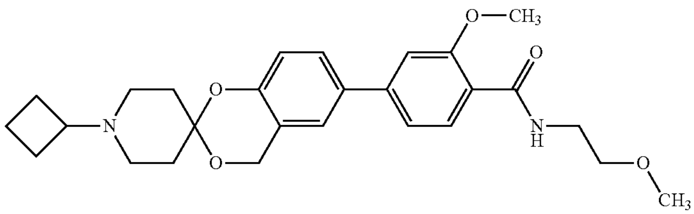 | 50-52 | 467 | +++ | +++ |
| 635 | 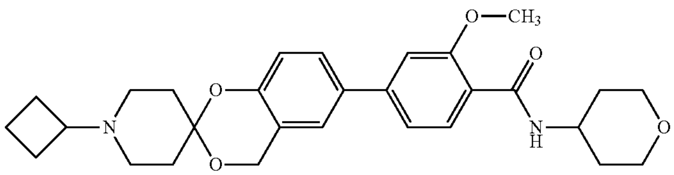 [SMILES: COc1cc(-c2ccc3c(c2)COC2(CCN(C4CCC4)CC2)O3)ccc1C(=O)NC1CCOCC1] | 86-88 | 493 | +++ | +++ |
| 636 | 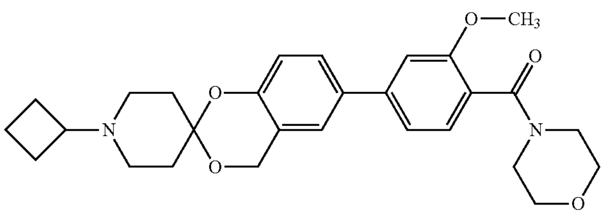 [SMILES: COc1cc(-c2ccc3c(c2)COC2(CCN(C4CCC4)CC2)O3)ccc1C(=O)N1CCOCC1] | 94-96 | 479 | +++ | +++ |
| 637 | 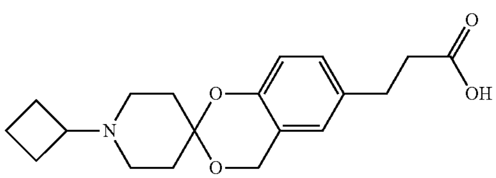 [SMILES: O=C(O)CCc1ccc2c(c1)COC1(CCN(C3CCC3)CC1)O2] | 235-237 | 331 | ++ | — |
| 638 | 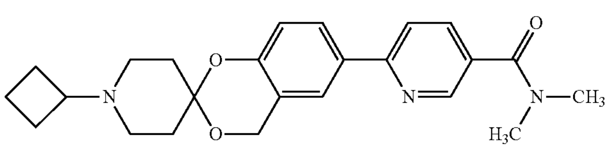 | 190-193 | 408 | +++ | +++ |
| 639 | 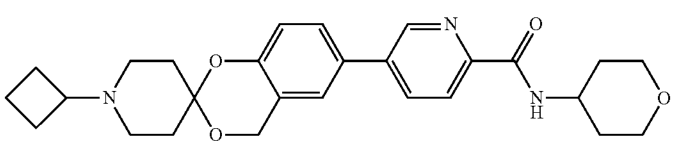 [SMILES: O=C(NC1CCOCC1)c1ccc(-c2ccc3c(c2)COC2(CCN(C4CCC4)CC2)O3)cn1] | 108-110 | 464 | +++ | +++ |
| 640 | 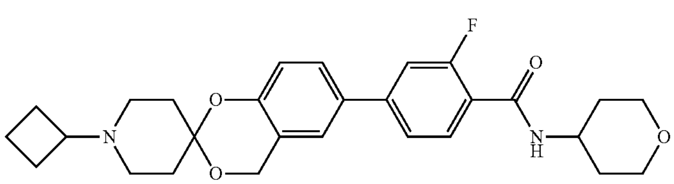 [SMILES: O=C(NC1CCOCC1)c1ccc(-c2ccc3c(c2)COC2(CCN(C4CCC4)CC2)O3)cc1F] | 165-167 | 481 | +++ | +++ |
| 641 | 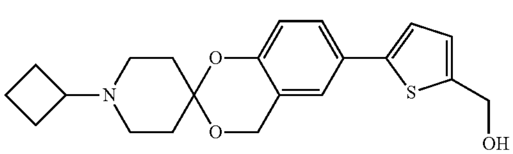 [SMILES: OCc1ccc(-c2ccc3c(c2)COC2(CCN(C4CCC4)CC2)O3)s1] | 168-169 | 372 | +++ | +++ |

TABLE D-continued
| Ex. No | Structure | MP (°C.) | (M + H) | Human H3 Ki (nM) | Rat H3 Ki (nM) |
|---|---|---|---|---|---|
| 642 | 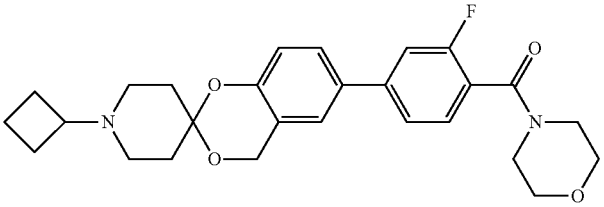 | 161-162 | 467 | +++ | +++ |
| 643 | 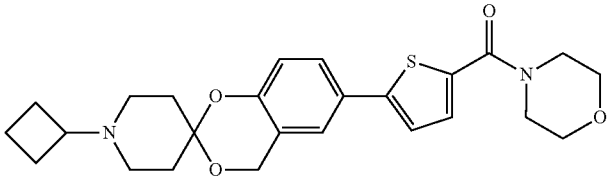 [SMILES: O=C(c1ccc(-c2ccc3c(c2)COC2(CCN(C4CCC4)CC2)O3)s1)N1CCOCC1] | 166-167 | 455 | +++ | +++ |
| 644 | 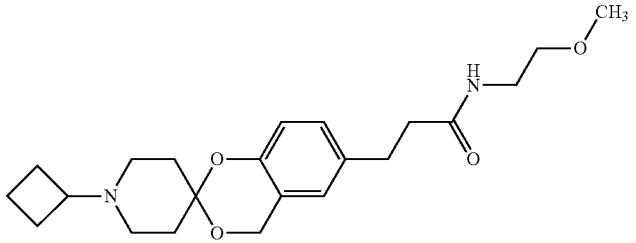 [SMILES: COCCNC(=O)CCc1ccc2c(c1)COC1(CCN(C3CCC3)CC1)O2] | 68-70 | 389 | +++ | ++ |
| 645 | 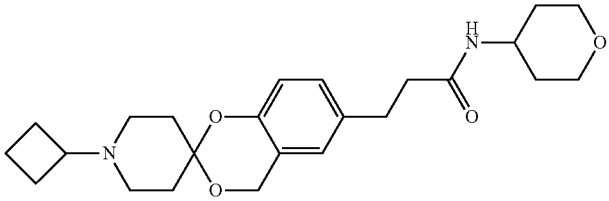 [SMILES: O=C(CCc1ccc2c(c1)COC1(CCN(C3CCC3)CC1)O2)NC1CCOCC1] | 167-169 | 415 | +++ | ++ |
| 646 | 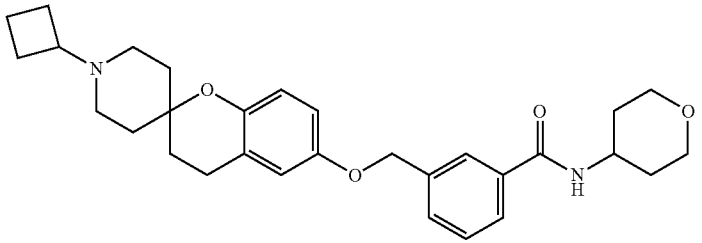 [SMILES: O=C(NC1CCOCC1)c1cccc(COc2ccc3c(c2)CCC2(CCN(C4CCC4)CC2)O3)c1] | 158-160 | 491 | +++ | +++ |
| 647 | 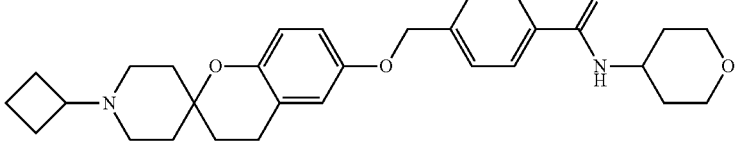 | 174-176 | 491 | +++ | +++ |
| 648 | 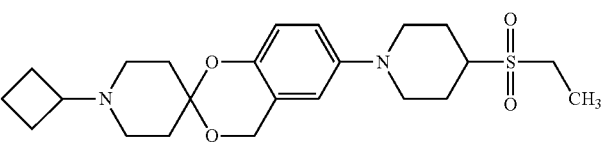 [SMILES: CCS(=O)(=O)C1CCN(c2ccc3c(c2)COC2(CCN(C4CCC4)CC2)O3)CC1] | 147.7-149.8 | 435 | +++ | +++ |

TABLE D-continued

| Ex. No | Structure | MP (°C.) | (M + H) | Human H3 Ki (nM) | Rat H3 Ki (nM) |
|---|---|---|---|---|---|
| 649 | 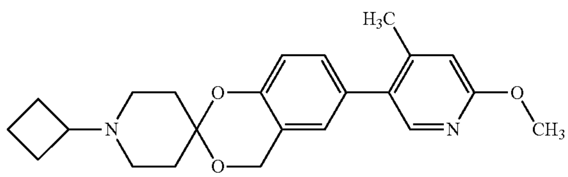 [SMILES: COc1cc(C)c(-c2ccc3c(c2)COC2(CCN(C4CCC4)CC2)O3)cn1] | | 417 | +++ | +++ |
| 650 | 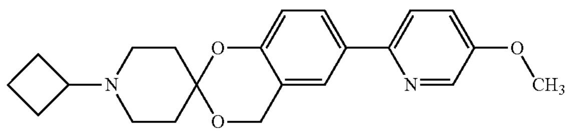 [SMILES: COc1ccc(-c2ccc3c(c2)COC2(CCN(C4CCC4)CC2)O3)nc1] | 123-126 | 367 | +++ | +++ |
| 651 | 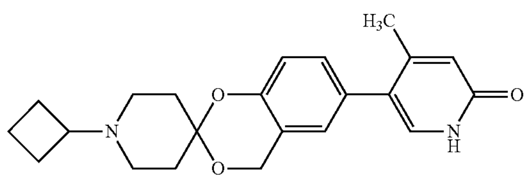 [SMILES: Cc1cc(=O)[nH]cc1-c1ccc2c(c1)COC1(CCN(C3CCC3)CC1)O2] | 217-220 | 367 | +++ | +++ |
| 652 | 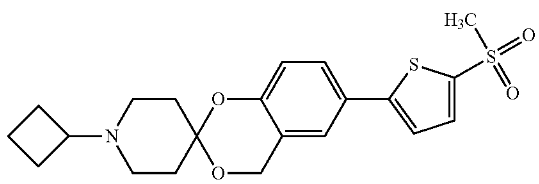 [SMILES: CS(=O)(=O)c1ccc(-c2ccc3c(c2)COC2(CCN(C4CCC4)CC2)O3)s1] | 159-161 | 420 | +++ | +++ |
| 653 | 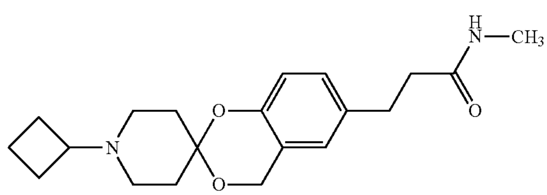 [SMILES: CNC(=O)CCc1ccc2c(c1)COC1(CCN(C3CCC3)CC1)O2] | 86-88 | 345 | +++ | +++ |
| 654 | 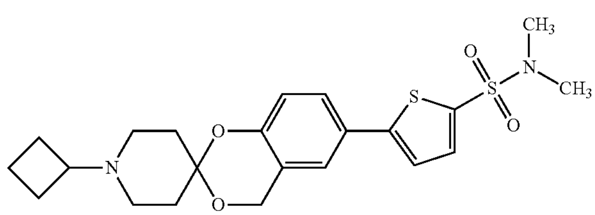 [SMILES: CN(C)S(=O)(=O)c1ccc(-c2ccc3c(c2)COC2(CCN(C4CCC4)CC2)O3)s1] | 189-192 | 449 | +++ | +++ |
| 655 | 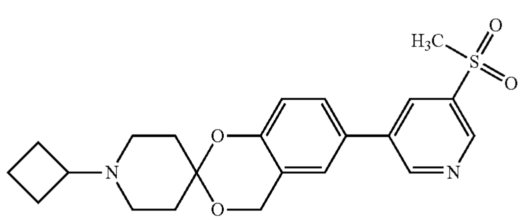 [SMILES: CS(=O)(=O)c1cncc(-c2ccc3c(c2)COC2(CCN(C4CCC4)CC2)O3)c1] | 148-149 | 415 | +++ | +++ |
| 656 | 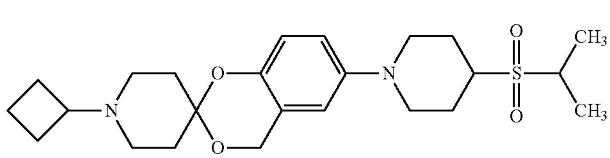 [SMILES: CC(C)S(=O)(=O)C1CCN(c2ccc3c(c2)COC2(CCN(C4CCC4)CC2)O3)CC1] | 142.6-145.1 | 449 | +++ | +++ |

TABLE D-continued

| Ex. No | Structure | MP (°C.) | (M + H) | Human H3 Ki (nM) | Rat H3 Ki (nM) |
|---|---|---|---|---|---|
| 657 | 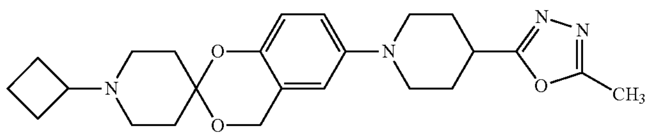 [SMILES: Cc1nnc(C2CCN(c3ccc4c(c3)COC3(CCN(C5CCC5)CC3)O4)CC2)o1] | 75.5-77.8 | 425 | +++ | +++ |
| 658 | 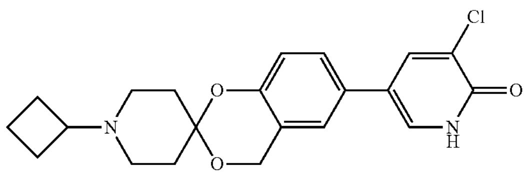 [SMILES: O=c1[nH]cc(-c2ccc3c(c2)COC2(CCN(C4CCC4)CC2)O3)cc1Cl] | 221.5-223.7 | 387 | +++ | +++ |
| 659 | 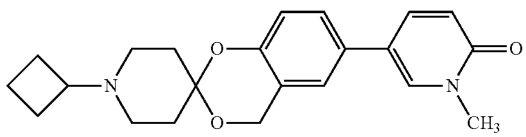 | 170-173 | 367 | +++ | +++ |
| 660 | 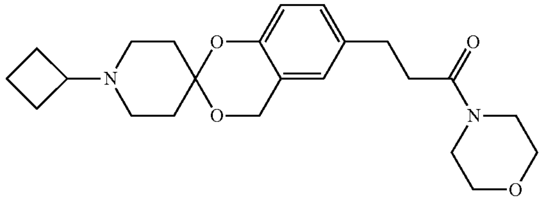 [SMILES: O=C(CCc1ccc2c(c1)COC1(CCN(C3CCC3)CC1)O2)N1CCOCC1] | 71-73 | 401 | +++ | +++ |
| 661 | 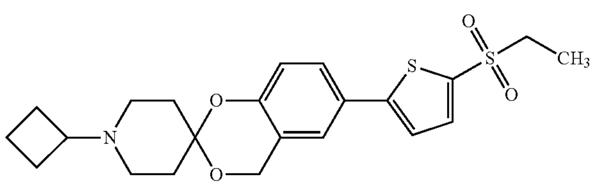 [SMILES: CCS(=O)(=O)c1ccc(-c2ccc3c(c2)COC2(CCN(C4CCC4)CC2)O3)s1] | 150-152 | 434 | +++ | +++ |
| 662 | 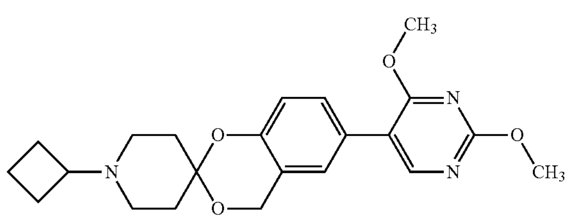 [SMILES: COc1ncc(-c2ccc3c(c2)COC2(CCN(C4CCC4)CC2)O3)c(OC)n1] | dec. 250 | 398 | +++ | +++ |
| 663 | 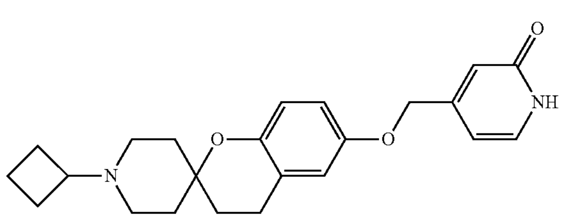 [SMILES: O=c1cc(COc2ccc3c(c2)CCC2(CCN(C4CCC4)CC2)O3)cc[nH]1] | 205-206 | 381 | +++ | +++ |
| 664 | 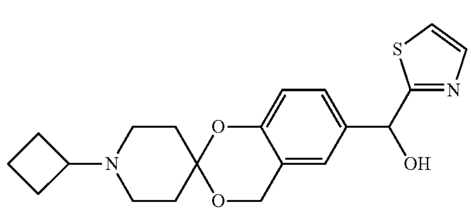 [SMILES: OC(c1ccc2c(c1)COC1(CCN(C3CCC3)CC1)O2)c1nccs1] | 70-72 | 373 | +++ | +++ |

TABLE D-continued

| Ex. No | Structure | MP (°C.) | (M + H) | Human H3 Ki (nM) | Rat H3 Ki (nM) |
|---|---|---|---|---|---|
| 665 | 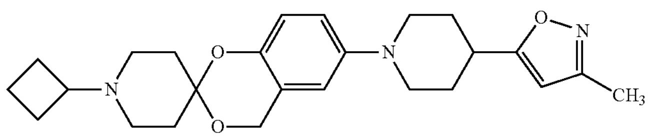 [SMILES: Cc1cc(C2CCN(c3ccc4c(c3)COC3(CCN(C5CCC5)CC3)O4)CC2)on1] | 135.9-137.2 | 424 | +++ | +++ |
| 666 | 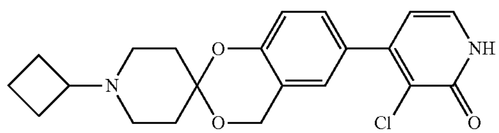 [SMILES: O=c1[nH]ccc(-c2ccc3c(c2)COC2(CCN(C4CCC4)CC2)O3)c1Cl] | 230-232 | 387 | +++ | +++ |
| 667 | 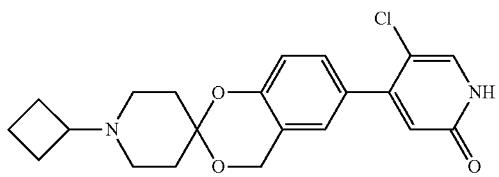 [SMILES: O=c1cc(-c2ccc3c(c2)COC2(CCN(C4CCC4)CC2)O3)c(Cl)c[nH]1] | 130-132 | 387 | +++ | +++ |
| 668 | 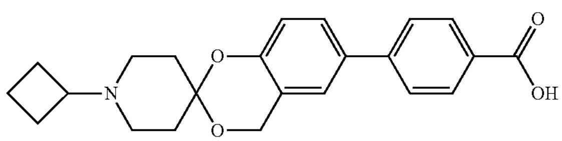 | 236-237 | 380 | +++ | +++ |
| 669 | 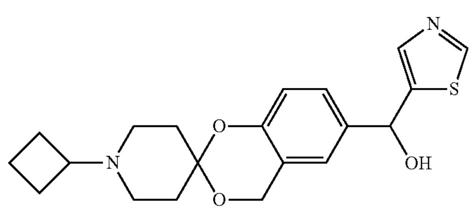 [SMILES: OC(c1ccc2c(c1)COC1(CCN(C3CCC3)CC1)O2)c1cncs1] | 72-75 | 373 | +++ | +++ |
| 670 | 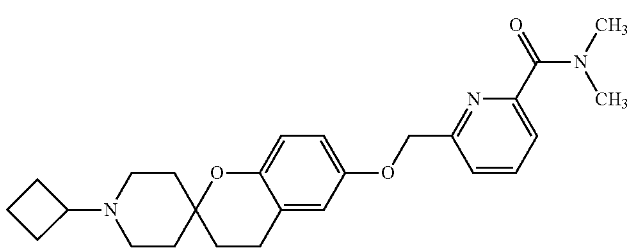 [SMILES: CN(C)C(=O)c1cccc(COc2ccc3c(c2)CCC2(CCN(C4CCC4)CC2)O3)n1] | 167-170 | 436 | +++ | +++ |
| 671 | 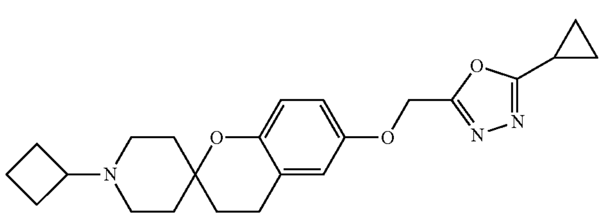 [SMILES: c1cc2c(cc1OCc1nnc(C3CC3)o1)CCC1(CCN(C3CCC3)CC1)O2] | 158-159 | 396 | +++ | +++ |
| 672 | 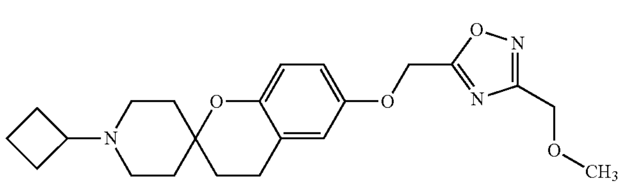 | 178-179 | 400 | +++ | +++ |

TABLE D-continued

| Ex. No | Structure | MP (°C.) | (M + H) | Human H3 Ki (nM) | Rat H3 Ki (nM) |
|---|---|---|---|---|---|
| 673 | 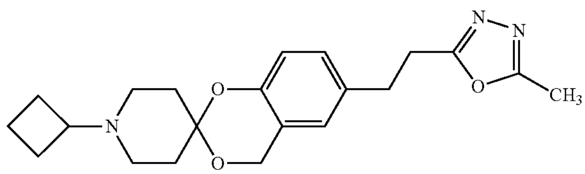 | 87-89 | 370 | +++ | +++ |
| 674 | 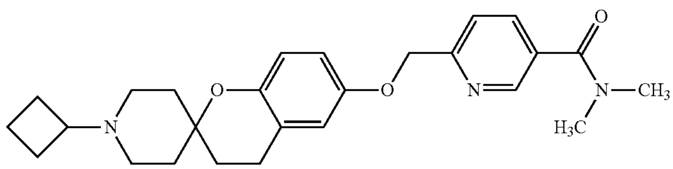 [SMILES: CN(C)C(=O)c1ccc(COc2ccc3c(c2)CCC2(CCN(C4CCC4)CC2)O3)nc1] | 75-78 | 436 | +++ | +++ |
| 675 | 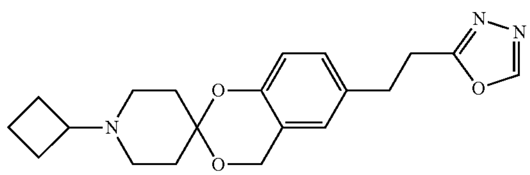 [SMILES: c1nnc(CCc2ccc3c(c2)COC2(CCN(C4CCC4)CC2)O3)o1] | 83-85 | 356 | +++ | +++ |
| 676 | 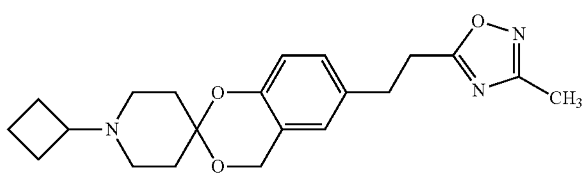 [SMILES: Cc1noc(CCc2ccc3c(c2)COC2(CCN(C4CCC4)CC2)O3)n1] | 74-76 | 370 | +++ | +++ |
| 677 | 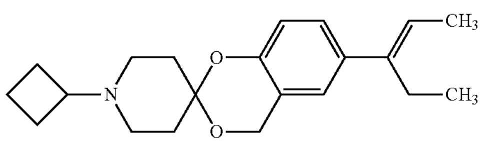 [SMILES: C/C=C(\CC)c1ccc2c(c1)COC1(CCN(C3CCC3)CC1)O2] | 223.5-225.8 | 327 | +++ | +++ |
| 678 | 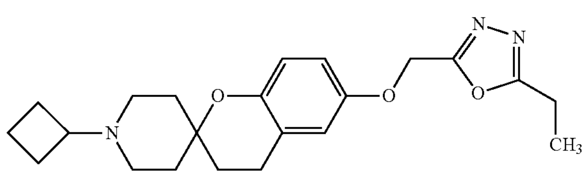 [SMILES: CCc1nnc(COc2ccc3c(c2)CCC2(CCN(C4CCC4)CC2)O3)o1] | 170-172 | 384 | +++ | +++ |
| 679 | 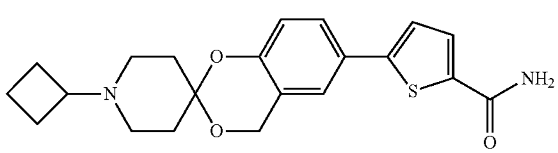 [SMILES: NC(=O)c1ccc(-c2ccc3c(c2)COC2(CCN(C4CCC4)CC2)O3)s1] | 250 dec | 385 | +++ | +++ |
| 680 | 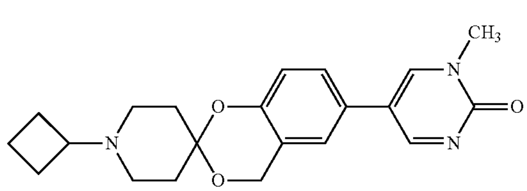 [SMILES: Cn1cc(-c2ccc3c(c2)COC2(CCN(C4CCC4)CC2)O3)cnc1=O] | 230-231 | 368 | +++ | +++ |
| 681 | 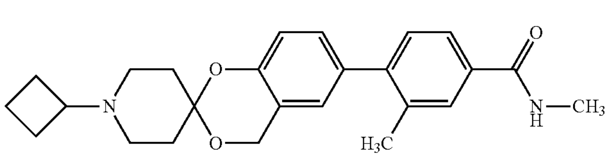 | 210-211 | 407 | +++ | +++ |

TABLE D-continued
| Ex. No | Structure | MP (°C.) | (M + H) | Human H3 Ki (nM) | Rat H3 Ki (nM) |
|---|---|---|---|---|---|
| 682 | 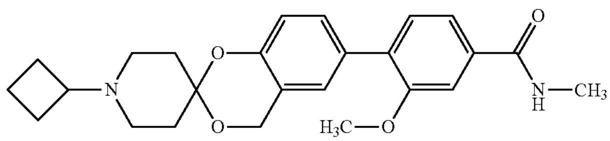 | 87-90 | 423 | +++ | +++ |
| 683 | 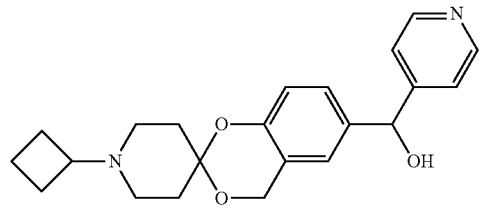 | 69-72 | 367 | +++ | +++ |
| 684 | 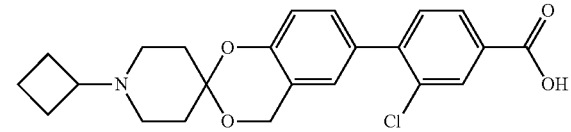 | 284-286 | 413 | +++ | +++ |
| 685 | 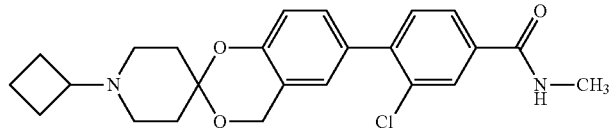 [SMILES: CNC(=O)c1ccc(-c2ccc3c(c2)COC2(CCN(C4CCC4)CC2)O3)c(Cl)c1] | 211-213 | 427 | +++ | +++ |
| 686 | 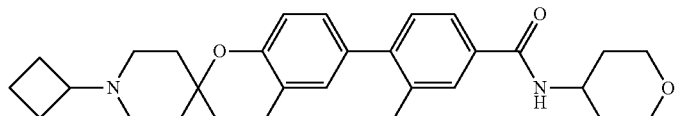 | 170-173 | 497 | +++ | +++ |
| 687 | 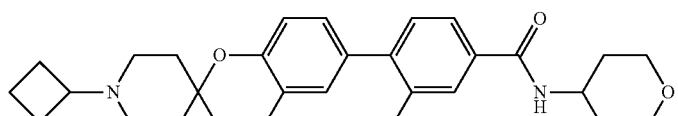 | 184-185 | 477 | +++ | +++ |
| 688 | 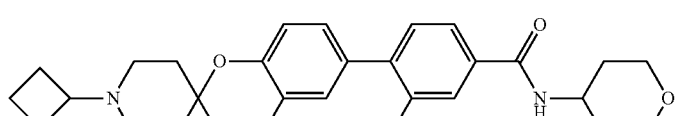 | 100-102 | 493 | +++ | +++ |
| 689 | 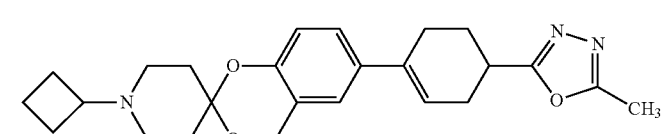 | 76.4-78.4 | 422 | +++ | +++ |
| 690 | 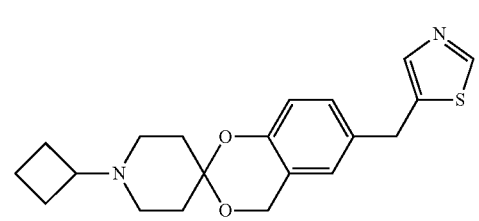 [SMILES: c1ncc(Cc2ccc3c(c2)COC2(CCN(C4CCC4)CC2)O3)s1] | NA | 357 | +++ | +++ |

TABLE D-continued

| Ex. No | Structure | MP (°C.) | (M + H) | Human H3 Ki (nM) | Rat H3 Ki (nM) |
|---|---|---|---|---|---|
| 691 | 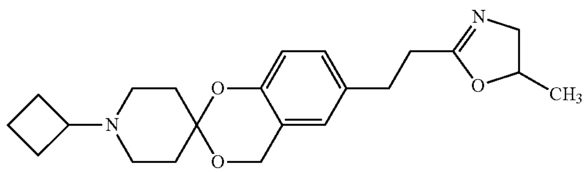 [SMILES: CC1CN=C(CCc2ccc3c(c2)COC2(CCN(C4CCC4)CC2)O3)O1] | 61-63 | 371 | +++ | +++ |
| 692 | 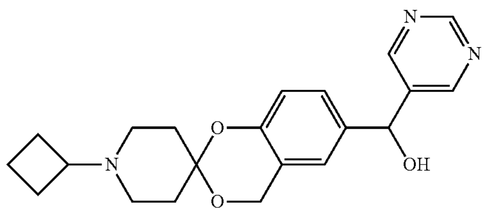 [SMILES: OC(c1cncnc1)c1ccc2c(c1)COC1(CCN(C3CCC3)CC1)O2] | 57-60 | 368 | +++ | +++ |
| 693 | 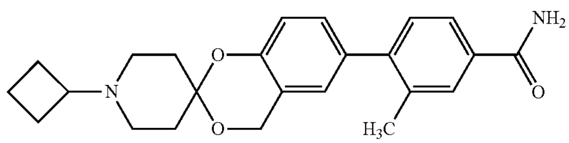 | 180-182 | 393 | +++ | +++ |
| 694 | 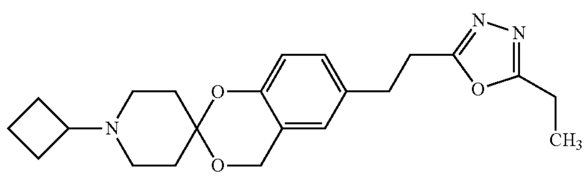 [SMILES: CCc1nnc(CCc2ccc3c(c2)COC2(CCN(C4CCC4)CC2)O3)o1] | 98-100 | 384 | +++ | +++ |
| 695 | 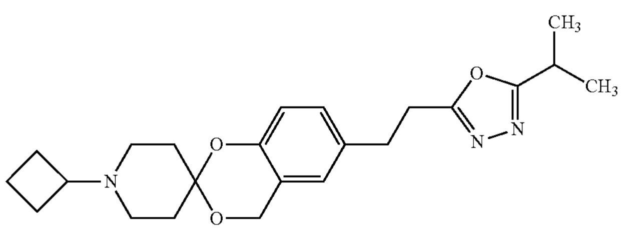 [SMILES: CC(C)c1nnc(CCc2ccc3c(c2)COC2(CCN(C4CCC4)CC2)O3)o1] | 101-103 | 398 | +++ | +++ |
| 696 | 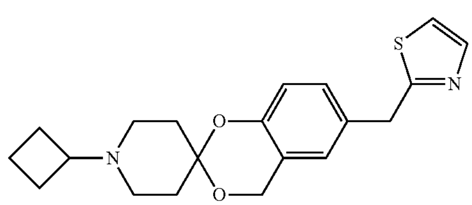 [SMILES: c1csc(Cc2ccc3c(c2)COC2(CCN(C4CCC4)CC2)O3)n1] | NA | 357 | +++ | +++ |
| 697 | 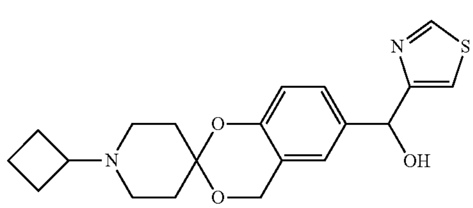 [SMILES: OC(c1ccc2c(c1)COC1(CCN(C3CCC3)CC1)O2)c1cscn1] | 63-68 | 373 | +++ | +++ |
| 698 | 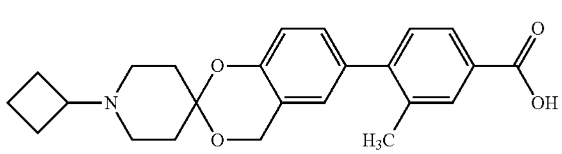 | 293-295 | 393 | +++ | +++ |

TABLE D-continued

| Ex. No | Structure | MP (°C.) | (M + H) | Human H3 Ki (nM) | Rat H3 Ki (nM) |
|---|---|---|---|---|---|
| 699 | 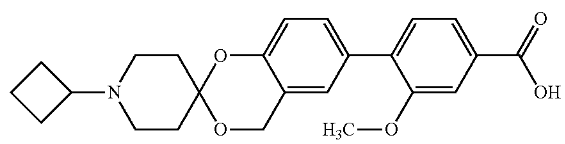 | 282-284 | 409 | +++ | +++ |
| 700 | 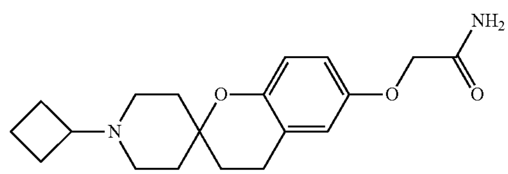 [SMILES: NC(=O)COc1ccc2c(c1)CCC1(CCN(C3CCC3)CC1)O2] | 121-125 | 331 | +++ | +++ |
| 701 | 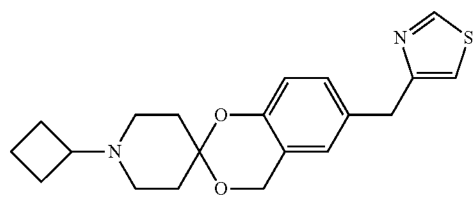 [SMILES: c1nc(Cc2ccc3c(c2)COC2(CCN(C4CCC4)CC2)O3)cs1] | NA | 357 | +++ | +++ |
| 702 | 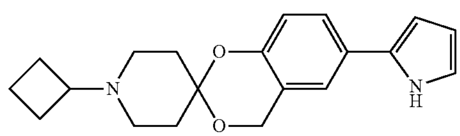 [SMILES: c1c[nH]c(-c2ccc3c(c2)COC2(CCN(C4CCC4)CC2)O3)c1] | 179-180 | 325 | +++ | +++ |
| 703 | 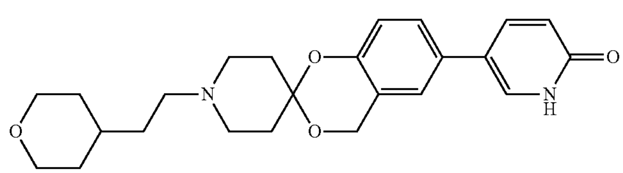 [SMILES: O=c1ccc(-c2ccc3c(c2)COC2(CCN(CCC4CCOCC4)CC2)O3)c[nH]1] | 214-216 | 411 | ++ | + |
| 704 | 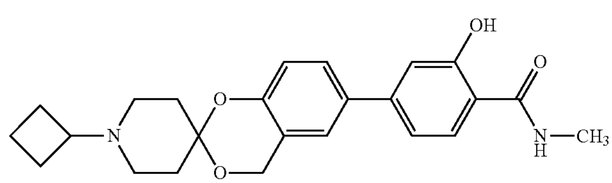 | 252-254 | 409 | +++ | +++ |
| 705 | 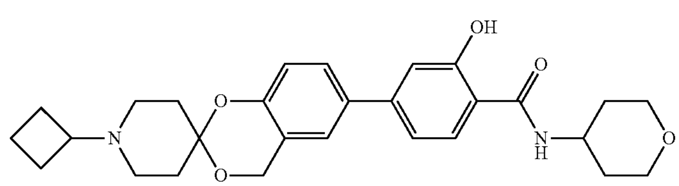 | 193-195 | 479 | +++ | +++ |
| 706 | 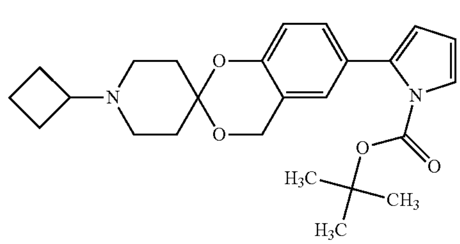 [SMILES: CC(C)(C)OC(=O)n1cccc1-c1ccc2c(c1)COC1(CCN(C3CCC3)CC1)O2] | thick oil | 425 | +++ | +++ |

TABLE D-continued

| Ex. No | Structure | MP (°C.) | (M + H) | Human H3 Ki (nM) | Rat H3 Ki (nM) |
|---|---|---|---|---|---|
| 707 | 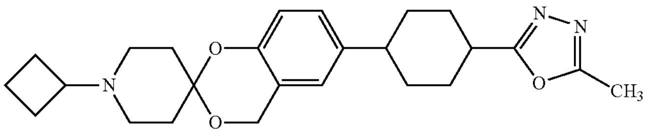 | 62.4-64.7 | 424 | +++ | +++ |
| 708 | 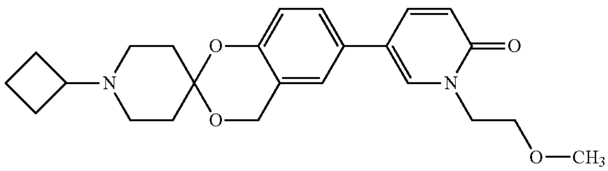 [SMILES: COCCn1cc(-c2ccc3c(c2)COC2(CCN(C4CCC4)CC2)O3)ccc1=O] | 141-142 | 411 | +++ | +++ |
| 709 | 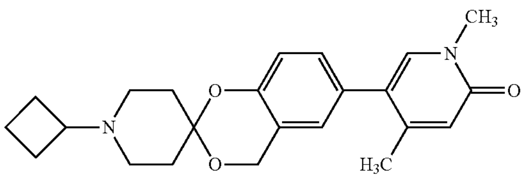 | 151-154 | 381 | +++ | +++ |
| 710 | 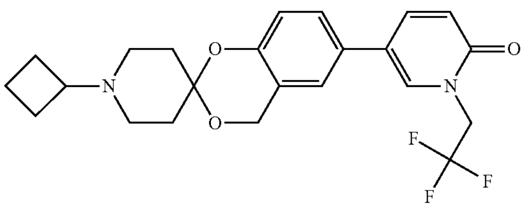 [SMILES: O=c1ccc(-c2ccc3c(c2)COC2(CCN(C4CCC4)CC2)O3)cn1CC(F)(F)F] | 158-160 | 435 | +++ | +++ |
| 711 | 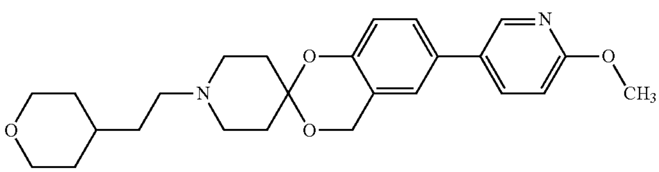 [SMILES: COc1ccc(-c2ccc3c(c2)COC2(CCN(CCC4CCOCC4)CC2)O3)cn1] | 143-145 | 425 | + | + |
| 712 | 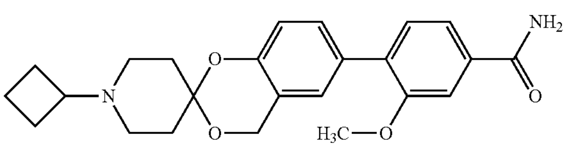 | 122-124 | 409 | +++ | +++ |
| 713 | 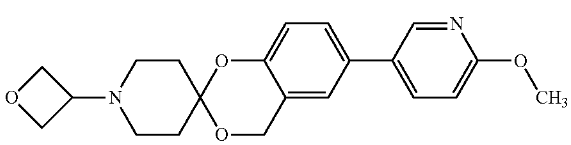 [SMILES: COc1ccc(-c2ccc3c(c2)COC2(CCN(C4COC4)CC2)O3)cn1] | 162-164 | 369 | ++ | + |
| 714 | 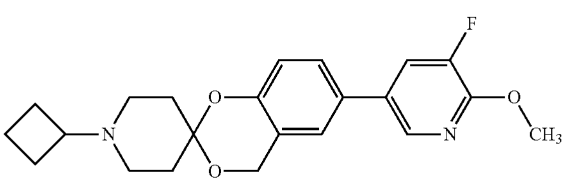 [SMILES: COc1ncc(-c2ccc3c(c2)COC2(CCN(C4CCC4)CC2)O3)cc1F] | 175-177 | 385 | +++ | +++ |
| 715 | 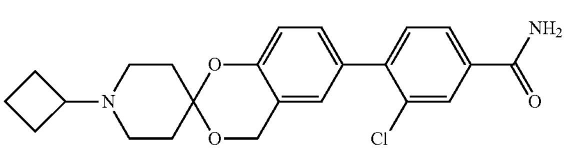 [SMILES: NC(=O)c1ccc(-c2ccc3c(c2)COC2(CCN(C4CCC4)CC2)O3)c(Cl)c1] | 112-114 | 413 | +++ | +++ |

TABLE D-continued

| Ex. No | Structure | MP (°C.) | (M + H) | Human H3 Ki (nM) | Rat H3 Ki (nM) |
|---|---|---|---|---|---|
| 716 | 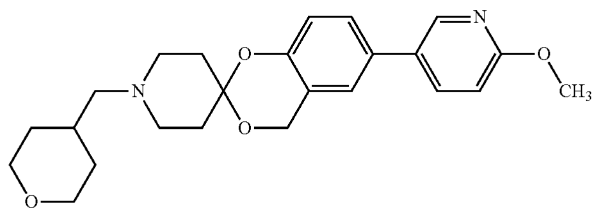 [SMILES: COc1ccc(-c2ccc3c(c2)COC2(CCN(CC4CCOCC4)CC2)O3)cn1] | 151-153 | 411 | + | + |
| 717 | 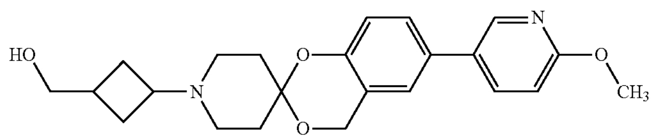 | 123-125 | 397 | ++ | ++ |
| 718 | 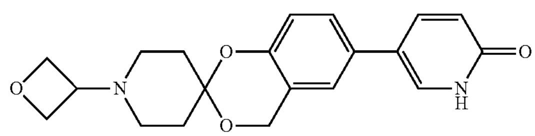 [SMILES: O=c1ccc(-c2ccc3c(c2)COC2(CCN(C4COC4)CC2)O3)c[nH]1] | 262-264 | 355 | + | + |
| 719 | 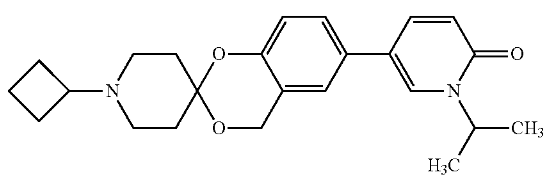 [SMILES: CC(C)n1cc(-c2ccc3c(c2)COC2(CCN(C4CCC4)CC2)O3)ccc1=O] | 176-177 | 395 | +++ | +++ |
| 720 | 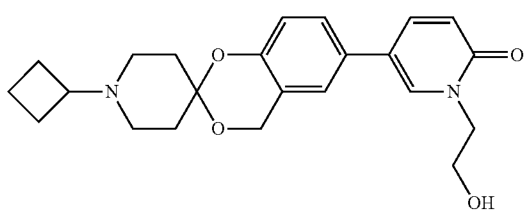 [SMILES: O=c1ccc(-c2ccc3c(c2)COC2(CCN(C4CCC4)CC2)O3)cn1CCO] | 129-130 | 397 | +++ | +++ |
| 721 | 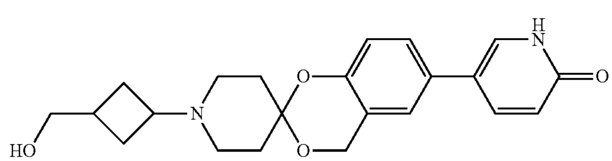 [SMILES: O=c1ccc(-c2ccc3c(c2)COC2(CCN(C4CC(CO)C4)CC2)O3)c[nH]1] | 228-230 | 383 | + | |
| 722 | 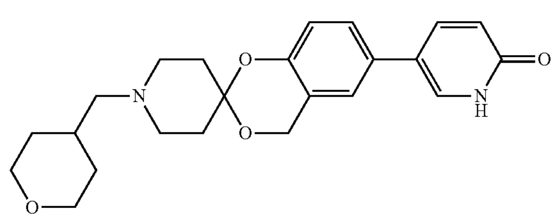 [SMILES: O=c1ccc(-c2ccc3c(c2)COC2(CCN(CC4CCOCC4)CC2)O3)c[nH]1] | 245-248 | 397 | ++ | + |
| 723 | 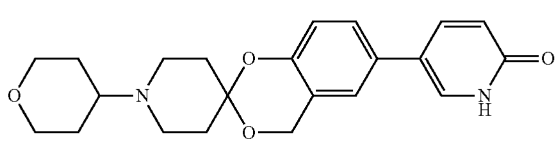 [SMILES: O=c1ccc(-c2ccc3c(c2)COC2(CCN(C4CCOCC4)CC2)O3)c[nH]1] | 230-232 | 383 | +++ | +++ |

TABLE D-continued

| Ex. No | Structure | MP (°C.) | (M + H) | Human H3 Ki (nM) | Rat H3 Ki (nM) |
|---|---|---|---|---|---|
| 724 | 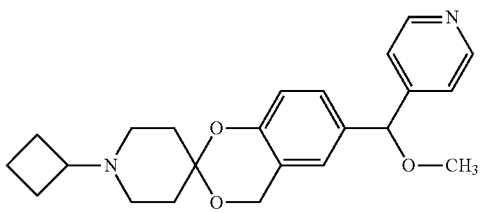 [SMILES: COC(c1ccncc1)c1ccc2c(c1)COC1(CCN(C3CCC3)CC1)O2] | NA | 381 | +++ | +++ |
| 725 | 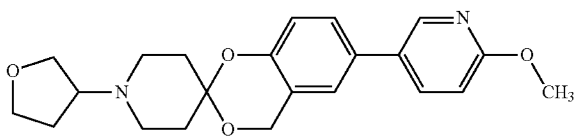 [SMILES: COc1ccc(-c2ccc3c(c2)COC2(CCN(C4CCOC4)CC2)O3)cn1] | 139-141 | 383 | ++ | ++ |
| 726 | 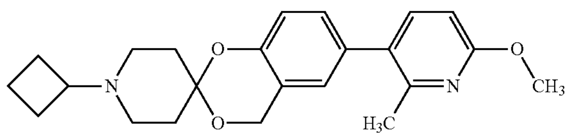 | 131-133 | 381 | +++ | +++ |
| 727 | 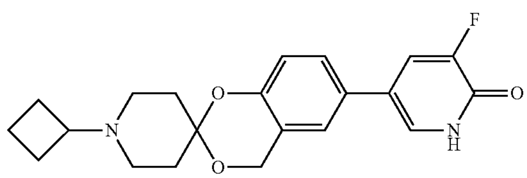 [SMILES: O=c1[nH]cc(-c2ccc3c(c2)COC2(CCN(C4CCC4)CC2)O3)cc1F] | 200-202 | 371 | +++ | +++ |
| 728 | 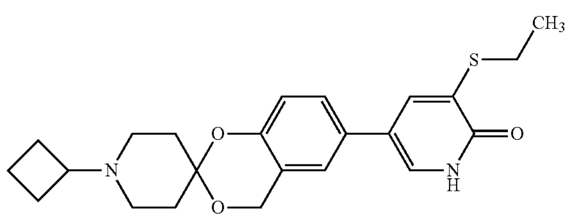 [SMILES: CCSc1cc(-c2ccc3c(c2)COC2(CCN(C4CCC4)CC2)O3)c[nH]c1=O] | 241-243 | 413 | +++ | +++ |
| 729 | 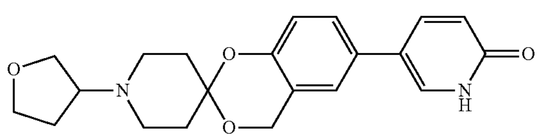 [SMILES: O=c1ccc(-c2ccc3c(c2)COC2(CCN(C4CCOC4)CC2)O3)c[nH]1] | 222-226 | 369 | ++ | ++ |
| 730 | 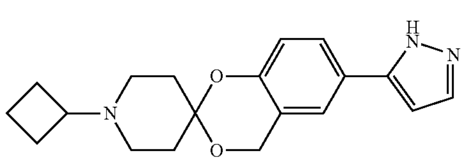 [SMILES: c1cc(-c2ccc3c(c2)COC2(CCN(C4CCC4)CC2)O3)[nH]n1] | 140-141 | 326 | +++ | +++ |
| 731 | 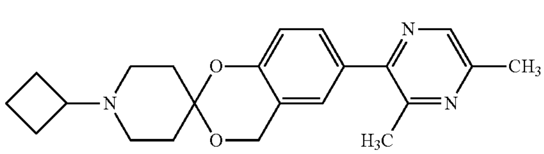 | 224-225 | 366 | +++ | +++ |
| 732 | 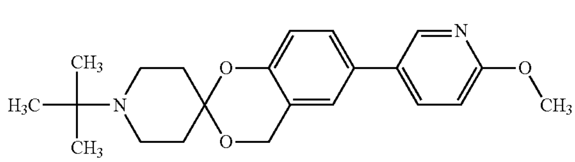 | 152-154 | 369 | +++ | +++ |

TABLE D-continued

| Ex. No | Structure | MP (°C.) | (M + H) | Human H3 Ki (nM) | Rat H3 Ki (nM) |
|---|---|---|---|---|---|
| 733 | 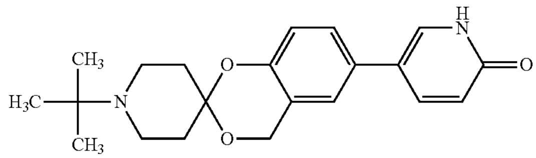 | 241-243 | 355 | +++ | +++ |
| 734 | 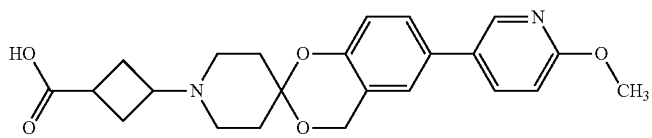 [SMILES: COc1ccc(-c2ccc3c(c2)COC2(CCN(C4CC(C(=O)O)C4)CC2)O3)cn1] | 260-262 | 411 | + | + |
| 735 | 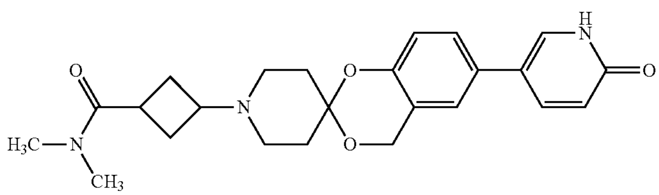 [SMILES: CN(C)C(=O)C1CC(N2CCC3(CC2)OCc2cc(-c4ccc(=O)[nH]c4)ccc2O3)C1] | 247-249 | 424 | + | + |
| 736 | 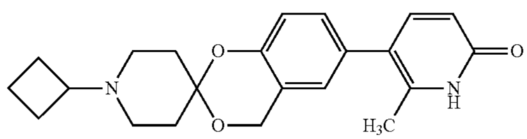 | 191-193 | 367 | +++ | +++ |
| 737 | 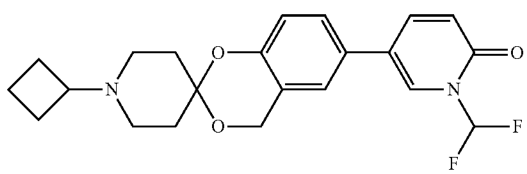 [SMILES: O=c1ccc(-c2ccc3c(c2)COC2(CCN(C4CCC4)CC2)O3)cn1C(F)F] | 125-127 | 403 | +++ | +++ |
| 738 | 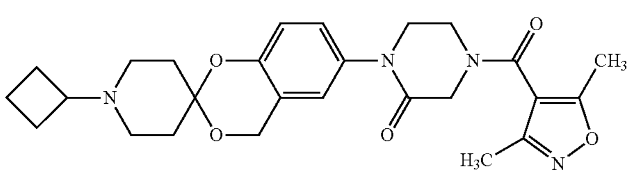 [SMILES: Cc1noc(C)c1C(=O)N1CCN(c2ccc3c(c2)COC2(CCN(C4CCC4)CC2)O3)C(=O)C1] | 103-106 | 481 | +++ | +++ |
| 739 | 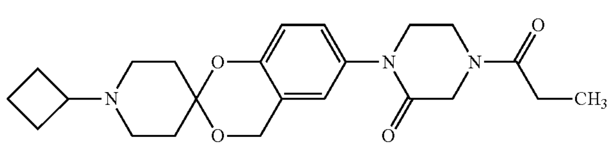 [SMILES: CCC(=O)N1CCN(c2ccc3c(c2)COC2(CCN(C4CCC4)CC2)O3)C(=O)C1] | 146-148 | 414 | +++ | +++ |
| 740 | 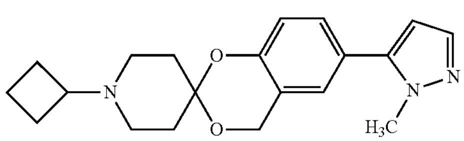 [SMILES: Cn1nccc1-c1ccc2c(c1)COC1(CCN(C3CCC3)CC1)O2] | 107-109 | 340 | +++ | +++ |
| 741 | 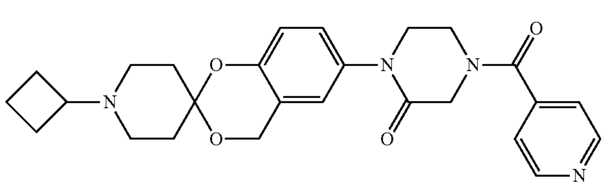 [SMILES: O=C(c1ccncc1)N1CCN(c2ccc3c(c2)COC2(CCN(C4CCC4)CC2)O3)C(=O)C1] | NA | 463 | +++ | +++ |

TABLE D-continued

| Ex. No | Structure | MP (°C.) | (M + H) | Human H3 Ki (nM) | Rat H3 Ki (nM) |
|---|---|---|---|---|---|
| 742 | 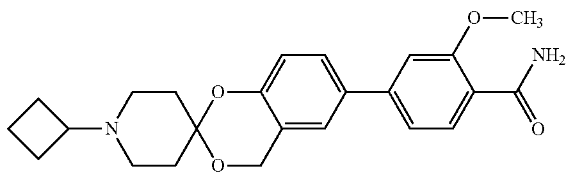 [SMILES: COc1cc(-c2ccc3c(c2)COC2(CCN(C4CCC4)CC2)O3)ccc1C(N)=O] | 212-214 | 409 | +++ | +++ |
| 743 | 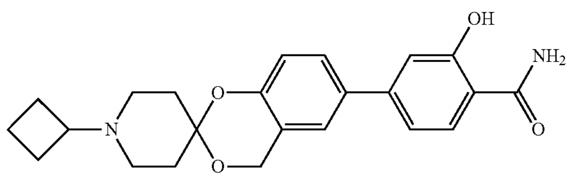 | 267-269 | 395 | +++ | +++ |
| 744 | 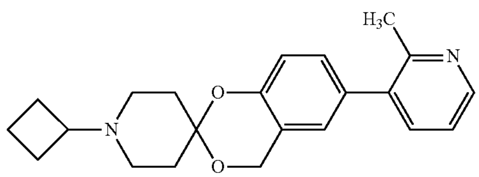 [SMILES: Cc1ncccc1-c1ccc2c(c1)COC1(CCN(C3CCC3)CC1)O2] | 197-199 | 351 | +++ | +++ |
| 745 | 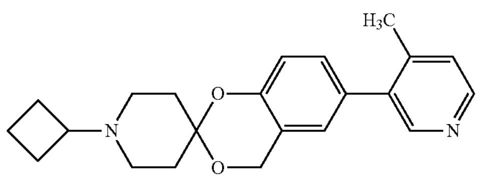 [SMILES: Cc1ccncc1-c1ccc2c(c1)COC1(CCN(C3CCC3)CC1)O2] | 200-202 | 351 | +++ | +++ |
| 746 | 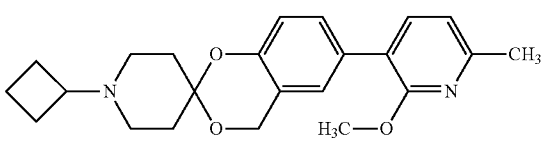 | 61-63 | 381 | +++ | +++ |
| 747 | 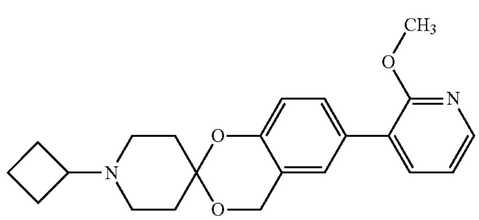 [SMILES: COc1ncccc1-c1ccc2c(c1)COC1(CCN(C3CCC3)CC1)O2] | 210-212 | 367 | +++ | +++ |
| 748 | 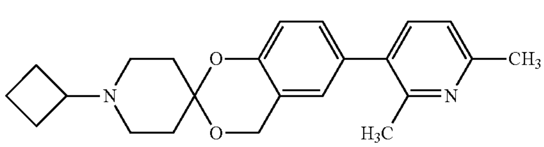 | 190-192 | 365 | +++ | +++ |
| 749 | 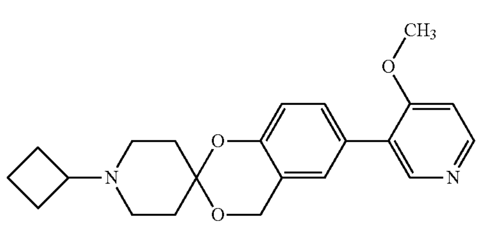 [SMILES: COc1ccncc1-c1ccc2c(c1)COC1(CCN(C3CCC3)CC1)O2] | 58-60 | 367 | +++ | +++ |

TABLE D-continued

| Ex. No | Structure | MP (°C.) | (M + H) | Human H3 Ki (nM) | Rat H3 Ki (nM) |
|---|---|---|---|---|---|
| 750 | 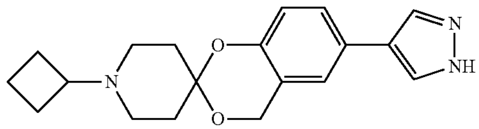 [SMILES: c1cc2c(cc1-c1cn[nH]c1)COC1(CCN(C3CCC3)CC1)O2] | 205-207 | 326 | +++ | +++ |
| 751 | 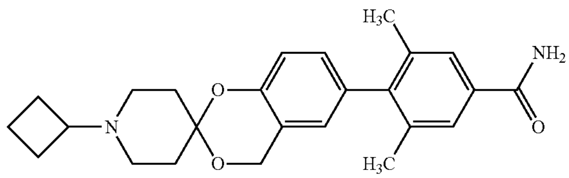 [SMILES: Cc1cc(C(N)=O)cc(C)c1-c1ccc2c(c1)COC1(CCN(C3CCC3)CC1)O2] | 156-158 | 407 | +++ | +++ |
| 752 | 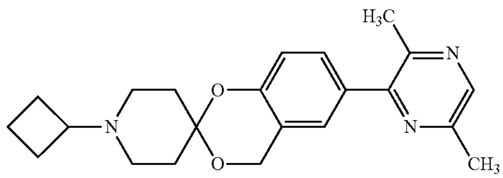 [SMILES: Cc1cnc(C)c(-c2ccc3c(c2)COC2(CCN(C4CCC4)CC2)O3)n1] | 102-103 | 366 | +++ | +++ |
| 753 | 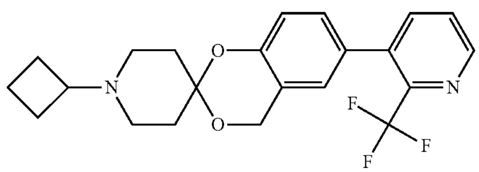 [SMILES: FC(F)(F)c1ncccc1-c1ccc2c(c1)COC1(CCN(C3CCC3)CC1)O2] | 190-192 | 405 | ++ | ++ |
| 754 | 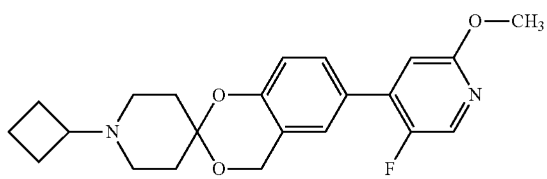 [SMILES: COc1cc(-c2ccc3c(c2)COC2(CCN(C4CCC4)CC2)O3)c(F)cn1] | 135-136 | 385 | +++ | +++ |
| 755 | 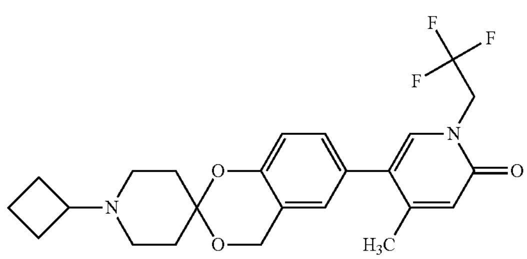 [SMILES: Cc1cc(=O)n(CC(F)(F)F)cc1-c1ccc2c(c1)COC1(CCN(C3CCC3)CC1)O2] | 60-62 | 449 | +++ | +++ |
| 756 | 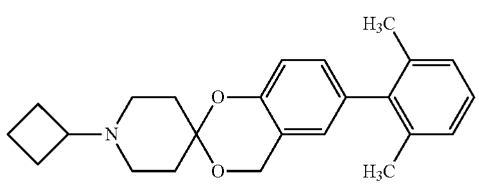 [SMILES: Cc1cccc(C)c1-c1ccc2c(c1)COC1(CCN(C3CCC3)CC1)O2] | 58-60 | 364 | +++ | ++ |
| 757 | 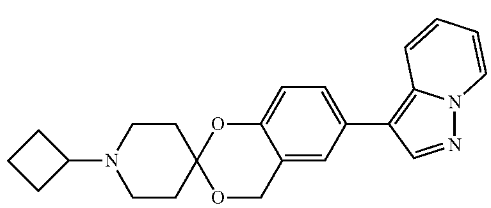 [SMILES: c1ccn2ncc(-c3ccc4c(c3)COC3(CCN(C5CCC5)CC3)O4)c2c1] | 158-160 | 376 | +++ | +++ |

TABLE D-continued

| Ex. No | Structure | MP (°C.) | (M + H) | Human H3 Ki (nM) | Rat H3 Ki (nM) |
|---|---|---|---|---|---|
| 758 | 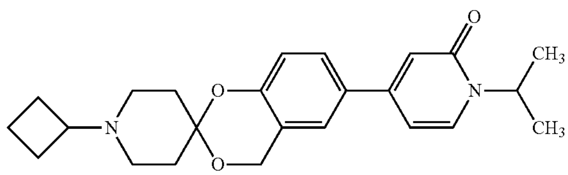 [SMILES: CC(C)n1ccc(-c2ccc3c(c2)COC2(CCN(C4CCC4)CC2)O3)cc1=O] | 218-220 | 395 | +++ | +++ |
| 759 | 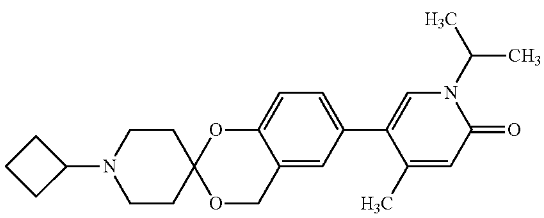 [SMILES: Cc1cc(=O)n(C(C)C)cc1-c1ccc2c(c1)COC1(CCN(C3CCC3)CC1)O2] | 65-68 | 409 | +++ | +++ |
| 760 | 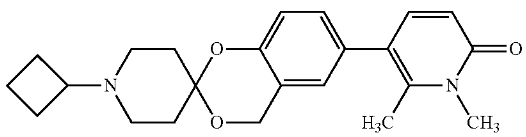 [SMILES: Cc1c(-c2ccc3c(c2)COC2(CCN(C4CCC4)CC2)O3)ccc(=O)n1C] | 59-61 | 381 | +++ | +++ |
| 761 | 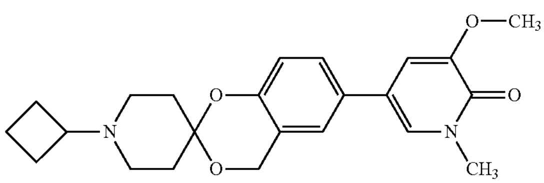 [SMILES: COc1cc(-c2ccc3c(c2)COC2(CCN(C4CCC4)CC2)O3)cn(C)c1=O] | 70-72 | 397 | +++ | +++ |
| 762 | 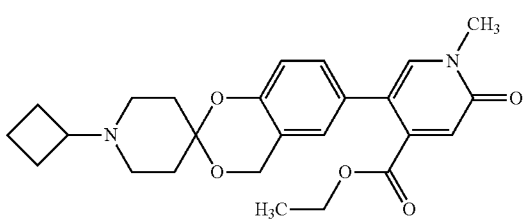 [SMILES: CCOC(=O)c1cc(=O)n(C)cc1-c1ccc2c(c1)COC1(CCN(C3CCC3)CC1)O2] | 71-74 | 439 | +++ | +++ |
| 763 | 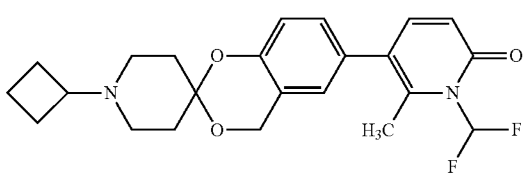 [SMILES: Cc1c(-c2ccc3c(c2)COC2(CCN(C4CCC4)CC2)O3)ccc(=O)n1C(F)F] | 143-145 | 417 | +++ | +++ |
| 764 | 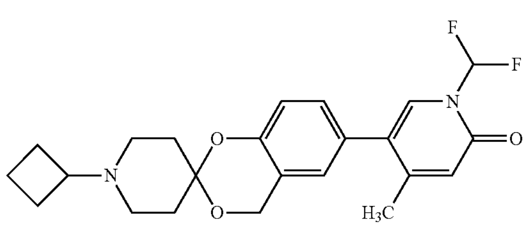 | 119-121 | 417 | +++ | +++ |

TABLE D-continued

| Ex. No | Structure | MP (°C.) | (M + H) | Human H3 Ki (nM) | Rat H3 Ki (nM) |
|---|---|---|---|---|---|
| 765 | 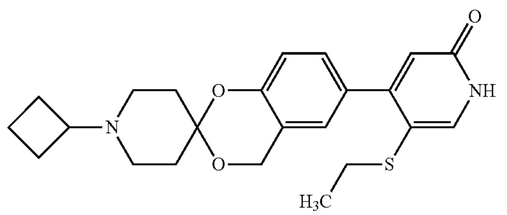 [SMILES: CCSc1c[nH]c(=O)cc1-c1ccc2c(c1)COC1(CCN(C3CCC3)CC1)O2] | 85-88 | 413 | +++ | +++ |
| 766 | 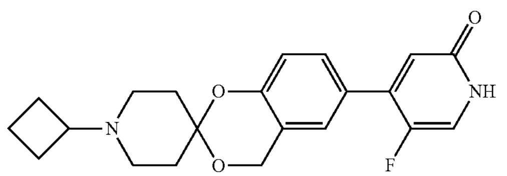 [SMILES: O=c1cc(-c2ccc3c(c2)COC2(CCN(C4CCC4)CC2)O3)c(F)c[nH]1] | 254-255 | 371 | +++ | +++ |
| 767 | 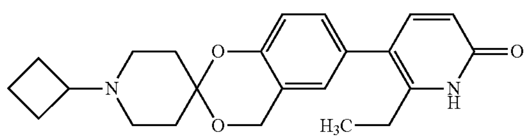 | 230-231 | 381 | +++ | +++ |
| 768 | 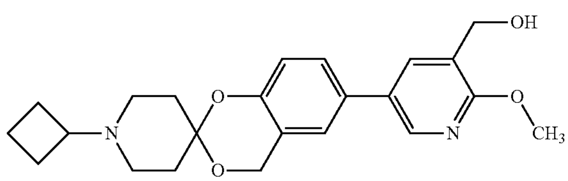 [SMILES: COc1ncc(-c2ccc3c(c2)COC2(CCN(C4CCC4)CC2)O3)cc1CO] | 150-151 | 397 | +++ | +++ |
| 769 | 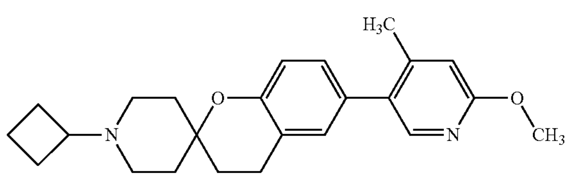 [SMILES: COc1cc(C)c(-c2ccc3c(c2)CCC2(CCN(C4CCC4)CC2)O3)cn1] | 127-128 | 379 | +++ | +++ |
| 770 | 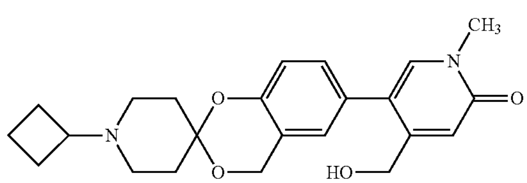 [SMILES: Cn1cc(-c2ccc3c(c2)COC2(CCN(C4CCC4)CC2)O3)c(CO)cc1=O] | 120-123 | 397 | +++ | +++ |
| 771 | 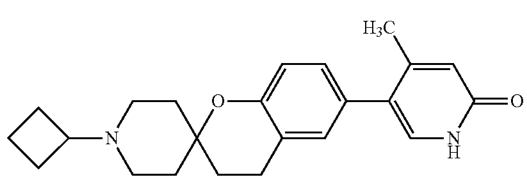 [SMILES: Cc1cc(=O)[nH]cc1-c1ccc2c(c1)CCC1(CCN(C3CCC3)CC1)O2] | 252-254 | 365 | +++ | +++ |
| 772 | 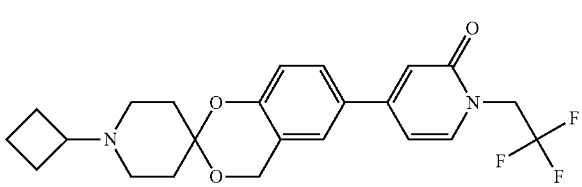 | 196-198 | 435 | +++ | +++ |

TABLE D-continued

| Ex. No | Structure | MP (°C.) | (M + H) | Human H3 Ki (nM) | Rat H3 Ki (nM) |
|---|---|---|---|---|---|
| 773 | 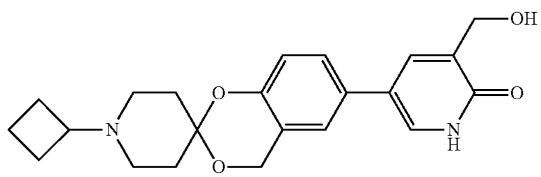 [SMILES: O=c1[nH]cc(-c2ccc3c(c2)COC2(CCN(C4CCC4)CC2)O3)cc1CO] | 228-230 | 383 | +++ | +++ |
| 774 | 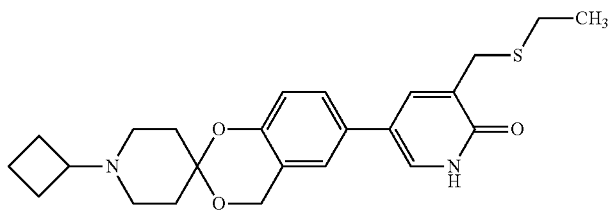 [SMILES: CCSCc1cc(-c2ccc3c(c2)COC2(CCN(C4CCC4)CC2)O3)c[nH]c1=O] | 205-207 | 427 | +++ | +++ |
| 775 | 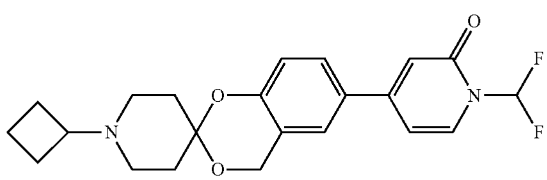 [SMILES: O=c1cc(-c2ccc3c(c2)COC2(CCN(C4CCC4)CC2)O3)ccn1C(F)F] | 175-177 | 403 | +++ | +++ |
| 776 | 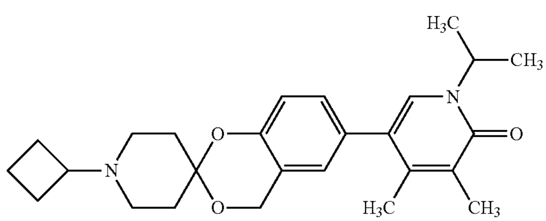 | 89-92 | 423 | +++ | +++ |
| 777 | 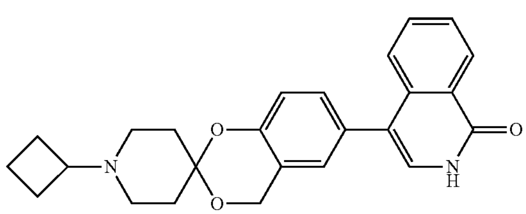 [SMILES: O=c1[nH]cc(-c2ccc3c(c2)COC2(CCN(C4CCC4)CC2)O3)c2ccccc12] | 202-204 | 403 | +++ | +++ |
| 778 | 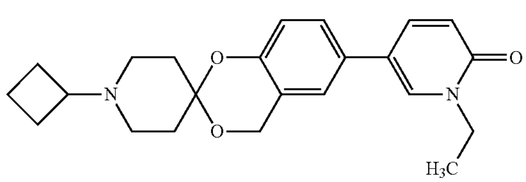 [SMILES: CCn1cc(-c2ccc3c(c2)COC2(CCN(C4CCC4)CC2)O3)ccc1=O] | 156-158 | 381 | +++ | +++ |
| 779 | 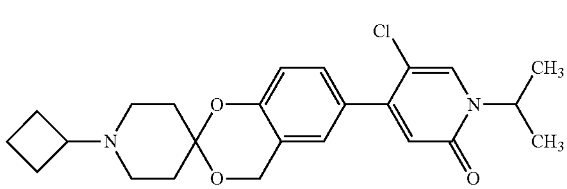 [SMILES: CC(C)n1cc(Cl)c(-c2ccc3c(c2)COC2(CCN(C4CCC4)CC2)O3)cc1=O] | 179-181 | 429 | +++ | +++ |

TABLE D-continued

| Ex. No | Structure | MP (°C.) | (M + H) | Human H3 Ki (nM) | Rat H3 Ki (nM) |
|---|---|---|---|---|---|
| 780 | 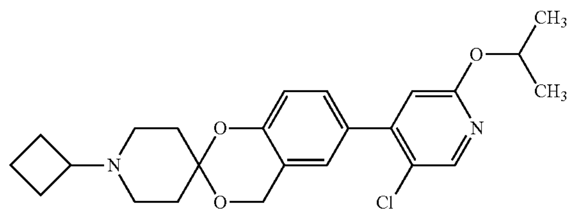 [SMILES: CC(C)Oc1cc(-c2ccc3c(c2)COC2(CCN(C4CCC4)CC2)O3)c(Cl)cn1] | 131-132 | 429 | +++ | +++ |
| 781 | 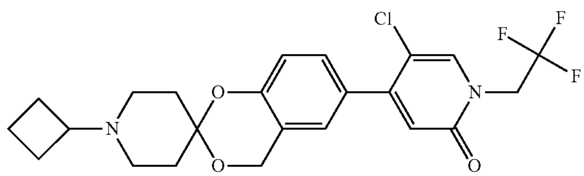 [SMILES: O=c1cc(-c2ccc3c(c2)COC2(CCN(C4CCC4)CC2)O3)c(Cl)cn1CC(F)(F)F] | 194-197 | 469 | +++ | +++ |
| 782 | 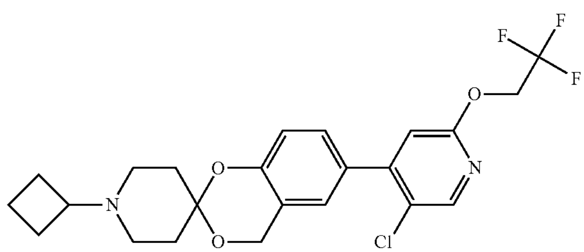 [SMILES: FC(F)(F)COc1cc(-c2ccc3c(c2)COC2(CCN(C4CCC4)CC2)O3)c(Cl)cn1] | 119-121 | 469 | +++ | +++ |
| 783 | 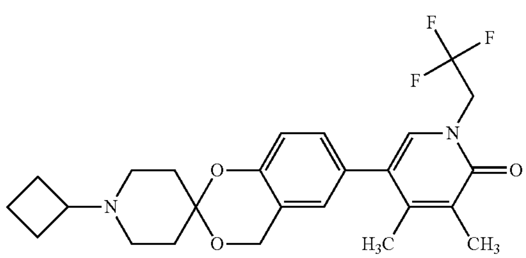 [SMILES: Cc1c(-c2ccc3c(c2)COC2(CCN(C4CCC4)CC2)O3)cn(CC(F)(F)F)c(=O)c1C] | 96-98 | 463 | +++ | +++ |
| 784 | 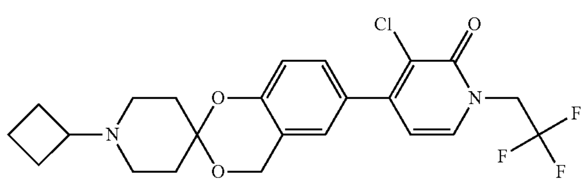 [SMILES: O=c1c(Cl)c(-c2ccc3c(c2)COC2(CCN(C4CCC4)CC2)O3)ccn1CC(F)(F)F] | 71.2-73.6 | 469 | +++ | +++ |
| 785 | 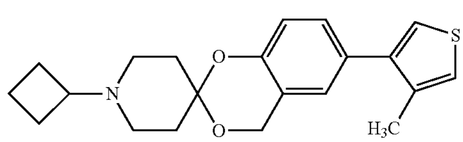 | 91-93 | 356 | +++ | +++ |
| 786 | 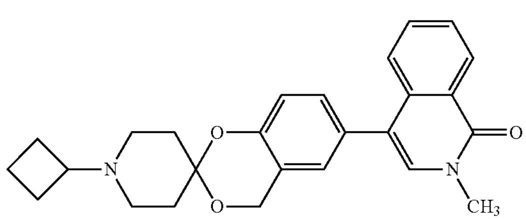 | 207-209 | 417 | +++ | +++ |

TABLE D-continued
| Ex. No | Structure | MP (°C.) | (M + H) | Human H3 Ki (nM) | Rat H3 Ki (nM) |
|---|---|---|---|---|---|
| 787 | 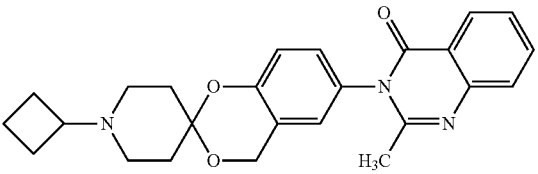 | 206-207 | 418 | +++ | +++ |
| 788 | 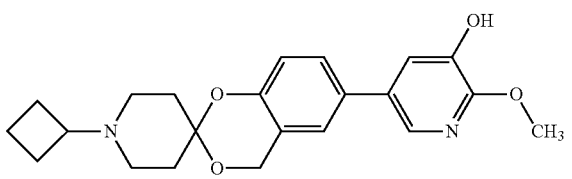 | 61-63 | 383 | +++ | +++ |
| 789 | 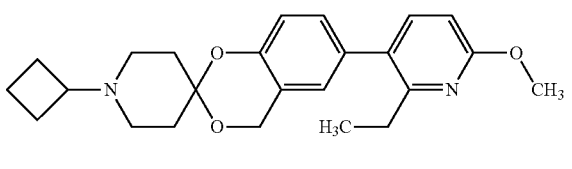 | 59-61 | 395 | +++ | +++ |
| 790 | 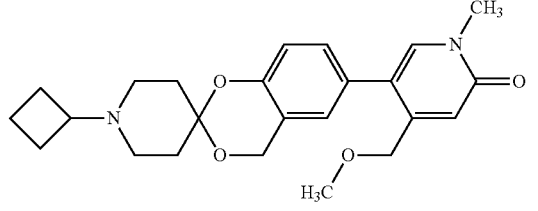 [SMILES: COCc1cc(=O)n(C)cc1-c1ccc2c(c1)COC1(CCN(C3CCC3)CC1)O2] | NA | 411 | +++ | +++ |
| 791 | 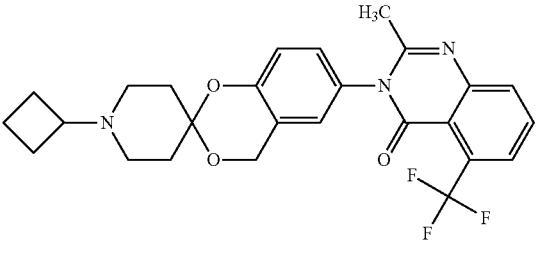 [SMILES: Cc1nc2cccc(C(F)(F)F)c2c(=O)n1-c1ccc2c(c1)COC1(CCN(C3CCC3)CC1)O2] | 221-222 | 486 | +++ | +++ |
| 792 | 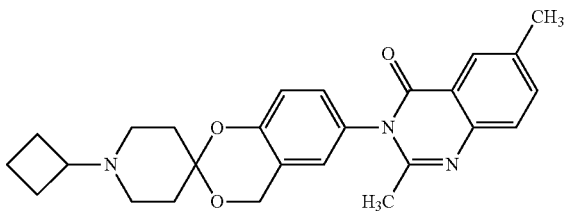 [SMILES: Cc1ccc2nc(C)n(-c3ccc4c(c3)COC3(CCN(C5CCC5)CC3)O4)c(=O)c2c1] | 149-152 | 432 | +++ | +++ |
| 793 | 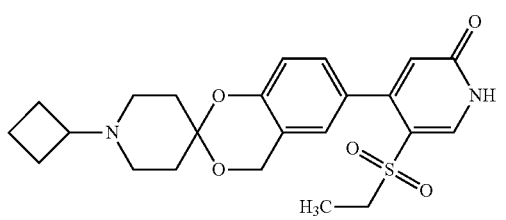 [SMILES: CCS(=O)(=O)c1c[nH]c(=O)cc1-c1ccc2c(c1)COC1(CCN(C3CCC3)CC1)O2] | 190-192 | 445 | +++ | +++ |

TABLE D-continued

| Ex. No | Structure | MP (°C.) | (M + H) | Human H3 Ki (nM) | Rat H3 Ki (nM) |
|---|---|---|---|---|---|
| 794 | 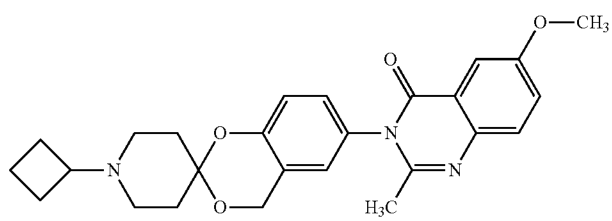 [SMILES: COc1ccc2nc(C)n(-c3ccc4c(c3)COC3(CCN(C5CCC5)CC3)O4)c(=O)c2c1] | 155-157 | 448 | +++ | +++ |
| 795 | 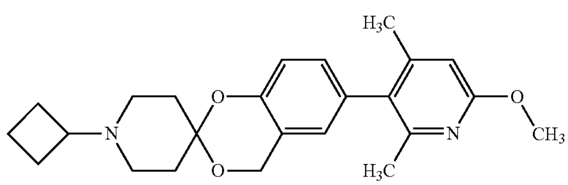 [SMILES: COc1cc(C)c(-c2ccc3c(c2)COC2(CCN(C4CCC4)CC2)O3)c(C)n1] | 149.8-150.4 | 395 | +++ | +++ |
| 796 | 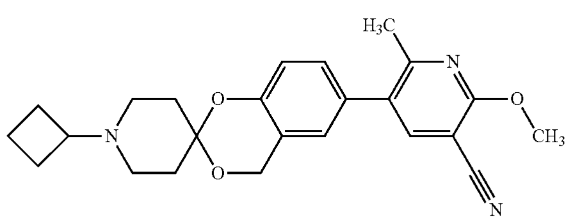 [SMILES: COc1nc(C)c(-c2ccc3c(c2)COC2(CCN(C4CCC4)CC2)O3)cc1C#N] | 215-217 | 406 | +++ | +++ |
| 797 | 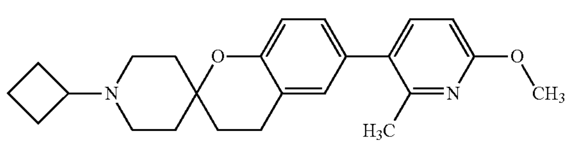 | 72-73 | 379 | +++ | +++ |
| 798 | 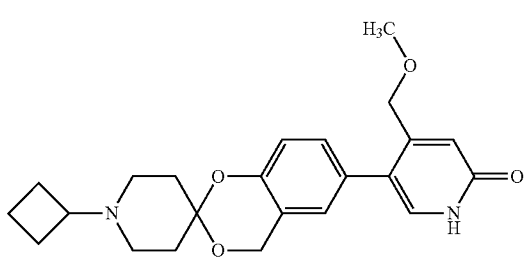 [SMILES: COCc1cc(=O)[nH]cc1-c1ccc2c(c1)COC1(CCN(C3CCC3)CC1)O2] | 217-219 | 397 | +++ | +++ |
| 799 | 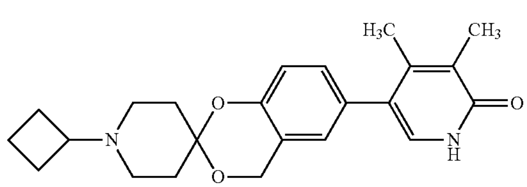 [SMILES: Cc1c(-c2ccc3c(c2)COC2(CCN(C4CCC4)CC2)O3)c[nH]c(=O)c1C] | 178-180 | 381 | +++ | +++ |
| 800 | 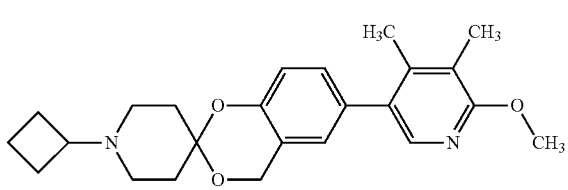 [SMILES: COc1ncc(-c2ccc3c(c2)COC2(CCN(C4CCC4)CC2)O3)c(C)c1C] | 233-235 | 395 | +++ | +++ |

TABLE D-continued

| Ex. No | Structure | MP (°C.) | (M + H) | Human H3 Ki (nM) | Rat H3 Ki (nM) |
|---|---|---|---|---|---|
| 801 | 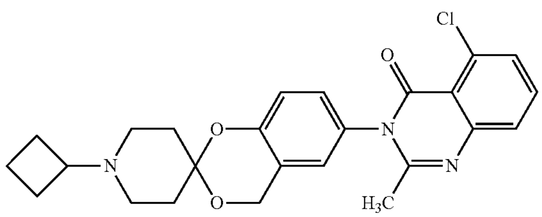 [SMILES: Cc1nc2cccc(Cl)c2c(=O)n1-c1ccc2c(c1)COC1(CCN(C3CCC3)CC1)O2] | 105-107 | 452 | +++ | +++ |
| 802 | 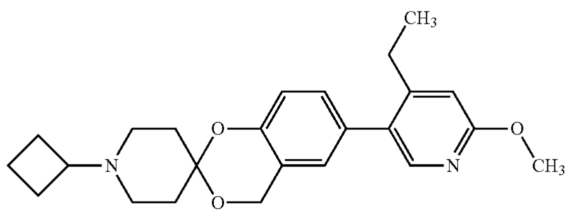 | 156-160 | 395 | +++ | +++ |
| 803 | 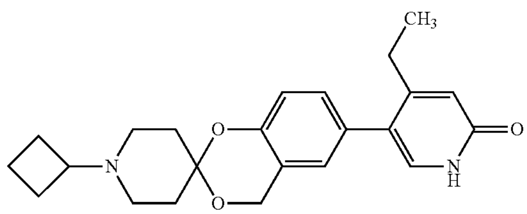 [SMILES: CCc1cc(=O)[nH]cc1-c1ccc2c(c1)COC1(CCN(C3CCC3)CC1)O2] | 107-109 | 381 | +++ | +++ |
| 804 | 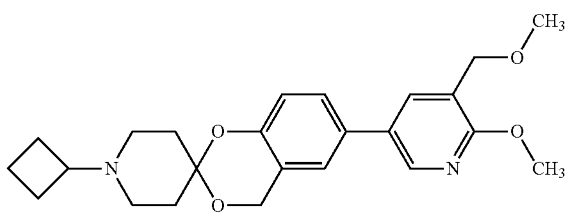 [SMILES: COCc1cc(-c2ccc3c(c2)COC2(CCN(C4CCC4)CC2)O3)cnc1OC] | 257 | 411 | +++ | +++ |
| 805 | 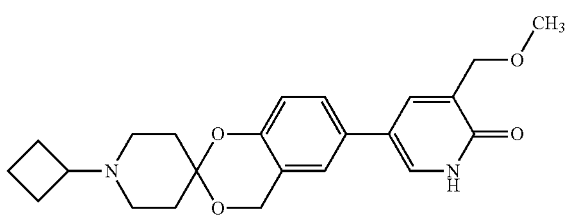 [SMILES: COCc1cc(-c2ccc3c(c2)COC2(CCN(C4CCC4)CC2)O3)c[nH]c1=O] | 212-214 | 397 | +++ | +++ |
| 806 | 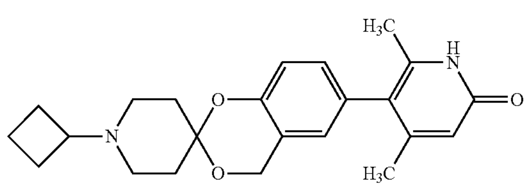 [SMILES: Cc1cc(=O)[nH]c(C)c1-c1ccc2c(c1)COC1(CCN(C3CCC3)CC1)O2] | 247-249 | 381 | +++ | +++ |
| 807 | 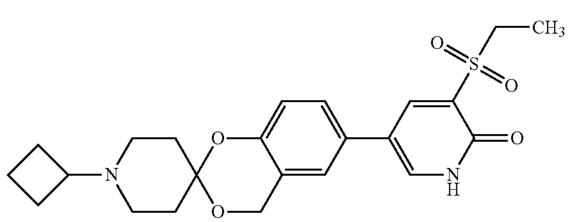 [SMILES: CCS(=O)(=O)c1cc(-c2ccc3c(c2)COC2(CCN(C4CCC4)CC2)O3)c[nH]c1=O] | DEC265-270 | 446 | +++ | +++ |

TABLE D-continued

| Ex. No | Structure | MP (°C.) | (M + H) | Human H3 Ki (nM) | Rat H3 Ki (nM) |
|---|---|---|---|---|---|
| 808 | 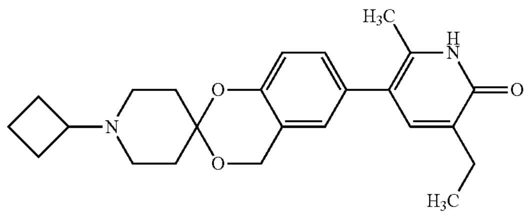 [SMILES: CCc1cc(-c2ccc3c(c2)COC2(CCN(C4CCC4)CC2)O3)c(C)[nH]c1=O] | 211-213 | 395 | +++ | +++ |

Dosage and Formulation

For therapeutic purposes, the compounds of the present invention can be administered by any means that results in the contact of the active agent with the agent's site of action in the body of the subject. The compounds may be administered by any conventional means available for use in conjunction with pharmaceuticals, either as individual therapeutic agents or in combination with other therapeutic agents, such as, for example, analgesics. The compounds of the present invention are preferably administered in therapeutically effective amounts for the treatment of the diseases and disorders described herein to a subject in need thereof.

A therapeutically effective amount can be readily determined by the attending diagnostician, as one skilled in the art, by the use of conventional techniques. The effective dose will vary depending upon a number of factors, including the type and extent of progression of the disease or disorder, the overall health status of the particular patient, the relative biological efficacy of the compound selected, the formulation of the active agent with appropriate excipients, and the route of administration. Typically, the compounds are administered at lower dosage levels, with a gradual increase until the desired effect is achieved.

Typical dose ranges are from about 0.01 mg/kg to about 100 mg/kg of body weight per day, with a preferred dose from about 0.01 mg/kg to 10 mg/kg of body weight per day. A preferred daily dose for adult humans includes about 25, 50, 100 and 200 mg, and an equivalent dose in a human child. The compounds may be administered in one or more unit dose forms. The unit dose ranges from about 1 to about 500 mg administered one to four times a day, preferably from about 10 mg to about 300 mg, two times a day. In an alternate method of describing an effective dose, an oral unit dose is one that is necessary to achieve a blood serum level of about 0.05 to 20 μg/ml in a subject, and preferably about 1 to 20 μg/ml.

The compounds of the present invention may be formulated into pharmaceutical compositions by admixture with one or more pharmaceutically acceptable excipients. The excipients are selected on the basis of the chosen route of administration and standard pharmaceutical practice, as described, for example, in *Remington: The Science and Practice of Pharmacy*, 20*th* ed.; Gennaro, A. R., Ed.; Lippincott Williams & Wilkins: Philadelphia, Pa., 2000. The compositions may be formulated to control and/or delay the release of the active agent(s), in fast-dissolve, modified-release, or sustained-release formulations. Such controlled-release, or extended-release compositions may utilize, for example biocompatible, biodegradable lactide polymers, lactide/glycolide copolymers, polyoxyethylene-polyoxypropylene copolymers, or other solid or semisolid polymeric matrices known in the art.

The compositions can be prepared for administration by oral means; parenteral means, including intravenous, intramuscular, and subcutaneous routes; topical or transdermal means; transmucosal means, including rectal, vaginal, sublingual and buccal routes; ophthalmic means; or inhalation means. Preferably the compositions are prepared for oral administration, particularly in the form of tablets, capsules or syrups; for parenteral administration, particularly in the form of liquid solutions, suspensions or emulsions; for intranasal administration, particularly in the form of powders, nasal drops, or aerosols; or for topical administration, such as creams, ointments, solutions, suspensions aerosols, powders and the like.

For oral administration, the tablets, pills, powders, capsules, troches and the like can contain one or more of the following: diluents or fillers such as starch, or cellulose; binders such as microcrystalline cellulose, gelatins, or polyvinylpyrrolidones; disintegrants such as starch or cellulose derivatives; lubricants such as talc or magnesium stearate; glidants such as colloidal silicon dioxide; sweetening agents such as sucrose or saccharin; or flavoring agents such as peppermint or cherry flavoring. Capsules may contain any of the afore listed excipients, and may additionally contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Nonaqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers, and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

REFERENCES

Alguacil L. F.; Perez-Garcia C. Histamine $H_3$ Receptor: A potential drug target for the treatment of central nervous systems disorders. *Current Drug Targets—CNS& Neurological Disorders* 2003, 2, 303-131.

Arrang, J. M.; Garbarg, M.; Schwartz, J. C., Auto-inhibition of brain histamine release mediated by a novel class ($H_3$) of histamine receptor. *Nature* 1983, 302, (5911), 832-7.

Celanire, S.; Wijtmans, M.; Talaga, P.; Leurs, R.; de Esch, I. J., Keynote review: histamine $H_3$ receptor antagonists reach out for the clinic. *Drug Discov Today* 2005, 10, (23-24), 1613-27.

Chazot P. L.; Hann V. $H_3$ histamine receptor isoforms: New therapeutic targets in the CNS? *Current Opinions in Investigational Drugs* 2001, 2, 1428-1431.

Chen Z. Effect of histamine $H_3$-receptor antagonist clobenprobit on spatial memory of radial maze performance in rats. *Acta Pharmacol Sin* 2000, 21, 905-910.

Esbenshade, T. A.; ox, G. B.; Cowart, M. D. Histamine $H_3$ receptor antagonists: Preclinical promise for treating obesity and cognitive disorders. *Molecular interventions* 2006, 6, 77-88.

Fox G. B.; Pan J. B.; Esbenshade T. A.; Bennani Y. L.; Black L. A.; Faghih R.; Hancock A. A.; Decker M. W. Effects of histamine $H_3$ receptor ligands GT-2331 and ciproxifan in a repeated acquisition response in the spontaneously hypertensive rat pup. *Behav. Brain Res.* 2002, 131, 151-161.

Fox G. B.; Pan J. B.; Radek R. J.; Lewis A. M.; Bitner R. S.; Esbenshade T. A.; Faghih R.; Bennani Y. L.; Williams M.; Yao B. B. Decker M. W.; Hancock A. A. Two novel and selective nonimidazole $H_3$ receptor Antagonists A-304121 and A-317920: II. In vivo behavioral and neurophysiological characterization. *J. Pharmacol. Exper. Ther.* 2003, 305, 897-908.

Hancock, A. A.; Esbenshade, T. A.; Krueger, K. M.; Yao, B. B., Genetic and pharmacological aspects of histamine $H_3$ receptor heterogeneity. *Life Sci* 2003, 73, (24), 3043-72.

Hancock, A. A.; Fox, G. B. Perspectives on cognitive domains, $H_3$ receptor ligands and neurological disease. *Expert Opin. Investig. Drugs,* 2004, 13, 1237-1248.

Komater V. A.; Browman K. E.; Curzon P.; Hancock A. A., Decker M. W.; Fox B. $H_3$ receptor blockade by thioperamide enhances cognition in rats without inducing locomotor sensitization. *Psychopharmacology* 2003, 167, 363-372.

Leurs R.; Blandina P.; Tedford C.; Timmerman H. Therapeutic potential of histamine $H_3$ receptor agonists and antagonists. *Trends in Pharmacology* 1998, 19, 177-183.

Leurs, R.; Bakker, R. A.; Timmerman, H.; de Esch, I. J., The histamine $H_3$ receptor: from gene cloning to $H_3$ receptor drugs. *Nat Rev Drug Discov* 2005, 4, (2), 107-20.

Lin, J. S.; Sakai, K.; Vanni-Mercier, G.; Arrang, J. M.; Garbarg, M.; Schwartz, J. C.; Jouvet, M., Involvement of histaminergic neurons in arousal mechanisms demonstrated with $H_3$-receptor ligands in the cat. *Brain Res* 1990, 523, (2), 325-30.

Lloyd G. K.; Williams M. Neuronal nicotinic acetylcholine receptors as novel drug targets. *J Pharmacol Exp Ther.* 2000, 292, 461-467.

Monti, J. M.; Jantos, H.; Ponzoni, A.; Monti, D., Sleep and waking during acute histamine $H_3$ agonist BP 2.94 or $H_3$ antagonist carboperamide (MR 16155) administration in rats. *Neuropsychopharmacology* 1996, 15, 31-5.

Orsetti M.; Ferretti C.; Gamalero S. R.; Ghi P. Histamine $H_3$-receptor blockade in the rat nucleus basalis magnocellularis improves place recognition memory. Psychopharmacology 2002, 159, 133-137.

Parmentier R.; Ohtsu H.; Djebbara-Hannas Z.; Valatx J-L.; Watanabe T.; Lin J-S. Anatomical, physiological, and pharmacological characteristics of histidine decarboxylase knock-out mice: evidence for the role of brain histamine in behavioral and sleep-wake control. *J. Neurosci.* 2002, 22, 7695-7711.

Passani, M. B.; Lin, J. S.; Hancock, A.; Crochet, S.; Blandina, P., The histamine $H_3$ receptor as a novel therapeutic target for cognitive and sleep disorders. *Trends Pharmacol Sci* 2004, 25, 618-25.

Repka-Ramirez M. S. New concepts of histamine receptors and actions. Current Allergy and Asthma Reports 2003, 3, 227-231.

Ritz A.; Curley J.; Robertson J.; Raber J. Anxiety and cognition in histamine $H_3$ receptor –/– mice. *Eur J Neurosci* 2004, 19, 1992-1996.

Rouleau, A.; Heron, A.; Cochois, V.; Pillot, C.; Schwartz, J. C.; Arrang, J. M., Cloning and expression of the mouse histamine $H_3$ receptor: evidence for multiple isoforms. *J Neurochem* 2004, 90, 1331-8.

Vanni-Merci G.; Gigout S.; Debilly G.; Lin J. S. Waking selective neurons in the posterior hypothalamus and their reponse to histamine $H_3$-receptor ligands: an electrophysiological study in freely moving cats. *Behav Brain Res* 2003, 144, 227-241.

Witkin, J. M.; Nelson, D. L., Selective histamine $H_3$ receptor antagonists for treatment of cognitive deficiencies and other disorders of the central nervous system. *Pharmacol Ther* 2004, 103, 1-20.

Yao, B. B.; Sharma, R.; Cassar, S.; Esbenshade, T. A.; Hancock, A. A., Cloning and pharmacological characterization of the monkey histamine $H_3$ receptor. *Eur J Pharmacol* 2003, 482, (1-3), 49-60.

What is claimed is:

1. A compound of the Formula (I):

$$\text{(I)}$$

or a stereoisomeric form, mixture of stereoisomeric forms, an N-oxide form, or a pharmaceutically acceptable salt thereof, wherein:

$R^1$ is cyclobutyl or cyclopentyl;

k is 0, 1, or 2; m is 0, 1, or 2; and the sum of m and k is 1, 2, or 3;

$Y^1$, $Y^2$, $Y^3$, and $Y^4$ are independently selected from —CH= and —N=;

provided that when $Y^1$, $Y^2$, $Y^3$, and $Y^4$ are independently selected from —N= with the proviso that no more than of $Y^1$, $Y^2$, $Y^3$, and $Y^4$ may be —N=;

W is —O—, —$CH_2$—, —$CH_2$—O—, —C(=O)—$CH_2$—, —C(OH)—$CH_2$—, —$CH_2$—$CH_2$—, —O—$CH_2$—$CH_2$— or —$CH_2$—$CH_2$—O—;

X is $R^2$, —$OR^2$, —($C_1$-$C_3$ alkyl)-$R^2$; —($C_2$-$C_6$ alkenyl)-$R^2$; —O($C_1$-$C_3$ alkyl)-$R^2$, —O($C_2$-$C_6$ alkenyl)-$R^2$; —$NR^{29}R^{29}$, —$NR^{29}R^2$, —$NR^{29}$($C_1$-$C_3$ alkyl)-$R^2$, —($C_1$-$C_3$ alkyl)$NR^{29}R^2$, —$NR^{29}C(=O)R^2$, —$NR^{29}C(=O)(C_1$-$C_3$ alkyl)-$R^2$, or —$NR^{29}C(=O)NHR^2$; wherein each of said ($C_1$-$C_3$ alkyl) is optionally substituted with —OH or —$OC_1$-$C_3$alkyl;

$R^2$ is selected from the group consisting of
$C_1$-$C_8$ alkyl optionally substituted with 1-3 $R^{20}$;
$C_2$-$C_6$ alkenyl optionally substituted with 1-3 $R^{20}$;
$C_3$-$C_{10}$ cycloalkyl optionally substituted with 1-3 $R^{20}$;
$C_6$-$C_{10}$ aryl optionally substituted with 1-3 $R^{20}$;
5 to 10 membered heteroaryl ring system containing one, two, or three heteroatoms selected from N, O, and S, wherein said heteroaryl ring system is optionally substituted with 1-3 $R^{20}$;
4 membered heterocycloalkyl ring system containing one heteroatom selected from N, O, S, SO, and $SO_2$, wherein said heterocycloalkyl ring system is optionally substituted with 1-3 R20; and
5 to 10 membered heterocycloalkyl ring system containing one, two, or three heteroatoms selected from N, O, S, SO, and $SO_2$, wherein said heterocycloalkyl ring system is optionally substituted with 1-3 $R^{20}$;
with the proviso that $R^2$ is not a substituted or unsubstituted pyridazine or pyridazinone;

$R^8$ is F, $C_1$-$C_3$ alkyl, or $C_1$-$C_3$ alkoxy;

$R^9$, at each occurrence, is independently, F, Cl, Br, $C_1$-$C_4$ alkyl, or $C_1$-$C_4$ alkoxy;

$R^{20}$ at each occurrence is independently selected from the group consisting of
—H, —F, —Cl, —Br, —I, —$OR^{21}$, —$NR^{23}R^{24}$, —NHOH, —$NO_2$, —CN, —$CF_3$, —$CHF_2$, —$CH_2F$, (=O), —C(=O)$R^{25}$, —C(=O)$OR^{25}$, —OC(=O)$R^{25}$, —OC(=O)$NR^{23}R^{24}$, —C(=O)$NR^{23}R^{24}$, —$NR^{27}C$(=O)$NR^{23}R^{24}$, —$NR^{27}C$(=O)$R^{25}$, —$NR^{27}C$(O)$OR^{25}$, —$NR^{27}C$(=S)$R^{25}$, —$SR^{25}$, —S(=O)$R^{25}$, —S(=O)$_2R^{25}$, —S(=O)$_2NR^{23}R^{24}$, —$NR^{27}SR^{25}$, —$NR^{27}S$(=O)$R^{25}$, —$NR^{27}S$(=O)$_2R^{25}$, methylenedioxy, ethylenedioxy, propylenedioxy, $C_1$-$C_6$ alkyl optionally substituted by 1-3 $R^{31}$;
$C_2$-$C_6$ alkenyl optionally substituted by 1-3 $R^{31}$;
$C_2$-$C_6$ alkynyl optionally substituted by 1-3 $R^{31}$;
$C_3$-$C_7$ cycloalkyl optionally substituted with 1-3 $R^{30}$;
$C_6$-$C_{10}$ aryl optionally substituted with 1-3 $R^{30}$;
5 to 6 membered heteroaryl ring system containing one, two, or three heteroatoms selected from N, O, and S, wherein said heteroaryl ring system is optionally substituted with 1-3 $R^{30}$;
4 membered heterocycloalkyl ring system containing one heteroatom selected from N, O, S, SO, and $SO_2$, wherein said heterocycloalkyl ring system is optionally substituted with 1-3 $R^{30}$; and
5 to 7 membered heterocycloalkyl ring system containing one, two, or three heteroatoms selected from N, O, S, SO, and $SO_2$, wherein said heterocycloalkyl ring system is optionally substituted with 1-3 $R^{30}$;

$R^{21}$ at each occurrence is independently H, $C_1$-$C_4$ haloalkyl, $C_1$-$C_4$ alkyl optionally substituted with 1-3 $R^{22}$; $C_2$-$C_6$ alkenyl optionally substituted with 1-3 $R^{22}$; $C_6$-$C_{10}$ aryl optionally substituted with 1-3 $R^{30}$; 5 to 6 membered heteroaryl ring system containing one, two, or three heteroatoms selected from N, O, and S, wherein said heteroaryl ring system is optionally substituted with 1-3 $R^{30}$;
4 membered heterocycloalkyl ring system containing one heteroatom selected from N, O, S, SO, and $SO_2$, wherein said heterocycloalkyl ring system is optionally substituted with 1-3 $R^{30}$; and
5 to 7 membered heterocycloalkyl ring system containing one, two, or three heteroatoms selected from N, O, S, SO, and $SO_2$, wherein said heterocycloalkyl ring system is optionally substituted with 1-3 $R^{30}$;

$R^{22}$ at each occurrence is independently selected from the group consisting of
—H, —F, —Cl, —Br, —I, —$C_1$-$C_6$ alkoxy, phenyl, —$NR^{23}R^{24}$, —NHOH, —$NO_2$, —CN, —$CF_3$, —$CHF_2$, —$CH_2F$, (=O), —C(=O)$R^{28}$, —C(=O)$OR^{28}$, —OC(=O)$R^{28}$, —OC(=O)$NR^{23}R^{24}$, —C(=O)$NR^{23}R^{24}$, —$NR^{27}C$(=O)$NR^{23}R^{24}$, —$NR^{27}C$(=O)$R^{28}$, —$NR^{27}C$(=O)$OR^{28}$, —$NR^{27}C$(=S)$R^{28}$, —$SR^{28}$, —S(=O)$R^{28}$, —S(=O)$_2R^{28}$, —S(=O)$_2NR^{23}R^{24}$, —$NR^{27}SR^{28}$, —$NR^{27}S$(=O)$R^{28}$, —$NR^{27}S$(=O)$_2R^{28}$, and $C_3$-$C_7$ cycloalkyl;

$R^{23}$ and $R^{24}$ at each occurrence are each independently selected from H, $C_1$-$C_6$ alkyl optionally substituted with 1-3 $R^{31}$; $C_3$-$C_7$ cycloalkyl; $C_6$-$C_{10}$ aryl optionally substituted with 1-3 $R^{30}$; 5 to 6 membered heteroaryl ring system containing one, two, or three heteroatoms selected from N, O, and S, said heteroaryl optionally substituted with 1-3 $R^{30}$;
4 membered heterocycloalkyl ring system containing one heteroatom selected from N, O, S, SO, and $SO_2$ said heterocycloalkyl optionally substituted with 1-3 $R^{30}$; and
5 to 7 membered heterocycloalkyl ring system containing one, two, or three heteroatoms selected from N, O, S, SO, and $SO_2$ said heterocycloalkyl optionally substituted with 1-3 $R^{30}$;

or $R^{23}$ and $R^{24}$, together with the nitrogen atom to which they are attached, may form a 3 to 7 membered heterocycloalkyl ring containing 1 nitrogen atom and optionally a second heteroatom selected from nitrogen, oxygen, and sulfur, wherein said heterocycloalkyl ring is optionally substituted with 1-3 $R^{30}$;

$R^{25}$ at each occurrence is independently H, $C_1$-$C_6$ alkyl, $C_1$-$C_4$ haloalkyl, —($C_1$-$C_3$ alkyl)$C_6$-$C_{10}$aryl, $C_6$-$C_{10}$ aryl, $C_3$-$C_7$ cycloalkyl, 5 to 6 membered heteroaryl ring system containing one, two, or three heteroatoms selected from N, O, and S;

4 membered heterocycloalkyl ring system containing one heteroatom selected from N, O, S, SO, and $SO_2$; or 5 to 7 membered heterocycloalkyl ring system containing one, two, or three heteroatoms selected from N, O, S, SO, and $SO_2$;

$R^{27}$ at each occurrence is independently H or $C_1$-$C_3$ alkyl;
$R^{28}$ at each occurrence is independently H or $C_1$-$C_3$ alkyl;
$R^{29}$ at each occurrence is independently H, $C_1$-$C_3$ alkyl, or —C(=O)$CH_3$;

$R^{30}$ at each occurrence is independently H, —F, —Cl, —Br, —I, —OH, =O, $C_1$-$C_6$ alkyl, $C_1$-$C_6$ alkoxy, $C_1$-$C_4$ haloalkyl, —C(=O)N($R^{32}$)$_2$, —NHC(=O)N($R^{32}$)$_2$, or —S(=O)$_2R^{32}$, $R^{31}$ at each occurrence is independently H, —F, —Cl, —Br, —I, —OH, =O, $C_1$-$C_6$ alkoxy, $C_1$-$C_4$ haloalkyl, —C(=O)N($R^{32}$)$_2$, —NHC(=O)N($R^{32}$)$_2$, $C_6$-$C_{10}$ aryl optionally substituted with 1-3 $R^{30}$; 3 to 4 membered heterocycloalkyl ring system containing one or two heteroatoms selected from N, O, S, SO, and $SO_2$; or 5 to 7 membered heterocycloalkyl ring system containing one, two, or three heteroatoms selected from N, O, S, SO, and $SO_2$;

$R^{32}$ at each occurrence is independently H, $C_1$-$C_3$ alkyl, or $C_1$-$C_3$ alkoxy;

n is 0, 1, 2, or 3; and
z is 0, 1, 2, 3, 4, 5, or 6.

2. The compound of claim 1 having the structure of Formula (II):

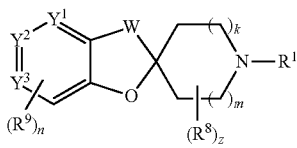

(II)

or a stereoisomeric form, mixture of stereoisomeric forms, N-oxide form, or a pharmaceutically acceptable salt thereof, wherein $Y^1$ is —CH= or —N=; and $Y^2$=$Y^3$ is —C(X)=CH— or —CH=C(X)—.

3. The compound of claim 2 wherein W is —$CH_2$—O— or —$CH_2$—$CH_2$—.

4. The compound of claim 1 wherein k is 0.
5. The compound of claim 1 wherein k is 1.
6. The compound of claim 1 wherein m is 0.
7. The compound of claim 1 wherein m is 1.
8. The compound of claim 1 wherein the sum of m and k is 1.
9. The compound of claim 1 wherein the sum of m and k is 2.
10. The compound of claim 1 wherein W is —O—, —$CH_2$—, —$CH_2$—O—, —C(=O)—$CH_2$—, —C(OH)—$CH_2$—, —$CH_2$—$CH_2$— or —$CH_2$—$CH_2$—O—.
11. The compound of claim 1 wherein W is —O—, —$CH_2$—O—, —$CH_2$—$CH_2$—, or —$CH_2$—$CH_2$—O—.
12. The compound of claim 1 wherein W is —$CH_2$—O— or —$CH_2$—$CH_2$—.
13. The compound of claim 1 wherein z is 0.

14. The compound of claim 1 having the structure of Formula (II):

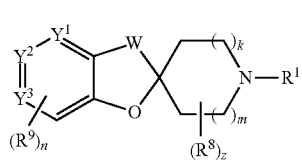

(II)

or a stereoisomeric form, mixture of stereoisomeric forms, an N-oxide form, or a pharmaceutically acceptable salt thereof.

15. The compound of claim 1 having the structure of Formula (III):

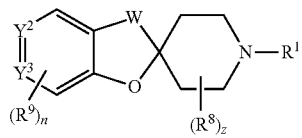

(III)

or a stereoisomeric form, mixture of stereoisomeric forms, an N-oxide form, or a pharmaceutically acceptable salt thereof, wherein $Y^2$=$Y^3$ is —C(X)=CH— or —CH=C(X)—.

16. The compound of claim 15 wherein W is —$CH_2$—O— or —$CH_2$—$CH_2$—.

17. The compound of claim 1 having the structure of Formula (III):

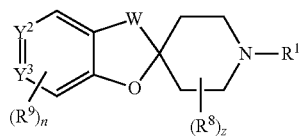

(III)

or a stereoisomeric form, mixture of stereoisomeric forms, an N-oxide form, or a pharmaceutically acceptable salt thereof.

18. The compound of claim 1 having the structure of Formula (IV):

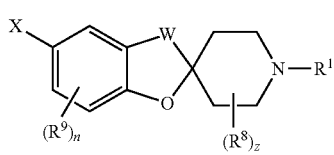

(IV)

or a stereoisomeric form, mixture of stereoisomeric forms, an N-oxide form, or a pharmaceutically acceptable salt thereof.

19. The compound of claim 18, or a stereoisomeric form, mixture of stereoisomeric forms, an N-oxide form, or a pharmaceutically acceptable salt thereof, wherein:

W is —O—, —$CH_2$—O—, —C(=O)—$CH_2$—, —C(OH)—$CH_2$—, —$CH_2$—$CH_2$—, or —$CH_2$—$CH_2$—O—;

$R^{23}$ at each occurrence are each independently selected from H, methyl, ethyl, and propyl; and $R^{24}$ at each occurrence are each independently selected from H, $C_1$-$C_6$ alkyl optionally substituted with 1-3 $R^{31}$;

$C_3$-$C_7$ cycloalkyl; $C_6$-$C_{10}$ aryl optionally substituted with 1-3 $R^{30}$; 5 to 6 membered heteroaryl ring system containing one, two, or three heteroatoms selected from N, O, and S, said heteroaryl optionally substituted with 1-3 $R^{30}$;

4 membered heterocycloalkyl ring system containing one heteroatom selected from N, O, S, SO, and $SO_2$ said heterocycloalkyl optionally substituted with 1-3 $R^{30}$; and 5 to 7 membered heterocycloalkyl ring system containing one, two, or three heteroatoms selected from N, O, S, SO, and $SO_2$ said heterocycloalkyl optionally substituted with 1-3 $R^{30}$;

or $R^{23}$ and $R^{24}$, together with the nitrogen atom to which they are attached, may form a 3 to 7 membered heterocycloalkyl ring containing 1 nitrogen atom and optionally a second heteroatom selected from nitrogen, oxygen, and sulfur, wherein said heterocycloalkyl ring is optionally substituted with 1-3 $R^{30}$.

20. The compound of claim 19, or a stereoisomeric form, mixture of stereoisomeric forms, an N-oxide form, or a pharmaceutically acceptable salt thereof, wherein W is —$CH_2$—O— or —$CH_2$—$CH_2$—.

21. The compound of claim 19, or a stereoisomeric form, mixture of stereoisomeric forms, an N-oxide form, or a pharmaceutically acceptable salt thereof, wherein X is $R^2$, —$OR^2$, —$OCH_2$—$R^2$, —OCH(OH)—$R^2$, —OCH($OCH_3$)—$R^2$, —($CH_2$—CH=CH—$CH_2$)—$R^2$, —O—($CH_2$—CH=CH—$CH_2$)—$R^2$, —$NR^{29}R^2$, —$N(R^{29})CH_2$—$R^2$, —$CH_2NR^{29}R^2$, —$NR^{29}C$(=O)$R^2$, —$NR^{29}C$(=O)$CH_2$—$R^2$, or —$NR^{29}C$(=O)$NHR^2$.

22. The compound of claim 18, or a stereoisomeric form, mixture of stereoisomeric forms, an N-oxide form, or a pharmaceutically acceptable salt thereof, wherein:

W is —$CH_2$—O— or —$CH_2$—$CH_2$—;
X is $R^2$, —$OR^2$, —$OCH_2$—$R^2$, —$NR^{29}R^2$, —$N(R^{29})CH_2$—$R^2$, —$CH_2NR^{29}R^2$, —$NR^{29}C$(=O)$R^2$, —$NR^{29}C$(=O)$CH_2$—$R^2$, or —$NR^{29}C$(=O)$NHR^2$;
$R^2$ is selected from the group consisting of:
phenyl optionally substituted with 1-3 $R^{20}$;
5 to 10 membered heteroaryl ring system selected from benzofuranyl, benzimidazolyl, benzothiazolyl, benzooxazolyl, benzooxadiazolyl, cinnolinyl, furanyl, imidazolyl, imidazopyridinyl, 1H-indazolyl, indolyl, isoxazolyl, isothiazolyl, oxazolyl, oxadiazolyl, pyrazolyl, pyrazinyl, pyridazinyl, pyridinyl, pyrimidinyl, pyrrolyl, thiazolyl, and thienyl, wherein said heteroaryl ring system is optionally substituted with 1-3 $R^{20}$; and
5 to 10 membered heterocycloalkyl ring system selected from azetidinyl, 1,1-dioxo-thiomorpholinyl, 1,4-diazapinyl, 2,3-dihydrobenzofuranyl, 3H-benzooxazolyl, imidazolidinyl, morpholinyl, piperidinyl, piperazinyl, pyrrolidinyl, oxazolidinyl, thiomorpholinyl, tetrahydropyranyl, tetrahydropyrazolopyridinyl, tetrahydro-1,3a, 7-triaza-azulenyl, and tetrahydrofuran, wherein said heterocycloalkyl ring system is optionally substituted with 1-3 $R^{20}$;
$R^9$, at each occurrence, is independently, F or Cl;
$R^{20}$ at each occurrence is independently selected from the group consisting of
—H, —F, —Cl, —$OR^{21}$, —$NR^{23}R^{24}$, —CN, —$CF_3$, (=O), —C(=O)$R^{25}$, —C(=O)$OR^{25}$, —OC(=O)$R^{25}$, —OC(=O)$NR^{23}R^{24}$, —C(=O)$NR^{23}R^{24}$, —$NR^{27}C$(=O)$NR^{23}R^{24}$, —$NR^{27}C$(=O)$R^{25}$, —$NR^{27}C$(=O)$OR^{25}$, —$NR^{27}C$(=S)$R^{25}$, —$SR^{25}$, —S(=O)$R^{25}$, —S(=O)$_2R^{25}$, —S(=O)$_2NR^{23}R^{24}$, —$NR^{27}SR^{25}$, —$NR^{27}S$(=O)$R^{25}$, —$NR^{27}S$(=O)$_2R^{25}$, methyl, ethyl, propyl, butyl, ethylenedioxy, methyl substituted with $R^{31}$; phenyl optionally substituted with 1-3 $R^{30}$; and 5 to 6 membered heteroaryl ring system selected from oxadiazolyl, thiazolyl, pyridinyl, pyridazinyl, pyrimidinyl, and pyrazinyl, wherein said heteroaryl ring system is optionally substituted with 1-3 $R^{30}$;

3 to 7 membered heterocycloalkyl ring system selected from dihydro-oxazolyl, morpholinyl, piperidinyl, piperazinyl, and pyrrolidinyl, wherein said heterocycloalkyl ring system is optionally substituted with 1-3 $R^{30}$;

$R^{21}$ at each occurrence is independently H, —$CF_3$, methyl, ethyl, propyl, butyl, methoxyethyl, cyclopropylmethyl, phenyl, or pyridyl;

$R^{22}$ at each occurrence is independently selected from the group consisting of —H, —F, —Cl, methoxy, ethoxy, propoxy, butoxy, —$NR^{23}R^{24}$, —NHOH, —$NO_2$, —CN, —$CF_3$, —$CHF_2$, —$CH_2F$, (=O), —C(=O)$R^{28}$, —C(=O)$OR^{28}$, —OC(=O)$R^{28}$, —OC(=O)$NR^{23}R^{24}$, —C(=O)$NR^{23}R^{24}$, —$NR^{27}C$(=O)$NR^{23}R^{24}$, —$NR^{27}C$(=O)$R^{28}$, —$NR^{27}C$(=O)$OR^{28}$, —$NR^{27}C$(=S)$R^{28}$, —$SR^{28}$, —S(=O)$R^{28}$, —S(=O)$_2R^{28}$, —S(=O)$_2NR^{23}R^{24}$, —$NR^{27}SR^{28}$, —$NR^{27}S$(=O)$R^{28}$, and —$NR^{27}S$(=O)$_2R^{28}$;

$R^{23}$ at each occurrence are each independently selected from H, methyl, ethyl, and propyl;

$R^{24}$ at each occurrence are each independently selected from H, methyl, ethyl, propyl, butyl, hydroxyethyl, methoxyethyl, ethoxyethyl, cyclopropyl, cyclobutyl, phenyl optionally substituted with 1-3 $R^{30}$; 3 to 7 membered heterocycloalkyl ring system selected from morpholinyl, piperidinyl, piperazinyl, pyrrolidinyl, tetrahydrofuranyl, and tetrahydropyranyl, said heterocycloalkyl optionally substituted with 1-3 $R^{30}$; or $R^{23}$ and $R^{24}$, together with the nitrogen atom to which they are attached, may form a 3 to 7 membered heterocycloalkyl ring selected from azetidinyl, morpholinyl, piperidinyl, piperazinyl, pyrrolidinyl, wherein said heterocycloalkyl ring is optionally substituted with 1-3 $R^{30}$;

$R^{25}$ at each occurrence is independently H, methyl, ethyl, propyl, butyl, $CF_3$, phenyl, cyclopropyl, cyclobutyl, cyclopentyl, cyclohexyl, morpholinyl and furanyl;

$R^{27}$ at each occurrence is independently H or methyl;

$R^{28}$ at each occurrence is independently H or methyl;

$R^{29}$ at each occurrence is independently H, methyl, ethyl, or —C(=O)$CH_3$;

$R^{30}$ at each occurrence is independently H, —F, —Cl, —OH, =O, methyl, ethyl, propyl, butyl, methoxy, ethoxy, propoxy, butoxy, $CF_3$, —C(=O)N($R^{32}$)$_2$, —NHC(=O)N($R^{32}$)$_2$, or —S(=O)$_2CH_3$;

$R^{31}$ at each occurrence is independently H, —F, —Cl, —OH, =O, methoxy, ethoxy, propoxy, butoxy, $CF_3$, —C(=O)N($R^{32}$)$_2$, —NHC(=O)N($R^{32}$)$_2$, phenyl optionally substituted with 1-3 $R^{30}$; or tetrahydrofuranyl;

$R^{32}$ at each occurrence is independently H or methyl;

n is 0, 1, or 2; and z is 0 or 1.

23. The compound of claim 1 having the structure of Formula (IV):

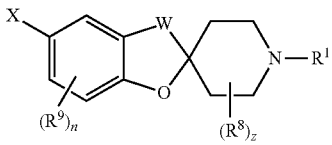

or a stereoisomeric form, mixture of stereoisomeric forms, an N-oxide form, or a pharmaceutically acceptable salt thereof, wherein:
W is —O—, —CH$_2$—O—, —C(=O)—CH$_2$—, —C(OH)—CH$_2$—, —CH$_2$—CH$_2$—, or —CH$_2$—CH$_2$—O—;
R$^2$ is selected from the group consisting of
C$_1$-C$_8$ alkyl optionally substituted with 1-3 R$^{20}$;
C$_2$-C$_6$ alkenyl optionally substituted with 1-3 R$^{20}$;
C$_3$-C$_{10}$ cycloalkyl optionally substituted with 1-3 R$^{20}$;
C$_6$-C$_{10}$ aryl optionally substituted with 1-3 R$^{20}$;
5 to 10 membered heteroaryl ring system containing one, two, or three heteroatoms selected from N, O, and S, wherein said heteroaryl ring system is optionally substituted with 1-3 R$^{20}$; and
5 to 10 membered heterocycloalkyl ring system containing one, two, or three heteroatoms selected from N, O, S, SO, and SO$_2$, wherein said heterocycloalkyl ring system is optionally substituted with 1-3 R$^{20}$;
with the proviso that R$^2$ is not a substituted or unsubstituted pyridazinone ring or a substituted or unsubstituted pyridazine ring;
R$^{23}$ at each occurrence are each independently selected from H, methyl, ethyl, and propyl;
R$^{24}$ at each occurrence are each independently selected from H, C$_1$-C$_6$ alkyl optionally substituted with 1-3 R$^{31}$; C$_3$-C$_7$ cycloalkyl; C$_6$-C$_{10}$ aryl optionally substituted with 1-3 R$^{30}$; 5 to 6 membered heteroaryl ring system containing one, two, or three heteroatoms selected from N, O, and S, said heteroaryl optionally substituted with 1-3 R$^{30}$;
4 membered heterocycloalkyl ring system containing one heteroatom selected from N, O, S, SO, and SO$_2$, said heterocycloalkyl optionally substituted with 1-3 R$^{30}$; and
5 to 7 membered heterocycloalkyl ring system containing one, two, or three heteroatoms selected from N, O, S, SO, and SO$_2$ said heterocycloalkyl optionally substituted with 1-3 R$^{30}$; or R$^{23}$ and R$^{24}$, together with the nitrogen atom to which they are attached, may form a 3 to 7 membered heterocycloalkyl ring containing 1 nitrogen atom and optionally a second heteroatom selected from nitrogen, oxygen, and sulfur, wherein said heterocycloalkyl ring is optionally substituted with 1-3 R$^{30}$.

24. The compound of claim 1 having the structure of Formula (V):

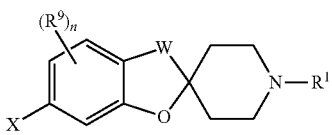

or a stereoisomeric form, mixture of stereoisomeric forms, an N-oxide form, or a pharmaceutically acceptable salt thereof.

25. The compound of claim 24, or a stereoisomeric form, mixture of stereoisomeric forms, an N-oxide form, or a pharmaceutically acceptable salt thereof, wherein:
W is —O—, —CH$_2$—O—, —C(=O)—CH$_2$—, —C(OH)—CH$_2$—, —CH$_2$—CH$_2$—, or —CH$_2$—CH$_2$—O—;
R$^{23}$ at each occurrence are each independently selected from H, methyl, ethyl, and propyl; and
R$^{24}$ at each occurrence are each independently selected from H, C$_1$-C$_6$ alkyl optionally substituted with 1-3 R$^{31}$; C$_3$-C$_7$ cycloalkyl; C$_6$-C$_{10}$ aryl optionally substituted with 1-3 R$^{30}$; 5 to 6 membered heteroaryl ring system containing one, two, or three heteroatoms selected from N, O, and S, said heteroaryl optionally substituted with 1-3 R$^{30}$; and 3 to 7 membered heterocycloalkyl ring system containing one, two, or three heteroatoms selected from N, O, S, SO, and SO$_2$ said heterocycloalkyl optionally substituted with 1-3 R$^{30}$;
or R$^{23}$ and R$^{24}$, together with the nitrogen atom to which they are attached, may form a 3 to 7 membered heterocycloalkyl ring containing 1 nitrogen atom and optionally a second heteroatom selected from nitrogen, oxygen, and sulfur, wherein said heterocycloalkyl ring is optionally substituted with 1-3 R$^{30}$.

26. The compound of claim 25, or a stereoisomeric form, mixture of stereoisomeric forms, an N-oxide form, or a pharmaceutically acceptable salt thereof, wherein W is —CH$_2$—O— or —CH$_2$—CH$_2$—.

27. The compound of claim 1, or a stereoisomeric form, mixture of stereoisomeric forms, an N-oxide form, or a pharmaceutically acceptable salt thereof, wherein X is R$^2$, —OR$^2$, —OCH$_2$—R$^2$, —OCH(OH)—R$^2$, —OCH(OCH$_3$)—R$^2$, —(CH$_2$—CH=CH—CH$_2$)—R$^2$, —O—(CH$_2$—CH=CH—CH$_2$)—R$^2$, —NR$^{29}$R$^2$, —N(R$^{29}$)CH$_2$—R$^2$, —CH$_2$NR$^{29}$R$^2$, —NR$^{29}$C(=O)R$^2$, —NR$^{29}$C(=O)CH$_2$—R$^2$, or —NR$^{29}$C(=O)NHR$^2$.

28. The compound of claim 27, or a stereoisomeric form, mixture of stereoisomeric forms, an N-oxide form, or a pharmaceutically acceptable salt thereof, wherein R$^8$ is H.

29. The compound of claim 24, or a stereoisomeric form, mixture of stereoisomeric forms, an N-oxide form, or a pharmaceutically acceptable salt thereof, wherein:
W is —CH$_2$—O— or —CH$_2$—CH$_2$—;
X is R$^2$, —OR$^2$, —OCH$_2$—R$^2$, —NR$^{29}$R$^2$, —N(R$^{29}$)CH$_2$—R$^2$, —CH$_2$NR$^{29}$R$^2$, —NR$^{29}$C(=O)R$^2$, —NR$^{29}$C(=O)CH$_2$—R$^2$, or —NR$^{29}$C(=O)NHR$^2$;
R$^2$ is selected from the group consisting of
phenyl optionally substituted with 1-3 R$^{20}$;
5 to 10 membered heteroaryl ring system selected from benzofuranyl, benzimidazolyl, benzothiazolyl, benzooxazolyl, benzooxadiazolyl, cinnolinyl, furanyl, imidazolyl, imidazopyridinyl, 1H-indazolyl, indolyl, isoxazolyl, isothiazolyl, oxazolyl, oxadiazolyl, pyrazolyl, pyrazinyl, pyridazinyl, pyridinyl, pyrimidinyl, pyrrolyl, thiazolyl, and thienyl, wherein said heteroaryl ring system is optionally substituted with 1-3 R$^{20}$; and
5 to 10 membered heterocycloalkyl ring system selected from azetidinyl, 1,1-dioxo-thiomorpholinyl, 1,4-diazapinyl, 2,3-dihydrobenzofuranyl, 3H-benzooxazolyl, imidazolidinyl, morpholinyl, piperidinyl, piperazinyl, pyrrolidinyl, oxazolidinyl, thiomorpholinyl, tetrahydropyranyl, tetrahydropyrazolopyridinyl, tetrahydro-1,3a,7-triaza-azulenyl, and tetrahydrofuran, wherein said heterocycloalkyl ring system is optionally substituted with 1-3 R$^{20}$;

$R^9$, at each occurrence, is independently, F or Cl;

$R^{20}$ at each occurrence is independently selected from the group consisting of —H, —F, —Cl, —OR$^{21}$, —NR$^{23}$R$^{24}$, —CN, —CF$_3$, (=O), —C(=O)R$^{25}$, —C(=O)OR$^{25}$, —OC(=O)R$^{25}$, —OC(=O)NR$^{23}$R$^{24}$, —C(=O)NR$^{23}$R$^{24}$, —NR$^{27}$C(=O)NR$^{23}$R$^{24}$, —NR$^{27}$C(=O)R$^{25}$, —NR$^{27}$C(=O)OR$^{25}$, —NR$^{27}$C(=S)R$^{25}$, —SR$^{25}$, —S(=O)R$^{25}$, —S(=O)$_2$R$^{25}$, —S(=O)$_2$NR$^{23}$R$^{24}$, —NR$^{27}$SR$^{25}$, —NR$^{27}$S(=O)R$^{25}$, —NR$^{27}$S(=O)$_2$R$^{25}$, methyl, ethyl, propyl, butyl, ethylenedioxy, methyl substituted with R$^{31}$;

phenyl optionally substituted with 1-3 R$^{30}$; and 5 to 6 membered heteroaryl ring system selected from oxadiazolyl, thiazolyl, pyridinyl, pyridazinyl, pyrimidinyl, and pyrazinyl, wherein said heteroaryl ring system is optionally substituted with 1-3 R$^{30}$;

3 to 7 membered heterocycloalkyl ring system selected from dihydro-oxazolyl, morpholinyl, piperidinyl, piperazinyl, and pyrrolidinyl, wherein said heterocycloalkyl ring system is optionally substituted with 1-3 R$^{30}$;

$R^{21}$ at each occurrence is independently H, —CF$_3$, methyl, ethyl, propyl, butyl, methoxyethyl, cyclopropylmethyl, phenyl, or pyridyl;

$R^{22}$ at each occurrence is independently selected from the group consisting of —H, —F, —Cl, methoxy, ethoxy, propoxy, butoxy, —NR$^{23}$R$^{24}$, —NHOH, —NO$_2$, —CN, —CF$_3$, —CHF$_2$, —CH$_2$F, (=O), —C(=O)R$^{28}$, —C(=O)OR$^{28}$, —OC(=O)R$^{28}$, —OC(=O)NR$^{23}$R$^{24}$, —C(=O)NR$^{23}$R$^{24}$, —NR$^{27}$C(=O)NR$^{23}$R$^{24}$, —NR$^{27}$C(=O)R$^{28}$, —NR$^{27}$C(=O)OR$^{28}$, —NR$^{27}$C(=S)R$^{28}$, —SR$^{28}$, —S(=O)R$^{28}$, —S(=O)$_2$R$^{28}$, —S(=O)$_2$NR$^{23}$R$^{24}$, —NR$^{27}$SR$^{28}$, —NR$^{27}$S(=O)R$^{28}$, and —NR$^{27}$S(=O)$_2$R$^{28}$;

$R^{23}$ at each occurrence are each independently selected from H, methyl, ethyl, and propyl;

$R^{24}$ at each occurrence are each independently selected from H, methyl, ethyl, propyl, butyl, hydroxyethyl, methoxyethyl, ethoxyethyl, cyclopropyl, cyclobutyl, phenyl optionally substituted with 1-3 R$^{30}$;

3 to 7 membered heterocycloalkyl ring system selected from morpholinyl, piperidinyl, piperazinyl, pyrrolidinyl, tetrahydrofuranyl, and tetrahydropyranyl, said heterocycloalkyl optionally substituted with 1-3 R$^{30}$; or R$^{23}$ and R$^{24}$, together with the nitrogen atom to which they are attached, may form a 3 to 7 membered heterocycloalkyl ring selected from azetidinyl, morpholinyl, piperidinyl, piperazinyl, pyrrolidinyl, wherein said heterocycloalkyl ring is optionally substituted with 1-3 R$^{30}$;

$R^{25}$ at each occurrence is independently H, methyl, ethyl, propyl, butyl, CF$_3$, phenyl, cyclopropyl, cyclobutyl, cyclopentyl, cyclohexyl, morpholinyl and furanyl;

$R^{27}$ at each occurrence is independently H or methyl;

$R^{28}$ at each occurrence is independently H or methyl;

$R^{29}$ at each occurrence is independently H, methyl, ethyl, or —C(=O)CH$_3$;

$R^{30}$ at each occurrence is independently H, —F, —Cl, —OH, =O, methyl, ethyl, propyl, butyl, methoxy, ethoxy, propoxy, butoxy, CF$_3$, —C(=O)N(R$^{32}$)$_2$, —NHC(=O) N(R$^{32}$)$_2$, or —S(=O)$_2$CH$_3$;

$R^{31}$ at each occurrence is independently H, —F, —Cl, —OH, =O, methoxy, ethoxy, propoxy, butoxy, CF$_3$, —C(=O)N(R$^{32}$)$_2$, —NHC(=O)N(R$^{32}$)$_2$, phenyl optionally substituted with 1-3 R$^{30}$; or tetrahydrofuranyl;

$R^{32}$ at each occurrence is independently H or methyl; and n is 0 or 1.

30. A pharmaceutical composition comprising a compound of claim 1, or a stereoisomeric form, mixture of stereoisomeric forms, an N-oxide form, or a pharmaceutically acceptable salt thereof, and one or more pharmaceutically acceptable excipients.

\* \* \* \* \*